US009933439B2

(12) United States Patent
Kentsis et al.

(10) Patent No.: US 9,933,439 B2
(45) Date of Patent: Apr. 3, 2018

(54) METHOD OF PREDICTING ACUTE APPENDICITIS

(71) Applicant: CHILDREN'S MEDICAL CENTER CORPORATION, Boston, MA (US)

(72) Inventors: Alex Kentsis, New York, NY (US); Hanno Steen, Cambridge, MA (US); Richard Bachur, North Reading, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 54 days.

(21) Appl. No.: 14/506,461

(22) Filed: Oct. 3, 2014

(65) Prior Publication Data

US 2015/0031049 A1 Jan. 29, 2015

Related U.S. Application Data

(60) Division of application No. 13/963,017, filed on Aug. 9, 2013, now Pat. No. 8,871,453, which is a continuation of application No. 13/142,598, filed as application No. PCT/US2009/069800 on Dec. 30, 2009, now Pat. No. 8,535,891.

(60) Provisional application No. 61/185,676, filed on Jun. 10, 2009, provisional application No. 61/141,283, filed on Dec. 30, 2008.

(51) Int. Cl.
*G01N 33/53* (2006.01)
*G01N 33/68* (2006.01)

(52) U.S. Cl.
CPC ..... *G01N 33/6893* (2013.01); *G01N 2800/06* (2013.01); *G01N 2800/50* (2013.01)

(58) Field of Classification Search
CPC .............. G06F 19/322; G01N 2800/06; G01N 2800/50; G01N 33/553
See application file for complete search history.

(56) References Cited

U.S. PATENT DOCUMENTS

| | | | |
|---|---|---|---|
| 7,623,910 | B2 | 11/2009 | Couderc et al. |
| 2008/0092094 | A1 | 4/2008 | Coolbaugh et al. |
| 2009/0018026 | A1 | 1/2009 | Kim et al. |
| 2009/0035875 | A1 | 2/2009 | Jemmerson |
| 2009/0104605 | A1 | 4/2009 | Siuzdak et al. |
| 2009/0175844 | A1 | 7/2009 | Nakamura et al. |
| 2010/0086932 | A1 | 4/2010 | Alcaraz Asensio et al. |
| 2010/0184049 | A1 | 7/2010 | Goodison et al. |
| 2010/0190662 | A1 | 7/2010 | Sutphen et al. |
| 2011/0117111 | A1* | 5/2011 | Kwon .................. C12N 15/111 424/172.1 |
| 2012/0009174 | A1* | 1/2012 | Van Eyk ........... G01N 33/6893 424/94.64 |

FOREIGN PATENT DOCUMENTS

WO 2006125973 11/2006

OTHER PUBLICATIONS

Budai et al, Anal Bioanal Chem 2009,393:991-998.*
Magid et al., 2005, Clin. Chem 51:11.*
Kumar et al.,"Dimeric S100A8 in human neutrophils is diminished after phagocytosis", Journal of Leukocyte Biology, 70(1):59-64 (2001).
Styrud et al., World J. Surg, 30(6):1033-1037 (2006). "Appendectomy versus antibiotic treatment in acute appendicitis. a prospective multicenter randomized controlled trial".
Groselj-Grenc et al., Scandinavian Journal of Clinical and Laboratory Investigation, 67(2):197-206 (2007). "Interleukin-6 and lipopolysaccharide-binding protein in acute appendicitis in children."
Lycopoulou et al., Clinical Chemistry and Laboratory Medicine, 43(1):49-53 (2005). "Serum amyloid A protein levels as a possible aid in the diagnosis of acute appendicitis in children."
Sack Ulrich et al., BMC Surgery, Biomed Central, 6(1):15-22 (2006). "Diagnostic value of blood inflammatory markers for detection of acute appendicitis in children."
Aspenbio Pharma, Inc., "Appendicitis product pipeline," http://www.aspenbiopharma.com/rdproduct/appendicitis/ accessed Apr. 7, 2009.
Kentsis et al., Annals of Emergency Medicine, 1-9.e4 (2009). "Discovery and validation of urine markers of acute pediatric appendicitis using high-accuracy mass spectrometry."
Mahmoud et al., Tikrit Medical Journal, 13(1):81-83 (2007).
O'Donnell et al., Journal of Leukocyte Biology, 72(3):478-485 (2002). "Molecular characterization and expression analysis of leucine-rich alpha2-glycoprotein, a novel marker of granulocytic differentiation".
Murphy et al., Nautre, 1(4), 2008.
Eguchi et al., Biochem J, 387:343-353 (2005). "Identification of adipocyte adhesion molecule (ACAM), a novel CTX gene family, implicated in adipocyte maturation and development of obesity".
Life Science Application, Life Technologies 2008 Catalog.

* cited by examiner

*Primary Examiner* — Tracy Vivlemore
*Assistant Examiner* — Carmencita M Belei
(74) *Attorney, Agent, or Firm* — Nixon Peabody LLP; David S. Resnick

(57) ABSTRACT

Embodiments of the invention provide method and devices for predicting the likelihood of acute appendicitis without invasive exploratory medical procedures. Several protein biomarkers: leucine-rich α-2-glycoprotein (LRG); S100-A8 (calgranulin); α-1-acid glycoprotein 1 (ORM); plasminogen (PLG); mannan-binding lectin serine protease 2 (MASP2); zinc-α-2-glycoprotein (AZGP1); Apolipoprotein D (ApoD); and α-1-antichymotrypsin (SERPINA3); are increased in the urine of patients with appendicitis. The method and devices comprise detecting the levels of these biomarkers and comparing with reference levels found in healthy individuals.

2 Claims, 22 Drawing Sheets

Figure 2A
Fig. 2
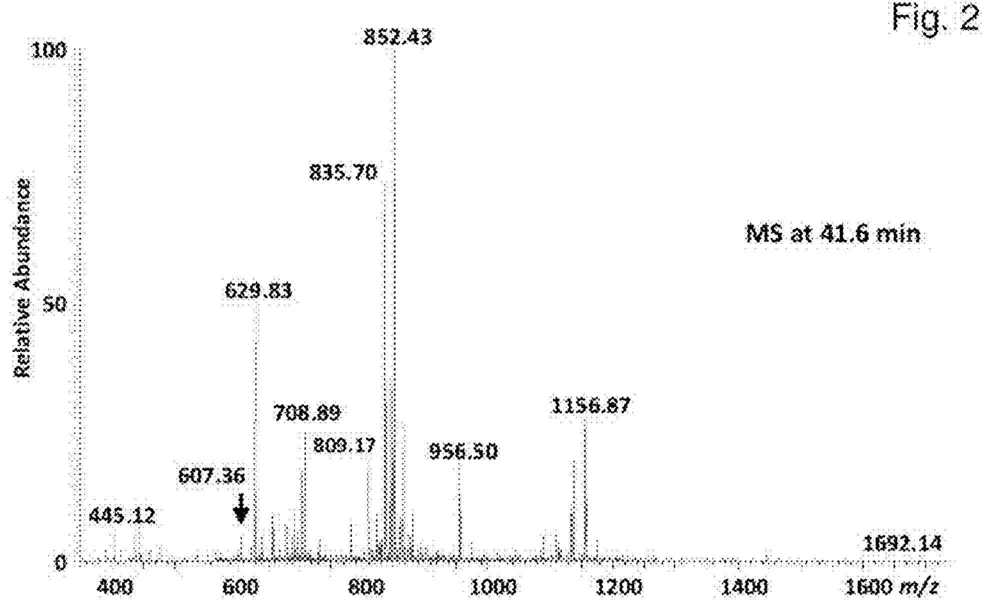
Figure 2B
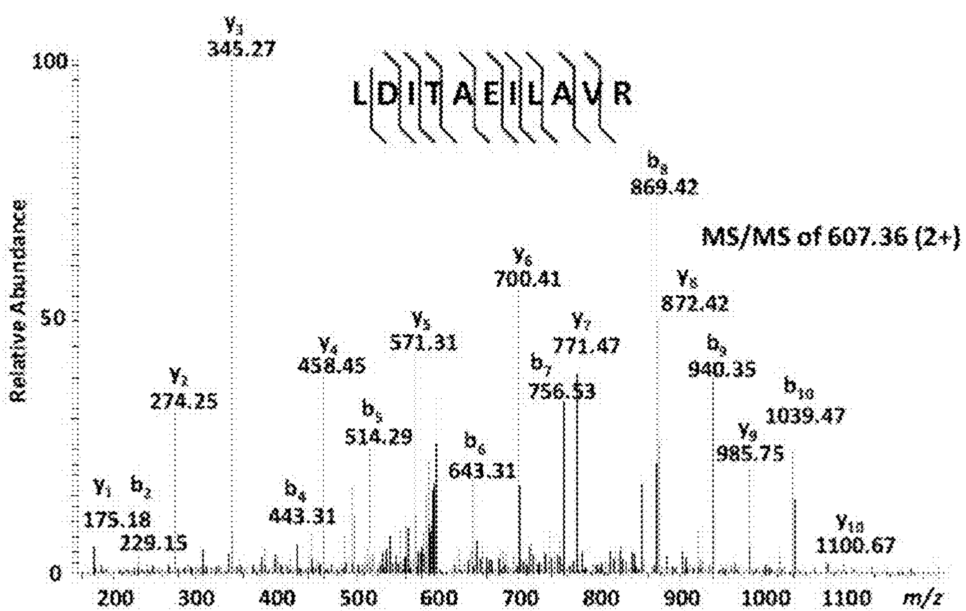

Current
2,362
Adachi *et al*
1,543
891
241
Pisitkun *et al*
258

Proteins
300
200
100
0
50
100
150
200
CV (%)
A
B (Top View)

(Cross Section View)

(Top View)

(Cross Section View)

SEQUENCE LISTING

```
<160> NUMBER OF SEQ ID NOS: 52

<210> SEQ ID NO 1
<211> LENGTH: 347
<212> TYPE: PRT
<213> ORGANISM: Homo sapiens

<400> SEQUENCE: 1

Met Ser Ser Trp Ser Arg Gln Arg Pro Lys Ser Pro Gly Gly Ile Gln
1               5                   10                  15

Pro His Val Ser Arg Thr Leu Phe Leu Leu Leu Leu Leu Ala Ala Ser
            20                  25                  30

Ala Trp Gly Val Thr Leu Ser Pro Lys Asp Cys Gln Val Phe Arg Ser
        35                  40                  45

Asp His Gly Ser Ser Ile Ser Cys Gln Pro Pro Ala Glu Ile Pro Gly
    50                  55                  60

Tyr Leu Pro Ala Asp Thr Val His Leu Ala Val Glu Phe Phe Asn Leu
65                  70                  75                  80
```

```
Thr His Leu Pro Ala Asn Leu Leu Gln Gly Ala Ser Lys Leu Gln Glu
                85                  90                  95

Leu His Leu Ser Ser Asn Gly Leu Glu Ser Leu Ser Pro Glu Phe Leu
            100                 105                 110

Arg Pro Val Pro Gln Leu Arg Val Leu Asp Leu Thr Arg Asn Ala Leu
        115                 120                 125

Thr Gly Leu Pro Pro Gly Leu Phe Gln Ala Ser Ala Thr Leu Asp Thr
    130                 135                 140

Leu Val Leu Lys Glu Asn Gln Leu Glu Val Leu Glu Val Ser Trp Leu
145                 150                 155                 160

His Gly Leu Lys Ala Leu Gly His Leu Asp Leu Ser Gly Asn Arg Leu
                165                 170                 175

Arg Lys Leu Pro Pro Gly Leu Leu Ala Asn Phe Thr Leu Leu Arg Thr
            180                 185                 190

Leu Asp Leu Gly Glu Asn Gln Leu Glu Thr Leu Pro Pro Asp Leu Leu
        195                 200                 205

Arg Gly Pro Leu Gln Leu Glu Arg Leu His Leu Glu Gly Asn Lys Leu
    210                 215                 220

Gln Val Leu Gly Lys Asp Leu Leu Leu Pro Gln Pro Asp Leu Arg Tyr
225                 230                 235                 240

Leu Phe Leu Asn Gly Asn Lys Leu Ala Arg Val Ala Ala Gly Ala Phe
                245                 250                 255

Gln Gly Leu Arg Gln Leu Asp Met Leu Asp Leu Ser Asn Asn Ser Leu
            260                 265                 270

Ala Ser Val Pro Glu Gly Leu Trp Ala Ser Leu Gly Gln Pro Asn Trp
        275                 280                 285

Asp Met Arg Asp Gly Phe Asp Ile Ser Gly Asn Pro Trp Ile Cys Asp
    290                 295                 300

Gln Asn Leu Ser Asp Leu Tyr Arg Trp Leu Gln Ala Gln Lys Asp Lys
305                 310                 315                 320

Met Phe Ser Gln Asn Asp Thr Arg Cys Ala Gly Pro Glu Ala Val Lys
                325                 330                 335

Gly Gln Thr Leu Leu Ala Val Ala Lys Ser Gln
            340                 345
```

<210> SEQ ID NO 2
<211> LENGTH: 93
<212> TYPE: PRT
<213> ORGANISM: Homo sapiens

<400> SEQUENCE: 2

```
Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90
```

<210> SEQ ID NO 3

```
<211> LENGTH: 201
<212> TYPE: PRT
<213> ORGANISM: Homo sapiens

<400> SEQUENCE: 3

Met Ala Leu Ser Trp Val Leu Thr Val Leu Ser Leu Leu Pro Leu Leu
1               5                   10                  15

Glu Ala Gln Ile Pro Leu Cys Ala Asn Leu Val Pro Val Pro Ile Thr
            20                  25                  30

Asn Ala Thr Leu Asp Gln Ile Thr Gly Lys Trp Phe Tyr Ile Ala Ser
        35                  40                  45

Ala Phe Arg Asn Glu Glu Tyr Asn Lys Ser Val Gln Glu Ile Gln Ala
    50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asp Gln Cys Ile Tyr Asn Thr Thr Tyr
                85                  90                  95

Leu Asn Val Gln Arg Glu Asn Gly Thr Ile Ser Arg Tyr Val Gly Gly
            100                 105                 110

Gln Glu His Phe Ala His Leu Leu Ile Leu Arg Asp Thr Lys Thr Tyr
        115                 120                 125

Met Leu Ala Phe Asp Val Asn Asp Glu Lys Asn Trp Gly Leu Ser Val
    130                 135                 140

Tyr Ala Asp Lys Pro Glu Thr Thr Lys Glu Gln Leu Gly Glu Phe Tyr
145                 150                 155                 160

Glu Ala Leu Asp Cys Leu Arg Ile Pro Lys Ser Asp Val Val Tyr Thr
                165                 170                 175

Asp Trp Lys Lys Asp Lys Cys Glu Pro Leu Glu Lys Gln His Glu Lys
            180                 185                 190

Glu Arg Lys Gln Glu Glu Gly Glu Ser
        195                 200


<210> SEQ ID NO 4
<211> LENGTH: 810
<212> TYPE: PRT
<213> ORGANISM: Homo sapiens

<400> SEQUENCE: 4

Met Glu His Lys Glu Val Val Leu Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140
```

```
Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
    290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
    450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560
```

```
Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810


<210> SEQ ID NO 5
<211> LENGTH: 185
<212> TYPE: PRT
<213> ORGANISM: Homo sapiens

<400> SEQUENCE: 5

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125
```

```
Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Glu Gln Ser Leu
            180                 185


<210> SEQ ID NO 6
<211> LENGTH: 298
<212> TYPE: PRT
<213> ORGANISM: Homo sapiens

<400> SEQUENCE: 6

Met Val Arg Met Val Pro Val Leu Leu Ser Leu Leu Leu Leu Leu Gly
1               5                   10                  15

Pro Ala Val Pro Gln Glu Asn Gln Asp Gly Arg Tyr Ser Leu Thr Tyr
            20                  25                  30

Ile Tyr Thr Gly Leu Ser Lys His Val Glu Asp Val Pro Ala Phe Gln
        35                  40                  45

Ala Leu Gly Ser Leu Asn Asp Leu Gln Phe Phe Arg Tyr Asn Ser Lys
    50                  55                  60

Asp Arg Lys Ser Gln Pro Met Gly Leu Trp Arg Gln Val Glu Gly Met
65                  70                  75                  80

Glu Asp Trp Lys Gln Asp Ser Gln Leu Gln Lys Ala Arg Glu Asp Ile
                85                  90                  95

Phe Met Glu Thr Leu Lys Asp Ile Val Glu Tyr Tyr Asn Asp Ser Asn
            100                 105                 110

Gly Ser His Val Leu Gln Gly Arg Phe Gly Cys Glu Ile Glu Asn Asn
        115                 120                 125

Arg Ser Ser Gly Ala Phe Trp Lys Tyr Tyr Tyr Asp Gly Lys Asp Tyr
    130                 135                 140

Ile Glu Phe Asn Lys Glu Ile Pro Ala Trp Val Pro Phe Asp Pro Ala
145                 150                 155                 160

Ala Gln Ile Thr Lys Gln Lys Trp Glu Ala Glu Pro Val Tyr Val Gln
                165                 170                 175

Arg Ala Lys Ala Tyr Leu Glu Glu Glu Cys Pro Ala Thr Leu Arg Lys
            180                 185                 190

Tyr Leu Lys Tyr Ser Lys Asn Ile Leu Asp Arg Gln Asp Pro Pro Ser
        195                 200                 205

Val Val Val Thr Ser His Gln Ala Pro Gly Glu Lys Lys Lys Leu Lys
    210                 215                 220

Cys Leu Ala Tyr Asp Phe Tyr Pro Gly Lys Ile Asp Val His Trp Thr
225                 230                 235                 240

Arg Ala Gly Glu Val Gln Glu Pro Glu Leu Arg Gly Asp Val Leu His
                245                 250                 255

Asn Gly Asn Gly Thr Tyr Gln Ser Trp Val Val Val Ala Val Pro Pro
            260                 265                 270

Gln Asp Thr Ala Pro Tyr Ser Cys His Val Gln His Ser Ser Leu Ala
        275                 280                 285

Gln Pro Leu Val Val Pro Trp Glu Ala Ser
    290                 295
```

```
<210> SEQ ID NO 7
<211> LENGTH: 189
<212> TYPE: PRT
<213> ORGANISM: Homo sapiens

<400> SEQUENCE: 7

Met Val Met Leu Leu Leu Leu Leu Ser Ala Leu Ala Gly Leu Phe Gly
1               5                   10                  15

Ala Ala Glu Gly Gln Ala Phe His Leu Gly Lys Cys Pro Asn Pro Pro
            20                  25                  30

Val Gln Glu Asn Phe Asp Val Asn Lys Tyr Leu Gly Arg Trp Tyr Glu
        35                  40                  45

Ile Glu Lys Ile Pro Thr Thr Phe Glu Asn Gly Arg Cys Ile Gln Ala
    50                  55                  60

Asn Tyr Ser Leu Met Glu Asn Gly Lys Ile Lys Val Leu Asn Gln Glu
65                  70                  75                  80

Leu Arg Ala Asp Gly Thr Val Asn Gln Ile Glu Gly Glu Ala Thr Pro
                85                  90                  95

Val Asn Leu Thr Glu Pro Ala Lys Leu Glu Val Lys Phe Ser Trp Phe
            100                 105                 110

Met Pro Ser Ala Pro Tyr Trp Ile Leu Ala Thr Asp Tyr Glu Asn Tyr
        115                 120                 125

Ala Leu Val Tyr Ser Cys Thr Cys Ile Ile Gln Leu Phe His Val Asp
    130                 135                 140

Phe Ala Trp Ile Leu Ala Arg Asn Pro Asn Leu Pro Pro Glu Thr Val
145                 150                 155                 160

Asp Ser Leu Lys Asn Ile Leu Thr Ser Asn Asn Ile Asp Val Lys Lys
                165                 170                 175

Met Thr Val Thr Asp Gln Val Asn Cys Pro Lys Leu Ser
            180                 185


<210> SEQ ID NO 8
<211> LENGTH: 448
<212> TYPE: PRT
<213> ORGANISM: Homo sapiens

<400> SEQUENCE: 8

Met Lys Ile His Tyr Ser Arg Gln Thr Ala Leu Glu Ser Thr Ser Tyr
1               5                   10                  15

Ile Gln Leu Pro Glu Ala Glu Leu Arg Met Glu Arg Met Leu Pro Leu
            20                  25                  30

Leu Ala Leu Gly Leu Leu Ala Ala Gly Phe Cys Pro Ala Val Leu Cys
        35                  40                  45

His Pro Asn Ser Pro Leu Asp Glu Glu Asn Leu Thr Gln Glu Asn Gln
    50                  55                  60

Asp Arg Gly Thr His Val Asp Leu Gly Leu Ala Ser Ala Asn Val Asp
65                  70                  75                  80

Phe Ala Phe Ser Leu Tyr Lys Gln Leu Val Leu Lys Ala Pro Asp Lys
                85                  90                  95

Asn Val Ile Phe Ser Pro Leu Ser Ile Ser Thr Ala Leu Ala Phe Leu
            100                 105                 110

Ser Leu Gly Ala His Asn Thr Thr Leu Thr Glu Ile Leu Lys Gly Leu
        115                 120                 125

Lys Phe Asn Leu Thr Glu Thr Ser Glu Ala Glu Ile His Gln Ser Phe
    130                 135                 140

Gln His Leu Leu Arg Thr Leu Asn Gln Ser Ser Asp Glu Leu Gln Leu
```

```
145                 150                 155                 160

Ser Met Gly Asn Ala Met Phe Val Lys Glu Gln Leu Ser Leu Leu Asp
                165                 170                 175

Arg Phe Thr Glu Asp Ala Lys Arg Leu Tyr Gly Ser Glu Ala Phe Ala
            180                 185                 190

Thr Asp Phe Gln Asp Ser Ala Ala Ala Lys Lys Leu Ile Asn Asp Tyr
        195                 200                 205

Val Lys Asn Gly Thr Arg Gly Lys Ile Thr Asp Leu Ile Lys Asp Leu
    210                 215                 220

Asp Ser Gln Thr Met Met Val Leu Val Asn Tyr Ile Phe Phe Lys Ala
225                 230                 235                 240

Lys Trp Glu Met Pro Phe Asp Pro Gln Asp Thr His Gln Ser Arg Phe
                245                 250                 255

Tyr Leu Ser Lys Lys Lys Trp Val Met Val Pro Met Met Ser Leu His
            260                 265                 270

His Leu Thr Ile Pro Tyr Phe Arg Asp Glu Glu Leu Ser Cys Thr Val
        275                 280                 285

Val Glu Leu Lys Tyr Thr Gly Asn Ala Ser Ala Leu Phe Ile Leu Pro
    290                 295                 300

Asp Gln Asp Lys Met Glu Glu Val Glu Ala Met Leu Leu Pro Glu Thr
305                 310                 315                 320

Leu Lys Arg Trp Arg Asp Ser Leu Glu Phe Arg Glu Ile Gly Glu Leu
                325                 330                 335

Tyr Leu Pro Lys Phe Ser Ile Ser Arg Asp Tyr Asn Leu Asn Asp Ile
            340                 345                 350

Leu Leu Gln Leu Gly Ile Glu Glu Ala Phe Thr Ser Lys Ala Asp Leu
        355                 360                 365

Ser Gly Ile Thr Gly Ala Arg Asn Leu Ala Val Ser Gln Val Val His
    370                 375                 380

Lys Ala Val Leu Asp Val Phe Glu Glu Gly Thr Glu Ala Ser Ala Ala
385                 390                 395                 400

Thr Ala Val Lys Ile Thr Leu Leu Ser Ala Leu Val Glu Thr Arg Thr
                405                 410                 415

Ile Val Arg Phe Asn Arg Pro Phe Leu Met Ile Ile Val Pro Thr Asp
            420                 425                 430

Thr Gln Asn Ile Phe Phe Met Ser Lys Val Thr Asn Pro Lys Gln Ala
        435                 440                 445


<210> SEQ ID NO 9
<211> LENGTH: 373
<212> TYPE: PRT
<213> ORGANISM: Homo sapiens

<400> SEQUENCE: 9

Met Ser Leu Leu Leu Leu Leu Leu Leu Val Ser Tyr Tyr Val Gly Thr
1               5                   10                  15

Leu Gly Thr His Thr Glu Ile Lys Arg Val Ala Glu Glu Lys Val Thr
            20                  25                  30

Leu Pro Cys His His Gln Leu Gly Leu Pro Glu Lys Asp Thr Leu Asp
        35                  40                  45

Ile Glu Trp Leu Leu Thr Asp Asn Glu Gly Asn Gln Lys Val Val Ile
    50                  55                  60

Thr Tyr Ser Ser Arg His Val Tyr Asn Asn Leu Thr Glu Glu Gln Lys
65                  70                  75                  80
```

```
Gly Arg Val Ala Phe Ala Ser Asn Phe Leu Ala Gly Asp Ala Ser Leu
                85                  90                  95

Gln Ile Glu Pro Leu Lys Pro Ser Asp Glu Gly Arg Tyr Thr Cys Lys
            100                 105                 110

Val Lys Asn Ser Gly Arg Tyr Val Trp Ser His Val Ile Leu Lys Val
        115                 120                 125

Leu Val Arg Pro Ser Lys Pro Lys Cys Glu Leu Glu Gly Glu Leu Thr
    130                 135                 140

Glu Gly Ser Asp Leu Thr Leu Gln Cys Glu Ser Ser Ser Gly Thr Glu
145                 150                 155                 160

Pro Ile Val Tyr Tyr Trp Gln Arg Ile Arg Glu Lys Glu Gly Glu Asp
                165                 170                 175

Glu Arg Leu Pro Pro Lys Ser Arg Ile Asp Tyr Asn His Pro Gly Arg
            180                 185                 190

Val Leu Leu Gln Asn Leu Thr Met Ser Tyr Ser Gly Leu Tyr Gln Cys
        195                 200                 205

Thr Ala Gly Asn Glu Ala Gly Lys Glu Ser Cys Val Val Arg Val Thr
    210                 215                 220

Val Gln Tyr Val Gln Ser Ile Gly Met Val Ala Gly Ala Val Thr Gly
225                 230                 235                 240

Ile Val Ala Gly Ala Leu Leu Ile Phe Leu Leu Val Trp Leu Leu Ile
                245                 250                 255

Arg Arg Lys Asp Lys Glu Arg Tyr Glu Glu Glu Glu Arg Pro Asn Glu
            260                 265                 270

Ile Arg Glu Asp Ala Glu Ala Pro Lys Ala Arg Leu Val Lys Pro Ser
        275                 280                 285

Ser Ser Ser Ser Gly Ser Arg Ser Ser Arg Ser Gly Ser Ser Ser Thr
    290                 295                 300

Arg Ser Thr Ala Asn Ser Ala Ser Arg Ser Gln Arg Thr Leu Ser Thr
305                 310                 315                 320

Asp Ala Ala Pro Gln Pro Gly Leu Ala Thr Gln Ala Tyr Ser Leu Val
                325                 330                 335

Gly Pro Glu Val Arg Gly Ser Glu Pro Lys Lys Val His His Ala Asn
            340                 345                 350

Leu Thr Lys Ala Glu Thr Thr Pro Ser Met Ile Pro Ser Gln Ser Arg
        355                 360                 365

Ala Phe Gln Thr Val
    370


<210> SEQ ID NO 10
<211> LENGTH: 352
<212> TYPE: PRT
<213> ORGANISM: Homo sapiens

<400> SEQUENCE: 10

Met Arg Ser Leu Gly Ala Leu Leu Leu Leu Leu Ser Ala Cys Leu Ala
1               5                   10                  15

Val Ser Ala Gly Pro Val Pro Thr Pro Pro Asp Asn Ile Gln Val Gln
            20                  25                  30

Glu Asn Phe Asn Ile Ser Arg Ile Tyr Gly Lys Trp Tyr Asn Leu Ala
        35                  40                  45

Ile Gly Ser Thr Cys Pro Trp Leu Lys Lys Ile Met Asp Arg Met Thr
    50                  55                  60

Val Ser Thr Leu Val Leu Gly Glu Gly Ala Thr Glu Ala Glu Ile Ser
65                  70                  75                  80
```

```
Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp
        115                 120                 125

Glu Tyr Ala Ile Phe Leu Thr Lys Lys Phe Ser Arg His His Gly Pro
    130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu
            180                 185                 190

Gln Glu Pro Glu Pro Ile Leu Ile Pro Arg Val Arg Arg Ala Val Leu
        195                 200                 205

Pro Gln Glu Glu Glu Gly Ser Gly Gly Gly Gln Leu Val Thr Glu Val
    210                 215                 220

Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255

Glu Thr Phe Gln Tyr Gly Gly Cys Met Gly Asn Gly Asn Asn Phe Val
            260                 265                 270

Thr Glu Lys Glu Cys Leu Gln Thr Cys Arg Thr Val Ala Ala Cys Asn
        275                 280                 285

Leu Pro Ile Val Arg Gly Pro Cys Arg Ala Phe Ile Gln Leu Trp Ala
    290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Glu Cys Arg Glu Tyr
                325                 330                 335

Cys Gly Val Pro Gly Asp Gly Asp Glu Glu Leu Leu Arg Phe Ser Asn
            340                 345                 350


<210> SEQ ID NO 11
<211> LENGTH: 763
<212> TYPE: PRT
<213> ORGANISM: Homo sapiens

<400> SEQUENCE: 11

Met Ala Ala Thr Gly Thr Ala Ala Ala Ala Ala Thr Gly Arg Leu Leu
1               5                   10                  15

Leu Leu Leu Leu Val Gly Leu Thr Ala Pro Ala Leu Ala Leu Ala Gly
            20                  25                  30

Tyr Ile Glu Ala Leu Ala Ala Asn Ala Gly Thr Gly Phe Ala Val Ala
        35                  40                  45

Glu Pro Gln Ile Ala Met Phe Cys Gly Lys Leu Asn Met His Val Asn
    50                  55                  60

Ile Gln Thr Gly Lys Trp Glu Pro Asp Pro Thr Gly Thr Lys Ser Cys
65                  70                  75                  80

Phe Glu Thr Lys Glu Glu Val Leu Gln Tyr Cys Gln Glu Met Tyr Pro
                85                  90                  95

Glu Leu Gln Ile Thr Asn Val Met Glu Ala Asn Gln Arg Val Ser Ile
```

```
            100                 105                 110

Asp Asn Trp Cys Arg Arg Asp Lys Lys Gln Cys Lys Ser Arg Phe Val
        115                 120                 125

Thr Pro Phe Lys Cys Leu Val Gly Glu Phe Val Ser Asp Val Leu Leu
    130                 135                 140

Val Pro Glu Lys Cys Gln Phe Phe His Lys Glu Arg Met Glu Val Cys
145                 150                 155                 160

Glu Asn His Gln His Trp His Thr Val Val Lys Glu Ala Cys Leu Thr
                165                 170                 175

Gln Gly Met Thr Leu Tyr Ser Tyr Gly Met Leu Leu Pro Cys Gly Val
            180                 185                 190

Asp Gln Phe His Gly Thr Glu Tyr Val Cys Cys Pro Gln Thr Lys Ile
        195                 200                 205

Ile Gly Ser Val Ser Lys Glu Glu Glu Glu Glu Asp Glu Glu Glu Glu
    210                 215                 220

Glu Glu Glu Asp Glu Glu Glu Asp Tyr Asp Val Tyr Lys Ser Glu Phe
225                 230                 235                 240

Pro Thr Glu Ala Asp Leu Glu Asp Phe Thr Glu Ala Ala Val Asp Glu
                245                 250                 255

Asp Asp Glu Asp Glu Glu Glu Gly Glu Glu Val Val Glu Asp Arg Asp
            260                 265                 270

Tyr Tyr Tyr Asp Thr Phe Lys Gly Asp Asp Tyr Asn Glu Glu Asn Pro
        275                 280                 285

Thr Glu Pro Gly Ser Asp Gly Thr Met Ser Asp Lys Glu Ile Thr His
    290                 295                 300

Asp Val Lys Ala Val Cys Ser Gln Glu Ala Met Thr Gly Pro Cys Arg
305                 310                 315                 320

Ala Val Met Pro Arg Trp Tyr Phe Asp Leu Ser Lys Gly Lys Cys Val
                325                 330                 335

Arg Phe Ile Tyr Gly Gly Cys Gly Gly Asn Arg Asn Asn Phe Glu Ser
            340                 345                 350

Glu Asp Tyr Cys Met Ala Val Cys Lys Ala Met Ile Pro Pro Thr Pro
        355                 360                 365

Leu Pro Thr Asn Asp Val Asp Val Tyr Phe Glu Thr Ser Ala Asp Asp
    370                 375                 380

Asn Glu His Ala Arg Phe Gln Lys Ala Lys Glu Gln Leu Glu Ile Arg
385                 390                 395                 400

His Arg Asn Arg Met Asp Arg Val Lys Lys Glu Trp Glu Glu Ala Glu
                405                 410                 415

Leu Gln Ala Lys Asn Leu Pro Lys Ala Glu Arg Gln Thr Leu Ile Gln
            420                 425                 430

His Phe Gln Ala Met Val Lys Ala Leu Glu Lys Glu Ala Ala Ser Glu
        435                 440                 445

Lys Gln Gln Leu Val Glu Thr His Leu Ala Arg Val Glu Ala Met Leu
    450                 455                 460

Asn Asp Arg Arg Arg Met Ala Leu Glu Asn Tyr Leu Ala Ala Leu Gln
465                 470                 475                 480

Ser Asp Pro Pro Arg Pro His Arg Ile Leu Gln Ala Leu Arg Arg Tyr
                485                 490                 495

Val Arg Ala Glu Asn Lys Asp Arg Leu His Thr Ile Arg His Tyr Gln
            500                 505                 510

His Val Leu Ala Val Asp Pro Glu Lys Ala Ala Gln Met Lys Ser Gln
        515                 520                 525
```

```
Val Met Thr His Leu His Val Ile Glu Glu Arg Arg Asn Gln Ser Leu
    530                 535                 540

Ser Leu Leu Tyr Lys Val Pro Tyr Val Ala Gln Glu Ile Gln Glu Glu
545                 550                 555                 560

Ile Asp Glu Leu Leu Gln Glu Gln Arg Ala Asp Met Asp Gln Phe Thr
                565                 570                 575

Ala Ser Ile Ser Glu Thr Pro Val Asp Val Arg Val Ser Ser Glu Glu
            580                 585                 590

Ser Glu Glu Ile Pro Pro Phe His Pro Phe His Pro Phe Pro Ala Leu
        595                 600                 605

Pro Glu Asn Glu Asp Thr Gln Pro Glu Leu Tyr His Pro Met Lys Lys
    610                 615                 620

Gly Ser Gly Val Gly Glu Gln Asp Gly Gly Leu Ile Gly Ala Glu Glu
625                 630                 635                 640

Lys Val Ile Asn Ser Lys Asn Lys Val Asp Glu Asn Met Val Ile Asp
                645                 650                 655

Glu Thr Leu Asp Val Lys Glu Met Ile Phe Asn Ala Glu Arg Val Gly
            660                 665                 670

Gly Leu Glu Glu Glu Arg Glu Ser Val Gly Pro Leu Arg Glu Asp Phe
        675                 680                 685

Ser Leu Ser Ser Ser Ala Leu Ile Gly Leu Leu Val Ile Ala Val Ala
    690                 695                 700

Ile Ala Thr Val Ile Val Ile Ser Leu Val Met Leu Arg Lys Arg Gln
705                 710                 715                 720

Tyr Gly Thr Ile Ser His Gly Ile Val Glu Val Asp Pro Met Leu Thr
                725                 730                 735

Pro Glu Glu Arg His Leu Asn Lys Met Gln Asn His Gly Tyr Glu Asn
            740                 745                 750

Pro Thr Tyr Lys Tyr Leu Glu Gln Met Gln Ile
        755                 760


<210> SEQ ID NO 12
<211> LENGTH: 805
<212> TYPE: PRT
<213> ORGANISM: Homo sapiens

<400> SEQUENCE: 12

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
```

```
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560
```

```
Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
        755                 760                 765

Lys Lys Lys Asn Lys Ala Arg Ser Gly Glu Asn Pro Tyr Ala Ser Ile
    770                 775                 780

Asp Ile Ser Lys Gly Glu Asn Asn Pro Gly Phe Gln Asn Thr Asp Asp
785                 790                 795                 800

Val Gln Thr Ser Phe
                805


<210> SEQ ID NO 13
<211> LENGTH: 1479
<212> TYPE: PRT
<213> ORGANISM: Homo sapiens

<400> SEQUENCE: 13

Met Ala Pro Leu Leu Gly Arg Lys Pro Phe Pro Leu Val Lys Pro Leu
1               5                   10                  15

Pro Gly Glu Glu Pro Leu Phe Thr Ile Pro His Thr Gln Glu Ala Phe
            20                  25                  30

Arg Thr Arg Glu Glu Tyr Glu Ala Arg Leu Glu Arg Tyr Ser Glu Arg
        35                  40                  45

Ile Trp Thr Cys Lys Ser Thr Gly Ser Ser Gln Leu Thr His Lys Glu
    50                  55                  60

Ala Trp Glu Glu Glu Gln Glu Val Ala Glu Leu Leu Lys Glu Glu Phe
65                  70                  75                  80

Pro Ala Trp Tyr Glu Lys Leu Val Leu Glu Met Val His His Asn Thr
                85                  90                  95

Ala Ser Leu Glu Lys Leu Val Asp Thr Ala Trp Leu Glu Ile Met Thr
            100                 105                 110

Lys Tyr Ala Val Gly Glu Glu Cys Asp Phe Glu Val Gly Lys Glu Lys
```

```
        115                 120                 125

Met Leu Lys Val Lys Ile Val Lys Ile His Pro Leu Glu Lys Val Asp
    130                 135                 140

Glu Glu Ala Thr Glu Lys Lys Ser Asp Gly Ala Cys Asp Ser Pro Ser
145                 150                 155                 160

Ser Asp Lys Glu Asn Ser Ser Gln Ile Ala Gln Asp His Gln Lys Lys
                165                 170                 175

Glu Thr Val Val Lys Glu Asp Glu Gly Arg Arg Glu Ser Ile Asn Asp
            180                 185                 190

Arg Ala Arg Arg Ser Pro Arg Lys Leu Pro Thr Ser Leu Lys Lys Gly
        195                 200                 205

Glu Arg Lys Trp Ala Pro Pro Lys Phe Leu Pro His Lys Tyr Asp Val
    210                 215                 220

Lys Leu Gln Asn Glu Asp Lys Ile Ile Ser Asn Val Pro Ala Asp Ser
225                 230                 235                 240

Leu Ile Arg Thr Glu Arg Pro Pro Asn Lys Glu Ile Val Arg Tyr Phe
                245                 250                 255

Ile Arg His Asn Ala Leu Arg Ala Gly Thr Gly Glu Asn Ala Pro Trp
            260                 265                 270

Val Val Glu Asp Glu Leu Val Lys Lys Tyr Ser Leu Pro Ser Lys Phe
        275                 280                 285

Ser Asp Phe Leu Leu Asp Pro Tyr Lys Tyr Met Thr Leu Asn Pro Ser
    290                 295                 300

Thr Lys Arg Lys Asn Thr Gly Ser Pro Asp Arg Lys Pro Ser Lys Lys
305                 310                 315                 320

Ser Lys Thr Asp Asn Ser Ser Leu Ser Ser Pro Leu Asn Pro Lys Leu
                325                 330                 335

Trp Cys His Val His Leu Lys Lys Ser Leu Ser Gly Ser Pro Leu Lys
            340                 345                 350

Val Lys Asn Ser Lys Asn Ser Lys Ser Pro Glu Glu His Leu Glu Glu
        355                 360                 365

Met Met Lys Met Met Ser Pro Asn Lys Leu His Thr Asn Phe His Ile
    370                 375                 380

Pro Lys Lys Gly Pro Pro Ala Lys Lys Pro Gly Lys His Ser Asp Lys
385                 390                 395                 400

Pro Leu Lys Ala Lys Gly Arg Ser Lys Gly Ile Leu Asn Gly Gln Lys
                405                 410                 415

Ser Thr Gly Asn Ser Lys Ser Pro Lys Lys Gly Leu Lys Thr Pro Lys
            420                 425                 430

Thr Lys Met Lys Gln Met Thr Leu Leu Asp Met Ala Lys Gly Thr Gln
        435                 440                 445

Lys Met Thr Arg Ala Pro Arg Asn Ser Gly Gly Thr Pro Arg Thr Ser
    450                 455                 460

Ser Lys Pro His Lys His Leu Pro Pro Ala Ala Leu His Leu Ile Ala
465                 470                 475                 480

Tyr Tyr Lys Glu Asn Lys Asp Arg Glu Asp Lys Arg Ser Ala Leu Ser
                485                 490                 495

Cys Val Ile Ser Lys Thr Ala Arg Leu Leu Ser Ser Glu Asp Arg Ala
            500                 505                 510

Arg Leu Pro Glu Glu Leu Arg Ser Leu Val Gln Lys Arg Tyr Glu Leu
        515                 520                 525

Leu Glu His Lys Lys Arg Trp Ala Ser Met Ser Glu Glu Gln Arg Lys
    530                 535                 540
```

```
Glu Tyr Leu Lys Lys Lys Arg Glu Glu Leu Lys Lys Lys Leu Lys Glu
545                 550                 555                 560

Lys Ala Lys Glu Arg Arg Glu Lys Glu Met Leu Glu Arg Leu Glu Lys
                565                 570                 575

Gln Lys Arg Tyr Glu Asp Gln Glu Leu Thr Gly Lys Asn Leu Pro Ala
            580                 585                 590

Phe Arg Leu Val Asp Thr Pro Glu Gly Leu Pro Asn Thr Leu Phe Gly
        595                 600                 605

Asp Val Ala Met Val Val Glu Phe Leu Ser Cys Tyr Ser Gly Leu Leu
    610                 615                 620

Leu Pro Asp Ala Gln Tyr Pro Ile Thr Ala Val Ser Leu Met Glu Ala
625                 630                 635                 640

Leu Ser Ala Asp Lys Gly Gly Phe Leu Tyr Leu Asn Arg Val Leu Val
                645                 650                 655

Ile Leu Leu Gln Asp Glu Ile Ala Glu Asp Tyr Gly Glu Leu Gly Met
            660                 665                 670

Lys Leu Ser Glu Ile Pro Leu Thr Leu His Ser Val Ser Glu Leu Val
        675                 680                 685

Arg Leu Cys Leu Arg Arg Ser Asp Val Gln Glu Glu Ser Glu Gly Ser
    690                 695                 700

Asp Thr Asp Asp Asn Lys Asp Ser Ala Ala Phe Glu Asp Asn Glu Val
705                 710                 715                 720

Gln Asp Glu Phe Leu Glu Lys Leu Glu Thr Ser Glu Phe Phe Glu Leu
                725                 730                 735

Thr Ser Glu Glu Lys Leu Gln Ile Leu Thr Ala Leu Cys His Arg Ile
            740                 745                 750

Leu Met Thr Tyr Ser Val Gln Asp His Met Glu Thr Arg Gln Gln Met
        755                 760                 765

Ser Ala Glu Leu Trp Lys Glu Arg Leu Ala Val Leu Lys Glu Glu Asn
    770                 775                 780

Asp Lys Lys Arg Ala Glu Lys Gln Lys Arg Lys Glu Met Glu Ala Lys
785                 790                 795                 800

Asn Lys Glu Asn Gly Lys Val Glu Asn Gly Leu Gly Lys Thr Asp Arg
                805                 810                 815

Lys Lys Glu Ile Val Lys Phe Glu Pro Gln Val Asp Thr Glu Ala Glu
            820                 825                 830

Asp Met Ile Ser Ala Val Lys Ser Arg Arg Leu Leu Ala Ile Gln Ala
        835                 840                 845

Lys Lys Glu Arg Glu Ile Gln Glu Arg Glu Met Lys Val Lys Leu Glu
    850                 855                 860

Arg Gln Ala Glu Glu Glu Arg Ile Arg Lys His Lys Ala Ala Ala Glu
865                 870                 875                 880

Lys Ala Phe Gln Glu Gly Ile Ala Lys Ala Lys Leu Val Met Arg Arg
                885                 890                 895

Thr Pro Ile Gly Thr Asp Arg Asn His Asn Arg Tyr Trp Leu Phe Ser
            900                 905                 910

Asp Glu Val Pro Gly Leu Phe Ile Glu Lys Gly Trp Val His Asp Ser
        915                 920                 925

Ile Asp Tyr Arg Phe Asn His His Cys Lys Asp His Thr Val Ser Gly
    930                 935                 940

Asp Glu Asp Tyr Cys Pro Arg Ser Lys Lys Ala Asn Leu Gly Lys Asn
945                 950                 955                 960
```

```
Ala Ser Met Asn Thr Gln His Gly Thr Ala Thr Glu Val Ala Val Glu
                965                 970                 975

Thr Thr Thr Pro Lys Gln Gly Gln Asn Leu Trp Phe Leu Cys Asp Ser
            980                 985                 990

Gln Lys Glu Leu Asp Glu Leu Leu  Asn Cys Leu His Pro  Gln Gly Ile
        995                 1000                 1005

Arg Glu  Ser Gln Leu Lys Glu  Arg Leu Glu Lys Arg  Tyr Gln Asp
    1010                 1015                 1020

Ile Ile  His Ser Ile His Leu  Ala Arg Lys Pro Asn  Leu Gly Leu
    1025                 1030                 1035

Lys Ser  Cys Asp Gly Asn Gln  Glu Leu Leu Asn Phe  Leu Arg Ser
    1040                 1045                 1050

Asp Leu  Ile Glu Val Ala Thr  Arg Leu Gln Lys Gly  Gly Leu Gly
    1055                 1060                 1065

Tyr Val  Glu Glu Thr Ser Glu  Phe Glu Ala Arg Val  Ile Ser Leu
    1070                 1075                 1080

Glu Lys  Leu Lys Asp Phe Gly  Glu Cys Val Ile Ala  Leu Gln Ala
    1085                 1090                 1095

Ser Val  Ile Lys Lys Phe Leu  Gln Gly Phe Met Ala  Pro Lys Gln
    1100                 1105                 1110

Lys Arg  Arg Lys Leu Gln Ser  Glu Asp Ser Ala Lys  Thr Glu Glu
    1115                 1120                 1125

Val Asp  Glu Glu Lys Lys Met  Val Glu Glu Ala Lys  Val Ala Ser
    1130                 1135                 1140

Ala Leu  Glu Lys Trp Lys Thr  Ala Ile Arg Glu Ala  Gln Thr Phe
    1145                 1150                 1155

Ser Arg  Met His Val Leu Leu  Gly Met Leu Asp Ala  Cys Ile Lys
    1160                 1165                 1170

Trp Asp  Met Ser Ala Glu Asn  Ala Arg Cys Lys Val  Cys Arg Lys
    1175                 1180                 1185

Lys Gly  Glu Asp Asp Lys Leu  Ile Leu Cys Asp Glu  Cys Asn Lys
    1190                 1195                 1200

Ala Phe  His Leu Phe Cys Leu  Arg Pro Ala Leu Tyr  Glu Val Pro
    1205                 1210                 1215

Asp Gly  Glu Trp Gln Cys Pro  Ala Cys Gln Pro Ala  Thr Ala Arg
    1220                 1225                 1230

Arg Asn  Ser Arg Gly Arg Asn  Tyr Thr Glu Glu Ser  Ala Ser Glu
    1235                 1240                 1245

Asp Ser  Glu Asp Asp Glu Ser  Asp Glu Glu Glu Glu  Glu Glu Glu
    1250                 1255                 1260

Glu Glu  Glu Glu Glu Glu Asp  Tyr Glu Val Ala Gly  Leu Arg Leu
    1265                 1270                 1275

Arg Pro  Arg Lys Thr Ile Arg  Gly Lys His Ser Val  Ile Pro Pro
    1280                 1285                 1290

Ala Ala  Arg Ser Gly Arg Arg  Pro Gly Lys Lys Pro  His Ser Thr
    1295                 1300                 1305

Arg Arg  Ser Gln Pro Lys Ala  Pro Pro Val Asp Asp  Ala Glu Val
    1310                 1315                 1320

Asp Glu  Leu Val Leu Gln Thr  Lys Arg Ser Ser Arg  Arg Gln Ser
    1325                 1330                 1335

Leu Glu  Leu Gln Lys Cys Glu  Glu Ile Leu His Lys  Ile Val Lys
    1340                 1345                 1350

Tyr Arg  Phe Ser Trp Pro Phe  Arg Glu Pro Val Thr  Arg Asp Glu
```

```
    1355                1360                1365

Ala Glu  Asp Tyr Tyr Asp Val  Ile Thr His Pro Met  Asp Phe Gln
    1370                1375                1380

Thr Val  Gln Asn Lys Cys Ser  Cys Gly Ser Tyr Arg  Ser Val Gln
    1385                1390                1395

Glu Phe  Leu Thr Asp Met Lys  Gln Val Phe Thr Asn  Ala Glu Val
    1400                1405                1410

Tyr Asn  Cys Arg Gly Ser His  Val Leu Ser Cys Met  Val Lys Thr
    1415                1420                1425

Glu Gln  Cys Leu Val Ala Leu  Leu His Lys His Leu  Pro Gly His
    1430                1435                1440

Pro Tyr  Val Arg Arg Lys Arg  Lys Lys Phe Pro Asp  Arg Leu Ala
    1445                1450                1455

Glu Asp  Glu Gly Asp Ser Glu  Pro Glu Ala Val Gly  Gln Ser Arg
    1460                1465                1470

Gly Arg  Arg Gln Lys Lys
    1475


<210> SEQ ID NO 14
<211> LENGTH: 261
<212> TYPE: PRT
<213> ORGANISM: Homo sapiens

<400> SEQUENCE: 14

Met Ala Ser Pro Asp Trp Gly Tyr Asp Asp Lys Asn Gly Pro Glu Gln
1               5                   10                  15

Trp Ser Lys Leu Tyr Pro Ile Ala Asn Gly Asn Asn Gln Ser Pro Val
            20                  25                  30

Asp Ile Lys Thr Ser Glu Thr Lys His Asp Thr Ser Leu Lys Pro Ile
        35                  40                  45

Ser Val Ser Tyr Asn Pro Ala Thr Ala Lys Glu Ile Ile Asn Val Gly
    50                  55                  60

His Ser Phe His Val Asn Phe Glu Asp Asn Asp Asn Arg Ser Val Leu
65                  70                  75                  80

Lys Gly Gly Pro Phe Ser Asp Ser Tyr Arg Leu Phe Gln Phe His Phe
                85                  90                  95

His Trp Gly Ser Thr Asn Glu His Gly Ser Glu His Thr Val Asp Gly
            100                 105                 110

Val Lys Tyr Ser Ala Glu Leu His Val Ala His Trp Asn Ser Ala Lys
        115                 120                 125

Tyr Ser Ser Leu Ala Glu Ala Ala Ser Lys Ala Asp Gly Leu Ala Val
    130                 135                 140

Ile Gly Val Leu Met Lys Val Gly Glu Ala Asn Pro Lys Leu Gln Lys
145                 150                 155                 160

Val Leu Asp Ala Leu Gln Ala Ile Lys Thr Lys Gly Lys Arg Ala Pro
                165                 170                 175

Phe Thr Asn Phe Asp Pro Ser Thr Leu Leu Pro Ser Ser Leu Asp Phe
            180                 185                 190

Trp Thr Tyr Pro Gly Ser Leu Thr His Pro Pro Leu Tyr Glu Ser Val
        195                 200                 205

Thr Trp Ile Ile Cys Lys Glu Ser Ile Ser Val Ser Ser Glu Gln Leu
    210                 215                 220

Ala Gln Phe Arg Ser Leu Leu Ser Asn Val Glu Gly Asp Asn Ala Val
225                 230                 235                 240
```

```
Pro Met Gln His Asn Asn Arg Pro Thr Gln Pro Leu Lys Gly Arg Thr
                245                 250                 255

Val Arg Ala Ser Phe
            260


<210> SEQ ID NO 15
<211> LENGTH: 375
<212> TYPE: PRT
<213> ORGANISM: Homo sapiens

<400> SEQUENCE: 15

Met Glu Arg Ala Ser Cys Leu Leu Leu Leu Leu Leu Pro Leu Val His
1               5                   10                  15

Val Ser Ala Thr Thr Pro Glu Pro Cys Glu Leu Asp Asp Glu Asp Phe
            20                  25                  30

Arg Cys Val Cys Asn Phe Ser Glu Pro Gln Pro Asp Trp Ser Glu Ala
        35                  40                  45

Phe Gln Cys Val Ser Ala Val Glu Val Glu Ile His Ala Gly Gly Leu
    50                  55                  60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
                85                  90                  95

Gly Ala Ala Gln Val Pro Ala Gln Leu Leu Val Gly Ala Leu Arg Val
            100                 105                 110

Leu Ala Tyr Ser Arg Leu Lys Glu Leu Thr Leu Glu Asp Leu Lys Ile
        115                 120                 125

Thr Gly Thr Met Pro Pro Leu Pro Leu Glu Ala Thr Gly Leu Ala Leu
    130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
                165                 170                 175

Ile Ala Gln Ala His Ser Pro Ala Phe Ser Cys Glu Gln Val Arg Ala
            180                 185                 190

Phe Pro Ala Leu Thr Ser Leu Asp Leu Ser Asp Asn Pro Gly Leu Gly
        195                 200                 205

Glu Arg Gly Leu Met Ala Ala Leu Cys Pro His Lys Phe Pro Ala Ile
    210                 215                 220

Gln Asn Leu Ala Leu Arg Asn Thr Gly Met Glu Thr Pro Thr Gly Val
225                 230                 235                 240

Cys Ala Ala Leu Ala Ala Ala Gly Val Gln Pro His Ser Leu Asp Leu
                245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
        275                 280                 285

Glu Gln Val Pro Lys Gly Leu Pro Ala Lys Leu Arg Val Leu Asp Leu
    290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
            340                 345                 350
```

```
Ala Arg Ser Thr Leu Ser Val Gly Val Ser Gly Thr Leu Val Leu Leu
        355                 360                 365

Gln Gly Ala Arg Gly Phe Ala
    370                 375


<210> SEQ ID NO 16
<211> LENGTH: 367
<212> TYPE: PRT
<213> ORGANISM: Homo sapiens

<400> SEQUENCE: 16

Glu Pro Arg Ala Gly Glu Leu Ala Gly Gly Ser Thr Asp Arg Arg Thr
1               5                   10                  15

His Ala Glu Ala Leu Arg Pro Gln Pro Arg Ala Gly Ala Thr Ala Ala
            20                  25                  30

Arg Pro Arg Pro Pro Val Gln Pro Pro Leu Ala Arg Cys Leu Gly Ala
        35                  40                  45

Arg Pro His Thr Ala Ser Cys Ser Ala Pro Gly Ser Ala Met Arg Ser
    50                  55                  60

Ala Ala Val Leu Ala Leu Leu Leu Cys Ala Gly Gln Val Thr Ala Leu
65                  70                  75                  80

Pro Val Asn Ser Pro Met Asn Lys Gly Asp Thr Glu Val Met Lys Cys
                85                  90                  95

Ile Val Glu Val Ile Ser Asp Thr Leu Ser Lys Pro Ser Pro Met Pro
            100                 105                 110

Val Ser Gln Glu Cys Phe Glu Thr Leu Arg Gly Asp Glu Arg Ile Leu
        115                 120                 125

Ser Ile Leu Arg His Gln Asn Leu Leu Lys Glu Leu Gln Asp Leu Ala
    130                 135                 140

Leu Gln Gly Ala Lys Glu Arg Ala His Gln Gln Lys Lys His Ser Gly
145                 150                 155                 160

Phe Glu Asp Glu Leu Ser Glu Val Leu Glu Asn Gln Ser Ser Gln Ala
                165                 170                 175

Glu Leu Lys Gly Arg Ser Glu Ala Leu Ala Val Asp Gly Ala Gly Lys
            180                 185                 190

Pro Gly Ala Glu Glu Ala Gln Asp Pro Glu Gly Lys Gly Glu Gln Glu
        195                 200                 205

His Ser Gln Gln Lys Glu Glu Glu Glu Glu Met Ala Val Val Pro Gln
    210                 215                 220

Gly Leu Phe Arg Gly Gly Lys Ser Gly Glu Leu Glu Gln Glu Glu Glu
225                 230                 235                 240

Arg Leu Ser Lys Glu Trp Glu Asp Ser Lys Arg Trp Ser Lys Met Asp
                245                 250                 255

Gln Leu Ala Lys Glu Leu Thr Ala Glu Lys Arg Leu Glu Gly Gln Glu
            260                 265                 270

Glu Glu Glu Asp Asn Arg Asp Ser Ser Met Lys Leu Ser Phe Arg Ala
        275                 280                 285

Arg Ala Tyr Gly Phe Arg Gly Pro Gly Pro Gln Leu Arg Arg Gly Trp
    290                 295                 300

Arg Pro Ser Ser Arg Glu Asp Ser Leu Glu Ala Gly Leu Pro Leu Gln
305                 310                 315                 320

Val Arg Gly Tyr Pro Glu Glu Lys Lys Glu Glu Glu Gly Ser Ala Asn
                325                 330                 335

Arg Arg Pro Glu Asp Gln Glu Leu Glu Ser Leu Ser Ala Ile Glu Ala
```

```
            340                 345                 350

Glu Leu Glu Lys Val Ala His Gln Leu Gln Ala Leu Arg Arg Gly
        355                 360                 365


<210> SEQ ID NO 17
<211> LENGTH: 439
<212> TYPE: PRT
<213> ORGANISM: Homo sapiens

<400> SEQUENCE: 17

Met Val Pro Ser Ser Pro Arg Ala Leu Phe Leu Leu Leu Leu Ile Leu
1               5                   10                  15

Ala Cys Pro Glu Pro Arg Ala Ser Gln Asn Cys Leu Ser Lys Gln Gln
            20                  25                  30

Leu Leu Ser Ala Ile Arg Gln Leu Gln Gln Leu Leu Lys Gly Gln Glu
        35                  40                  45

Thr Arg Phe Ala Glu Gly Ile Arg His Met Lys Ser Arg Leu Ala Ala
    50                  55                  60

Leu Gln Asn Ser Val Gly Arg Val Gly Pro Asp Ala Leu Pro Val Ser
65                  70                  75                  80

Cys Pro Ala Leu Asn Thr Pro Ala Asp Gly Arg Lys Phe Gly Ser Lys
                85                  90                  95

Tyr Leu Val Asp His Glu Val His Phe Thr Cys Asn Pro Gly Phe Arg
            100                 105                 110

Leu Val Gly Pro Ser Ser Val Val Cys Leu Pro Asn Gly Thr Trp Thr
        115                 120                 125

Gly Glu Gln Pro His Cys Arg Gly Ile Ser Glu Cys Ser Ser Gln Pro
    130                 135                 140

Cys Gln Asn Gly Gly Thr Cys Val Glu Gly Val Asn Gln Tyr Arg Cys
145                 150                 155                 160

Ile Cys Pro Pro Gly Arg Thr Gly Asn Arg Cys Gln His Gln Ala Gln
                165                 170                 175

Thr Ala Ala Pro Glu Gly Ser Val Ala Gly Asp Ser Ala Phe Ser Arg
            180                 185                 190

Ala Pro Arg Cys Ala Gln Val Glu Arg Ala Gln His Cys Ser Cys Glu
        195                 200                 205

Ala Gly Phe His Leu Ser Gly Ala Ala Gly Asp Ser Val Cys Gln Asp
    210                 215                 220

Val Asn Glu Cys Glu Leu Tyr Gly Gln Glu Gly Arg Pro Arg Leu Cys
225                 230                 235                 240

Met His Ala Cys Val Asn Thr Pro Gly Ser Tyr Arg Cys Thr Cys Pro
                245                 250                 255

Gly Gly Tyr Arg Thr Leu Ala Asp Gly Lys Ser Cys Glu Asp Val Asp
            260                 265                 270

Glu Cys Val Gly Leu Gln Pro Val Cys Pro Gln Gly Thr Thr Cys Ile
        275                 280                 285

Asn Thr Gly Gly Ser Phe Gln Cys Val Ser Pro Glu Cys Pro Glu Gly
    290                 295                 300

Ser Gly Asn Val Ser Tyr Val Lys Thr Ser Pro Phe Gln Cys Glu Arg
305                 310                 315                 320

Asn Pro Cys Pro Met Asp Ser Arg Pro Cys Arg His Leu Pro Lys Thr
                325                 330                 335

Ile Ser Phe His Tyr Leu Ser Leu Pro Ser Asn Leu Lys Thr Pro Ile
            340                 345                 350
```

```
Thr Leu Phe Arg Met Ala Thr Ala Ser Ala Pro Gly Arg Ala Gly Pro
        355                 360                 365

Asn Ser Leu Arg Phe Gly Ile Val Gly Gly Asn Ser Arg Gly His Phe
    370                 375                 380

Val Met Gln Arg Ser Asp Arg Gln Thr Gly Asp Leu Ile Leu Val Gln
385                 390                 395                 400

Asn Leu Glu Gly Pro Gln Thr Leu Glu Val Asp Val Asp Met Ser Glu
                405                 410                 415

Tyr Leu Asp Arg Ser Phe Gln Ala Asn His Val Ser Lys Val Thr Ile
            420                 425                 430

Phe Val Ser Pro Tyr Asp Phe
        435


<210> SEQ ID NO 18
<211> LENGTH: 698
<212> TYPE: PRT
<213> ORGANISM: Homo sapiens

<400> SEQUENCE: 18

Met Gly Gly Leu Ala Ser Gly Gly Asp Val Glu Pro Gly Leu Pro Val
1               5                   10                  15

Glu Val Arg Gly Ser Asn Gly Ala Phe Tyr Lys Gly Phe Val Lys Asp
            20                  25                  30

Val His Glu Asp Ser Val Thr Ile Phe Phe Glu Asn Asn Trp Gln Ser
        35                  40                  45

Glu Arg Gln Ile Pro Phe Gly Asp Val Arg Leu Pro Pro Pro Ala Asp
    50                  55                  60

Tyr Asn Lys Glu Ile Thr Glu Gly Asp Glu Val Glu Val Tyr Ser Arg
65                  70                  75                  80

Ala Asn Glu Gln Glu Pro Cys Gly Trp Trp Leu Ala Arg Val Arg Met
                85                  90                  95

Met Lys Gly Asp Phe Tyr Val Ile Glu Tyr Ala Ala Cys Asp Ala Thr
            100                 105                 110

Tyr Asn Glu Ile Val Thr Leu Glu Arg Leu Arg Pro Val Asn Pro Asn
        115                 120                 125

Pro Leu Ala Thr Lys Gly Ser Phe Phe Lys Val Thr Met Ala Val Pro
    130                 135                 140

Glu Asp Leu Arg Glu Ala Cys Ser Asn Glu Asn Val His Lys Glu Phe
145                 150                 155                 160

Lys Lys Ala Leu Gly Ala Asn Cys Ile Phe Leu Asn Ile Thr Asn Ser
                165                 170                 175

Glu Leu Phe Ile Leu Ser Thr Thr Glu Ala Pro Val Lys Arg Ala Ser
            180                 185                 190

Leu Leu Gly Asp Met His Phe Arg Ser Leu Arg Thr Lys Leu Leu Leu
        195                 200                 205

Met Ser Arg Asn Glu Glu Ala Thr Lys His Leu Glu Thr Ser Lys Gln
    210                 215                 220

Leu Ala Ala Ala Phe Gln Glu Glu Phe Thr Val Arg Glu Asp Leu Met
225                 230                 235                 240

Gly Leu Ala Ile Gly Thr His Gly Ala Asn Ile Gln Gln Ala Arg Lys
                245                 250                 255

Val Pro Gly Val Thr Ala Ile Glu Leu Gly Glu Glu Thr Cys Thr Phe
            260                 265                 270

Arg Ile Tyr Gly Glu Thr Pro Glu Ala Cys Arg Gln Ala Arg Ser Tyr
        275                 280                 285
```

```
Leu Glu Phe Ser Glu Asp Ser Val Gln Val Pro Arg Asn Leu Val Gly
    290                 295                 300

Lys Val Ile Gly Lys Asn Gly Lys Val Ile Gln Glu Ile Val Asp Lys
305                 310                 315                 320

Ser Gly Val Val Arg Val Arg Val Glu Gly Asp Asn Asp Lys Lys Asn
                325                 330                 335

Pro Arg Glu Glu Gly Met Val Pro Phe Ile Phe Val Gly Thr Arg Glu
            340                 345                 350

Asn Ile Ser Asn Ala Gln Ala Leu Leu Glu Tyr His Leu Ser Tyr Leu
        355                 360                 365

Gln Glu Val Glu Gln Leu Arg Leu Glu Arg Leu Gln Ile Asp Glu Gln
    370                 375                 380

Leu Arg Gln Ile Gly Leu Gly Phe Arg Pro Pro Gly Ser Gly Arg Gly
385                 390                 395                 400

Ser Gly Gly Ser Asp Lys Ala Gly Tyr Ser Thr Asp Glu Ser Ser Ser
                405                 410                 415

Ser Ser Leu His Ala Thr Arg Thr Tyr Gly Gly Ser Tyr Gly Gly Arg
            420                 425                 430

Gly Arg Gly Arg Arg Thr Gly Gly Pro Ala Tyr Gly Pro Ser Ser Asp
        435                 440                 445

Val Ser Thr Ala Ser Glu Thr Glu Ser Glu Lys Arg Glu Glu Pro Asn
    450                 455                 460

Arg Ala Gly Pro Gly Asp Arg Asp Pro Pro Thr Arg Gly Glu Glu Ser
465                 470                 475                 480

Arg Arg Arg Pro Thr Gly Gly Arg Gly Arg Gly Pro Pro Pro Ala Pro
                485                 490                 495

Arg Pro Thr Ser Arg Tyr Asn Ser Ser Ser Ile Ser Ser Val Leu Lys
            500                 505                 510

Asp Pro Asp Ser Asn Pro Tyr Ser Leu Leu Asp Thr Ser Glu Pro Glu
        515                 520                 525

Pro Pro Val Asp Ser Glu Pro Gly Glu Pro Pro Pro Ala Ser Ala Arg
    530                 535                 540

Arg Arg Arg Ser Arg Arg Arg Arg Thr Asp Glu Asp Arg Thr Val Met
545                 550                 555                 560

Asp Gly Gly Leu Glu Ser Asp Gly Pro Asn Met Thr Glu Asn Gly Leu
                565                 570                 575

Glu Asp Glu Ser Arg Pro Gln Arg Arg Asn Arg Ser Arg Arg Arg Arg
            580                 585                 590

Asn Arg Gly Asn Arg Thr Asp Gly Ser Ile Ser Gly Asp Arg Gln Pro
        595                 600                 605

Val Thr Val Ala Asp Tyr Ile Ser Arg Ala Glu Ser Gln Ser Arg Gln
    610                 615                 620

Arg Pro Pro Leu Glu Arg Thr Lys Pro Ser Glu Asp Ser Leu Ser Gly
625                 630                 635                 640

Gln Lys Gly Asp Ser Val Ser Lys Leu Pro Lys Gly Pro Ser Glu Asn
                645                 650                 655

Gly Glu Leu Ser Ala Pro Leu Glu Leu Gly Ser Met Val Glu Trp Gly
            660                 665                 670

Phe Ile Lys Pro Pro Thr Cys Thr Pro Pro Phe Ser Ile Ser Leu Ala
        675                 680                 685

Ala Gln His His Gly Pro His Arg Pro Asn
    690                 695
```

<210> SEQ ID NO 19
<211> LENGTH: 142
<212> TYPE: PRT
<213> ORGANISM: Homo sapiens

<400> SEQUENCE: 19

Met Val Leu Ser Pro Ala Asp Lys Thr Asn Val Lys Ala Ala Trp Gly
1               5                   10                  15

Lys Val Gly Ala His Ala Gly Glu Tyr Gly Ala Glu Ala Leu Glu Arg
            20                  25                  30

Met Phe Leu Ser Phe Pro Thr Thr Lys Thr Tyr Phe Pro His Phe Asp
        35                  40                  45

Leu Ser His Gly Ser Ala Gln Val Lys Gly His Gly Lys Lys Val Ala
    50                  55                  60

Asp Ala Leu Thr Asn Ala Val Ala His Val Asp Asp Met Pro Asn Ala
65                  70                  75                  80

Leu Ser Ala Leu Ser Asp Leu His Ala His Lys Leu Arg Val Asp Pro
                85                  90                  95

Val Asn Phe Lys Leu Leu Ser His Cys Leu Leu Val Thr Leu Ala Ala
            100                 105                 110

His Leu Pro Ala Glu Phe Thr Pro Ala Val His Ala Ser Leu Asp Lys
        115                 120                 125

Phe Leu Ala Ser Val Ser Thr Val Leu Thr Ser Lys Tyr Arg
    130                 135                 140

<210> SEQ ID NO 20
<211> LENGTH: 147
<212> TYPE: PRT
<213> ORGANISM: Homo sapiens

<400> SEQUENCE: 20

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145

<210> SEQ ID NO 21
<211> LENGTH: 177
<212> TYPE: PRT
<213> ORGANISM: Homo sapiens

<400> SEQUENCE: 21

```
Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

<210> SEQ ID NO 22
<211> LENGTH: 914
<212> TYPE: PRT
<213> ORGANISM: Homo sapiens

<400> SEQUENCE: 22

```
Met Lys Pro Pro Arg Pro Val Arg Thr Cys Ser Lys Val Leu Val Leu
1               5                   10                  15

Leu Ser Leu Leu Ala Ile His Gln Thr Thr Thr Ala Glu Lys Asn Gly
            20                  25                  30

Ile Asp Ile Tyr Ser Leu Thr Val Asp Ser Arg Val Ser Ser Arg Phe
        35                  40                  45

Ala His Thr Val Val Thr Ser Arg Val Val Asn Arg Ala Asn Thr Val
    50                  55                  60

Gln Glu Ala Thr Phe Gln Met Glu Leu Pro Lys Lys Ala Phe Ile Thr
65                  70                  75                  80

Asn Phe Ser Met Ile Ile Asp Gly Met Thr Tyr Pro Gly Ile Ile Lys
                85                  90                  95

Glu Lys Ala Glu Ala Gln Ala Gln Tyr Ser Ala Ala Val Ala Lys Gly
            100                 105                 110

Lys Ser Ala Gly Leu Val Lys Ala Thr Gly Arg Asn Met Glu Gln Phe
        115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr
```

-continued

```
            180                 185                 190

Phe Met Thr Asn Gln Leu Val Asp Ala Leu Thr Thr Trp Gln Asn Lys
        195                 200                 205

Thr Lys Ala His Ile Arg Phe Lys Pro Thr Leu Ser Gln Gln Gln Lys
    210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
                245                 250                 255

Gly Tyr Phe Val His Tyr Phe Ala Pro Glu Gly Leu Thr Thr Met Pro
            260                 265                 270

Lys Asn Val Val Phe Val Ile Asp Lys Ser Gly Ser Met Ser Gly Arg
        275                 280                 285

Lys Ile Gln Gln Thr Arg Glu Ala Leu Ile Lys Ile Leu Asp Asp Leu
    290                 295                 300

Ser Pro Arg Asp Gln Phe Asn Leu Ile Val Phe Ser Thr Glu Ala Thr
305                 310                 315                 320

Gln Trp Arg Pro Ser Leu Val Pro Ala Ser Ala Glu Asn Val Asn Lys
                325                 330                 335

Ala Arg Ser Phe Ala Ala Gly Ile Gln Ala Leu Gly Gly Thr Asn Ile
            340                 345                 350

Asn Asp Ala Met Leu Met Ala Val Gln Leu Leu Asp Ser Ser Asn Gln
        355                 360                 365

Glu Glu Arg Leu Pro Glu Gly Ser Val Ser Leu Ile Ile Leu Leu Thr
    370                 375                 380

Asp Gly Asp Pro Thr Val Gly Glu Thr Asn Pro Arg Ser Ile Gln Asn
385                 390                 395                 400

Asn Val Arg Glu Ala Val Ser Gly Arg Tyr Ser Leu Phe Cys Leu Gly
                405                 410                 415

Phe Gly Phe Asp Val Ser Tyr Ala Phe Leu Glu Lys Leu Ala Leu Asp
            420                 425                 430

Asn Gly Gly Leu Ala Arg Arg Ile His Glu Asp Ser Asp Ser Ala Leu
        435                 440                 445

Gln Leu Gln Asp Phe Tyr Gln Glu Val Ala Asn Pro Leu Leu Thr Ala
    450                 455                 460

Val Thr Phe Glu Tyr Pro Ser Asn Ala Val Glu Glu Val Thr Gln Asn
465                 470                 475                 480

Asn Phe Arg Leu Leu Phe Lys Gly Ser Glu Met Val Val Ala Gly Lys
                485                 490                 495

Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
        515                 520                 525

Gln Glu Ala Glu Phe Gln Ser Pro Lys Tyr Ile Phe His Asn Phe Met
    530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
                565                 570                 575

Asn Leu Ser Leu Ala Tyr Ser Phe Val Thr Pro Leu Thr Ser Met Val
            580                 585                 590

Val Thr Lys Pro Asp Asp Gln Glu Gln Ser Gln Val Ala Glu Lys Pro
        595                 600                 605
```

```
Met Glu Gly Glu Ser Arg Asn Arg Asn Val His Ser Ala Gly Ala Ala
    610                 615                 620

Gly Ser Arg Met Asn Phe Arg Pro Gly Val Leu Ser Ser Arg Gln Leu
625                 630                 635                 640

Gly Leu Pro Gly Pro Pro Asp Val Pro Asp His Ala Ala Tyr His Pro
                645                 650                 655

Phe Arg Arg Leu Ala Ile Leu Pro Ala Ser Ala Pro Pro Ala Thr Ser
            660                 665                 670

Asn Pro Asp Pro Ala Val Ser Arg Val Met Asn Met Lys Ile Glu Glu
        675                 680                 685

Thr Thr Met Thr Thr Gln Thr Pro Ala Cys Pro Ser Cys Ser Arg Ser
    690                 695                 700

Arg Ala Pro Ala Val Pro Ala Pro Ile Gln Ala Pro Ser Ala Ile Leu
705                 710                 715                 720

Pro Leu Pro Gly Gln Ser Val Glu Arg Leu Cys Val Asp Pro Arg His
                725                 730                 735

Arg Gln Gly Pro Val Asn Leu Leu Ser Asp Pro Glu Gln Gly Val Glu
            740                 745                 750

Val Thr Gly Gln Tyr Glu Arg Glu Lys Ala Gly Phe Ser Trp Ile Glu
        755                 760                 765

Val Thr Phe Lys Asn Pro Leu Val Trp Val His Ala Ser Pro Glu His
    770                 775                 780

Val Val Val Thr Arg Asn Arg Arg Ser Ser Ala Tyr Lys Trp Lys Glu
785                 790                 795                 800

Thr Leu Phe Ser Val Met Pro Gly Leu Lys Met Thr Met Asp Lys Thr
                805                 810                 815

Gly Leu Leu Leu Leu Ser Asp Pro Asp Lys Val Thr Ile Gly Leu Leu
            820                 825                 830

Phe Trp Asp Gly Arg Gly Glu Gly Leu Arg Leu Leu Leu Arg Asp Thr
        835                 840                 845

Asp Arg Phe Ser Ser His Val Gly Gly Thr Leu Gly Gln Phe Tyr Gln
    850                 855                 860

Glu Val Leu Trp Gly Ser Pro Ala Ala Ser Asp Asp Gly Arg Arg Thr
865                 870                 875                 880

Leu Arg Val Gln Gly Asn Asp His Ser Ala Thr Arg Glu Arg Arg Leu
                885                 890                 895

Asp Tyr Gln Glu Gly Pro Pro Gly Val Glu Ile Ser Cys Trp Ser Val
            900                 905                 910

Glu Leu


<210> SEQ ID NO 23
<211> LENGTH: 481
<212> TYPE: PRT
<213> ORGANISM: Homo sapiens

<400> SEQUENCE: 23

Met Gly Ala Leu Ala Arg Ala Leu Pro Ser Ile Leu Leu Ala Leu Leu
1               5                   10                  15

Leu Thr Ser Thr Pro Glu Ala Leu Gly Ala Asn Pro Gly Leu Val Ala
            20                  25                  30

Arg Ile Thr Asp Lys Gly Leu Gln Tyr Ala Ala Gln Glu Gly Leu Leu
        35                  40                  45

Ala Leu Gln Ser Glu Leu Leu Arg Ile Thr Leu Pro Asp Phe Thr Gly
    50                  55                  60
```

```
Asp Leu Arg Ile Pro His Val Gly Arg Gly Arg Tyr Glu Phe His Ser
65                  70                  75                  80

Leu Asn Ile His Ser Cys Glu Leu Leu His Ser Ala Leu Arg Pro Val
                85                  90                  95

Pro Gly Gln Gly Leu Ser Leu Ser Ile Ser Asp Ser Ser Ile Arg Val
            100                 105                 110

Gln Gly Arg Trp Lys Val Arg Lys Ser Phe Phe Lys Leu Gln Gly Ser
        115                 120                 125

Phe Asp Val Ser Val Lys Gly Ile Ser Ile Ser Val Asn Leu Leu Leu
    130                 135                 140

Gly Ser Glu Ser Ser Gly Arg Pro Thr Val Thr Ala Ser Ser Cys Ser
145                 150                 155                 160

Ser Asp Ile Ala Asp Val Glu Val Asp Met Ser Gly Asp Leu Gly Trp
                165                 170                 175

Leu Leu Asn Leu Phe His Asn Gln Ile Glu Ser Lys Phe Gln Lys Val
            180                 185                 190

Leu Glu Ser Arg Ile Cys Glu Met Ile Gln Lys Ser Val Ser Ser Asp
        195                 200                 205

Leu Gln Pro Tyr Leu Gln Thr Leu Pro Val Thr Thr Glu Ile Asp Ser
    210                 215                 220

Phe Ala Asp Ile Asp Tyr Ser Leu Val Glu Ala Pro Arg Ala Thr Ala
225                 230                 235                 240

Gln Met Leu Glu Val Met Phe Lys Gly Glu Ile Phe His Arg Asn His
                245                 250                 255

Arg Ser Pro Val Thr Leu Leu Ala Ala Val Met Ser Leu Pro Glu Glu
            260                 265                 270

His Asn Lys Met Val Tyr Phe Ala Ile Ser Asp Tyr Val Phe Asn Thr
        275                 280                 285

Ala Ser Leu Val Tyr His Glu Glu Gly Tyr Leu Asn Phe Ser Ile Thr
    290                 295                 300

Asp Asp Met Ile Pro Pro Asp Ser Asn Ile Arg Leu Thr Thr Lys Ser
305                 310                 315                 320

Phe Arg Pro Phe Val Pro Arg Leu Ala Arg Leu Tyr Pro Asn Met Asn
                325                 330                 335

Leu Glu Leu Gln Gly Ser Val Pro Ser Ala Pro Leu Leu Asn Phe Ser
            340                 345                 350

Pro Gly Asn Leu Ser Val Asp Pro Tyr Met Glu Ile Asp Ala Phe Val
        355                 360                 365

Leu Leu Pro Ser Ser Ser Lys Glu Pro Val Phe Arg Leu Ser Val Ala
    370                 375                 380

Thr Asn Val Ser Ala Thr Leu Thr Phe Asn Thr Ser Lys Ile Thr Gly
385                 390                 395                 400

Phe Leu Lys Pro Gly Lys Val Lys Val Glu Leu Lys Glu Ser Lys Val
                405                 410                 415

Gly Leu Phe Asn Ala Glu Leu Leu Glu Ala Leu Leu Asn Tyr Tyr Ile
            420                 425                 430

Leu Asn Thr Phe Tyr Pro Lys Phe Asn Asp Lys Leu Ala Glu Gly Phe
        435                 440                 445

Pro Leu Pro Leu Leu Lys Arg Val Gln Leu Tyr Asp Leu Gly Leu Gln
    450                 455                 460

Ile His Lys Asp Phe Leu Phe Leu Gly Ala Asn Val Gln Tyr Met Arg
465                 470                 475                 480
```

Val

<210> SEQ ID NO 24
<211> LENGTH: 322
<212> TYPE: PRT
<213> ORGANISM: Homo sapiens

<400> SEQUENCE: 24

```
Met Ala Arg Cys Phe Ser Leu Val Leu Leu Leu Thr Ser Ile Trp Thr
1               5                   10                  15

Thr Arg Leu Leu Val Gln Gly Ser Leu Arg Ala Glu Glu Leu Ser Ile
            20                  25                  30

Gln Val Ser Cys Arg Ile Met Gly Ile Thr Leu Val Ser Lys Lys Ala
        35                  40                  45

Asn Gln Gln Leu Asn Phe Thr Glu Ala Lys Glu Ala Cys Arg Leu Leu
    50                  55                  60

Gly Leu Ser Leu Ala Gly Lys Asp Gln Val Glu Thr Ala Leu Lys Ala
65                  70                  75                  80

Ser Phe Glu Thr Cys Ser Tyr Gly Trp Val Gly Asp Gly Phe Val Val
                85                  90                  95

Ile Ser Arg Ile Ser Pro Asn Pro Lys Cys Gly Lys Asn Gly Val Gly
            100                 105                 110

Val Leu Ile Trp Lys Val Pro Val Ser Arg Gln Phe Ala Ala Tyr Cys
        115                 120                 125

Tyr Asn Ser Ser Asp Thr Trp Thr Asn Ser Cys Ile Pro Glu Ile Ile
    130                 135                 140

Thr Thr Lys Asp Pro Ile Phe Asn Thr Gln Thr Ala Thr Gln Thr Thr
145                 150                 155                 160

Glu Phe Ile Val Ser Asp Ser Thr Tyr Ser Val Ala Ser Pro Tyr Ser
                165                 170                 175

Thr Ile Pro Ala Pro Thr Thr Thr Pro Pro Ala Pro Ala Ser Thr Ser
            180                 185                 190

Ile Pro Arg Arg Lys Lys Leu Ile Cys Val Thr Glu Val Phe Met Glu
        195                 200                 205

Thr Ser Thr Met Ser Thr Glu Thr Glu Pro Phe Val Glu Asn Lys Ala
    210                 215                 220

Ala Phe Lys Asn Glu Ala Ala Gly Phe Gly Gly Val Pro Thr Ala Leu
225                 230                 235                 240

Leu Val Leu Ala Leu Leu Phe Phe Gly Ala Ala Ala Gly Leu Gly Phe
                245                 250                 255

Cys Tyr Val Lys Arg Tyr Val Lys Ala Phe Pro Phe Thr Asn Lys Asn
            260                 265                 270

Gln Gln Lys Glu Met Ile Glu Thr Lys Val Val Lys Glu Glu Lys Ala
        275                 280                 285

Asn Asp Ser Asn Pro Asn Glu Glu Ser Lys Lys Thr Asp Lys Asn Pro
    290                 295                 300

Glu Glu Ser Lys Ser Pro Ser Lys Thr Thr Val Arg Cys Leu Glu Ala
305                 310                 315                 320

Glu Val
```

<210> SEQ ID NO 25
<211> LENGTH: 471
<212> TYPE: PRT
<213> ORGANISM: Homo sapiens

<400> SEQUENCE: 25

```
Met Glu Asn Leu Lys His Ile Ile Thr Leu Gly Gln Val Ile His Lys
1               5                   10                  15

Arg Cys Glu Glu Met Lys Tyr Cys Lys Lys Gln Cys Arg Arg Leu Gly
            20                  25                  30

His Arg Val Leu Gly Leu Ile Lys Pro Leu Glu Met Leu Gln Asp Gln
        35                  40                  45

Gly Lys Arg Ser Val Pro Ser Glu Lys Leu Thr Thr Ala Met Asn Arg
    50                  55                  60

Phe Lys Ala Ala Leu Glu Glu Ala Asn Gly Glu Ile Glu Lys Phe Ser
65                  70                  75                  80

Asn Arg Ser Asn Ile Cys Arg Phe Leu Thr Ala Ser Gln Asp Lys Ile
                85                  90                  95

Leu Phe Lys Asp Val Asn Arg Lys Leu Ser Asp Val Trp Lys Glu Leu
            100                 105                 110

Ser Leu Leu Leu Gln Val Glu Gln Arg Met Pro Val Ser Pro Ile Ser
        115                 120                 125

Gln Gly Ala Ser Trp Ala Gln Glu Asp Gln Gln Asp Ala Asp Glu Asp
    130                 135                 140

Arg Arg Ala Phe Gln Met Leu Arg Arg Asp Asn Glu Lys Ile Glu Ala
145                 150                 155                 160

Ser Leu Arg Arg Leu Glu Ile Asn Met Lys Glu Ile Lys Glu Thr Leu
                165                 170                 175

Arg Gln Tyr Leu Pro Pro Lys Cys Met Gln Glu Ile Pro Gln Glu Gln
            180                 185                 190

Ile Lys Glu Ile Lys Lys Glu Gln Leu Ser Gly Ser Pro Trp Ile Leu
        195                 200                 205

Leu Arg Glu Asn Glu Val Ser Thr Leu Tyr Lys Gly Glu Tyr His Arg
    210                 215                 220

Ala Pro Val Ala Ile Lys Val Phe Lys Lys Leu Gln Ala Gly Ser Ile
225                 230                 235                 240

Ala Ile Val Arg Gln Thr Phe Asn Lys Glu Ile Lys Thr Met Lys Lys
                245                 250                 255

Phe Glu Ser Pro Asn Ile Leu Arg Ile Phe Gly Ile Cys Ile Asp Glu
            260                 265                 270

Thr Val Thr Pro Pro Gln Phe Ser Ile Val Met Glu Tyr Cys Glu Leu
        275                 280                 285

Gly Thr Leu Arg Glu Leu Leu Asp Arg Glu Lys Asp Leu Thr Leu Gly
    290                 295                 300

Lys Arg Met Val Leu Val Leu Gly Ala Ala Arg Gly Leu Tyr Arg Leu
305                 310                 315                 320

His His Ser Glu Ala Pro Glu Leu His Gly Lys Ile Arg Ser Ser Asn
                325                 330                 335

Phe Leu Val Thr Gln Gly Tyr Gln Val Lys Leu Ala Gly Phe Glu Leu
            340                 345                 350

Arg Lys Thr Gln Thr Ser Met Ser Leu Gly Thr Thr Arg Glu Lys Thr
        355                 360                 365

Asp Arg Val Lys Ser Thr Ala Tyr Leu Ser Pro Gln Glu Leu Glu Asp
    370                 375                 380

Val Phe Tyr Gln Tyr Asp Val Lys Ser Glu Ile Tyr Ser Phe Gly Ile
385                 390                 395                 400

Val Leu Trp Glu Ile Ala Thr Gly Asp Ile Pro Phe Gln Gly Cys Asn
                405                 410                 415
```

```
Ser Glu Lys Ile Arg Lys Leu Val Ala Val Lys Arg Gln Gln Glu Pro
            420                 425                 430

Leu Gly Glu Asp Cys Pro Ser Glu Leu Arg Glu Ile Ile Asp Glu Cys
        435                 440                 445

Arg Ala His Asp Pro Ser Val Arg Pro Ser Val Asp Glu Ile Leu Lys
    450                 455                 460

Lys Leu Ser Thr Phe Ser Lys
465                 470


<210> SEQ ID NO 26
<211> LENGTH: 709
<212> TYPE: PRT
<213> ORGANISM: Homo sapiens

<400> SEQUENCE: 26

Met Ala Thr Ala Gly Gly Gly Ser Gly Ala Asp Pro Gly Ser Arg Gly
1               5                   10                  15

Leu Leu Arg Leu Leu Ser Phe Cys Val Leu Leu Ala Gly Leu Cys Arg
            20                  25                  30

Gly Asn Ser Val Glu Arg Lys Ile Tyr Ile Pro Leu Asn Lys Thr Ala
        35                  40                  45

Pro Cys Val Arg Leu Leu Asn Ala Thr His Gln Ile Gly Cys Gln Ser
    50                  55                  60

Ser Ile Ser Gly Asp Thr Gly Val Ile His Val Val Glu Lys Glu Glu
65                  70                  75                  80

Asp Leu Gln Trp Val Leu Thr Asp Gly Pro Asn Pro Pro Tyr Met Val
                85                  90                  95

Leu Leu Glu Ser Lys His Phe Thr Arg Asp Leu Met Glu Lys Leu Lys
            100                 105                 110

Gly Arg Thr Ser Arg Ile Ala Gly Leu Ala Val Ser Leu Thr Lys Pro
        115                 120                 125

Ser Pro Ala Ser Gly Phe Ser Pro Ser Val Gln Cys Pro Asn Asp Gly
    130                 135                 140

Phe Gly Val Tyr Ser Asn Ser Tyr Gly Pro Glu Phe Ala His Cys Arg
145                 150                 155                 160

Glu Ile Gln Trp Asn Ser Leu Gly Asn Gly Leu Ala Tyr Glu Asp Phe
                165                 170                 175

Ser Phe Pro Ile Phe Leu Leu Glu Asp Glu Asn Glu Thr Lys Val Ile
            180                 185                 190

Lys Gln Cys Tyr Gln Asp His Asn Leu Ser Gln Asn Gly Ser Ala Pro
        195                 200                 205

Thr Phe Pro Leu Cys Ala Met Gln Leu Phe Ser His Met His Ala Val
    210                 215                 220

Ile Ser Thr Ala Thr Cys Met Arg Arg Ser Ser Ile Gln Ser Thr Phe
225                 230                 235                 240

Ser Ile Asn Pro Glu Ile Val Cys Asp Pro Leu Ser Asp Tyr Asn Val
                245                 250                 255

Trp Ser Met Leu Lys Pro Ile Asn Thr Thr Gly Thr Leu Lys Pro Asp
            260                 265                 270

Asp Arg Val Val Val Ala Ala Thr Arg Leu Asp Ser Arg Ser Phe Phe
        275                 280                 285

Trp Asn Val Ala Pro Gly Ala Glu Ser Ala Val Ala Ser Phe Val Thr
    290                 295                 300

Gln Leu Ala Ala Ala Glu Ala Leu Gln Lys Ala Pro Asp Val Thr Thr
305                 310                 315                 320
```

```
Leu Pro Arg Asn Val Met Phe Val Phe Phe Gln Gly Glu Thr Phe Asp
                325                 330                 335

Tyr Ile Gly Ser Ser Arg Met Val Tyr Asp Met Glu Lys Gly Lys Phe
            340                 345                 350

Pro Val Gln Leu Glu Asn Val Asp Ser Phe Val Glu Leu Gly Gln Val
        355                 360                 365

Ala Leu Arg Thr Ser Leu Glu Leu Trp Met His Thr Asp Pro Val Ser
    370                 375                 380

Gln Lys Asn Glu Ser Val Arg Asn Gln Val Glu Asp Leu Leu Ala Thr
385                 390                 395                 400

Leu Glu Lys Ser Gly Ala Gly Val Pro Ala Val Ile Leu Arg Arg Pro
                405                 410                 415

Asn Gln Ser Gln Pro Leu Pro Pro Ser Ser Leu Gln Arg Phe Leu Arg
            420                 425                 430

Ala Arg Asn Ile Ser Gly Val Val Leu Ala Asp His Ser Gly Ala Phe
        435                 440                 445

His Asn Lys Tyr Tyr Gln Ser Ile Tyr Asp Thr Ala Glu Asn Ile Asn
    450                 455                 460

Val Ser Tyr Pro Glu Trp Leu Ser Pro Glu Glu Asp Leu Asn Phe Val
465                 470                 475                 480

Thr Asp Thr Ala Lys Ala Leu Ala Asp Val Ala Thr Val Leu Gly Arg
                485                 490                 495

Ala Leu Tyr Glu Leu Ala Gly Gly Thr Asn Phe Ser Asp Thr Val Gln
            500                 505                 510

Ala Asp Pro Gln Thr Val Thr Arg Leu Leu Tyr Gly Phe Leu Ile Lys
        515                 520                 525

Ala Asn Asn Ser Trp Phe Gln Ser Ile Leu Arg Gln Asp Leu Arg Ser
    530                 535                 540

Tyr Leu Gly Asp Gly Pro Leu Gln His Tyr Ile Ala Val Ser Ser Pro
545                 550                 555                 560

Thr Asn Thr Thr Tyr Val Val Gln Tyr Ala Leu Ala Asn Leu Thr Gly
                565                 570                 575

Thr Val Val Asn Leu Thr Arg Glu Gln Cys Gln Asp Pro Ser Lys Val
            580                 585                 590

Pro Ser Glu Asn Lys Asp Leu Tyr Glu Tyr Ser Trp Val Gln Gly Pro
        595                 600                 605

Leu His Ser Asn Glu Thr Asp Arg Leu Pro Arg Cys Val Arg Ser Thr
    610                 615                 620

Ala Arg Leu Ala Arg Ala Leu Ser Pro Ala Phe Glu Leu Ser Gln Trp
625                 630                 635                 640

Ser Ser Thr Glu Tyr Ser Thr Trp Thr Glu Ser Arg Trp Lys Asp Ile
                645                 650                 655

Arg Ala Arg Ile Phe Leu Ile Ala Ser Lys Glu Leu Glu Leu Ile Thr
            660                 665                 670

Leu Thr Val Gly Phe Gly Ile Leu Ile Phe Ser Leu Ile Val Thr Tyr
        675                 680                 685

Cys Ile Asn Ala Lys Ala Asp Val Leu Phe Ile Ala Pro Arg Glu Pro
    690                 695                 700

Gly Ala Val Ser Tyr
705

<210> SEQ ID NO 27
<211> LENGTH: 469
```

<212> TYPE: PRT
<213> ORGANISM: Homo sapiens

<400> SEQUENCE: 27

```
Met Ala Ala Ala Ser Pro Leu Arg Asp Cys Gln Ala Trp Lys Asp Ala
1               5                   10                  15

Arg Leu Pro Leu Ser Thr Thr Ser Asn Glu Ala Cys Lys Leu Phe Asp
            20                  25                  30

Ala Thr Leu Thr Gln Tyr Val Lys Trp Thr Asn Asp Lys Ser Leu Gly
        35                  40                  45

Gly Ile Glu Gly Cys Leu Ser Lys Leu Lys Ala Ala Asp Pro Thr Phe
    50                  55                  60

Val Met Gly His Ala Met Ala Thr Gly Leu Val Leu Ile Gly Thr Gly
65                  70                  75                  80

Ser Ser Val Lys Leu Asp Lys Glu Leu Asp Leu Ala Val Lys Thr Met
                85                  90                  95

Val Glu Ile Ser Arg Thr Gln Pro Leu Thr Arg Arg Glu Gln Leu His
            100                 105                 110

Val Ser Ala Val Glu Thr Phe Ala Asn Gly Asn Phe Pro Lys Ala Cys
        115                 120                 125

Glu Leu Trp Glu Gln Ile Leu Gln Asp His Pro Thr Asp Met Leu Ala
    130                 135                 140

Leu Lys Phe Ser His Asp Ala Tyr Phe Tyr Leu Gly Tyr Gln Glu Gln
145                 150                 155                 160

Met Arg Asp Ser Val Ala Arg Ile Tyr Pro Phe Trp Thr Pro Asp Ile
                165                 170                 175

Pro Leu Ser Ser Tyr Val Lys Gly Ile Tyr Ser Phe Gly Leu Met Glu
            180                 185                 190

Thr Asn Phe Tyr Asp Gln Ala Glu Lys Leu Ala Lys Glu Ala Leu Ser
        195                 200                 205

Ile Asn Pro Thr Asp Ala Trp Ser Val His Thr Val Ala His Ile His
    210                 215                 220

Glu Met Lys Ala Glu Ile Lys Asp Gly Leu Glu Phe Met Gln His Ser
225                 230                 235                 240

Glu Thr Phe Trp Lys Asp Ser Asp Met Leu Ala Cys His Asn Tyr Trp
                245                 250                 255

His Trp Ala Leu Tyr Leu Ile Glu Lys Gly Glu Tyr Glu Ala Ala Leu
            260                 265                 270

Thr Ile Tyr Asp Thr His Ile Leu Pro Ser Leu Gln Ala Asn Asp Ala
        275                 280                 285

Met Leu Asp Val Val Asp Ser Cys Ser Met Leu Tyr Arg Leu Gln Met
    290                 295                 300

Glu Gly Val Ser Val Gly Gln Arg Trp Gln Asp Val Leu Pro Val Ala
305                 310                 315                 320

Arg Lys His Ser Arg Asp His Ile Leu Leu Phe Asn Asp Ala His Phe
                325                 330                 335

Leu Met Ala Ser Leu Gly Ala His Asp Pro Gln Thr Thr Gln Glu Leu
            340                 345                 350

Leu Thr Thr Leu Arg Asp Ala Ser Glu Ser Pro Gly Glu Asn Cys Gln
        355                 360                 365

His Leu Leu Ala Arg Asp Val Gly Leu Pro Leu Cys Gln Ala Leu Val
    370                 375                 380

Glu Ala Glu Asp Gly Asn Pro Asp Arg Val Leu Glu Leu Leu Leu Pro
385                 390                 395                 400
```

```
Ile Arg Tyr Arg Ile Val Gln Leu Gly Gly Ser Asn Ala Gln Arg Asp
                405                 410                 415

Val Phe Asn Gln Leu Leu Ile His Ala Ala Leu Asn Cys Thr Ser Ser
            420                 425                 430

Val His Lys Asn Val Ala Arg Ser Leu Leu Met Glu Arg Asp Ala Leu
        435                 440                 445

Lys Pro Asn Ser Pro Leu Thr Glu Arg Leu Ile Arg Lys Ala Ala Thr
    450                 455                 460

Val His Leu Met Gln
465


<210> SEQ ID NO 28
<211> LENGTH: 114
<212> TYPE: PRT
<213> ORGANISM: Homo sapiens

<400> SEQUENCE: 28

Met Ser Ala Leu Ser Leu Leu Ile Leu Gly Leu Leu Thr Ala Val Pro
1               5                   10                  15

Pro Ala Ser Cys Gln Gln Gly Leu Gly Asn Leu Gln Pro Trp Met Gln
            20                  25                  30

Gly Leu Ile Ala Val Ala Val Phe Leu Val Leu Val Ala Ile Ala Phe
        35                  40                  45

Ala Val Asn His Phe Trp Cys Gln Glu Glu Pro Glu Pro Ala His Met
    50                  55                  60

Ile Leu Thr Val Gly Asn Lys Ala Asp Gly Val Leu Val Gly Thr Asp
65                  70                  75                  80

Gly Arg Tyr Ser Ser Met Ala Ala Ser Phe Arg Ser Ser Glu His Glu
                85                  90                  95

Asn Ala Tyr Glu Asn Val Pro Glu Glu Glu Gly Lys Val Arg Ser Thr
            100                 105                 110

Pro Met


<210> SEQ ID NO 29
<211> LENGTH: 2080
<212> TYPE: PRT
<213> ORGANISM: Homo sapiens

<400> SEQUENCE: 29

Met Ser Ser Ser Pro Ser Arg Ser Ala Ala Asp Ile Tyr Ile Arg Glu
1               5                   10                  15

Tyr Phe His Ser His Val Ser Gly Gly His Pro Glu Ala Thr Pro Leu
            20                  25                  30

Arg Val Met Tyr Thr Asp Arg Pro Leu Ser Gln Thr Asp Pro Val Thr
        35                  40                  45

Leu Gln Tyr Cys Cys Leu Thr Asp Asp Arg Gln Ala Phe Arg Pro Pro
    50                  55                  60

Thr Arg Ala Glu Leu Ala Arg His Arg Val Val Val Thr Thr Thr Ser
65                  70                  75                  80

Gln Ala Arg Glu Leu Arg Val Pro Val Gly Phe Phe Ser His Ile Leu
                85                  90                  95

Ile Asp Glu Ala Ala Gln Met Leu Glu Cys Glu Ala Leu Thr Pro Leu
            100                 105                 110

Ala Tyr Ala Ser His Gly Thr Arg Leu Val Leu Ala Gly Asp His Met
        115                 120                 125
```

```
Gln Val Thr Pro Arg Leu Phe Ser Val Ala Arg Ala Arg Ala Ala Glu
    130                 135                 140

His Thr Leu Leu His Arg Leu Phe Leu Cys Tyr Gln Gln Glu Thr His
145                 150                 155                 160

Glu Val Ala Arg Gln Ser Arg Leu Val Phe His Glu Asn Tyr Arg Cys
                165                 170                 175

Thr Asp Ala Ile Val Ser Phe Ile Ser Arg His Phe Tyr Val Ala Lys
            180                 185                 190

Gly Asn Pro Ile His Ala Arg Gly Lys Val Pro Pro His Pro Arg His
        195                 200                 205

Tyr Pro Leu Met Phe Cys His Val Ala Gly Asn Pro Asp Arg Asp Met
    210                 215                 220

Ser Met Ala Ser Trp Leu Asn Leu Ala Glu Ile Ala Gln Val Val Glu
225                 230                 235                 240

Lys Val Gln Glu Ala Tyr Asn Thr Trp Pro Ser Cys Trp Gly Gly Arg
                245                 250                 255

Glu Gln Arg Cys Ile Cys Val Val Ser His Gly Ala Gln Val Ser Ala
            260                 265                 270

Leu Arg Gln Glu Leu Arg Arg Arg Asp Leu Gly Gln Val Ser Val Gly
        275                 280                 285

Ser Phe Glu Ile Leu Pro Gly Arg Gln Phe Arg Val Val Val Leu Ser
    290                 295                 300

Thr Val His Thr Cys Gln Ser Leu Leu Ser Pro Gly Ala Leu Ala Pro
305                 310                 315                 320

Glu Phe Phe Thr Asp Ala Arg Val Leu Asn Thr Val Leu Thr Arg Ala
                325                 330                 335

Gln Ser Gln Leu Val Val Val Gly Asp Ala Val Ala Leu Cys Ser Phe
            340                 345                 350

Gly Ala Cys Gly Lys Leu Trp Glu Ser Phe Ile Arg Glu Cys Val Glu
        355                 360                 365

Arg His Ser Val Cys Pro Glu Gly Leu Ser Met Glu Gln Val Glu Gln
    370                 375                 380

Gly Val Ala Gln Arg Arg Arg Trp Pro Pro Arg Gly Thr Gln Ala Gly
385                 390                 395                 400

Ala Ala Gly Asn Trp Glu Ala Ala Pro Glu Pro Val Gly Asp Leu Ala
                405                 410                 415

Glu Glu Gln Ala Ala Val Val Thr Ala Met Val Lys Ala Glu Pro Gly
            420                 425                 430

Asp Glu Ala Leu Ser Pro Ala Ser Arg Asp Ile Thr Ala Thr Thr Ala
        435                 440                 445

Gln Thr Glu Ala Ala Ala Ala Pro Ala Gly Asp Ala Val Lys Glu Asp
    450                 455                 460

Val Val Pro Gly Ala Cys Ala Ala Gly Ala Ala Ala Ala Ala Gly Val
465                 470                 475                 480

Glu Ser Thr Glu Ala Glu Asp Ala Glu Ala Asp Phe Trp Pro Trp Asp
                485                 490                 495

Gly Glu Leu Asn Ala Asp Asp Ala Ile Leu Arg Glu Leu Leu Asp Glu
            500                 505                 510

Ser Gln Lys Val Met Val Thr Val Gly Glu Asp Gly Leu Leu Asp Thr
        515                 520                 525

Val Ala Arg Pro Glu Ser Leu Gln Gln Ala Arg Leu Tyr Glu Asn Leu
    530                 535                 540

Pro Pro Ala Ala Leu Arg Lys Leu Leu Arg Ala Glu Pro Glu Arg Tyr
```

```
545                 550                 555                 560

Arg His Cys Ser Phe Val Pro Glu Thr Phe Glu Arg Ala Ser Ala Ile
                565                 570                 575

Pro Leu Asp Asp Ala Ser Ser Gly Pro Ile Gln Val Arg Gly Arg Leu
            580                 585                 590

Asp Cys Gly Met Ala Phe Ala Gly Asp Glu Val Leu Val Gln Leu Leu
        595                 600                 605

Ser Gly Asp Lys Ala Pro Glu Gly Arg Leu Arg Gly Arg Val Leu Gly
    610                 615                 620

Val Leu Lys Arg Lys Arg His Glu Leu Ala Phe Val Cys Arg Met Asp
625                 630                 635                 640

Thr Trp Asp Pro Arg Ile Met Val Pro Ile Asn Gly Ser Val Thr Lys
                645                 650                 655

Ile Phe Val Ala Glu Leu Lys Asp Pro Ser Gln Val Pro Ile Tyr Ser
            660                 665                 670

Leu Arg Lys Gly Arg Leu Gln Arg Val Gly Leu Glu Arg Leu Thr Ala
        675                 680                 685

Glu Ala Arg His Ser Arg Leu Phe Trp Val Gln Ile Val Leu Trp Arg
    690                 695                 700

Gln Gly Phe Tyr Tyr Pro Leu Gly Ile Val Arg Glu Val Leu Pro Glu
705                 710                 715                 720

Ala Ser Thr Trp Glu Gln Gly Leu Arg Ile Leu Gly Leu Glu Tyr Ser
                725                 730                 735

Leu Arg Val Pro Pro Ser Asp Gln Ala Thr Ile Thr Lys Val Leu Gln
            740                 745                 750

Lys Tyr His Thr Glu Leu Gly Arg Val Ala Gly Arg Arg Glu Asp Cys
        755                 760                 765

Arg Ala Phe Leu Thr Phe Thr Val Asp Pro Gln Gly Ala Cys Asn Leu
    770                 775                 780

Asp Asp Ala Leu Ser Val Arg Asp Leu Gly Pro Arg Cys Glu Val Ala
785                 790                 795                 800

Val His Ile Thr Asp Val Ala Ser Phe Val Pro Arg Asp Gly Val Leu
                805                 810                 815

Asp Val Glu Ala Arg Arg Gln Gly Ala Ala Phe Tyr Ala Pro Gly Arg
            820                 825                 830

Glu Pro Val Pro Met Leu Pro Ala Ser Leu Cys Gln Asp Val Leu Ser
        835                 840                 845

Leu Leu Pro Gly Arg Asp Arg Leu Ala Ile Ser Leu Phe Leu Thr Met
    850                 855                 860

Glu Lys Ala Ser Gly Gln Leu Lys Ser Leu Arg Phe Ala Pro Ser Val
865                 870                 875                 880

Val Gln Ser Asp Arg Gln Leu Ser Tyr Glu Glu Ala Glu Glu Val Ile
                885                 890                 895

Arg Gln His Pro Gly Ala Gly Arg Glu Leu Pro Ala Arg Leu Asp Ser
            900                 905                 910

Val Asp Ala Cys Val Val Ala Ala Cys Tyr Phe Ser Arg Leu Leu Arg
        915                 920                 925

Arg His Arg Leu Arg Ser Asp Cys Phe Tyr Glu Gln Pro Asp Glu Asp
    930                 935                 940

Gly Thr Leu Gly Phe Arg Ala Ala His Ile Met Val Lys Glu Tyr Met
945                 950                 955                 960

Ile Gln Phe Asn Arg Leu Val Ala Glu Phe Leu Val Gly Ser Glu Cys
                965                 970                 975
```

```
Thr Arg Thr Val Thr Pro Leu Arg Trp Gln Pro Ala Pro Arg Ser Gln
            980                 985                 990

Gln Leu Lys Ala Leu Cys Glu Lys  His Gly Asp Arg Val  Pro Leu Ser
        995                 1000                 1005

Leu His  Leu Gly His His Leu  His Gly Gly Gly Gly  Ser Pro Pro
    1010                 1015                 1020

Asp Thr  Arg Leu His Leu Leu  Ala Ser Leu Trp Lys  Gln Val Gln
    1025                 1030                 1035

Phe Ala  Ala Arg Thr Gln Asp  Tyr Glu Gln Met Val  Asp Leu Val
    1040                 1045                 1050

Thr Thr  Asp Asp Met His Pro  Phe Leu Ala Pro Ala  Gly Arg Asp
    1055                 1060                 1065

Leu Arg  Lys Ala Leu Glu Arg  Ser Ala Phe Gly Arg  Cys Ala Arg
    1070                 1075                 1080

Gly His  Gln Gln Gln Gly Gly  His Tyr Ser Leu Gln  Val Asp Trp
    1085                 1090                 1095

Tyr Thr  Trp Ala Thr Ser Pro  Ile Arg Arg Tyr Leu  Asp Val Val
    1100                 1105                 1110

Leu Gln  Arg Gln Ile Leu Leu  Ala Leu Gly His Gly  Gly Ser Ala
    1115                 1120                 1125

Tyr Ser  Ala Arg Asp Ile Asp  Gly Leu Cys Gln Ala  Phe Ser Leu
    1130                 1135                 1140

Gln His  Ala Leu Ala Gln Ser  Tyr Gln Arg Arg Ala  Arg Ser Leu
    1145                 1150                 1155

His Leu  Ala Val Gln Leu Lys  Ala Gln Pro Leu Asp  Lys Leu Gly
    1160                 1165                 1170

Phe Val  Val Asp Val Glu Ala  Gly Ser Arg Cys Phe  Arg Leu Leu
    1175                 1180                 1185

Phe Pro  Ser Asn Arg Glu Thr  Leu Pro Asp Pro Cys  Pro Val Pro
    1190                 1195                 1200

Tyr Gly  Ser Leu Gln Leu Ala  Glu His Pro His Ala  Leu Ala Gly
    1205                 1210                 1215

Arg Pro  Gly Leu Arg Leu Leu  Trp Arg Arg Arg Val  Tyr Ser Ala
    1220                 1225                 1230

Gln Gly  Ser Ser Pro Pro Leu  Pro Leu Pro Gly Thr  Val Pro Asp
    1235                 1240                 1245

Pro His  Thr Leu Ala Val Glu  Thr Ala Leu Trp Lys  Gln Leu Leu
    1250                 1255                 1260

Glu Leu  Val Glu Leu Gln Arg  Trp Pro Glu Ala Ala  Ala Leu Ile
    1265                 1270                 1275

Gln Glu  Lys Gly Glu Ala Ser  Gln Arg Arg Glu Leu  Val Gln Val
    1280                 1285                 1290

Gln Arg  Ser His Cys Gly His  Phe Leu Glu Val Ala  Arg Glu Leu
    1295                 1300                 1305

Gly Ser  Gly Asp Thr Leu Gln  Val Gln Leu Gly Thr  Ser Leu Gln
    1310                 1315                 1320

His Gly  Phe Leu Val Pro Ser  Pro Gln Leu Trp Thr  Val Ala Pro
    1325                 1330                 1335

Gly Phe  Ser Leu Cys Leu Glu  His Val Glu Arg Pro  Gly Asp Cys
    1340                 1345                 1350

Phe Ser  Gly Arg Val Tyr Arg  Ala Pro Arg Asp Arg  Tyr Arg Asp
    1355                 1360                 1365
```

```
Val Asp  Glu Tyr Ala Cys Val  Trp Glu Pro Phe Cys  Ala Leu Glu
    1370                 1375                 1380

Ser Ala  Thr Gly Ala Val Ala  Glu Asn Asp Ser Val  Thr Leu Gln
    1385                 1390                 1395

His Leu  Ser Val Ser Trp Glu  Ala Ser Arg Thr Pro  Gln Gly Gln
    1400                 1405                 1410

Leu Gln  Gly Ala Phe Arg Leu  Glu Ala Ala Phe Leu  Glu Glu Asn
    1415                 1420                 1425

Cys Ala  Asp Ile Asn Phe Ser  Cys Cys Tyr Leu Cys  Ile Arg Leu
    1430                 1435                 1440

Glu Gly  Leu Pro Ala Pro Thr  Ala Ser Pro Arg Pro  Gly Pro Ser
    1445                 1450                 1455

Ser Leu  Gly Pro Gly Leu Asn  Val Asp Pro Gly Thr  Tyr Thr Trp
    1460                 1465                 1470

Val Ala  His Gly Gln Thr Gln  Asp Trp Asp Gln Glu  Arg Arg Ala
    1475                 1480                 1485

Asp Arg  Gln Glu Ala Pro Arg  Arg Val His Leu Phe  Val His His
    1490                 1495                 1500

Met Gly  Met Glu Lys Val Pro  Glu Glu Val Leu Arg  Pro Gly Thr
    1505                 1510                 1515

Leu Phe  Thr Val Glu Leu Leu  Pro Lys Gln Leu Pro  Asp Leu Arg
    1520                 1525                 1530

Lys Glu  Glu Ala Val Arg Gly  Leu Glu Glu Ala Ser  Pro Leu Val
    1535                 1540                 1545

Thr Ser  Ile Ala Leu Gly Arg  Pro Val Pro Gln Pro  Leu Cys Arg
    1550                 1555                 1560

Val Ile  Pro Ser Arg Phe Leu  Glu Arg Gln Thr Tyr  Asn Ile Pro
    1565                 1570                 1575

Gly Gly  Arg His Lys Leu Asn  Pro Ser Gln Asn Val  Ala Val Arg
    1580                 1585                 1590

Glu Ala  Leu Glu Lys Pro Phe  Thr Val Ile Gln Gly  Pro Pro Gly
    1595                 1600                 1605

Thr Gly  Lys Thr Ile Val Gly  Leu His Ile Val Phe  Trp Phe His
    1610                 1615                 1620

Lys Ser  Asn Gln Glu Gln Val  Gln Pro Gly Gly Pro  Pro Arg Gly
    1625                 1630                 1635

Glu Lys  Arg Leu Gly Gly Pro  Cys Ile Leu Tyr Cys  Gly Pro Ser
    1640                 1645                 1650

Asn Lys  Ser Val Asp Val Leu  Ala Gly Leu Leu Leu  Arg Arg Met
    1655                 1660                 1665

Glu Leu  Lys Pro Leu Arg Val  Tyr Ser Glu Gln Ala  Glu Ala Ser
    1670                 1675                 1680

Glu Phe  Pro Val Pro Arg Val  Gly Ser Arg Lys Leu  Leu Arg Lys
    1685                 1690                 1695

Ser Pro  Arg Glu Gly Arg Pro  Asn Gln Ser Leu Arg  Ser Ile Thr
    1700                 1705                 1710

Leu His  His Arg Ile Arg Gln  Ala Pro Asn Pro Tyr  Ser Ser Glu
    1715                 1720                 1725

Ile Lys  Ala Phe Asp Thr Arg  Leu Gln Arg Gly Glu  Leu Phe Ser
    1730                 1735                 1740

Arg Glu  Asp Leu Val Trp Tyr  Lys Lys Val Leu Trp  Glu Ala Arg
    1745                 1750                 1755

Lys Phe  Glu Leu Asp Arg His  Glu Val Ile Leu Cys  Thr Cys Ser
```

```
    1760                1765                1770

Cys Ala  Ala Ser Ala Ser Leu  Lys Ile Leu Asp Val  Arg Gln Ile
    1775                1780                1785

Leu Val  Asp Glu Ala Gly Met  Ala Thr Glu Pro Glu  Thr Leu Ile
    1790                1795                1800

Pro Leu  Val Gln Phe Pro Gln  Ala Glu Lys Val Val  Leu Leu Gly
    1805                1810                1815

Asp His  Lys Gln Leu Arg Pro  Val Val Lys Asn Glu  Arg Leu Gln
    1820                1825                1830

Asn Leu  Gly Leu Asp Arg Ser  Leu Phe Glu Arg Tyr  His Glu Asp
    1835                1840                1845

Ala His  Met Leu Asp Thr Gln  Tyr Arg Met His Glu  Gly Ile Cys
    1850                1855                1860

Ala Phe  Pro Ser Val Ala Phe  Tyr Lys Ser Lys Leu  Lys Thr Trp
    1865                1870                1875

Gln Gly  Leu Arg Arg Pro Pro  Ser Val Leu Gly His  Ala Gly Lys
    1880                1885                1890

Glu Ser  Cys Pro Val Ile Phe  Gly His Val Gln Gly  His Glu Arg
    1895                1900                1905

Ser Leu  Leu Val Ser Thr Asp  Glu Gly Asn Glu Asn  Ser Lys Ala
    1910                1915                1920

Asn Leu  Glu Glu Val Ala Glu  Val Val Arg Ile Thr  Lys Gln Leu
    1925                1930                1935

Thr Leu  Gly Arg Thr Val Glu  Pro Gln Asp Ile Ala  Val Leu Thr
    1940                1945                1950

Pro Tyr  Asn Ala Gln Ala Ser  Glu Ile Ser Lys Ala  Leu Arg Arg
    1955                1960                1965

Glu Gly  Ile Ala Gly Val Ala  Val Ser Ser Ile Thr  Lys Ser Gln
    1970                1975                1980

Gly Ser  Glu Trp Arg Tyr Val  Leu Val Ser Thr Val  Arg Thr Cys
    1985                1990                1995

Ala Lys  Ser Asp Leu Asp Gln  Arg Pro Thr Lys Ser  Trp Leu Lys
    2000                2005                2010

Lys Phe  Leu Gly Phe Val Val  Asp Pro Asn Gln Val  Asn Val Ala
    2015                2020                2025

Val Thr  Arg Ala Gln Glu Gly  Leu Cys Leu Ile Gly  Asp His Leu
    2030                2035                2040

Leu Leu  Arg Cys Cys Pro Leu  Trp Arg Ser Leu Leu  Asp Phe Cys
    2045                2050                2055

Glu Ala  Gln Gln Thr Leu Val  Pro Ala Gly Gln Val  Arg Val Cys
    2060                2065                2070

Arg Arg  Pro Thr Met Pro Ser
    2075                2080


<210> SEQ ID NO 30
<211> LENGTH: 190
<212> TYPE: PRT
<213> ORGANISM: Homo sapiens

<400> SEQUENCE: 30

Met Ala Thr His His Thr Leu Trp Met Gly Leu Ala Leu Leu Gly Val
1               5                   10                  15

Leu Gly Asp Leu Gln Ala Ala Pro Glu Ala Gln Val Ser Val Gln Pro
            20                  25                  30
```

```
Asn Phe Gln Gln Asp Lys Phe Leu Gly Arg Trp Phe Ser Ala Gly Leu
        35                  40                  45

Ala Ser Asn Ser Ser Trp Leu Arg Glu Lys Lys Ala Ala Leu Ser Met
    50                  55                  60

Cys Lys Ser Val Val Ala Pro Ala Thr Asp Gly Gly Leu Asn Leu Thr
65                  70                  75                  80

Ser Thr Phe Leu Arg Lys Asn Gln Cys Glu Thr Arg Thr Met Leu Leu
                85                  90                  95

Gln Pro Ala Gly Ser Leu Gly Ser Tyr Ser Tyr Arg Ser Pro His Trp
            100                 105                 110

Gly Ser Thr Tyr Ser Val Ser Val Val Glu Thr Asp Tyr Asp Gln Tyr
        115                 120                 125

Ala Leu Leu Tyr Ser Gln Gly Ser Lys Gly Pro Gly Glu Asp Phe Arg
    130                 135                 140

Met Ala Thr Leu Tyr Ser Arg Thr Gln Thr Pro Arg Ala Glu Leu Lys
145                 150                 155                 160

Glu Lys Phe Thr Ala Phe Cys Lys Ala Gln Gly Phe Thr Glu Asp Thr
                165                 170                 175

Ile Val Phe Leu Pro Gln Thr Asp Lys Cys Met Thr Glu Gln
            180                 185                 190


<210> SEQ ID NO 31
<211> LENGTH: 174
<212> TYPE: PRT
<213> ORGANISM: Homo sapiens

<400> SEQUENCE: 31

Met Ala Ala Ala Met Val Pro Gly Arg Ser Glu Ser Trp Glu Arg Gly
1               5                   10                  15

Glu Pro Gly Arg Pro Ala Leu Tyr Phe Cys Gly Ser Ile Arg Gly Gly
            20                  25                  30

Arg Glu Asp Arg Thr Leu Tyr Glu Arg Ile Val Ser Arg Leu Arg Arg
        35                  40                  45

Phe Gly Thr Val Leu Thr Glu His Val Ala Ala Ala Glu Leu Gly Ala
    50                  55                  60

Arg Gly Glu Glu Ala Ala Gly Gly Asp Arg Leu Ile His Glu Gln Asp
65                  70                  75                  80

Leu Glu Trp Leu Gln Gln Ala Asp Val Val Val Ala Glu Val Thr Gln
                85                  90                  95

Pro Ser Leu Gly Val Gly Tyr Glu Leu Gly Arg Ala Val Ala Phe Asn
            100                 105                 110

Lys Arg Ile Leu Cys Leu Phe Arg Pro Gln Ser Gly Arg Val Leu Ser
        115                 120                 125

Ala Met Ile Arg Gly Ala Ala Asp Gly Ser Arg Phe Gln Val Trp Asp
    130                 135                 140

Tyr Glu Glu Gly Glu Val Glu Ala Leu Leu Asp Arg Tyr Phe Glu Ala
145                 150                 155                 160

Asp Pro Pro Gly Gln Val Ala Ala Ser Pro Asp Pro Thr Thr
                165                 170


<210> SEQ ID NO 32
<211> LENGTH: 114
<212> TYPE: PRT
<213> ORGANISM: Homo sapiens

<400> SEQUENCE: 32
```

```
Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro


<210> SEQ ID NO 33
<211> LENGTH: 122
<212> TYPE: PRT
<213> ORGANISM: Homo sapiens

<400> SEQUENCE: 33

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Val Trp Ala Ala Glu Ala Ile Ser Asp Ala Arg
65                  70                  75                  80

Glu Asn Ile Gln Arg Phe Phe Gly His Gly Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120


<210> SEQ ID NO 34
<211> LENGTH: 602
<212> TYPE: PRT
<213> ORGANISM: Homo sapiens

<400> SEQUENCE: 34

Met Ala Ala Leu Ala Ala Ala Ala Lys Lys Val Trp Ser Ala Arg Arg
1               5                   10                  15

Leu Leu Val Leu Leu Phe Thr Pro Leu Ala Leu Leu Pro Val Val Phe
            20                  25                  30

Ala Leu Pro Pro Lys Glu Gly Arg Cys Leu Phe Val Ile Leu Leu Met
        35                  40                  45

Ala Val Tyr Trp Cys Thr Glu Ala Leu Pro Leu Ser Val Thr Ala Leu
    50                  55                  60

Leu Pro Ile Val Leu Phe Pro Phe Met Gly Ile Leu Pro Ser Asn Lys
65                  70                  75                  80

Val Cys Pro Gln Tyr Phe Leu Asp Thr Asn Phe Leu Phe Leu Ser Gly
```

```
                85                  90                  95

Leu Ile Met Ala Ser Ala Ile Glu Glu Trp Asn Leu His Arg Arg Ile
            100                 105                 110

Ala Leu Lys Ile Leu Met Leu Val Gly Val Gln Pro Ala Arg Leu Ile
        115                 120                 125

Leu Gly Met Met Val Thr Thr Ser Phe Leu Ser Met Trp Leu Ser Asn
    130                 135                 140

Thr Ala Ser Thr Ala Met Met Leu Pro Ile Ala Asn Ala Ile Leu Lys
145                 150                 155                 160

Ser Leu Phe Gly Gln Lys Glu Val Arg Lys Asp Pro Ser Gln Glu Ser
                165                 170                 175

Glu Glu Asn Thr Ala Ala Val Arg Arg Asn Gly Leu His Thr Val Pro
            180                 185                 190

Thr Glu Met Gln Phe Leu Ala Ser Thr Glu Ala Lys Asp His Pro Gly
        195                 200                 205

Glu Thr Glu Val Pro Leu Asp Leu Pro Ala Asp Ser Arg Lys Glu Asp
    210                 215                 220

Glu Tyr Arg Arg Asn Ile Trp Lys Gly Phe Leu Ile Ser Ile Pro Tyr
225                 230                 235                 240

Ser Ala Ser Ile Gly Gly Thr Ala Thr Leu Thr Gly Thr Ala Pro Asn
                245                 250                 255

Leu Ile Leu Leu Gly Gln Leu Lys Ser Phe Phe Pro Gln Cys Asp Val
            260                 265                 270

Val Asn Phe Gly Ser Trp Phe Ile Phe Ala Phe Pro Leu Met Leu Leu
        275                 280                 285

Phe Leu Leu Ala Gly Trp Leu Trp Ile Ser Phe Leu Tyr Gly Gly Leu
    290                 295                 300

Ser Phe Arg Gly Trp Arg Lys Asn Lys Ser Glu Ile Arg Thr Asn Ala
305                 310                 315                 320

Glu Asp Arg Ala Arg Ala Val Ile Arg Glu Glu Tyr Gln Asn Leu Gly
                325                 330                 335

Pro Ile Lys Phe Ala Glu Gln Ala Val Phe Ile Leu Phe Cys Met Phe
            340                 345                 350

Ala Ile Leu Leu Phe Thr Arg Asp Pro Lys Phe Ile Pro Gly Trp Ala
        355                 360                 365

Ser Leu Phe Asn Pro Gly Phe Leu Ser Asp Ala Val Thr Gly Val Ala
    370                 375                 380

Ile Val Thr Ile Leu Phe Phe Phe Pro Ser Gln Arg Pro Ser Leu Lys
385                 390                 395                 400

Trp Trp Phe Asp Phe Lys Ala Pro Asn Thr Glu Thr Glu Pro Leu Leu
                405                 410                 415

Thr Trp Lys Lys Ala Gln Glu Thr Val Pro Trp Asn Ile Ile Leu Leu
            420                 425                 430

Leu Gly Gly Gly Phe Ala Met Ala Lys Gly Cys Glu Glu Ser Gly Leu
        435                 440                 445

Ser Val Trp Ile Gly Gly Gln Leu His Pro Leu Glu Asn Val Pro Pro
    450                 455                 460

Ala Leu Ala Val Leu Leu Ile Thr Val Val Ile Ala Phe Phe Thr Glu
465                 470                 475                 480

Phe Ala Ser Asn Thr Ala Thr Ile Ile Ile Phe Leu Pro Val Leu Ala
                485                 490                 495

Glu Leu Ala Ile Arg Leu Arg Val His Pro Leu Tyr Leu Met Ile Pro
            500                 505                 510
```

Gly Thr Val Gly Cys Ser Phe Ala Phe Met Leu Pro Val Ser Thr Pro
515 520 525

Pro Asn Ser Ile Ala Phe Ala Ser Gly His Leu Leu Val Lys Asp Met
530 535 540

Val Arg Thr Gly Leu Leu Met Asn Leu Met Gly Val Leu Leu Leu Ser
545 550 555 560

Leu Ala Met Asn Thr Trp Ala Gln Thr Ile Phe Gln Leu Gly Thr Phe
565 570 575

Pro Asp Trp Ala Asp Met Tyr Ser Val Asn Val Thr Ala Leu Pro Pro
580 585 590

Thr Leu Ala Asn Asp Thr Phe Arg Thr Leu
595 600

<210> SEQ ID NO 35
<211> LENGTH: 492
<212> TYPE: PRT
<213> ORGANISM: Homo sapiens

<400> SEQUENCE: 35

Met Glu Pro Ser Ser Lys Lys Leu Thr Gly Arg Leu Met Leu Ala Val
1 5 10 15

Gly Gly Ala Val Leu Gly Ser Leu Gln Phe Gly Tyr Asn Thr Gly Val
20 25 30

Ile Asn Ala Pro Gln Lys Val Ile Glu Glu Phe Tyr Asn Gln Thr Trp
35 40 45

Val His Arg Tyr Gly Glu Ser Ile Leu Pro Thr Thr Leu Thr Thr Leu
50 55 60

Trp Ser Leu Ser Val Ala Ile Phe Ser Val Gly Gly Met Ile Gly Ser
65 70 75 80

Phe Ser Val Gly Leu Phe Val Asn Arg Phe Gly Arg Arg Asn Ser Met
85 90 95

Leu Met Met Asn Leu Leu Ala Phe Val Ser Ala Val Leu Met Gly Phe
100 105 110

Ser Lys Leu Gly Lys Ser Phe Glu Met Leu Ile Leu Gly Arg Phe Ile
115 120 125

Ile Gly Val Tyr Cys Gly Leu Thr Thr Gly Phe Val Pro Met Tyr Val
130 135 140

Gly Glu Val Ser Pro Thr Ala Leu Arg Gly Ala Leu Gly Thr Leu His
145 150 155 160

Gln Leu Gly Ile Val Val Gly Ile Leu Ile Ala Gln Val Phe Gly Leu
165 170 175

Asp Ser Ile Met Gly Asn Lys Asp Leu Trp Pro Leu Leu Leu Ser Ile
180 185 190

Ile Phe Ile Pro Ala Leu Leu Gln Cys Ile Val Leu Pro Phe Cys Pro
195 200 205

Glu Ser Pro Arg Phe Leu Leu Ile Asn Arg Asn Glu Glu Asn Arg Ala
210 215 220

Lys Ser Val Leu Lys Lys Leu Arg Gly Thr Ala Asp Val Thr His Asp
225 230 235 240

Leu Gln Glu Met Lys Glu Glu Ser Arg Gln Met Met Arg Glu Lys Lys
245 250 255

Val Thr Ile Leu Glu Leu Phe Arg Ser Pro Ala Tyr Arg Gln Pro Ile
260 265 270

Leu Ile Ala Val Val Leu Gln Leu Ser Gln Gln Leu Ser Gly Ile Asn

```
        275                 280                 285

Ala Val Phe Tyr Tyr Ser Thr Ser Ile Phe Glu Lys Ala Gly Val Gln
    290                 295                 300

Gln Pro Val Tyr Ala Thr Ile Gly Ser Gly Ile Val Asn Thr Ala Phe
305                 310                 315                 320

Thr Val Val Ser Leu Phe Val Val Glu Arg Ala Gly Arg Arg Thr Leu
                325                 330                 335

His Leu Ile Gly Leu Ala Gly Met Ala Gly Cys Ala Ile Leu Met Thr
            340                 345                 350

Ile Ala Leu Ala Leu Leu Glu Gln Leu Pro Trp Met Ser Tyr Leu Ser
        355                 360                 365

Ile Val Ala Ile Phe Gly Phe Val Ala Phe Phe Glu Val Gly Pro Gly
    370                 375                 380

Pro Ile Pro Trp Phe Ile Val Ala Glu Leu Phe Ser Gln Gly Pro Arg
385                 390                 395                 400

Pro Ala Ala Ile Ala Val Ala Gly Phe Ser Asn Trp Thr Ser Asn Phe
                405                 410                 415

Ile Val Gly Met Cys Phe Gln Tyr Val Glu Gln Leu Cys Gly Pro Tyr
            420                 425                 430

Val Phe Ile Ile Phe Thr Val Leu Leu Val Leu Phe Phe Ile Phe Thr
        435                 440                 445

Tyr Phe Lys Val Pro Glu Thr Lys Gly Arg Thr Phe Asp Glu Ile Ala
    450                 455                 460

Ser Gly Phe Arg Gln Gly Gly Ala Ser Gln Ser Asp Lys Thr Pro Glu
465                 470                 475                 480

Glu Leu Phe His Pro Leu Gly Ala Asp Ser Gln Val
                485                 490


<210> SEQ ID NO 36
<211> LENGTH: 524
<212> TYPE: PRT
<213> ORGANISM: Homo sapiens

<400> SEQUENCE: 36

Met Thr Glu Asp Lys Val Thr Gly Thr Leu Val Phe Thr Val Ile Thr
1               5                   10                  15

Ala Val Leu Gly Ser Phe Gln Phe Gly Tyr Asp Ile Gly Val Ile Asn
            20                  25                  30

Ala Pro Gln Gln Val Ile Ile Ser His Tyr Arg His Val Leu Gly Val
        35                  40                  45

Pro Leu Asp Asp Arg Lys Ala Ile Asn Asn Tyr Val Ile Asn Ser Thr
    50                  55                  60

Asp Glu Leu Pro Thr Ile Ser Tyr Ser Met Asn Pro Lys Pro Thr Pro
65                  70                  75                  80

Trp Ala Glu Glu Glu Thr Val Ala Ala Ala Gln Leu Ile Thr Met Leu
                85                  90                  95

Trp Ser Leu Ser Val Ser Ser Phe Ala Val Gly Gly Met Thr Ala Ser
            100                 105                 110

Phe Phe Gly Gly Trp Leu Gly Asp Thr Leu Gly Arg Ile Lys Ala Met
        115                 120                 125

Leu Val Ala Asn Ile Leu Ser Leu Val Gly Ala Leu Leu Met Gly Phe
    130                 135                 140

Ser Lys Leu Gly Pro Ser His Ile Leu Ile Ile Ala Gly Arg Ser Ile
145                 150                 155                 160
```

```
Ser Gly Leu Tyr Cys Gly Leu Ile Ser Gly Leu Val Pro Met Tyr Ile
                165                 170                 175

Gly Glu Ile Ala Pro Thr Ala Leu Arg Gly Ala Leu Gly Thr Phe His
            180                 185                 190

Gln Leu Ala Ile Val Thr Gly Ile Leu Ile Ser Gln Ile Ile Gly Leu
        195                 200                 205

Glu Phe Ile Leu Gly Asn Tyr Asp Leu Trp His Ile Leu Leu Gly Leu
    210                 215                 220

Ser Gly Val Arg Ala Ile Leu Gln Ser Leu Leu Leu Phe Phe Cys Pro
225                 230                 235                 240

Glu Ser Pro Arg Tyr Leu Tyr Ile Lys Leu Asp Glu Glu Val Lys Ala
                245                 250                 255

Lys Gln Ser Leu Lys Arg Leu Arg Gly Tyr Asp Asp Val Thr Lys Asp
            260                 265                 270

Ile Asn Glu Met Arg Lys Glu Arg Glu Glu Ala Ser Ser Glu Gln Lys
        275                 280                 285

Val Ser Ile Ile Gln Leu Phe Thr Asn Ser Ser Tyr Arg Gln Pro Ile
    290                 295                 300

Leu Val Ala Leu Met Leu His Val Ala Gln Gln Phe Ser Gly Ile Asn
305                 310                 315                 320

Gly Ile Phe Tyr Tyr Ser Thr Ser Ile Phe Gln Thr Ala Gly Ile Ser
                325                 330                 335

Lys Pro Val Tyr Ala Thr Ile Gly Val Gly Ala Val Asn Met Val Phe
            340                 345                 350

Thr Ala Val Ser Val Phe Leu Val Glu Lys Ala Gly Arg Arg Ser Leu
        355                 360                 365

Phe Leu Ile Gly Met Ser Gly Met Phe Val Cys Ala Ile Phe Met Ser
    370                 375                 380

Val Gly Leu Val Leu Leu Asn Lys Phe Ser Trp Met Ser Tyr Val Ser
385                 390                 395                 400

Met Ile Ala Ile Phe Leu Phe Val Ser Phe Phe Glu Ile Gly Pro Gly
                405                 410                 415

Pro Ile Pro Trp Phe Met Val Ala Glu Phe Phe Ser Gln Gly Pro Arg
            420                 425                 430

Pro Ala Ala Leu Ala Ile Ala Ala Phe Ser Asn Trp Thr Cys Asn Phe
        435                 440                 445

Ile Val Ala Leu Cys Phe Gln Tyr Ile Ala Asp Phe Cys Gly Pro Tyr
    450                 455                 460

Val Phe Phe Leu Phe Ala Gly Val Leu Leu Ala Phe Thr Leu Phe Thr
465                 470                 475                 480

Phe Phe Lys Val Pro Glu Thr Lys Gly Lys Ser Phe Glu Glu Ile Ala
                485                 490                 495

Ala Glu Phe Gln Lys Lys Ser Gly Ser Ala His Arg Pro Lys Ala Ala
            500                 505                 510

Val Glu Met Lys Phe Leu Gly Ala Thr Glu Thr Val
        515                 520
```

<210> SEQ ID NO 37
<211> LENGTH: 929
<212> TYPE: PRT
<213> ORGANISM: Homo sapiens

<400> SEQUENCE: 37

```
Met Leu Gly Ala Gln Ile Thr Val Asp Asn Trp Thr Leu Arg Thr Thr
1               5                   10                  15
```

```
Pro Trp Arg Ser Cys Arg Gln Asp Asp Tyr Glu Asp Met Met Glu Glu
            20                  25                  30

Asn Leu Glu Gln Glu Glu Tyr Glu Asp Pro Asp Ile Pro Glu Ser Gln
        35                  40                  45

Met Glu Glu Pro Ala Ala His Asp Thr Glu Ala Thr Ala Thr Asp Tyr
    50                  55                  60

His Thr Thr Ser His Pro Gly Thr His Lys Val Tyr Val Glu Leu Gln
65                  70                  75                  80

Glu Leu Val Met Asp Glu Lys Asn Gln Glu Leu Arg Trp Met Glu Ala
                85                  90                  95

Ala Arg Trp Val Gln Leu Glu Glu Asn Leu Gly Glu Asn Gly Ala Trp
            100                 105                 110

Gly Arg Pro His Leu Ser His Leu Thr Phe Trp Ser Leu Leu Glu Leu
        115                 120                 125

Arg Arg Val Phe Thr Lys Gly Thr Val Leu Leu Asp Leu Gln Glu Thr
    130                 135                 140

Ser Leu Ala Gly Val Ala Asn Gln Leu Leu Asp Arg Phe Ile Phe Glu
145                 150                 155                 160

Asp Gln Ile Arg Pro Gln Asp Arg Glu Glu Leu Leu Arg Ala Leu Leu
                165                 170                 175

Leu Lys His Ser His Ala Gly Glu Leu Glu Ala Leu Gly Gly Val Lys
            180                 185                 190

Pro Ala Val Leu Thr Arg Ser Gly Asp Pro Ser Gln Pro Leu Leu Pro
        195                 200                 205

Gln His Ser Ser Leu Glu Thr Gln Leu Phe Cys Glu Gln Gly Asp Gly
    210                 215                 220

Gly Thr Glu Gly His Ser Pro Ser Gly Ile Leu Glu Lys Ile Pro Pro
225                 230                 235                 240

Asp Ser Glu Ala Thr Leu Val Leu Val Gly Arg Ala Asp Phe Leu Glu
                245                 250                 255

Gln Pro Val Leu Gly Phe Val Arg Leu Gln Glu Ala Ala Glu Leu Glu
            260                 265                 270

Ala Val Glu Leu Pro Val Pro Ile Arg Phe Leu Phe Val Leu Leu Gly
        275                 280                 285

Pro Glu Ala Pro His Ile Asp Tyr Thr Gln Leu Gly Arg Ala Ala Ala
    290                 295                 300

Thr Leu Met Ser Glu Arg Val Phe Arg Ile Asp Ala Tyr Met Ala Gln
305                 310                 315                 320

Ser Arg Gly Glu Leu Leu His Ser Leu Glu Gly Phe Leu Asp Cys Ser
                325                 330                 335

Leu Val Leu Pro Pro Thr Asp Ala Pro Ser Glu Gln Ala Leu Leu Ser
            340                 345                 350

Leu Val Pro Val Gln Arg Glu Leu Leu Arg Arg Arg Tyr Gln Ser Ser
        355                 360                 365

Pro Ala Lys Pro Asp Ser Ser Phe Tyr Lys Gly Leu Asp Leu Asn Gly
    370                 375                 380

Gly Pro Asp Asp Pro Leu Gln Gln Thr Gly Gln Leu Phe Gly Gly Leu
385                 390                 395                 400

Val Arg Asp Ile Arg Arg Arg Tyr Pro Tyr Tyr Leu Ser Asp Ile Thr
                405                 410                 415

Asp Ala Phe Ser Pro Gln Val Leu Ala Ala Val Ile Phe Ile Tyr Phe
            420                 425                 430
```

```
Ala Ala Leu Ser Pro Ala Ile Thr Phe Gly Gly Leu Leu Gly Glu Lys
        435                 440                 445

Thr Arg Asn Gln Met Gly Val Ser Glu Leu Leu Ile Ser Thr Ala Val
    450                 455                 460

Gln Gly Ile Leu Phe Ala Leu Leu Gly Ala Gln Pro Leu Leu Val Val
465                 470                 475                 480

Gly Phe Ser Gly Pro Leu Leu Val Phe Glu Glu Ala Phe Phe Ser Phe
                485                 490                 495

Cys Glu Thr Asn Gly Leu Glu Tyr Ile Val Gly Arg Val Trp Ile Gly
            500                 505                 510

Phe Trp Leu Ile Leu Leu Val Val Leu Val Val Ala Phe Glu Gly Ser
        515                 520                 525

Phe Leu Val Arg Phe Ile Ser Arg Tyr Thr Gln Glu Ile Phe Ser Phe
    530                 535                 540

Leu Ile Ser Leu Ile Phe Ile Tyr Glu Thr Phe Ser Lys Leu Ile Lys
545                 550                 555                 560

Ile Phe Gln Asp His Pro Leu Gln Lys Thr Tyr Asn Tyr Asn Val Leu
                565                 570                 575

Met Val Pro Lys Pro Gln Gly Pro Leu Pro Asn Thr Ala Leu Leu Ser
            580                 585                 590

Leu Val Leu Met Ala Gly Thr Phe Phe Phe Ala Met Met Leu Arg Lys
        595                 600                 605

Phe Lys Asn Ser Ser Tyr Phe Pro Gly Lys Leu Arg Arg Val Ile Gly
    610                 615                 620

Asp Phe Gly Val Pro Ile Ser Ile Leu Ile Met Val Leu Val Asp Phe
625                 630                 635                 640

Phe Ile Gln Asp Thr Tyr Thr Gln Lys Leu Ser Val Pro Asp Gly Phe
                645                 650                 655

Lys Val Ser Asn Ser Ser Ala Arg Gly Trp Val Ile His Pro Leu Gly
            660                 665                 670

Leu Arg Ser Glu Phe Pro Ile Trp Met Met Phe Ala Ser Ala Leu Pro
        675                 680                 685

Ala Leu Leu Val Phe Ile Leu Ile Phe Leu Glu Ser Gln Ile Thr Thr
    690                 695                 700

Leu Ile Val Ser Lys Pro Glu Arg Lys Met Val Lys Gly Ser Gly Phe
705                 710                 715                 720

His Leu Asp Leu Leu Leu Val Val Gly Met Gly Gly Val Ala Ala Leu
                725                 730                 735

Phe Gly Met Pro Trp Leu Ser Ala Thr Thr Val Arg Ser Val Thr His
            740                 745                 750

Ala Asn Ala Leu Thr Val Met Gly Lys Ala Ser Thr Pro Gly Ala Ala
        755                 760                 765

Ala Gln Ile Gln Glu Val Lys Glu Gln Arg Ile Ser Gly Leu Leu Val
    770                 775                 780

Ala Val Leu Val Gly Leu Ser Ile Leu Met Glu Pro Ile Leu Ser Arg
785                 790                 795                 800

Ile Pro Leu Ala Val Leu Phe Gly Ile Phe Leu Tyr Met Gly Val Thr
                805                 810                 815

Ser Leu Ser Gly Ile Gln Leu Phe Asp Arg Ile Leu Leu Leu Phe Lys
            820                 825                 830

Pro Pro Lys Tyr His Pro Asp Val Pro Tyr Val Lys Arg Val Lys Thr
        835                 840                 845

Trp Arg Met His Leu Phe Thr Gly Ile Gln Ile Ile Cys Leu Ala Val
```

```
    850                 855                 860

Leu Trp Val Val Lys Ser Thr Pro Ala Ser Leu Ala Leu Pro Phe Val
865                 870                 875                 880

Leu Ile Leu Thr Val Pro Leu Arg Arg Val Leu Leu Pro Leu Ile Phe
                885                 890                 895

Arg Asn Val Glu Leu Gln Cys Leu Asp Ala Asp Asp Ala Lys Ala Thr
            900                 905                 910

Phe Asp Glu Glu Glu Gly Arg Asp Glu Tyr Asp Glu Val Ala Met Pro
        915                 920                 925

Val


<210> SEQ ID NO 38
<211> LENGTH: 834
<212> TYPE: PRT
<213> ORGANISM: Homo sapiens

<400> SEQUENCE: 38

Met Trp Gly Leu Gly Ala Arg Gly Pro Asp Arg Gly Leu Leu Leu Ala
1               5                   10                  15

Leu Ala Leu Gly Gly Leu Ala Arg Ala Gly Gly Val Glu Val Glu Pro
            20                  25                  30

Gly Gly Ala His Gly Glu Ser Gly Gly Phe Gln Val Val Thr Phe Glu
        35                  40                  45

Trp Ala His Val Gln Asp Pro Tyr Val Ile Ala Leu Trp Ile Leu Val
    50                  55                  60

Ala Ser Leu Ala Lys Ile Gly Phe His Leu Ser His Lys Val Thr Ser
65                  70                  75                  80

Val Val Pro Glu Ser Ala Leu Leu Ile Val Leu Gly Leu Val Leu Gly
                85                  90                  95

Gly Ile Val Trp Ala Ala Asp His Ile Ala Ser Phe Thr Leu Thr Pro
            100                 105                 110

Thr Val Phe Phe Phe Tyr Leu Leu Pro Pro Ile Val Leu Asp Ala Gly
        115                 120                 125

Tyr Phe Met Pro Asn Arg Leu Phe Phe Gly Asn Leu Gly Thr Ile Leu
    130                 135                 140

Leu Tyr Ala Val Val Gly Thr Val Trp Asn Ala Ala Thr Thr Gly Leu
145                 150                 155                 160

Ser Leu Tyr Gly Val Phe Leu Ser Gly Leu Met Gly Asp Leu Gln Ile
                165                 170                 175

Gly Leu Leu Asp Phe Leu Leu Phe Gly Ser Leu Met Ala Ala Val Asp
            180                 185                 190

Pro Val Ala Val Leu Ala Val Phe Glu Glu Val His Val Asn Glu Val
        195                 200                 205

Leu Phe Ile Ile Val Phe Gly Glu Ser Leu Leu Asn Asp Ala Val Thr
    210                 215                 220

Val Val Leu Tyr Asn Val Phe Glu Ser Phe Val Ala Leu Gly Gly Asp
225                 230                 235                 240

Asn Val Thr Gly Val Asp Cys Val Lys Gly Ile Val Ser Phe Phe Val
                245                 250                 255

Val Ser Leu Gly Gly Thr Leu Val Gly Val Val Phe Ala Phe Leu Leu
            260                 265                 270

Ser Leu Val Thr Arg Phe Thr Lys His Val Arg Ile Ile Glu Pro Gly
        275                 280                 285

Phe Val Phe Ile Ile Ser Tyr Leu Ser Tyr Leu Thr Ser Glu Met Leu
```

```
    290                 295                 300

Ser Leu Ser Ala Ile Leu Ala Ile Thr Phe Cys Gly Ile Cys Cys Gln
305                 310                 315                 320

Lys Tyr Val Lys Ala Asn Ile Ser Glu Gln Ser Ala Thr Thr Val Arg
                325                 330                 335

Tyr Thr Met Lys Met Leu Ala Ser Ser Ala Glu Thr Ile Ile Phe Met
            340                 345                 350

Phe Leu Gly Ile Ser Ala Val Asn Pro Phe Ile Trp Thr Trp Asn Thr
        355                 360                 365

Ala Phe Val Leu Leu Thr Leu Val Phe Ile Ser Val Tyr Arg Ala Ile
    370                 375                 380

Gly Val Val Leu Gln Thr Trp Leu Leu Asn Arg Tyr Arg Met Val Gln
385                 390                 395                 400

Leu Glu Pro Ile Asp Gln Val Val Leu Ser Tyr Gly Gly Leu Arg Gly
                405                 410                 415

Ala Val Ala Phe Ala Leu Val Val Leu Leu Asp Gly Asp Lys Val Lys
            420                 425                 430

Glu Lys Asn Leu Phe Val Ser Thr Thr Ile Ile Val Val Phe Phe Thr
        435                 440                 445

Val Ile Phe Gln Gly Leu Thr Ile Lys Pro Leu Val Gln Trp Leu Lys
    450                 455                 460

Val Lys Arg Ser Glu His Arg Glu Pro Arg Leu Asn Glu Lys Leu His
465                 470                 475                 480

Gly Arg Ala Phe Asp His Ile Leu Ser Ala Ile Glu Asp Ile Ser Gly
                485                 490                 495

Gln Ile Gly His Asn Tyr Leu Arg Asp Lys Trp Ser His Phe Asp Arg
            500                 505                 510

Lys Phe Leu Ser Arg Val Leu Met Arg Arg Ser Ala Gln Lys Ser Arg
        515                 520                 525

Asp Arg Ile Leu Asn Val Phe His Glu Leu Asn Leu Lys Asp Ala Ile
    530                 535                 540

Ser Tyr Val Ala Glu Gly Glu Arg Arg Gly Ser Leu Ala Phe Ile Arg
545                 550                 555                 560

Ser Pro Ser Thr Asp Asn Val Val Asn Val Asp Phe Thr Pro Arg Ser
                565                 570                 575

Ser Thr Val Glu Ala Ser Val Ser Tyr Leu Leu Arg Glu Asn Val Ser
            580                 585                 590

Ala Val Cys Leu Asp Met Gln Ser Leu Glu Gln Arg Arg Arg Ser Ile
        595                 600                 605

Arg Asp Ala Glu Asp Met Val Thr His His Thr Leu Gln Gln Tyr Leu
    610                 615                 620

Tyr Lys Pro Arg Gln Glu Tyr Lys His Leu Tyr Ser Arg His Glu Leu
625                 630                 635                 640

Thr Pro Thr Glu Asp Glu Lys Gln Asp Arg Glu Ile Phe His Arg Thr
                645                 650                 655

Met Arg Lys Arg Leu Glu Ser Phe Lys Ser Thr Lys Leu Gly Leu Asn
            660                 665                 670

Gln Asn Lys Lys Ala Ala Lys Leu Tyr Lys Arg Glu Arg Ala Gln Lys
        675                 680                 685

Arg Arg Asn Ser Ser Ile Pro Asn Gly Lys Leu Pro Met Glu Ser Pro
    690                 695                 700

Ala Gln Asn Phe Thr Ile Lys Glu Lys Asp Leu Glu Leu Ser Asp Thr
705                 710                 715                 720
```

```
Glu Glu Pro Pro Asn Tyr Asp Glu Glu Met Ser Gly Gly Ile Glu Phe
                725                 730                 735

Leu Ala Ser Val Thr Lys Asp Thr Ala Ser Asp Ser Pro Ala Gly Ile
            740                 745                 750

Asp Asn Pro Val Phe Ser Pro Asp Glu Ala Leu Asp Arg Ser Leu Leu
        755                 760                 765

Ala Arg Leu Pro Pro Trp Leu Ser Pro Gly Glu Thr Val Val Pro Ser
    770                 775                 780

Gln Arg Ala Arg Thr Gln Ile Pro Tyr Ser Pro Gly Thr Phe Cys Arg
785                 790                 795                 800

Leu Met Pro Phe Arg Leu Ser Ser Lys Ser Val Asp Ser Phe Leu Gln
                805                 810                 815

Ala Asp Gly Pro Glu Glu Arg Pro Pro Ala Ala Leu Pro Glu Ser Thr
            820                 825                 830

His Met


<210> SEQ ID NO 39
<211> LENGTH: 781
<212> TYPE: PRT
<213> ORGANISM: Homo sapiens

<400> SEQUENCE: 39

Met Ser Ser Glu Cys Asp Gly Gly Ser Lys Ala Val Met Asn Gly Leu
1               5                   10                  15

Ala Pro Gly Ser Asn Gly Gln Asp Lys Ala Thr Ala Asp Pro Leu Arg
            20                  25                  30

Ala Arg Ser Ile Ser Ala Val Lys Ile Ile Pro Val Lys Thr Val Lys
        35                  40                  45

Asn Ala Ser Gly Leu Val Leu Pro Thr Asp Met Asp Pro Thr Lys Ile
    50                  55                  60

Cys Thr Gly Lys Gly Ala Val Thr Leu Arg Ala Ser Ser Ser Tyr Arg
65                  70                  75                  80

Glu Thr Pro Ser Ser Ser Pro Ala Ser Pro Gln Glu Thr Arg Gln His
                85                  90                  95

Glu Ser Lys Pro Gly Leu Glu Pro Glu Pro Ser Ser Ala Asp Glu Trp
            100                 105                 110

Arg Leu Ser Ser Ser Ala Asp Ala Asn Gly Asn Ala Gln Pro Ser Ser
        115                 120                 125

Leu Ala Ala Lys Gly Tyr Arg Ser Val His Pro Asn Leu Pro Ser Asp
    130                 135                 140

Lys Ser Gln Asp Ser Ser Pro Leu Leu Asn Glu Val Ser Ser Ser Leu
145                 150                 155                 160

Ile Gly Thr Asp Ser Gln Ala Phe Pro Ser Val Ser Lys Pro Ser Ser
                165                 170                 175

Ala Tyr Pro Ser Thr Thr Ile Val Asn Pro Thr Ile Val Leu Leu Gln
            180                 185                 190

His Asn Arg Glu Gln Gln Lys Arg Leu Ser Ser Leu Ser Asp Pro Val
        195                 200                 205

Ser Glu Arg Arg Val Gly Glu Gln Asp Ser Ala Pro Thr Gln Glu Lys
    210                 215                 220

Pro Thr Ser Pro Gly Lys Ala Ile Glu Lys Arg Ala Lys Asp Asp Ser
225                 230                 235                 240

Arg Arg Val Val Lys Ser Thr Gln Asp Leu Ser Asp Val Ser Met Asp
                245                 250                 255
```

```
Glu Val Gly Ile Pro Leu Arg Asn Thr Glu Arg Ser Lys Asp Trp Tyr
            260                 265                 270

Lys Thr Met Phe Lys Gln Ile His Lys Leu Asn Arg Asp Asp Asp Ser
        275                 280                 285

Asp Leu Tyr Ser Pro Arg Tyr Ser Phe Ser Glu Asp Thr Lys Ser Pro
    290                 295                 300

Leu Ser Val Pro Arg Ser Lys Ser Glu Met Ser Tyr Ile Asp Gly Glu
305                 310                 315                 320

Lys Val Val Lys Arg Ser Ala Thr Leu Pro Leu Pro Ala Arg Ser Ser
                325                 330                 335

Ser Leu Lys Ser Ser Ser Glu Arg Asn Asp Trp Glu Pro Pro Asp Lys
            340                 345                 350

Lys Val Asp Thr Arg Lys Tyr Arg Ala Glu Pro Lys Ser Ile Tyr Glu
        355                 360                 365

Tyr Gln Pro Gly Lys Ser Ser Val Leu Thr Asn Glu Lys Met Ser Ser
    370                 375                 380

Ala Ile Ser Pro Thr Pro Glu Ile Ser Ser Glu Thr Pro Gly Tyr Ile
385                 390                 395                 400

Tyr Ser Ser Asn Phe His Ala Val Lys Arg Glu Ser Asp Gly Ala Pro
                405                 410                 415

Gly Asp Leu Thr Ser Leu Glu Asn Glu Arg Gln Ile Tyr Lys Ser Val
            420                 425                 430

Leu Glu Gly Gly Asp Ile Pro Leu Gln Gly Leu Ser Gly Leu Lys Arg
        435                 440                 445

Pro Ser Ser Ser Ala Ser Thr Lys Asp Ser Glu Ser Pro Arg His Phe
    450                 455                 460

Ile Pro Ala Asp Tyr Leu Glu Ser Thr Glu Glu Phe Ile Arg Arg Arg
465                 470                 475                 480

His Asp Asp Lys Glu Lys Leu Leu Ala Asp Gln Arg Arg Leu Lys Arg
                485                 490                 495

Glu Gln Glu Glu Ala Asp Ile Ala Ala Arg Arg His Thr Gly Val Ile
            500                 505                 510

Pro Thr His His Gln Phe Ile Thr Asn Glu Arg Phe Gly Asp Leu Leu
        515                 520                 525

Asn Ile Asp Asp Thr Ala Lys Arg Lys Ser Gly Ser Glu Met Arg Pro
    530                 535                 540

Ala Arg Ala Lys Phe Asp Phe Lys Ala Gln Thr Leu Lys Glu Leu Pro
545                 550                 555                 560

Leu Gln Lys Gly Asp Ile Val Tyr Ile Tyr Lys Gln Ile Asp Gln Asn
                565                 570                 575

Trp Tyr Glu Gly Glu His His Gly Arg Val Gly Ile Phe Pro Arg Thr
            580                 585                 590

Tyr Ile Glu Leu Leu Pro Pro Ala Glu Lys Ala Gln Pro Lys Lys Leu
        595                 600                 605

Thr Pro Val Gln Val Leu Glu Tyr Gly Glu Ala Ile Ala Lys Phe Asn
    610                 615                 620

Phe Asn Gly Asp Thr Gln Val Glu Met Ser Phe Arg Lys Gly Glu Arg
625                 630                 635                 640

Ile Thr Leu Leu Arg Gln Val Asp Glu Asn Trp Tyr Glu Gly Arg Ile
                645                 650                 655

Pro Gly Thr Ser Arg Gln Gly Ile Phe Pro Ile Thr Tyr Val Asp Val
            660                 665                 670
```

```
Ile Lys Arg Pro Leu Val Lys Asn Pro Val Asp Tyr Met Asp Leu Pro
        675                 680                 685

Phe Ser Ser Ser Pro Ser Arg Ser Ala Thr Ala Ser Pro Gln Gln Pro
    690                 695                 700

Gln Ala Gln Gln Arg Arg Val Thr Pro Asp Arg Ser Gln Thr Ser Gln
705                 710                 715                 720

Asp Leu Phe Ser Tyr Gln Ala Leu Tyr Ser Tyr Ile Pro Gln Asn Asp
                725                 730                 735

Asp Glu Leu Glu Leu Arg Asp Gly Asp Ile Val Asp Val Met Glu Lys
            740                 745                 750

Cys Asp Asp Gly Trp Phe Val Gly Thr Ser Arg Arg Thr Lys Gln Phe
        755                 760                 765

Gly Thr Phe Pro Gly Asn Tyr Val Lys Pro Leu Tyr Leu
    770                 775                 780


<210> SEQ ID NO 40
<211> LENGTH: 465
<212> TYPE: PRT
<213> ORGANISM: Homo sapiens

<400> SEQUENCE: 40

Met Ala Ser Gln Leu Thr Gln Arg Gly Ala Leu Phe Leu Leu Phe Phe
1               5                   10                  15

Leu Thr Pro Ala Val Thr Pro Thr Trp Tyr Ala Gly Ser Gly Tyr Tyr
            20                  25                  30

Pro Asp Glu Ser Tyr Asn Glu Val Tyr Ala Glu Glu Val Pro Gln Ala
        35                  40                  45

Pro Ala Leu Asp Tyr Arg Val Pro Arg Trp Cys Tyr Thr Leu Asn Ile
    50                  55                  60

Gln Asp Gly Glu Ala Thr Cys Tyr Ser Pro Lys Gly Gly Asn Tyr His
65                  70                  75                  80

Ser Ser Leu Gly Thr Arg Cys Glu Leu Ser Cys Asp Arg Gly Phe Arg
                85                  90                  95

Leu Ile Gly Arg Arg Ser Val Gln Cys Leu Pro Ser Arg Arg Trp Ser
            100                 105                 110

Gly Thr Ala Tyr Cys Arg Gln Met Arg Cys His Ala Leu Pro Phe Ile
        115                 120                 125

Thr Ser Gly Thr Tyr Thr Cys Thr Asn Gly Val Leu Leu Asp Ser Arg
    130                 135                 140

Cys Asp Tyr Ser Cys Ser Ser Gly Tyr His Leu Glu Gly Asp Arg Ser
145                 150                 155                 160

Arg Ile Cys Met Glu Asp Gly Arg Trp Ser Gly Gly Glu Pro Val Cys
                165                 170                 175

Val Asp Ile Asp Pro Pro Lys Ile Arg Cys Pro His Ser Arg Glu Lys
            180                 185                 190

Met Ala Glu Pro Glu Lys Leu Thr Ala Arg Val Tyr Trp Asp Pro Pro
        195                 200                 205

Leu Val Lys Asp Ser Ala Asp Gly Thr Ile Thr Arg Val Thr Leu Arg
    210                 215                 220

Gly Pro Glu Pro Gly Ser His Phe Pro Glu Gly Glu His Val Ile Arg
225                 230                 235                 240

Tyr Thr Ala Tyr Asp Arg Ala Tyr Asn Arg Ala Ser Cys Lys Phe Ile
                245                 250                 255

Val Lys Val Gln Val Arg Arg Cys Pro Thr Leu Lys Pro Pro Gln His
            260                 265                 270
```

```
Gly Tyr Leu Thr Cys Thr Ser Ala Gly Asp Asn Tyr Gly Ala Thr Cys
        275                 280                 285

Glu Tyr His Cys Asp Gly Gly Tyr Asp Arg Gln Gly Thr Pro Ser Arg
    290                 295                 300

Val Cys Gln Ser Ser Arg Gln Trp Ser Gly Ser Pro Pro Ile Cys Ala
305                 310                 315                 320

Pro Met Lys Ile Asn Val Asn Val Asn Ser Ala Ala Gly Leu Leu Asp
                325                 330                 335

Gln Phe Tyr Glu Lys Gln Arg Leu Leu Ile Ile Ser Ala Pro Asp Pro
            340                 345                 350

Ser Asn Arg Tyr Tyr Lys Met Gln Ile Ser Met Leu Gln Gln Ser Thr
        355                 360                 365

Cys Gly Leu Asp Leu Arg His Val Thr Ile Ile Glu Leu Val Gly Gln
    370                 375                 380

Pro Pro Gln Glu Val Gly Arg Ile Arg Glu Gln Gln Leu Ser Ala Asn
385                 390                 395                 400

Ile Ile Glu Glu Leu Arg Gln Phe Gln Arg Leu Thr Arg Ser Tyr Phe
                405                 410                 415

Asn Met Val Leu Ile Asp Lys Gln Gly Ile Asp Arg Asp Arg Tyr Met
            420                 425                 430

Glu Pro Val Thr Pro Glu Glu Ile Phe Thr Phe Ile Asp Asp Tyr Leu
        435                 440                 445

Leu Ser Asn Gln Glu Leu Thr Gln Arg Arg Glu Gln Arg Asp Ile Cys
    450                 455                 460

Glu
465


<210> SEQ ID NO 41
<211> LENGTH: 2214
<212> TYPE: PRT
<213> ORGANISM: Homo sapiens

<400> SEQUENCE: 41

Met Lys Arg Lys Glu Arg Ile Ala Arg Arg Leu Glu Gly Ile Glu Asn
1               5                   10                  15

Asp Thr Gln Pro Ile Leu Leu Gln Ser Cys Thr Gly Leu Val Thr His
            20                  25                  30

Arg Leu Leu Glu Glu Asp Thr Pro Arg Tyr Met Arg Ala Ser Asp Pro
        35                  40                  45

Ala Ser Pro His Ile Gly Arg Ser Asn Glu Glu Glu Glu Thr Ser Asp
    50                  55                  60

Ser Ser Leu Glu Lys Gln Thr Arg Ser Lys Tyr Cys Thr Glu Thr Ser
65                  70                  75                  80

Gly Val His Gly Asp Ser Pro Tyr Gly Ser Gly Thr Met Asp Thr His
                85                  90                  95

Ser Leu Glu Ser Lys Ala Glu Arg Ile Ala Arg Tyr Lys Ala Glu Arg
            100                 105                 110

Arg Arg Gln Leu Ala Glu Lys Tyr Gly Leu Thr Leu Asp Pro Glu Ala
        115                 120                 125

Asp Ser Glu Tyr Leu Ser Arg Tyr Thr Lys Ser Arg Lys Glu Pro Asp
    130                 135                 140

Ala Val Glu Lys Arg Gly Gly Lys Ser Asp Lys Gln Glu Glu Ser Ser
145                 150                 155                 160

Arg Asp Ala Ser Ser Leu Tyr Pro Gly Thr Glu Thr Met Gly Leu Arg
```

```
                165                 170                 175

Thr Cys Ala Gly Glu Ser Lys Asp Tyr Ala Leu His Val Gly Asp Gly
            180                 185                 190

Ser Ser Asp Pro Glu Val Leu Leu Asn Ile Glu Asn Gln Arg Arg Gly
        195                 200                 205

Gln Glu Leu Ser Ala Thr Arg Gln Ala His Asp Leu Ser Pro Ala Ala
    210                 215                 220

Glu Ser Ser Ser Thr Phe Ser Phe Ser Gly Arg Asp Ser Ser Phe Thr
225                 230                 235                 240

Glu Val Pro Arg Ser Pro Lys His Ala His Ser Ser Ser Leu Gln Gln
                245                 250                 255

Ala Ala Ser Arg Ser Pro Ser Phe Gly Asp Pro Gln Leu Ser Pro Glu
            260                 265                 270

Ala Arg Pro Ser Thr Gly Lys Pro Lys His Glu Trp Phe Leu Gln Lys
        275                 280                 285

Asp Ser Glu Gly Asp Thr Pro Ser Leu Ile Asn Trp Pro Ser Arg Val
    290                 295                 300

Lys Val Arg Glu Lys Leu Val Lys Glu Glu Ser Ala Arg Asn Ser Pro
305                 310                 315                 320

Glu Leu Ala Ser Glu Ser Val Thr Gln Arg Arg His Gln Pro Ala Pro
                325                 330                 335

Val His Tyr Val Ser Phe Gln Ser Glu His Ser Ala Phe Asp Arg Val
            340                 345                 350

Pro Ser Lys Ala Ala Gly Ser Thr Arg Gln Pro Ile Arg Gly Tyr Val
        355                 360                 365

Gln Pro Ala Asp Thr Gly His Thr Ala Lys Leu Val Thr Pro Glu Thr
    370                 375                 380

Pro Glu Asn Ala Ser Glu Cys Ser Trp Val Ala Ser Ala Thr Gln Asn
385                 390                 395                 400

Val Pro Lys Pro Pro Ser Leu Thr Val Leu Glu Gly Asp Gly Arg Asp
                405                 410                 415

Ser Pro Val Leu His Val Cys Glu Ser Lys Ala Glu Glu Glu Glu Gly
            420                 425                 430

Glu Gly Glu Gly Glu Glu Lys Glu Glu Asp Val Cys Phe Thr Glu Ala
        435                 440                 445

Leu Glu Gln Ser Lys Lys Thr Leu Leu Ala Leu Glu Gly Asp Gly Leu
    450                 455                 460

Val Arg Ser Pro Glu Asp Pro Ser Arg Asn Glu Asp Phe Gly Lys Pro
465                 470                 475                 480

Ala Val Ser Thr Val Thr Leu Glu His Gln Lys Glu Leu Glu Asn Val
                485                 490                 495

Ala Gln Pro Pro Gln Ala Pro His Gln Pro Thr Glu Arg Thr Gly Arg
            500                 505                 510

Ser Glu Met Val Leu Tyr Ile Gln Ser Glu Pro Val Ser Gln Asp Ala
        515                 520                 525

Lys Pro Thr Gly His Asn Arg Glu Ala Ser Lys Lys Arg Lys Val Arg
    530                 535                 540

Thr Arg Ser Leu Ser Asp Phe Thr Gly Pro Pro Gln Leu Gln Ala Leu
545                 550                 555                 560

Lys Tyr Lys Asp Pro Ala Ser Arg Arg Glu Leu Glu Leu Pro Ser Ser
                565                 570                 575

Lys Thr Glu Gly Pro Tyr Gly Glu Ile Ser Met Leu Asp Thr Lys Val
            580                 585                 590
```

```
Ser Val Ala Gln Leu Arg Ser Ala Phe Leu Ala Ser Ala Asn Ala Cys
        595                 600                 605

Arg Arg Pro Glu Leu Lys Ser Arg Val Glu Arg Ser Ala Glu Gly Pro
    610                 615                 620

Gly Leu Pro Thr Gly Val Glu Arg Glu Arg Gly Ser Arg Lys Pro Arg
625                 630                 635                 640

Arg Tyr Phe Ser Pro Gly Glu Ser Arg Lys Thr Ser Glu Arg Phe Arg
                645                 650                 655

Thr Gln Pro Ile Thr Ser Ala Glu Arg Lys Glu Ser Asp Arg Cys Thr
            660                 665                 670

Ser His Ser Glu Thr Pro Thr Val Asp Asp Glu Glu Lys Val Asp Glu
        675                 680                 685

Arg Ala Lys Leu Ser Val Ala Ala Lys Arg Leu Leu Phe Arg Glu Met
    690                 695                 700

Glu Lys Ser Phe Asp Glu Gln Asn Val Pro Lys Arg Arg Ser Arg Asn
705                 710                 715                 720

Thr Ala Val Glu Gln Arg Leu Arg Arg Leu Gln Asp Arg Ser Leu Thr
                725                 730                 735

Gln Pro Ile Thr Thr Glu Glu Val Val Ile Ala Ala Thr Glu Pro Ile
            740                 745                 750

Pro Ala Ser Cys Ser Gly Gly Thr His Pro Val Met Ala Arg Leu Pro
        755                 760                 765

Ser Pro Thr Val Ala Arg Ser Ala Val Gln Pro Ala Arg Leu Gln Ala
    770                 775                 780

Ser Ala His Gln Lys Ala Leu Ala Lys Asp Gln Thr Asn Glu Gly Lys
785                 790                 795                 800

Glu Leu Ala Glu Gln Gly Glu Pro Asp Ser Ser Thr Leu Ser Leu Ala
                805                 810                 815

Glu Lys Leu Ala Leu Phe Asn Lys Leu Ser Gln Pro Val Ser Lys Ala
            820                 825                 830

Ile Ser Thr Arg Asn Arg Ile Asp Thr Arg Gln Arg Arg Met Asn Ala
        835                 840                 845

Arg Tyr Gln Thr Gln Pro Val Thr Leu Gly Glu Val Glu Gln Val Gln
    850                 855                 860

Ser Gly Lys Leu Ile Pro Phe Ser Pro Ala Val Asn Thr Ser Val Ser
865                 870                 875                 880

Thr Val Ala Ser Thr Val Ala Pro Met Tyr Ala Gly Asp Leu Arg Thr
                885                 890                 895

Lys Pro Pro Leu Asp His Asn Ala Ser Ala Thr Asp Tyr Lys Phe Ser
            900                 905                 910

Ser Ser Ile Glu Asn Ser Asp Ser Pro Val Arg Ser Ile Leu Lys Ser
        915                 920                 925

Gln Ala Trp Gln Pro Leu Val Glu Gly Ser Glu Asn Lys Gly Met Leu
    930                 935                 940

Arg Glu Tyr Gly Glu Thr Glu Ser Lys Arg Ala Leu Thr Gly Arg Asp
945                 950                 955                 960

Ser Gly Met Glu Lys Tyr Gly Ser Phe Glu Glu Ala Glu Ala Ser Tyr
                965                 970                 975

Pro Ile Leu Asn Arg Ala Arg Glu Gly Asp Ser His Lys Glu Ser Lys
            980                 985                 990

Tyr Ala Val Pro Arg Arg Gly Ser  Leu Glu Arg Ala Asn  Pro Pro Ile
        995                 1000                1005
```

```
Thr His  Leu Gly Asp Glu Pro  Lys Glu Phe Ser Met  Ala Lys Met
    1010                 1015                 1020

Asn Ala  Gln Gly Asn Leu Asp  Leu Arg Asp Arg Leu  Pro Phe Glu
    1025                 1030                 1035

Glu Lys  Val Glu Val Glu Asn  Val Met Lys Arg Lys  Phe Ser Leu
    1040                 1045                 1050

Arg Ala  Ala Glu Phe Gly Glu  Pro Thr Ser Glu Gln  Thr Gly Thr
    1055                 1060                 1065

Ala Ala  Gly Lys Thr Ile Ala  Gln Thr Thr Ala Pro  Val Ser Trp
    1070                 1075                 1080

Lys Pro  Gln Asp Ser Ser Glu  Gln Pro Gln Glu Lys  Leu Cys Lys
    1085                 1090                 1095

Asn Pro  Cys Ala Met Phe Ala  Ala Gly Glu Ile Lys  Thr Pro Thr
    1100                 1105                 1110

Gly Glu  Gly Leu Leu Asp Ser  Pro Ser Lys Thr Met  Ser Ile Lys
    1115                 1120                 1125

Glu Arg  Leu Ala Leu Leu Lys  Lys Ser Gly Glu Glu  Asp Trp Arg
    1130                 1135                 1140

Asn Arg  Leu Ser Arg Arg Gln  Glu Gly Gly Lys Ala  Pro Ala Ser
    1145                 1150                 1155

Ser Leu  His Thr Gln Glu Ala  Gly Arg Ser Leu Ile  Lys Lys Arg
    1160                 1165                 1170

Val Thr  Glu Ser Arg Glu Ser  Gln Met Thr Ile Glu  Glu Arg Lys
    1175                 1180                 1185

Gln Leu  Ile Thr Val Arg Glu  Glu Ala Trp Lys Thr  Arg Gly Arg
    1190                 1195                 1200

Gly Ala  Ala Asn Asp Ser Thr  Gln Phe Thr Val Ala  Gly Arg Met
    1205                 1210                 1215

Val Lys  Lys Gly Leu Ala Ser  Pro Thr Ala Ile Thr  Pro Val Ala
    1220                 1225                 1230

Ser Pro  Ile Cys Gly Lys Thr  Arg Gly Thr Thr Pro  Val Ser Lys
    1235                 1240                 1245

Pro Leu  Glu Asp Ile Glu Ala  Arg Pro Asp Met Gln  Leu Glu Ser
    1250                 1255                 1260

Asp Leu  Lys Leu Asp Arg Leu  Glu Thr Phe Leu Arg  Arg Leu Asn
    1265                 1270                 1275

Asn Lys  Val Gly Gly Met His  Glu Thr Val Leu Thr  Val Thr Gly
    1280                 1285                 1290

Lys Ser  Val Lys Glu Val Met  Lys Pro Asp Asp Asp  Glu Thr Phe
    1295                 1300                 1305

Ala Lys  Phe Tyr Arg Ser Val  Asp Tyr Asn Met Pro  Arg Ser Pro
    1310                 1315                 1320

Val Glu  Met Asp Glu Asp Phe  Asp Val Ile Phe Asp  Pro Tyr Ala
    1325                 1330                 1335

Pro Lys  Leu Thr Ser Ser Val  Ala Glu His Lys Arg  Ala Val Arg
    1340                 1345                 1350

Pro Lys  Arg Arg Val Gln Ala  Ser Lys Asn Pro Leu  Lys Met Leu
    1355                 1360                 1365

Ala Ala  Arg Glu Asp Leu Leu  Gln Glu Tyr Thr Glu  Gln Arg Leu
    1370                 1375                 1380

Asn Val  Ala Phe Met Glu Ser  Lys Arg Met Lys Val  Glu Lys Met
    1385                 1390                 1395

Ser Ser  Asn Ser Asn Phe Ser  Glu Val Thr Leu Ala  Gly Leu Ala
```

```
    1400                1405                1410

Ser Lys  Glu Asn Phe Ser Asn  Val Ser Leu Arg Ser  Val Asn Leu
    1415                1420                1425

Thr Glu  Gln Asn Ser Asn Asn  Ser Ala Val Pro Tyr  Lys Arg Leu
    1430                1435                1440

Met Leu  Leu Gln Ile Lys Gly  Arg Arg His Val Gln  Thr Arg Leu
    1445                1450                1455

Val Glu  Pro Arg Ala Ser Ala  Leu Asn Ser Gly Asp  Cys Phe Leu
    1460                1465                1470

Leu Leu  Ser Pro His Cys Cys  Phe Leu Trp Val Gly  Glu Phe Ala
    1475                1480                1485

Asn Val  Ile Glu Lys Ala Lys  Ala Ser Glu Leu Ala  Thr Leu Ile
    1490                1495                1500

Gln Thr  Lys Arg Glu Leu Gly  Cys Arg Ala Thr Tyr  Ile Gln Thr
    1505                1510                1515

Ile Glu  Glu Gly Ile Asn Thr  His Thr His Ala Ala  Lys Asp Phe
    1520                1525                1530

Trp Lys  Leu Leu Gly Gly Gln  Thr Ser Tyr Gln Ser  Ala Gly Asp
    1535                1540                1545

Pro Lys  Glu Asp Glu Leu Tyr  Glu Ala Ala Ile Ile  Glu Thr Asn
    1550                1555                1560

Cys Ile  Tyr Arg Leu Met Asp  Asp Lys Leu Val Pro  Asp Asp Asp
    1565                1570                1575

Tyr Trp  Gly Lys Ile Pro Lys  Cys Ser Leu Leu Gln  Pro Lys Glu
    1580                1585                1590

Val Leu  Val Phe Asp Phe Gly  Ser Glu Val Tyr Val  Trp His Gly
    1595                1600                1605

Lys Glu  Val Thr Leu Ala Gln  Arg Lys Ile Ala Phe  Gln Leu Ala
    1610                1615                1620

Lys His  Leu Trp Asn Gly Thr  Phe Asp Tyr Glu Asn  Cys Asp Ile
    1625                1630                1635

Asn Pro  Leu Asp Pro Gly Glu  Cys Asn Pro Leu Ile  Pro Arg Lys
    1640                1645                1650

Gly Gln  Gly Arg Pro Asp Trp  Ala Ile Phe Gly Arg  Leu Thr Glu
    1655                1660                1665

His Asn  Glu Thr Ile Leu Phe  Lys Glu Lys Phe Leu  Asp Trp Thr
    1670                1675                1680

Glu Leu  Lys Arg Ser Asn Glu  Lys Asn Pro Gly Glu  Leu Ala Gln
    1685                1690                1695

His Lys  Glu Asp Pro Arg Thr  Asp Val Lys Ala Tyr  Asp Val Thr
    1700                1705                1710

Arg Met  Val Ser Met Pro Gln  Thr Thr Ala Gly Thr  Ile Leu Asp
    1715                1720                1725

Gly Val  Asn Val Gly Arg Gly  Tyr Gly Leu Val Glu  Gly His Asp
    1730                1735                1740

Arg Arg  Gln Phe Glu Ile Thr  Ser Val Ser Val Asp  Val Trp His
    1745                1750                1755

Ile Leu  Glu Phe Asp Tyr Ser  Arg Leu Pro Lys Gln  Ser Ile Gly
    1760                1765                1770

Gln Phe  His Glu Gly Asp Ala  Tyr Val Val Lys Trp  Lys Phe Met
    1775                1780                1785

Val Ser  Thr Ala Val Gly Ser  Arg Gln Lys Gly Glu  His Ser Val
    1790                1795                1800
```

```
Arg Ala  Ala Gly Lys Glu Lys  Cys Val Tyr Phe Phe  Trp Gln Gly
    1805                 1810                 1815

Arg His  Ser Thr Val Ser Glu  Lys Gly Thr Ser Ala  Leu Met Thr
    1820                 1825                 1830

Val Glu  Leu Asp Glu Glu Arg  Gly Ala Gln Val Gln  Val Leu Gln
    1835                 1840                 1845

Gly Lys  Glu Pro Pro Cys Phe  Leu Gln Cys Phe Gln  Gly Gly Met
    1850                 1855                 1860

Val Val  His Ser Gly Arg Arg  Glu Glu Glu Glu Glu  Asn Val Gln
    1865                 1870                 1875

Ser Glu  Trp Arg Leu Tyr Cys  Val Arg Gly Glu Val  Pro Val Glu
    1880                 1885                 1890

Gly Asn  Leu Leu Glu Val Ala  Cys His Cys Ser Ser  Leu Arg Ser
    1895                 1900                 1905

Arg Thr  Ser Met Val Val Leu  Asn Val Asn Lys Ala  Leu Ile Tyr
    1910                 1915                 1920

Leu Trp  His Gly Cys Lys Ala  Gln Ala His Thr Lys  Glu Val Gly
    1925                 1930                 1935

Arg Thr  Ala Ala Asn Lys Ile  Lys Glu Gln Cys Pro  Leu Glu Ala
    1940                 1945                 1950

Gly Leu  His Ser Ser Ser Lys  Val Thr Ile His Glu  Cys Asp Glu
    1955                 1960                 1965

Gly Ser  Glu Pro Leu Gly Phe  Trp Asp Ala Leu Gly  Arg Arg Asp
    1970                 1975                 1980

Arg Lys  Ala Tyr Asp Cys Met  Leu Gln Asp Pro Gly  Ser Phe Asn
    1985                 1990                 1995

Phe Ala  Pro Arg Leu Phe Ile  Leu Ser Ser Ser Ser  Gly Asp Phe
    2000                 2005                 2010

Ala Ala  Thr Glu Phe Val Tyr  Pro Ala Arg Ala Pro  Ser Val Val
    2015                 2020                 2025

Ser Ser  Met Pro Phe Leu Gln  Glu Asp Leu Tyr Ser  Ala Pro Gln
    2030                 2035                 2040

Pro Ala  Leu Phe Leu Val Asp  Asn His His Glu Val  Tyr Leu Trp
    2045                 2050                 2055

Gln Gly  Trp Trp Pro Ile Glu  Asn Lys Ile Thr Gly  Ser Ala Arg
    2060                 2065                 2070

Ile Arg  Trp Ala Ser Asp Arg  Lys Ser Ala Met Glu  Thr Val Leu
    2075                 2080                 2085

Gln Tyr  Cys Lys Gly Lys Asn  Leu Lys Lys Pro Ala  Pro Lys Ser
    2090                 2095                 2100

Tyr Leu  Ile His Ala Gly Leu  Glu Pro Leu Thr Phe  Thr Asn Met
    2105                 2110                 2115

Phe Pro  Ser Trp Glu His Arg  Glu Asp Ile Ala Glu  Ile Thr Glu
    2120                 2125                 2130

Met Asp  Thr Glu Val Ser Asn  Gln Ile Thr Leu Val  Glu Asp Val
    2135                 2140                 2145

Leu Ala  Lys Leu Cys Lys Thr  Ile Tyr Pro Leu Ala  Asp Leu Leu
    2150                 2155                 2160

Ala Arg  Pro Leu Pro Glu Gly  Val Asp Pro Leu Lys  Leu Glu Ile
    2165                 2170                 2175

Tyr Leu  Thr Asp Glu Asp Phe  Glu Phe Ala Leu Asp  Met Thr Arg
    2180                 2185                 2190
```

```
Asp Glu  Tyr Asn Ala Leu Pro  Ala Trp Lys Gln Val  Asn Leu Lys
    2195                 2200                 2205

Lys Ala  Lys Gly Leu Phe
    2210


<210> SEQ ID NO 42
<211> LENGTH: 103
<212> TYPE: PRT
<213> ORGANISM: Homo sapiens

<400> SEQUENCE: 42

Met Ile Leu Pro Leu His Asn Leu Gly Asn Gly Val Arg Ser His Asn
1               5                   10                  15

Phe Ser Phe Leu Tyr Phe Ile Leu Glu Asp Ala Ala Ser Pro Lys Cys
            20                  25                  30

Ile Met Lys Glu Lys Lys Lys Pro Gly Glu Thr Phe Phe Met Cys Ser
        35                  40                  45

Cys Ser Ser Asp Glu Cys Asn Asp Asn Ile Ile Phe Ser Glu Glu Tyr
    50                  55                  60

Asn Thr Ser Asn Pro Asp Leu Leu Leu Val Ile Phe Gln Val Thr Gly
65                  70                  75                  80

Ile Ser Leu Leu Pro Pro Leu Gly Val Ala Ile Ser Val Ile Ile Ile
                85                  90                  95

Phe Tyr Cys Tyr Arg Val Asn
            100


<210> SEQ ID NO 43
<211> LENGTH: 523
<212> TYPE: PRT
<213> ORGANISM: Homo sapiens

<400> SEQUENCE: 43

Met Ala Gly Val Ser Tyr Ala Ala Pro Trp Trp Val Ser Leu Leu His
1               5                   10                  15

Arg Leu Pro His Phe Asp Leu Ser Trp Glu Ala Thr Ser Ser Gln Phe
            20                  25                  30

Arg Pro Glu Asp Thr Asp Tyr Gln Gln Ala Leu Leu Leu Leu Gly Ala
        35                  40                  45

Ala Ala Leu Ala Cys Leu Ala Leu Asp Leu Leu Phe Leu Leu Phe Tyr
    50                  55                  60

Ser Phe Trp Leu Cys Cys Arg Arg Arg Lys Ser Glu Glu His Leu Asp
65                  70                  75                  80

Ala Asp Cys Cys Cys Thr Ala Trp Cys Val Ile Ile Ala Thr Leu Val
                85                  90                  95

Cys Ser Ala Gly Ile Ala Val Gly Phe Tyr Gly Asn Gly Glu Thr Ser
            100                 105                 110

Asp Gly Ile His Arg Ala Thr Tyr Ser Leu Arg His Ala Asn Arg Thr
        115                 120                 125

Val Ala Gly Val Gln Asp Arg Val Trp Asp Thr Ala Val Gly Leu Asn
    130                 135                 140

His Thr Ala Glu Pro Ser Leu Gln Thr Leu Glu Arg Gln Leu Ala Gly
145                 150                 155                 160

Arg Pro Glu Pro Leu Arg Ala Val Gln Arg Leu Gln Gly Leu Leu Glu
                165                 170                 175

Thr Leu Leu Gly Tyr Thr Ala Ala Ile Pro Phe Trp Arg Asn Thr Ala
            180                 185                 190
```

```
Val Ser Leu Glu Val Leu Ala Glu Gln Val Asp Leu Tyr Asp Trp Tyr
        195                 200                 205

Arg Trp Leu Gly Tyr Leu Gly Leu Leu Leu Leu Asp Val Ile Ile Cys
    210                 215                 220

Leu Leu Val Leu Val Gly Leu Ile Arg Ser Ser Lys Gly Ile Leu Val
225                 230                 235                 240

Gly Val Cys Leu Leu Gly Val Leu Ala Leu Val Ile Ser Trp Gly Ala
                245                 250                 255

Leu Gly Leu Glu Leu Ala Val Ser Val Gly Ser Ser Asp Phe Cys Val
            260                 265                 270

Asp Pro Asp Ala Tyr Val Thr Lys Met Val Glu Glu Tyr Ser Val Leu
        275                 280                 285

Ser Gly Asp Ile Leu Gln Tyr Tyr Leu Ala Cys Ser Pro Arg Ala Ala
    290                 295                 300

Asn Pro Phe Gln Gln Lys Leu Ser Gly Ser His Lys Ala Leu Val Glu
305                 310                 315                 320

Met Gln Asp Val Val Ala Glu Leu Leu Arg Thr Val Pro Trp Glu Gln
                325                 330                 335

Pro Ala Thr Lys Asp Pro Leu Leu Arg Val Gln Glu Val Leu Asn Gly
            340                 345                 350

Thr Glu Val Asn Leu Gln His Leu Thr Ala Leu Val Asp Cys Arg Ser
        355                 360                 365

Leu His Leu Asp Tyr Val Gln Ala Leu Thr Gly Phe Cys Tyr Asp Gly
    370                 375                 380

Val Glu Gly Leu Ile Tyr Leu Ala Leu Phe Ser Phe Val Thr Ala Leu
385                 390                 395                 400

Met Phe Ser Ser Ile Val Cys Ser Val Pro His Thr Trp Gln Gln Lys
                405                 410                 415

Arg Gly Pro Asp Glu Asp Gly Glu Glu Glu Ala Ala Pro Gly Pro Arg
            420                 425                 430

Gln Ala His Asp Ser Leu Tyr Arg Val His Met Pro Ser Leu Tyr Ser
        435                 440                 445

Cys Gly Ser Ser Tyr Gly Ser Glu Thr Ser Ile Pro Ala Ala Ala His
    450                 455                 460

Thr Val Ser Asn Ala Pro Val Thr Glu Tyr Met Ser Gln Asn Ala Asn
465                 470                 475                 480

Phe Gln Asn Pro Arg Cys Glu Asn Thr Pro Leu Ile Gly Arg Glu Ser
                485                 490                 495

Pro Pro Pro Ser Tyr Thr Ser Ser Met Arg Ala Lys Tyr Leu Ala Thr
            500                 505                 510

Ser Gln Pro Arg Pro Asp Ser Ser Gly Ser His
        515                 520


<210> SEQ ID NO 44
<211> LENGTH: 351
<212> TYPE: PRT
<213> ORGANISM: Homo sapiens

<400> SEQUENCE: 44

Met Ser Phe Phe Pro Glu Leu Tyr Phe Asn Val Asp Asn Gly Tyr Leu
1               5                   10                  15

Glu Gly Leu Val Arg Gly Leu Lys Ala Gly Val Leu Ser Gln Ala Asp
            20                  25                  30

Tyr Leu Asn Leu Val Gln Cys Glu Thr Leu Glu Asp Leu Lys Leu His
        35                  40                  45
```

```
Leu Gln Ser Thr Asp Tyr Gly Asn Phe Leu Ala Asn Glu Ala Ser Pro
    50                  55                  60

Leu Thr Val Ser Val Ile Asp Asp Arg Leu Lys Glu Lys Met Val Val
65                  70                  75                  80

Glu Phe Arg His Met Arg Asn His Ala Tyr Glu Pro Leu Ala Ser Phe
                85                  90                  95

Leu Asp Phe Ile Thr Tyr Ser Tyr Met Ile Asp Asn Val Ile Leu Leu
            100                 105                 110

Ile Thr Gly Thr Leu His Gln Arg Ser Ile Ala Glu Leu Val Pro Lys
        115                 120                 125

Cys His Pro Leu Gly Ser Phe Glu Gln Met Glu Ala Val Asn Ile Ala
    130                 135                 140

Gln Thr Pro Ala Glu Leu Tyr Asn Ala Ile Leu Val Asp Thr Pro Leu
145                 150                 155                 160

Ala Ala Phe Phe Gln Asp Cys Ile Ser Glu Gln Asp Leu Asp Glu Met
                165                 170                 175

Asn Ile Glu Ile Ile Arg Asn Thr Leu Tyr Lys Ala Tyr Leu Glu Ser
            180                 185                 190

Phe Tyr Lys Phe Cys Thr Leu Leu Gly Gly Thr Thr Ala Asp Ala Met
        195                 200                 205

Cys Pro Ile Leu Glu Phe Glu Ala Asp Arg Arg Ala Phe Ile Ile Thr
    210                 215                 220

Ile Asn Ser Phe Gly Thr Glu Leu Ser Lys Glu Asp Arg Ala Lys Leu
225                 230                 235                 240

Phe Pro His Cys Gly Arg Leu Tyr Pro Glu Gly Leu Ala Gln Leu Ala
                245                 250                 255

Arg Ala Asp Asp Tyr Glu Gln Val Lys Asn Val Ala Asp Tyr Tyr Pro
            260                 265                 270

Glu Tyr Lys Leu Leu Phe Glu Gly Ala Gly Ser Asn Pro Gly Asp Lys
        275                 280                 285

Thr Leu Glu Asp Arg Phe Phe Glu His Glu Val Lys Leu Asn Lys Leu
    290                 295                 300

Ala Phe Leu Asn Gln Phe His Phe Gly Val Phe Tyr Ala Phe Val Lys
305                 310                 315                 320

Leu Lys Glu Gln Glu Cys Arg Asn Ile Val Trp Ile Ala Glu Cys Ile
                325                 330                 335

Ala Gln Arg His Arg Ala Lys Ile Asp Asn Tyr Ile Pro Ile Phe
            340                 345                 350


<210> SEQ ID NO 45
<211> LENGTH: 739
<212> TYPE: PRT
<213> ORGANISM: Homo sapiens

<400> SEQUENCE: 45

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu
```

-continued

```
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
        355                 360                 365

Thr Leu Ser Pro Val Ser Phe Glu Asn Glu His Ser Tyr Leu Cys Thr
    370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
            420                 425                 430

Leu Asp Arg Leu Glu Ile Glu Leu Leu Lys Gly Glu Thr Ile Leu Glu
        435                 440                 445

Asn Ile Glu Phe Leu Glu Asp Thr Asp Met Lys Ser Leu Glu Asn Lys
    450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495
```

```
Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
        515                 520                 525

Ser Val Asn Met Thr Cys Leu Ser Gln Gly Phe Pro Ala Pro Lys Ile
    530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
        595                 600                 605

Pro Ser Glu Ser Val Lys Glu Gly Asp Thr Val Ile Ile Ser Cys Thr
    610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
        675                 680                 685

Glu Asn Asn Lys Asp Tyr Phe Ser Pro Glu Leu Leu Val Leu Tyr Phe
    690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val


<210> SEQ ID NO 46
<211> LENGTH: 3396
<212> TYPE: PRT
<213> ORGANISM: Homo sapiens

<400> SEQUENCE: 46

Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
            20                  25                  30

Arg Gly Ser Leu Ser Gly Lys Val Ser Leu Pro Cys His Phe Ser Thr
        35                  40                  45

Met Pro Thr Leu Pro Pro Ser Tyr Asn Thr Ser Glu Phe Leu Arg Ile
    50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
            100                 105                 110

Ala Ser Leu Thr Val Val Lys Leu Leu Ala Ser Asp Ala Gly Leu Tyr
        115                 120                 125
```

```
Arg Cys Asp Val Met Tyr Gly Ile Glu Asp Thr Gln Asp Thr Val Ser
    130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

Pro Ile Arg Ala Pro Arg Val Gly Cys Tyr Gly Asp Lys Met Gly Lys
    210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Ala Lys Glu Cys Glu Asn
            260                 265                 270

Gln Asp Ala Arg Leu Ala Thr Val Gly Glu Leu Gln Ala Ala Trp Arg
        275                 280                 285

Asn Gly Phe Asp Gln Cys Asp Tyr Gly Trp Leu Ser Asp Ala Ser Val
    290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Pro Lys Glu Ala Thr
            340                 345                 350

Thr Ile Asp Leu Ser Ile Leu Ala Glu Thr Ala Ser Pro Ser Leu Ser
        355                 360                 365

Lys Glu Pro Gln Met Val Ser Asp Arg Thr Thr Pro Ile Ile Pro Leu
    370                 375                 380

Val Asp Glu Leu Pro Val Ile Pro Thr Glu Phe Pro Pro Val Gly Asn
385                 390                 395                 400

Ile Val Ser Phe Glu Gln Lys Ala Thr Val Gln Pro Gln Ala Ile Thr
                405                 410                 415

Asp Ser Leu Ala Thr Lys Leu Pro Thr Pro Thr Gly Ser Thr Lys Lys
            420                 425                 430

Pro Trp Asp Met Asp Asp Tyr Ser Pro Ser Ala Ser Gly Pro Leu Gly
        435                 440                 445

Lys Leu Asp Ile Ser Glu Ile Lys Glu Glu Val Leu Gln Ser Thr Thr
    450                 455                 460

Gly Val Ser His Tyr Ala Thr Asp Ser Trp Asp Gly Val Val Glu Asp
465                 470                 475                 480

Lys Gln Thr Gln Glu Ser Val Thr Gln Ile Glu Gln Ile Glu Val Gly
                485                 490                 495

Pro Leu Val Thr Ser Met Glu Ile Leu Lys His Ile Pro Ser Lys Glu
            500                 505                 510

Phe Pro Val Thr Glu Thr Pro Leu Val Thr Ala Arg Met Ile Leu Glu
        515                 520                 525

Ser Lys Thr Glu Lys Lys Met Val Ser Thr Val Ser Glu Leu Val Thr
    530                 535                 540
```

```
Thr Gly His Tyr Gly Phe Thr Leu Gly Glu Glu Asp Asp Glu Asp Arg
545                 550                 555                 560

Thr Leu Thr Val Gly Ser Asp Glu Ser Thr Leu Ile Phe Asp Gln Ile
                565                 570                 575

Pro Glu Val Ile Thr Val Ser Lys Thr Ser Glu Asp Thr Ile His Thr
            580                 585                 590

His Leu Glu Asp Leu Glu Ser Val Ser Ala Ser Thr Thr Val Ser Pro
        595                 600                 605

Leu Ile Met Pro Asp Asn Asn Gly Ser Ser Met Asp Asp Trp Glu Glu
    610                 615                 620

Arg Gln Thr Ser Gly Arg Ile Thr Glu Glu Phe Leu Gly Lys Tyr Leu
625                 630                 635                 640

Ser Thr Thr Pro Phe Pro Ser Gln His Arg Thr Glu Ile Glu Leu Phe
                645                 650                 655

Pro Tyr Ser Gly Asp Lys Ile Leu Val Glu Gly Ile Ser Thr Val Ile
            660                 665                 670

Tyr Pro Ser Leu Gln Thr Glu Met Thr His Arg Arg Glu Arg Thr Glu
        675                 680                 685

Thr Leu Ile Pro Glu Met Arg Thr Asp Thr Tyr Thr Asp Glu Ile Gln
    690                 695                 700

Glu Glu Ile Thr Lys Ser Pro Phe Met Gly Lys Thr Glu Glu Glu Val
705                 710                 715                 720

Phe Ser Gly Met Lys Leu Ser Thr Ser Leu Ser Glu Pro Ile His Val
                725                 730                 735

Thr Glu Ser Ser Val Glu Met Thr Lys Ser Phe Asp Phe Pro Thr Leu
            740                 745                 750

Ile Thr Lys Leu Ser Ala Glu Pro Thr Glu Val Arg Asp Met Glu Glu
        755                 760                 765

Asp Phe Thr Ala Thr Pro Gly Thr Thr Lys Tyr Asp Glu Asn Ile Thr
    770                 775                 780

Thr Val Leu Leu Ala His Gly Thr Leu Ser Val Glu Ala Ala Thr Val
785                 790                 795                 800

Ser Lys Trp Ser Trp Asp Glu Asp Asn Thr Thr Ser Lys Pro Leu Glu
                805                 810                 815

Ser Thr Glu Pro Ser Ala Ser Ser Lys Leu Pro Pro Ala Leu Leu Thr
            820                 825                 830

Thr Val Gly Met Asn Gly Lys Asp Lys Asp Ile Pro Ser Phe Thr Glu
        835                 840                 845

Asp Gly Ala Asp Glu Phe Thr Leu Ile Pro Asp Ser Thr Gln Lys Gln
    850                 855                 860

Leu Glu Glu Val Thr Asp Glu Asp Ile Ala Ala His Gly Lys Phe Thr
865                 870                 875                 880

Ile Arg Phe Gln Pro Thr Thr Ser Thr Gly Ile Ala Glu Lys Ser Thr
                885                 890                 895

Leu Arg Asp Ser Thr Thr Glu Glu Lys Val Pro Pro Ile Thr Ser Thr
            900                 905                 910

Glu Gly Gln Val Tyr Ala Thr Met Glu Gly Ser Ala Leu Gly Glu Val
        915                 920                 925

Glu Asp Val Asp Leu Ser Lys Pro Val Ser Thr Val Pro Gln Phe Ala
    930                 935                 940

His Thr Ser Glu Val Glu Gly Leu Ala Phe Val Ser Tyr Ser Ser Thr
945                 950                 955                 960

Gln Glu Pro Thr Thr Tyr Val Asp Ser Ser His Thr Ile Pro Leu Ser
```

```
                965                 970                 975

Val Ile Pro Lys Thr Asp Trp Gly Val Leu Val Pro Ser Val Pro Ser
            980                 985                 990

Glu Asp Glu Val Leu Gly Glu Pro  Ser Gln Asp Ile Leu  Val Ile Asp
        995                 1000                1005

Gln Thr  Arg Leu Glu Ala Thr  Ile Ser Pro Glu Thr  Met Arg Thr
    1010                1015                1020

Thr Lys  Ile Thr Glu Gly Thr  Thr Gln Glu Glu Phe  Pro Trp Lys
    1025                1030                1035

Glu Gln  Thr Ala Glu Lys Pro  Val Pro Ala Leu Ser  Ser Thr Ala
    1040                1045                1050

Trp Thr  Pro Lys Glu Ala Val  Thr Pro Leu Asp Glu  Gln Glu Gly
    1055                1060                1065

Asp Gly  Ser Ala Tyr Thr Val  Ser Glu Asp Glu Leu  Leu Thr Gly
    1070                1075                1080

Ser Glu  Arg Val Pro Val Leu  Glu Thr Thr Pro Val  Gly Lys Ile
    1085                1090                1095

Asp His  Ser Val Ser Tyr Pro  Pro Gly Ala Val Thr  Glu His Lys
    1100                1105                1110

Val Lys  Thr Asp Glu Val Val  Thr Leu Thr Pro Arg  Ile Gly Pro
    1115                1120                1125

Lys Val  Ser Leu Ser Pro Gly  Pro Glu Gln Lys Tyr  Glu Thr Glu
    1130                1135                1140

Gly Ser  Ser Thr Thr Gly Phe  Thr Ser Ser Leu Ser  Pro Phe Ser
    1145                1150                1155

Thr His  Ile Thr Gln Leu Met  Glu Glu Thr Thr Thr  Glu Lys Thr
    1160                1165                1170

Ser Leu  Glu Asp Ile Asp Leu  Gly Ser Gly Leu Phe  Glu Lys Pro
    1175                1180                1185

Lys Ala  Thr Glu Leu Ile Glu  Phe Ser Thr Ile Lys  Val Thr Val
    1190                1195                1200

Pro Ser  Asp Ile Thr Thr Ala  Phe Ser Ser Val Asp  Arg Leu His
    1205                1210                1215

Thr Thr  Ser Ala Phe Lys Pro  Ser Ser Ala Ile Thr  Lys Lys Pro
    1220                1225                1230

Pro Leu  Ile Asp Arg Glu Pro  Gly Glu Glu Thr Thr  Ser Asp Met
    1235                1240                1245

Val Ile  Ile Gly Glu Ser Thr  Ser His Val Pro Pro  Thr Thr Leu
    1250                1255                1260

Glu Asp  Ile Val Ala Lys Glu  Thr Glu Thr Asp Ile  Asp Arg Glu
    1265                1270                1275

Tyr Phe  Thr Thr Ser Ser Pro  Pro Ala Thr Gln Pro  Thr Arg Pro
    1280                1285                1290

Pro Thr  Val Glu Asp Lys Glu  Ala Phe Gly Pro Gln  Ala Leu Ser
    1295                1300                1305

Thr Pro  Gln Pro Pro Ala Ser  Thr Lys Phe His Pro  Asp Ile Asn
    1310                1315                1320

Val Tyr  Ile Ile Glu Val Arg  Glu Asn Lys Thr Gly  Arg Met Ser
    1325                1330                1335

Asp Leu  Ser Val Ile Gly His  Pro Ile Asp Ser Glu  Ser Lys Glu
    1340                1345                1350

Asp Glu  Pro Cys Ser Glu Glu  Thr Asp Pro Val His  Asp Leu Met
    1355                1360                1365
```

```
Ala Glu  Ile Leu Pro Glu Phe  Pro Asp Ile Ile Glu  Ile Asp Leu
    1370                 1375                 1380

Tyr His  Ser Glu Glu Asn Glu  Glu Glu Glu Glu Glu  Cys Ala Asn
    1385                 1390                 1395

Ala Thr  Asp Val Thr Thr Thr  Pro Ser Val Gln Tyr  Ile Asn Gly
    1400                 1405                 1410

Lys His  Leu Val Thr Thr Val  Pro Lys Asp Pro Glu  Ala Ala Glu
    1415                 1420                 1425

Ala Arg  Arg Gly Gln Phe Glu  Ser Val Ala Pro Ser  Gln Asn Phe
    1430                 1435                 1440

Ser Asp  Ser Ser Glu Ser Asp  Thr His Pro Phe Val  Ile Ala Lys
    1445                 1450                 1455

Thr Glu  Leu Ser Thr Ala Val  Gln Pro Asn Glu Ser  Thr Glu Thr
    1460                 1465                 1470

Thr Glu  Ser Leu Glu Val Thr  Trp Lys Pro Glu Thr  Tyr Pro Glu
    1475                 1480                 1485

Thr Ser  Glu His Phe Ser Gly  Gly Glu Pro Asp Val  Phe Pro Thr
    1490                 1495                 1500

Val Pro  Phe His Glu Glu Phe  Glu Ser Gly Thr Ala  Lys Lys Gly
    1505                 1510                 1515

Ala Glu  Ser Val Thr Glu Arg  Asp Thr Glu Val Gly  His Gln Ala
    1520                 1525                 1530

His Glu  His Thr Glu Pro Val  Ser Leu Phe Pro Glu  Glu Ser Ser
    1535                 1540                 1545

Gly Glu  Ile Ala Ile Asp Gln  Glu Ser Gln Lys Ile  Ala Phe Ala
    1550                 1555                 1560

Arg Ala  Thr Glu Val Thr Phe  Gly Glu Glu Val Glu  Lys Ser Thr
    1565                 1570                 1575

Ser Val  Thr Tyr Thr Pro Thr  Ile Val Pro Ser Ser  Ala Ser Ala
    1580                 1585                 1590

Tyr Val  Ser Glu Glu Glu Ala  Val Thr Leu Ile Gly  Asn Pro Trp
    1595                 1600                 1605

Pro Asp  Asp Leu Leu Ser Thr  Lys Glu Ser Trp Val  Glu Ala Thr
    1610                 1615                 1620

Pro Arg  Gln Val Val Glu Leu  Ser Gly Ser Ser Ser  Ile Pro Ile
    1625                 1630                 1635

Thr Glu  Gly Ser Gly Glu Ala  Glu Glu Asp Glu Asp  Thr Met Phe
    1640                 1645                 1650

Thr Met  Val Thr Asp Leu Ser  Gln Arg Asn Thr Thr  Asp Thr Leu
    1655                 1660                 1665

Ile Thr  Leu Asp Thr Ser Arg  Ile Ile Thr Glu Ser  Phe Phe Glu
    1670                 1675                 1680

Val Pro  Ala Thr Thr Ile Tyr  Pro Val Ser Glu Gln  Pro Ser Ala
    1685                 1690                 1695

Lys Val  Val Pro Thr Lys Phe  Val Ser Glu Thr Asp  Thr Ser Glu
    1700                 1705                 1710

Trp Ile  Ser Ser Thr Thr Val  Glu Glu Lys Lys Arg  Lys Glu Glu
    1715                 1720                 1725

Glu Gly  Thr Thr Gly Thr Ala  Ser Thr Phe Glu Val  Tyr Ser Ser
    1730                 1735                 1740

Thr Gln  Arg Ser Asp Gln Leu  Ile Leu Pro Phe Glu  Leu Glu Ser
    1745                 1750                 1755
```

```
Pro Asn Val Ala Thr Ser Ser Asp Ser Gly Thr Arg Lys Ser Phe
    1760                1765                1770

Met Ser Leu Thr Thr Pro Thr Gln Ser Glu Arg Glu Met Thr Asp
    1775                1780                1785

Ser Thr Pro Val Phe Thr Glu Thr Asn Thr Leu Glu Asn Leu Gly
    1790                1795                1800

Ala Gln Thr Thr Glu His Ser Ser Ile His Gln Pro Gly Val Gln
    1805                1810                1815

Glu Gly Leu Thr Thr Leu Pro Arg Ser Pro Ala Ser Val Phe Met
    1820                1825                1830

Glu Gln Gly Ser Gly Glu Ala Ala Ala Asp Pro Glu Thr Thr Thr
    1835                1840                1845

Val Ser Ser Phe Ser Leu Asn Val Glu Tyr Ala Ile Gln Ala Glu
    1850                1855                1860

Lys Glu Val Ala Gly Thr Leu Ser Pro His Val Glu Thr Thr Phe
    1865                1870                1875

Ser Thr Glu Pro Thr Gly Leu Val Leu Ser Thr Val Met Asp Arg
    1880                1885                1890

Val Val Ala Glu Asn Ile Thr Gln Thr Ser Arg Glu Ile Val Ile
    1895                1900                1905

Ser Glu Arg Leu Gly Glu Pro Asn Tyr Gly Ala Glu Ile Arg Gly
    1910                1915                1920

Phe Ser Thr Gly Phe Pro Leu Glu Glu Asp Phe Ser Gly Asp Phe
    1925                1930                1935

Arg Glu Tyr Ser Thr Val Ser His Pro Ile Ala Lys Glu Glu Thr
    1940                1945                1950

Val Met Met Glu Gly Ser Gly Asp Ala Ala Phe Arg Asp Thr Gln
    1955                1960                1965

Thr Ser Pro Ser Thr Val Pro Thr Ser Val His Ile Ser His Ile
    1970                1975                1980

Ser Asp Ser Glu Gly Pro Ser Ser Thr Met Val Ser Thr Ser Ala
    1985                1990                1995

Phe Pro Trp Glu Glu Phe Thr Ser Ser Ala Glu Gly Ser Gly Glu
    2000                2005                2010

Gln Leu Val Thr Val Ser Ser Ser Val Val Pro Val Leu Pro Ser
    2015                2020                2025

Ala Val Gln Lys Phe Ser Gly Thr Ala Ser Ser Ile Ile Asp Glu
    2030                2035                2040

Gly Leu Gly Glu Val Gly Thr Val Asn Glu Ile Asp Arg Arg Ser
    2045                2050                2055

Thr Ile Leu Pro Thr Ala Glu Val Glu Gly Thr Lys Ala Pro Val
    2060                2065                2070

Glu Lys Glu Glu Val Lys Val Ser Gly Thr Val Ser Thr Asn Phe
    2075                2080                2085

Pro Gln Thr Ile Glu Pro Ala Lys Leu Trp Ser Arg Gln Glu Val
    2090                2095                2100

Asn Pro Val Arg Gln Glu Ile Glu Ser Glu Thr Thr Ser Glu Glu
    2105                2110                2115

Gln Ile Gln Glu Glu Lys Ser Phe Glu Ser Pro Gln Asn Ser Pro
    2120                2125                2130

Ala Thr Glu Gln Thr Ile Phe Asp Ser Gln Thr Phe Thr Glu Thr
    2135                2140                2145

Glu Leu Lys Thr Thr Asp Tyr Ser Val Leu Thr Thr Lys Lys Thr
```

```
    2150                2155                2160

Tyr Ser  Asp Asp Lys Glu Met  Lys Glu Glu Asp Thr  Ser Leu Val
    2165                2170                2175

Asn Met  Ser Thr Pro Asp Pro  Asp Ala Asn Gly Leu  Glu Ser Tyr
    2180                2185                2190

Thr Thr  Leu Pro Glu Ala Thr  Glu Lys Ser His Phe  Phe Leu Ala
    2195                2200                2205

Thr Ala  Leu Val Thr Glu Ser  Ile Pro Ala Glu His  Val Val Thr
    2210                2215                2220

Asp Ser  Pro Ile Lys Lys Glu  Glu Ser Thr Lys His  Phe Pro Lys
    2225                2230                2235

Gly Met  Arg Pro Thr Ile Gln  Glu Ser Asp Thr Glu  Leu Leu Phe
    2240                2245                2250

Ser Gly  Leu Gly Ser Gly Glu  Glu Val Leu Pro Thr  Leu Pro Thr
    2255                2260                2265

Glu Ser  Val Asn Phe Thr Glu  Val Glu Gln Ile Asn  Asn Thr Leu
    2270                2275                2280

Tyr Pro  His Thr Ser Gln Val  Glu Ser Thr Ser Ser  Asp Lys Ile
    2285                2290                2295

Glu Asp  Phe Asn Arg Met Glu  Asn Val Ala Lys Glu  Val Gly Pro
    2300                2305                2310

Leu Val  Ser Gln Thr Asp Ile  Phe Glu Gly Ser Gly  Ser Val Thr
    2315                2320                2325

Ser Thr  Thr Leu Ile Glu Ile  Leu Ser Asp Thr Gly  Ala Glu Gly
    2330                2335                2340

Pro Thr  Val Ala Pro Leu Pro  Phe Ser Thr Asp Ile  Gly His Pro
    2345                2350                2355

Gln Asn  Gln Thr Val Arg Trp  Ala Glu Glu Ile Gln  Thr Ser Arg
    2360                2365                2370

Pro Gln  Thr Ile Thr Glu Gln  Asp Ser Asn Lys Asn  Ser Ser Thr
    2375                2380                2385

Ala Glu  Ile Asn Glu Thr Thr  Thr Ser Ser Thr Asp  Phe Leu Ala
    2390                2395                2400

Arg Ala  Tyr Gly Phe Glu Met  Ala Lys Glu Phe Val  Thr Ser Ala
    2405                2410                2415

Pro Lys  Pro Ser Asp Leu Tyr  Tyr Glu Pro Ser Gly  Glu Gly Ser
    2420                2425                2430

Gly Glu  Val Asp Ile Val Asp  Ser Phe His Thr Ser  Ala Thr Thr
    2435                2440                2445

Gln Ala  Thr Arg Gln Glu Ser  Ser Thr Thr Phe Val  Ser Asp Gly
    2450                2455                2460

Ser Leu  Glu Lys His Pro Glu  Val Pro Ser Ala Lys  Ala Val Thr
    2465                2470                2475

Ala Asp  Gly Phe Pro Thr Val  Ser Val Met Leu Pro  Leu His Ser
    2480                2485                2490

Glu Gln  Asn Lys Ser Ser Pro  Asp Pro Thr Ser Thr  Leu Ser Asn
    2495                2500                2505

Thr Val  Ser Tyr Glu Arg Ser  Thr Asp Gly Ser Phe  Gln Asp Arg
    2510                2515                2520

Phe Arg  Glu Phe Glu Asp Ser  Thr Leu Lys Pro Asn  Arg Lys Lys
    2525                2530                2535

Pro Thr  Glu Asn Ile Ile Ile  Asp Leu Asp Lys Glu  Asp Lys Asp
    2540                2545                2550
```

```
Leu Ile  Leu Thr Ile Thr Glu  Ser Thr Ile Leu Glu  Ile Leu Pro
    2555                 2560                 2565

Glu Leu  Thr Ser Asp Lys Asn  Thr Ile Ile Asp Ile  Asp His Thr
    2570                 2575                 2580

Lys Pro  Val Tyr Glu Asp Ile  Leu Gly Met Gln Thr  Asp Ile Asp
    2585                 2590                 2595

Thr Glu  Val Pro Ser Glu Pro  His Asp Ser Asn Asp  Glu Ser Asn
    2600                 2605                 2610

Asp Asp  Ser Thr Gln Val Gln  Glu Ile Tyr Glu Ala  Ala Val Asn
    2615                 2620                 2625

Leu Ser  Leu Thr Glu Glu Thr  Phe Glu Gly Ser Ala  Asp Val Leu
    2630                 2635                 2640

Ala Ser  Tyr Thr Gln Ala Thr  His Asp Glu Ser Met  Thr Tyr Glu
    2645                 2650                 2655

Asp Arg  Ser Gln Leu Asp His  Met Gly Phe His Phe  Thr Thr Gly
    2660                 2665                 2670

Ile Pro  Ala Pro Ser Thr Glu  Thr Glu Leu Asp Val  Leu Leu Pro
    2675                 2680                 2685

Thr Ala  Thr Ser Leu Pro Ile  Pro Arg Lys Ser Ala  Thr Val Ile
    2690                 2695                 2700

Pro Glu  Ile Glu Gly Ile Lys  Ala Glu Ala Lys Ala  Leu Asp Asp
    2705                 2710                 2715

Met Phe  Glu Ser Ser Thr Leu  Ser Asp Gly Gln Ala  Ile Ala Asp
    2720                 2725                 2730

Gln Ser  Glu Ile Ile Pro Thr  Leu Gly Gln Phe Glu  Arg Thr Gln
    2735                 2740                 2745

Glu Glu  Tyr Glu Asp Lys Lys  His Ala Gly Pro Ser  Phe Gln Pro
    2750                 2755                 2760

Glu Phe  Ser Ser Gly Ala Glu  Glu Ala Leu Val Asp  His Thr Pro
    2765                 2770                 2775

Tyr Leu  Ser Ile Ala Thr Thr  His Leu Met Asp Gln  Ser Val Thr
    2780                 2785                 2790

Glu Val  Pro Asp Val Met Glu  Gly Ser Asn Pro Pro  Tyr Tyr Thr
    2795                 2800                 2805

Asp Thr  Thr Leu Ala Val Ser  Thr Phe Ala Lys Leu  Ser Ser Gln
    2810                 2815                 2820

Thr Pro  Ser Ser Pro Leu Thr  Ile Tyr Ser Gly Ser  Glu Ala Ser
    2825                 2830                 2835

Gly His  Thr Glu Ile Pro Gln  Pro Ser Ala Leu Pro  Gly Ile Asp
    2840                 2845                 2850

Val Gly  Ser Ser Val Met Ser  Pro Gln Asp Ser Phe  Lys Glu Ile
    2855                 2860                 2865

His Val  Asn Ile Glu Ala Thr  Phe Lys Pro Ser Ser  Glu Glu Tyr
    2870                 2875                 2880

Leu His  Ile Thr Glu Pro Pro  Ser Leu Ser Pro Asp  Thr Lys Leu
    2885                 2890                 2895

Glu Pro  Ser Glu Asp Asp Gly  Lys Pro Glu Leu Leu  Glu Glu Met
    2900                 2905                 2910

Glu Ala  Ser Pro Thr Glu Leu  Ile Ala Val Glu Gly  Thr Glu Ile
    2915                 2920                 2925

Leu Gln  Asp Phe Gln Asn Lys  Thr Asp Gly Gln Val  Ser Gly Glu
    2930                 2935                 2940
```

```
Ala Ile  Lys Met Phe Pro Thr  Ile Lys Thr Pro Glu  Ala Gly Thr
    2945                 2950                 2955

Val Ile  Thr Thr Ala Asp Glu  Ile Glu Leu Glu Gly  Ala Thr Gln
    2960                 2965                 2970

Trp Pro  His Ser Thr Ser Ala  Ser Ala Thr Tyr Gly  Val Glu Ala
    2975                 2980                 2985

Gly Val  Val Pro Trp Leu Ser  Pro Gln Thr Ser Glu  Arg Pro Thr
    2990                 2995                 3000

Leu Ser  Ser Ser Pro Glu Ile  Asn Pro Glu Thr Gln  Ala Ala Leu
    3005                 3010                 3015

Ile Arg  Gly Gln Asp Ser Thr  Ile Ala Ala Ser Glu  Gln Gln Val
    3020                 3025                 3030

Ala Ala  Arg Ile Leu Asp Ser  Asn Asp Gln Ala Thr  Val Asn Pro
    3035                 3040                 3045

Val Glu  Phe Asn Thr Glu Val  Ala Thr Pro Pro Phe  Ser Leu Leu
    3050                 3055                 3060

Glu Thr  Ser Asn Glu Thr Asp  Phe Leu Ile Gly Ile  Asn Glu Glu
    3065                 3070                 3075

Ser Val  Glu Gly Thr Ala Ile  Tyr Leu Pro Gly Pro  Asp Arg Cys
    3080                 3085                 3090

Lys Met  Asn Pro Cys Leu Asn  Gly Gly Thr Cys Tyr  Pro Thr Glu
    3095                 3100                 3105

Thr Ser  Tyr Val Cys Thr Cys  Val Pro Gly Tyr Ser  Gly Asp Gln
    3110                 3115                 3120

Cys Glu  Leu Asp Phe Asp Glu  Cys His Ser Asn Pro  Cys Arg Asn
    3125                 3130                 3135

Gly Ala  Thr Cys Val Asp Gly  Phe Asn Thr Phe Arg  Cys Leu Cys
    3140                 3145                 3150

Leu Pro  Ser Tyr Val Gly Ala  Leu Cys Glu Gln Asp  Thr Glu Thr
    3155                 3160                 3165

Cys Asp  Tyr Gly Trp His Lys  Phe Gln Gly Gln Cys  Tyr Lys Tyr
    3170                 3175                 3180

Phe Ala  His Arg Arg Thr Trp  Asp Ala Ala Glu Arg  Glu Cys Arg
    3185                 3190                 3195

Leu Gln  Gly Ala His Leu Thr  Ser Ile Leu Ser His  Glu Glu Gln
    3200                 3205                 3210

Met Phe  Val Asn Arg Val Gly  His Asp Tyr Gln Trp  Ile Gly Leu
    3215                 3220                 3225

Asn Asp  Lys Met Phe Glu His  Asp Phe Arg Trp Thr  Asp Gly Ser
    3230                 3235                 3240

Thr Leu  Gln Tyr Glu Asn Trp  Arg Pro Asn Gln Pro  Asp Ser Phe
    3245                 3250                 3255

Phe Ser  Ala Gly Glu Asp Cys  Val Val Ile Ile Trp  His Glu Asn
    3260                 3265                 3270

Gly Gln  Trp Asn Asp Val Pro  Cys Asn Tyr His Leu  Thr Tyr Thr
    3275                 3280                 3285

Cys Lys  Lys Gly Thr Val Ala  Cys Gly Gln Pro Pro  Val Val Glu
    3290                 3295                 3300

Asn Ala  Lys Thr Phe Gly Lys  Met Lys Pro Arg Tyr  Glu Ile Asn
    3305                 3310                 3315

Ser Leu  Ile Arg Tyr His Cys  Lys Asp Gly Phe Ile  Gln Arg His
    3320                 3325                 3330

Leu Pro  Thr Ile Arg Cys Leu  Gly Asn Gly Arg Trp  Ala Ile Pro
```

```
    3335                3340                3345

Lys Ile  Thr Cys Met Asn Pro  Ser Ala Tyr Gln Arg  Thr Tyr Ser
    3350                3355                3360

Met Lys  Tyr Phe Lys Asn Ser  Ser Ser Ala Lys Asp  Asn Ser Ile
    3365                3370                3375

Asn Thr  Ser Lys His Asp His  Arg Trp Ser Arg Arg  Trp Gln Glu
    3380                3385                3390

Ser Arg  Arg
    3395


<210> SEQ ID NO 47
<211> LENGTH: 356
<212> TYPE: PRT
<213> ORGANISM: Homo sapiens

<400> SEQUENCE: 47

Met Ala Ala Glu Gly Trp Ile Trp Arg Trp Gly Trp Gly Arg Arg Cys
1               5                   10                  15

Leu Gly Arg Pro Gly Leu Leu Gly Pro Gly Pro Gly Pro Thr Thr Pro
            20                  25                  30

Leu Phe Leu Leu Leu Leu Leu Gly Ser Val Thr Ala Asp Ile Thr Asp
        35                  40                  45

Gly Asn Ser Glu His Leu Lys Arg Glu His Ser Leu Ile Lys Pro Tyr
    50                  55                  60

Gln Gly Val Gly Ser Ser Ser Met Pro Leu Trp Asp Phe Gln Gly Ser
65                  70                  75                  80

Thr Met Leu Thr Ser Gln Tyr Val Arg Leu Thr Pro Asp Glu Arg Ser
                85                  90                  95

Lys Glu Gly Ser Ile Trp Asn His Gln Pro Cys Phe Leu Lys Asp Trp
            100                 105                 110

Glu Met His Val His Phe Lys Val His Gly Thr Gly Lys Lys Asn Leu
        115                 120                 125

His Gly Asp Gly Ile Ala Leu Trp Tyr Thr Arg Asp Arg Leu Val Pro
    130                 135                 140

Gly Pro Val Phe Gly Ser Lys Asp Asn Phe His Gly Leu Ala Ile Phe
145                 150                 155                 160

Leu Asp Thr Tyr Pro Asn Asp Glu Thr Thr Glu Arg Val Phe Pro Tyr
                165                 170                 175

Ile Ser Val Met Val Asn Asn Gly Ser Leu Ser Tyr Asp His Ser Lys
            180                 185                 190

Asp Gly Arg Trp Thr Glu Leu Ala Gly Cys Thr Ala Asp Phe Arg Asn
        195                 200                 205

Arg Asp His Asp Thr Phe Leu Ala Val Arg Tyr Ser Arg Gly Arg Leu
    210                 215                 220

Thr Val Met Thr Asp Leu Glu Asp Lys Asn Glu Trp Lys Asn Cys Ile
225                 230                 235                 240

Asp Ile Thr Gly Val Arg Leu Pro Thr Gly Tyr Tyr Phe Gly Ala Ser
                245                 250                 255

Ala Gly Thr Gly Asp Leu Ser Asp Asn His Asp Ile Ile Ser Met Lys
            260                 265                 270

Leu Phe Gln Leu Met Val Glu His Thr Pro Asp Glu Glu Ser Ile Asp
        275                 280                 285

Trp Thr Lys Ile Glu Pro Ser Val Asn Phe Leu Lys Ser Pro Lys Asp
    290                 295                 300
```

```
Asn Val Asp Asp Pro Thr Gly Asn Phe Arg Ser Gly Pro Leu Thr Gly
305                 310                 315                 320

Trp Arg Val Phe Leu Leu Leu Leu Cys Ala Leu Leu Gly Ile Val Val
                325                 330                 335

Cys Ala Val Val Gly Ala Val Val Phe Gln Lys Arg Gln Glu Arg Asn
            340                 345                 350

Lys Arg Phe Tyr
        355


<210> SEQ ID NO 48
<211> LENGTH: 201
<212> TYPE: PRT
<213> ORGANISM: Homo sapiens

<400> SEQUENCE: 48

Met Ala Leu Ser Trp Val Leu Thr Val Leu Ser Leu Leu Pro Leu Leu
1               5                   10                  15

Glu Ala Gln Ile Pro Leu Cys Ala Asn Leu Val Pro Val Pro Ile Thr
            20                  25                  30

Asn Ala Thr Leu Asp Arg Ile Thr Gly Lys Trp Phe Tyr Ile Ala Ser
        35                  40                  45

Ala Phe Arg Asn Glu Glu Tyr Asn Lys Ser Val Gln Glu Ile Gln Ala
    50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asn Gln Cys Phe Tyr Asn Ser Ser Tyr
                85                  90                  95

Leu Asn Val Gln Arg Glu Asn Gly Thr Val Ser Arg Tyr Glu Gly Gly
            100                 105                 110

Arg Glu His Val Ala His Leu Leu Phe Leu Arg Asp Thr Lys Thr Leu
        115                 120                 125

Met Phe Gly Ser Tyr Leu Asp Asp Glu Lys Asn Trp Gly Leu Ser Phe
    130                 135                 140

Tyr Ala Asp Lys Pro Glu Thr Thr Lys Glu Gln Leu Gly Glu Phe Tyr
145                 150                 155                 160

Glu Ala Leu Asp Cys Leu Cys Ile Pro Arg Ser Asp Val Met Tyr Thr
                165                 170                 175

Asp Trp Lys Lys Asp Lys Cys Glu Pro Leu Glu Lys Gln His Glu Lys
            180                 185                 190

Glu Arg Lys Gln Glu Glu Gly Glu Ser
        195                 200


<210> SEQ ID NO 49
<211> LENGTH: 310
<212> TYPE: PRT
<213> ORGANISM: Homo sapiens

<400> SEQUENCE: 49

Met Ala Phe Pro Lys Met Arg Leu Met Tyr Ile Cys Leu Leu Val Leu
1               5                   10                  15

Gly Ala Leu Cys Leu Tyr Phe Ser Met Tyr Ser Leu Asn Pro Phe Lys
            20                  25                  30

Glu Gln Ser Phe Val Tyr Lys Lys Asp Gly Asn Phe Leu Lys Leu Pro
        35                  40                  45

Asp Thr Asp Cys Arg Gln Thr Pro Pro Phe Leu Val Leu Leu Val Thr
    50                  55                  60
```

```
Ser Ser His Lys Gln Leu Ala Glu Arg Met Ala Ile Arg Gln Thr Trp
65                  70                  75                  80

Gly Lys Glu Arg Met Val Lys Gly Lys Gln Leu Lys Thr Phe Phe Leu
                85                  90                  95

Leu Gly Thr Thr Ser Ser Ala Ala Glu Thr Lys Glu Val Asp Gln Glu
            100                 105                 110

Ser Gln Arg His Gly Asp Ile Ile Gln Lys Asp Phe Leu Asp Val Tyr
        115                 120                 125

Tyr Asn Leu Thr Leu Lys Thr Met Met Gly Ile Glu Trp Val His Arg
    130                 135                 140

Phe Cys Pro Gln Ala Ala Phe Val Met Lys Thr Asp Ser Asp Met Phe
145                 150                 155                 160

Ile Asn Val Asp Tyr Leu Thr Glu Leu Leu Leu Lys Lys Asn Arg Thr
                165                 170                 175

Thr Arg Phe Phe Thr Gly Phe Leu Lys Leu Asn Glu Phe Pro Ile Arg
            180                 185                 190

Gln Pro Phe Ser Lys Trp Phe Val Ser Lys Ser Glu Tyr Pro Trp Asp
        195                 200                 205

Arg Tyr Pro Pro Phe Cys Ser Gly Thr Gly Tyr Val Phe Ser Gly Asp
    210                 215                 220

Val Ala Ser Gln Val Tyr Asn Val Ser Lys Ser Val Pro Tyr Ile Lys
225                 230                 235                 240

Leu Glu Asp Val Phe Val Gly Leu Cys Leu Glu Arg Leu Asn Ile Arg
                245                 250                 255

Leu Glu Glu Leu His Ser Gln Pro Thr Phe Phe Pro Gly Gly Leu Arg
            260                 265                 270

Phe Ser Val Cys Leu Phe Arg Arg Ile Val Ala Cys His Phe Ile Lys
        275                 280                 285

Pro Arg Thr Leu Leu Asp Tyr Trp Gln Ala Leu Glu Asn Ser Arg Gly
    290                 295                 300

Glu Asp Cys Pro Pro Val
305                 310


<210> SEQ ID NO 50
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Leu Asp Ile Thr Ala Glu Ile Leu Ala Val Arg
1               5                   10


<210> SEQ ID NO 51
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Val Ala Thr Val Ser Leu Pro Arg
1               5
```

-continued

```
<210> SEQ ID NO 52
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 52

His His His His His His
1               5
```

METHOD OF PREDICTING ACUTE APPENDICITIS

CROSS REFERENCE TO RELATED APPLICATIONS

This application is a divisional application of U.S. patent application Ser. No. 13/963,017 filed on Aug. 9, 2013, which is a continuation of U.S. patent application Ser. No. 13/142,598 filed on Oct. 14, 2011, now U.S. Pat. No. 8,535,891 issued on Sep. 17, 2013, which is 35 U.S.C. § 371 U.S. National Entry of International Application No. PCT/US2009/069800 filed on Dec. 30, 2009, which claims benefit under 35 U.S.C. § 119(e) of U.S. Provisional Application No. 61/141,283 filed on Dec. 30, 2008, and U.S. Provisional Application No. 61/185,676 filed on Jun. 10, 2009, the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Aug. 8, 2013, is named 701039-064449_SequenceListing.txt and is 244,089 bytes in size.

BACKGROUND

Appendicitis is a condition characterized by inflammation of the appendix. All cases require removal of the inflamed appendix, either by laparotomy or laparoscopy. Untreated, mortality is high, mainly because of peritonitis and shock.

Appendicitis is among many human diseases, for which the diagnosis is complicated by the heterogeneity of its clinical presentation. Patients with many other disorders can present with symptoms similar to those of appendicitis. Examples include the following: pelvic inflammatory disease (PID) or tubo-ovarian abscess, Endometriosis, ovarian cyst or torsion, ureterolithiasis and renal colic, degenerating uterine leiomyomata, diverticulitis, Crohn's disease, colonic carcinoma, rectus sheath hematoma, cholecystitis, bacterial enteritis, mesenteric adenitis, and omental torsion. It remains the most common surgical emergency of children, with initial diagnosis accuracy additionally challenged because of non-specific but similar symptoms of many other childhood conditions. Delays in accurate diagnosis lead to increased mortality, morbidity, and costs associated with the complications of appendicitis.

The use of high resolution computed tomography (CT) to identify appendiceal inflammation was hoped to improve both the diagnosis and treatment of acute appendicitis. Though variable, these improvements have been modest at best, with rates of unnecessary appendectomies and ruptures of 3-30% and 30-45%, respectively. In addition, availability of and experience with CT limit the usefulness of this approach. Furthermore, recently its use has been re-evaluated due to concerns of cancer risk.

Development of non-invasive diagnostics are therefore needed and desirable.

SUMMARY OF THE INVENTION

The present invention generally relates to devices, kits and methods to determine acute appendicitis in a subject, such as a human subject. In particular, the inventors have discovered a set of appendicitis biomarkers which are present in a urine sample obtained from a subject with acute appendicitis. As such, one aspect of the present invention provides devices, kits and methods to detect the presence of such appendicitis biomarkers in a urine sample from a subject, such as a human subject. In some embodiments, the device is in the format of a dipstick test, in particular, a lateral flow immunoassay.

In some embodiments, an appendicitis biomarker is leucine α-2 glycoprotein (LRG). In some embodiments, an appendicitis biomarker is mannan-binding lectin serine protease 2 (MASP2). In some embodiments, an appendicitis biomarker is α-1-acid glycoprotein 1 (ORM). In some embodiments, an appendicitis biomarker is selected from the groups selected from leucine-rich α-2-glycoprotein (LRG); S100-A8 (calgranulin); α-1-acid glycoprotein 1 (ORM); plasminogen (PLG); mannan-binding lectin serine protease 2 (MASP2); zinc-α-2-glycoprotein (AZGP1); apolipoprotein D (ApoD); and α-1-antichymotrypsin (SERPINA3). In some embodiments, an appendicitis biomarker is selected from at least 1, or at least about 2, or at least about 3, or at least about 4, or at least about 5, or more than 5 of any and all combinations of appendicitis biomarkers disclosed in Table 1.

One aspect of the present invention relates to a device for detecting at least one protein biomarker in a urine sample from a subject to identify if the subject is likely to have acute appendicitis, the device comprising: (a) at least one protein-binding agent which specifically binds to at least one biomarker protein selected from the group of: leucine α-2 glycoprotein (LRG), mannan-binding lectin serine protease 2 (MASP2), α-1-acid glycoprotein 1 (ORM); and (b) at least one solid support for the at least one protein binding-agent in (a), wherein the protein-binding agent is deposited on the solid support. In some embodiments, a protein-binding agent deposited on the solid support specifically binds the leucine α-2 glycoprotein (LRG) of SEQ ID NO: 1. In another embodiment, a protein-binding agent deposited on the solid support specifically binds to the polypeptide of α-1-acid glycoprotein 1 (ORM) of SEQ ID NO: 3. In another embodiment, a protein-binding agent deposited on the solid support specifically binds to the polypeptide of mannan-binding lectin serine protease 2 (MASP2) of SEQ ID NO: 5.

In some embodiment, the device is useful for detecting multiple appendicitis biomarkers, for example where the device further comprises at least one additional different protein-binding agent deposited on the solid support, wherein the additional protein-binding agent specifically binds to a biomarker protein selected from the group consisting of: leucine-rich α-2-glycoprotein (LRG); S100-A8 (calgranulin); α-1-acid glycoprotein 1 (ORM); plasminogen (PLG); mannan-binding lectin serine protease 2 (MASP2); zinc-α-2-glycoprotein (AZGP1); Apolipoprotein D (ApoD); and α-1-antichymotrypsin (SERPINA3).

In some embodiment, the device is useful for detecting multiple appendicitis biomarkers, for example where the device further comprises at least one additional different protein-binding agent deposited on the solid support, wherein the additional protein-binding agent specifically binds to a biomarker protein selected from the group consisting of: adipocyte specific adhesion molecule; AMBP; amyloid-like protein 2; angiotensin converting enzyme 2; BAZ1B; carbonic anhydrase 1; CD14; chromogranin A; FBLN7; FXR2; hemoglobin α; hemoglobin β; interleukin-1 receptor antagonist protein; inter-α-trypsin inhibitor; lipopolysaccharide binding protein; lymphatic vessel endothelial hyaluronan acid receptor 1; MLKL; nicastrin; novel protein (Accession No: IPI00550644); PDZK1 interacting protein 1; PRIC285; prostaglandin-H2 D-isomerase; Rcl; S100-A9; serum amyloid A protein; SLC13A3; SLC2A1; SLC2A2; SLC4A1; SLC9A3; SORBS1; SPRX2; supervillin; TGFbeta2R; TTYH3; VA0D1; vascular adhesion molecule 1; versican; VIP36; α-1-acid glycoprotein 2; β-1,3-galactosyltransferase, also disclosed in Table 1.

In some embodiments, the solid support of the device is in the format of a dipstick, a microfluidic chip or a cartridge. In some embodiments, the dipstick is a lateral flaw immunoassay test strip. In some embodiments, a single test strip tests for one appendicitis biomarker, such as LRG or ORM or S100-A8. In other embodiments, a single test strip test for several appendicitis biomarkers, for example, a single test strip test for all three appendicitis biomarkers: LRG, ORM and S100-A8; or a single test strip test for two appendicitis biomarkers: LRG and ORM; LRG and S100-A8; or ORM and S100-A8.

In some embodiments, a protein-binding agent is an antibody, antibody fragment, aptamer, small molecule or variant or fragment thereof. In some embodiments, a subject is a mammalian subject such as a human subject. In some embodiments, a subject with at least one symptom of appendicitis, as disclosed herein.

In some embodiments, a protein-binding agent deposited on the device specifically binds to the specific appendicitis biomarker protein when the level of the appendicitis biomarker protein is at least 2-fold above a reference level for that appendicitis biomarker protein. Typically, a reference level for a particular appendicitis biomarker is an average level of the appendicitis biomarker protein in a plurality of urine samples from a population of healthy humans not having acute appendicitis.

Another aspect of the present invention relates to the use of a device as disclosed herein to identify if a subject has acute appendicitis, wherein if at least one biomarker specifically binds to at least one protein-binding agent, the subject is likely to have acute appendicitis.

Another aspect of the present invention provides a kit, where the kit comprises (a) a device as disclosed herein, and (b) a first agent, wherein the first agent produces a detectable signal in the presence of a protein-binding agent which deposited on the device is specifically bound to a biomarker protein. In some embodiments, a kit optionally further comprises a second agent, wherein the second agent produces a different detectable signal in the presence of a second protein-binding agent deposited on the device which is specifically bound to a second biomarker protein.

Another aspect of the present invention relates to a method to identify the likelihood of a subject to have acute appendicitis comprising: (a) measuring the level of at least one appendicitis biomarker protein selected from the group listed in Table 1 in a urine sample from the human subject; (b) comparing the level of the at least one biomarker protein measured in step (a) to a reference level for the measured appendicitis biomarker, where if the level of a measured appendicitis biomarker is at least 2-fold increased than the reference level for the particular appendicitis biomarker measured, it identifies that the subject is likely to have acute appendicitis. In some embodiments, the method can be used to guide a clinician to direct an appropriate therapy to a subject which is identified to have acute appendicitis.

In some embodiments, the method further comprises determining the level of albumin in the urine sample from the human subject. In some embodiments, the subject is a human subject and the human subject has exhibited at least one symptom of acute appendicitis.

In some embodiments, the method comprises measuring an appendicitis biomarker level by any method known by one of ordinary skill in the art, such as for example with the use of an immunoassay or an automated immunoassay, or a dipstick test, as disclosed herein. In some embodiments, the method comprises measuring the level of the appendicitis biomarker leucine α-2 glycoprotein (LRG). In some embodiments, the method comprises measuring the level of the appendicitis biomarker α-1-acid glycoprotein 1 (ORM). In some embodiments, the method comprises measuring the level of the appendicitis biomarker mannan-binding lectin serine protease 2 (MASP2).

In some embodiments, the method comprises measuring the level of at least one the appendicitis biomarker selected from a group consisting of leucine α-2 glycoprotein (LRG), calgranulin A (S100-A8), α-1-acid glycoprotein 1 (ORM), plasminogen (PLG), mannan-binding lectin serine protease 2 (MASP2), zinc-α-2-glycoprotein (AZGP1), α-1-antichymotrypsin (SERPINA3) and apolipoprotein D (ApoD).

In some embodiments, the reference level in the method is a level of the particular appendicitis biomarker measured in a urine sample of a healthy human not having acute appendicitis. In some embodiments, the reference level is an average level of the appendicitis biomarker in a plurality of urine samples from a population of healthy humans not having acute appendicitis. In some embodiments, the reference level is a normalized level of the appendicitis biomarker in a urine sample of a healthy human not having acute appendicitis, wherein the normalization is performed against the level of albumin in the urine sample of a healthy human not having acute appendicitis.

In some embodiments, the method comprises measuring the level of at least one the appendicitis biomarker in a urine sample is collected in mid-stream. In some embodiments, the method comprises measuring the level of at least one the appendicitis biomarker by depositing the urine sample from the subject on a device, such as a test strip or dipstick device, as disclosed herein.

BRIEF DESCRIPTION OF THE DRAWINGS

FIGS. 2A-2B show representative mass spectra. FIG. 2A is the relative ion intensity as a function of m/z values of precursor ions (MS), with the doubly charged peptide LDITAEILAVR from plunc labeled by arrow, and FIG. 2B is the fragmentation spectrum with fragment ions labeled as y- and b-series fragment ions (MS/MS).

FIG. 3A is a cumulative probability graph of the mass accuracy error, and FIG. 3B is the histogram of the LTQ-Orbitrap mass accuracy error, as assessed by comparison of observed masses of the trypsin autolysis peptide VATVSLPR, as compared to its expected monoisotopic mass, indicating that most peptides have apparent mass errors of less than 2 ppm.

FIG. 9A shows receiver operating characteristics of appendicitis protein biomarkers from urine validated by target mass spectrometry, demonstrating the relative diagnostic performance of leucine-rich α-2-glycoprotein (LRG), calgranulin A (S100-A8), α-1-acid glycoprotein 1 (ORM), and apolipoprotein D (ApoD). FIG. 9B shows the enrichment of LRG in a random sample of urine of patients with histologically proven appendicitis (+) as compared to those without (−) by using Western immunoblotting. LRG signal was observed in 5/5 patients with appendicitis and no signal was observed in 5/6 patients without appendicitis.

FIG. 10A is a boxplot showing the relative appendicitis protein biomarker abundance (normalized ion current units) of leucine-rich α-2-glycoprotein (LRG) (top panel) and calgranulin A (S100-A8) (bottom panel) as a function of appendicitis severity, as assessed using histologic classification. Note that the group with histologically normal appendices includes both patients who underwent appendectomies and patients without clinical diagnosis of appendicitis. FIG. 10B shows representative micrographs of appendectomy specimens and immunohistochemistry staining against LRG, demonstrating increased LRG signal in appendectomy specimens with more severe grade of appendicitis.

DETAILED DESCRIPTION OF THE INVENTION

Figure 1:
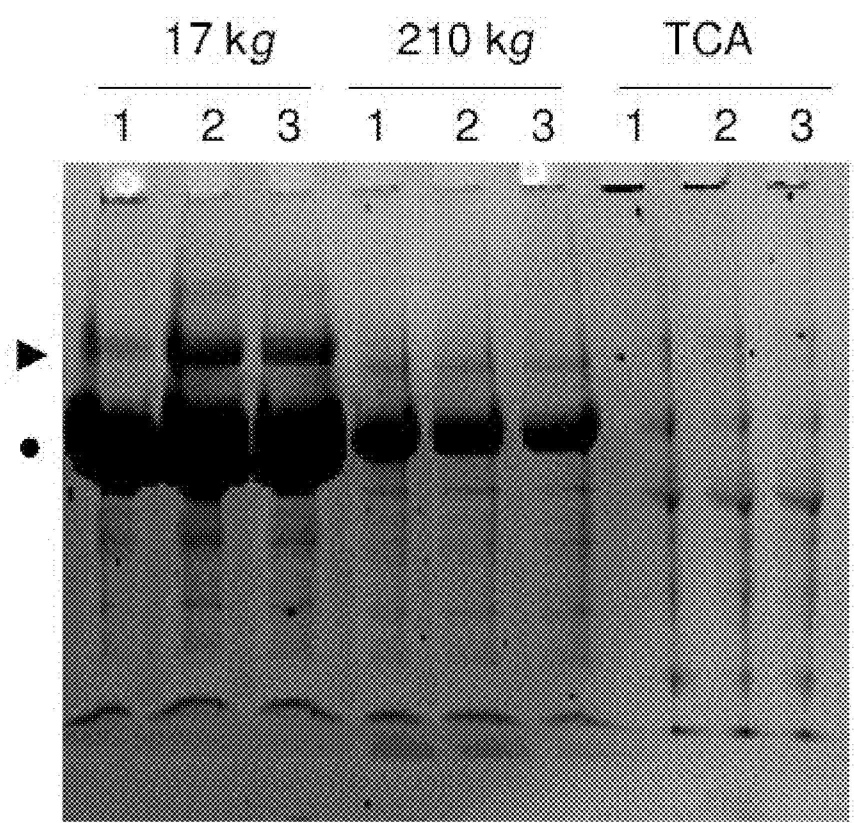
FIG. 1 is a representative SDS-PAGE separation of 17,000 g, 210,000 g, and TCA fractions of three urine specimens (1, 2, 3) demonstrating small differences in total protein abundance among different urine specimens, and preferential fractionation of albumin (●) and uromodulin (▸) in the 17,000 g fraction, enabling improved detection of the remaining urinary proteins. The majority of albumin and uromodulin appears to sediment at 17,000 g, demonstrating that they exist in high molecular weight complexes, consistent with uromodulin's ability to polymerize in urine.

Embodiments of the present invention are based on the discovery of eight biomarkers whose increase in urinary concentration correlate accurately with acute appendicitis. These eight biomarkers are leucine-rich α 2-glycoprotein (LRG), calgranulin A (S100-A8), α-1-acid glycoprotein 1 (orosomucoid) (ORM), plasminogen (PLG), mannan-binding lectin serine protease 2 (MASP2), zinc-α-2-glycoprotein (AZGP1), α-1-antichymotrypsin (SERPINA3) and apolipoprotein D (ApoD). These appendicitis biomarker proteins have been confirmed by Western immunoblotting (Example 2, FIGS. 9 and 10) and further validated by target mass spectrometry (Example 2).

Accordingly, in some embodiments, these biomarkers can be used as indicators of acute appendicitis. By simply measuring the levels of these biomarkers in a urine sample from an individual having some symptoms of acute appendicitis or that is suspected of having acute appendicitis, a physician can quickly make a diagnosis and administer appropriate medical treatment in a timely manner. When the levels of these biomarkers in an individual is greater than the reference level or reference value of the respective biomarkers, at least one order of magnitude greater than that found in healthy individual not having acute appendicitis, it is indicative that the individual is indeed having acute appendicitis.

In one embodiment, a subject or individual is a mammalian subject, such as a human.

Non-limiting symptoms of acute appendicitis include pain starting centrally (periumbilical) before localizing to the right iliac fossa (the lower right side of the abdomen); loss of appetite and fever; nausea or vomiting; the feeling of drowsiness; the feeling of general bad health; pain beginning and staying in the right iliac fossa, diarrhea and a more prolonged, smoldering course; increased frequency of urination; marked retching; tenesmus or "downward urge" (the feeling that a bowel movement will relieve discomfort); positive Rovsing's sign, Psoas sign, and/or Obturator sign.

In one embodiment, the invention provides a kit for predicting acute appendicitis in a human comprising an indicator or device that is responsive to a level of at least one biomarker in a sample of urine from a human upon contact with the sample of urine, wherein the appendicitis biomarker protein in a sample of urine is selected from a group consisting of leucine α-2 glycoprotein (LRG), calgranulin A (S100-A8), α-1-acid glycoprotein 1 (ORM), plasminogen (PLG), mannan-binding lectin serine protease 2 (MASP2), zinc-α-2-glycoprotein (AZGP1), α-1-antichymotrypsin (SERPINA3) and apolipoprotein D (ApoD), and wherein the indicator provides a positive test result when the appendicitis biomarker level exceeds a reference value.

In some embodiments, the present invention provides a kit or device for predicting acute appendicitis in a subject, (e.g. a human subject) that are responsive to at least one marker selected from the list of appendicitis biomarkers listed in Table 1. In one embodiment, the kit or device for predicting acute appendicitis in a subject is responsive to leucine α-2 glycoprotein (LRG). In one embodiment, the kit or device for predicting acute appendicitis in a subject, is responsive to leucine α-2 glycoprotein (LRG) and at least one marker selected from α-1-acid glycoprotein 1 (ORM), and/or mannan-binding lectin serine protease 2 (MASP2). In some embodiments, the kit or device for predicting acute appendicitis in a subject, is responsive to leucine α-2 glycoprotein (LRG) and at least one marker selected from the group consisting of calgranulin A (S100-A8), α-1-acid glycoprotein 1 (ORM), plasminogen (PLG), mannan-binding lectin serine protease 2 (MASP2), zinc-α-2-glycoprotein (AZGP1), α-1-antichymotrypsin (SERPINA3) and apolipoprotein D (ApoD). As used herein, the term "responsive" refers to the ability to detect the level of an appendicitis biomarkers of interest in a urine sample.

In another embodiment, the kit or device for predicting acute appendicitis in a subject, is responsive to leucine α-2 glycoprotein (LRG) and at least 1, or a least 2 or at least 3, or at least 4 or at least 5, or at least 6, or at least 7, or at least 8, or at least 9, or at least 10 other marker(s), in all and any combination, selected from the group consisting of the list of biomarkers listed in Table 1. In another embodiment, the kit or device for predicting acute appendicitis in a subject, is responsive to leucine α-2 glycoprotein (LRG) and at least one marker selected from the group consisting of adipocyte specific adhesion molecule; AMBP; amyloid-like protein 2; angiotensin converting enzyme 2; BAZ1B; carbonic anhydrase 1; CD14; chromogranin A; FBLN7; FXR2; hemoglobin α; hemoglobin β; interleukin-1 receptor antagonist protein; inter-α-trypsin inhibitor; lipopolysaccharide binding protein; lymphatic vessel endothelial hyaluronan acid receptor 1; MLKL; nicastrin; novel protein (Accession No: IPI00550644); PDZK1 interacting protein 1; PRIC285; prostaglandin-H2 D-isomerase; Rcl; S100-A9; serum amyloid A protein; SLC13A3; SLC2A1; SLC2A2; SLC4A1; SLC9A3; SORBS1; SPRX2; supervillin; TGFbeta2R; TTYH3; VA0D1; vascular adhesion molecule 1; versican; VIP36; α-1-acid glycoprotein 2; and β-1,3-galactosyltransferase.

In one embodiment, the indicator is in the form of a test strip such as a dipstick. In one embodiment, the test strip is a lateral flow immunoassay (LFIA). In one embodiment, the test strip is a double sandwich LFIA. In another embodiment, test strip is a competitive LFIA.

In one embodiment, the reference value is an average level of the appendicitis biomarker in urine samples from a population of healthy humans not having acute appendicitis. In some embodiments, healthy humans not having acute appendicitis do not exhibit any symptom associated with acute appendicitis as disclosed herein.

In one embodiment, the responsiveness of the indicator of the kit is by way of an immunoassay. In one embodiment, the immunoassay is a lateral flow immunoassay test, also known as the immunochromatographic assay, or strip test.

In one embodiment, the invention provides a method of predicting acute appendicitis in a human comprising the steps of: (a) determining the level of at least one biomarker protein in a sample of urine from the human; and comparing the level of step (a) to a reference value to determine whether the human is suffering from acute appendicitis.

In one embodiment, the invention further comprises determining the level of albumin in the sample of urine from the human.

In one embodiment, the sample of urine is collected by the human.

In one embodiment, the human exhibits at least one symptom of acute appendicitis described herein.

In one embodiment, the human had an inconclusive CT to determine inflammation of the appendix.

In one embodiment, the human did not have a CT to determine inflammation of the appendix.

In one embodiment, the determination of the appendicitis biomarker level is completed with the use of an immunoassay. In some embodiments, the immunoassay is a lateral flow immunoassay test, also known as the immunochromatographic assay, or strip test. In some embodiments, the lateral flow immunoassay is a double antibody sandwich assay, a competitive assay, a quantitative assay or variations thereof.

In one embodiment, the appendicitis biomarker protein is leucine α-2 glycoprotein (LRG). In one embodiment, the appendicitis biomarker protein is selected from a group consisting of leucine α-2 glycoprotein (LRG), calgranulin A (S100-A8), α-1-acid glycoprotein 1 (ORM), plasminogen (PLG), mannan-binding lectin serine protease 2 (MASP2), zinc-α-2-glycoprotein (AZGP1), α-1-antichymotrypsin (SERPINA3) and apolipoprotein D (ApoD). In another embodiment, the appendicitis biomarker is selected from the group of biomarkers selected from any of those listed in Table 1.

In other embodiments, for the method and kit or devices, various combinations of appendicitis biomarkers can be selected. For examples: LRG and S100-8A; LRG and ORM; ORM and S100-A8, LRG and PLG; LRG and MASP2; LRG and AZGP1; LRG and SERPINA3; LRG and ApoD; LRG, MASP2 and ORM; ORM and MASP2, LRG, S100-A8 and ORM; LRG, ORM and PLG; LRG, ORM and ApoD; LRG, S100-A8, and PLG; LRG, S100-A8, and ApoD; LRG, S100-A8, ORM and SERPINA3; LRG, S100-8A and SERPINA3; LRG, SERPINA3 and AZGP1; LRG, SERPINA3 and Apo D and so forth.

In one embodiment, the method of predicting acute appendicitis in a human comprises the step of determining the level of leucine-rich α-2-glycoprotein (LRG) in a sample of urine from the human.

In one embodiment, the method of predicting acute appendicitis in a human comprises the step of determining the levels of LRG and S100-A8 (calgranulin) in a sample of urine from the human.

In one embodiment, the method of predicting acute appendicitis in a human comprises the step of determining the levels of LRG and α-1-acid glycoprotein 1 (ORM) in a sample of urine from the human.

In one embodiment, the method of predicting acute appendicitis in a human comprises the step of determining the levels of LRG and plasminogen (PLG) in a sample of urine from the human.

In one embodiment, the method of predicting acute appendicitis in a human comprises the step of determining the levels of LRG and mannan-binding lectin serine protease 2 (MASP2) in a sample of urine from the human.

In one embodiment, the method of predicting acute appendicitis in a human comprises the step of determining the levels of LRG and zinc-α-2-glycoprotein (AZGP1) in a sample of urine from the human.

In one embodiment, the method of predicting acute appendicitis in a human comprises the step of determining the levels of LRG and apolipoprotein D (ApoD) in a sample of urine from the human.

In one embodiment, the method of predicting acute appendicitis in a human comprises the step of determining the levels of ORM and S100-A8 in a sample of urine from the human.

In one embodiment, the method of predicting acute appendicitis in a human comprises the step of determining the levels of LRG, ORM and S100-A8 in a sample of urine from the human.

In one embodiment, the method of predicting acute appendicitis in a human comprises the step of determining the levels of LRG and α-1-antichymotrypsin (SERPINA3) in a sample of urine from the human.

TABLE 1

List of appendicitis biomarkers for use in the kits, devices and methods as disclosed herein for predicting acute appendicitisin the subject, for example a human subject. The SEQ ID NO refers to the amino acid sequence encoding the protein biomarker, and are incorporated herein by reference.

| Protein biomarker | Accession no | SEQ ID |
|---|---|---|
| Leucine-rich α-2-glycoprotein (LRG) | IPI00022417 | 1 |
| S100-A8 (calgranulin) | IPI00007047 | 2 |
| α-1-acid glycoprotein 1 (ORM) | IPI00022429 | 3 |
| Plasminogen | IPI00019580 | 4 |
| Mannan-binding lectin serine protease 2 (MASP2) | IPI00306378 | 5 |
| Zinc-α-2-glycoprotein (AZGP1) | IPI00166729 | 6 |
| Apolipoprotein D (ApoD) | IPI00006662 | 7 |
| α-1-antichymotrypsin (SERPINA3) | IPI00550991 | 8 |
| Adipocyte specific adhesion molecule | IPI00024929 | 9 |
| AMBP | IPI00022426 | 10 |
| Amyloid-like protein 2 | IPI00031030 | 11 |
| Angiotensin converting enzyme 2 | IPI00465187 | 12 |
| BAZ1B | IPI00216695 | 13 |
| Carbonic anhydrase 1 | IPI00215983 | 14 |
| CD14 | IPI00029260 | 15 |
| chromogranin A | IPI00383975 | 16 |
| FBLN7 | IPI00167710 | 17 |
| FXR2 | IPI00016250 | 18 |
| Hemoglobin α | IPI00410714 | 19 |
| Hemoglobin β | IPI00654755 | 20 |
| Interleukin-1 receptor antagonist protein | IPI00000045 | 21 |
| Inter-α-trypsin inhibitor | IPI00218192 | 22 |
| Lipopolysaccharide binding protein | IPI00032311 | 23 |
| Lymphatic vessel endothelial hyaruronan acid receptor 1 | IPI00290856 | 24 |
| MLKL | IPI00180781 | 25 |
| Nicastrin | IPI00021983 | 26 |
| Novel protein | IPI00550644 | 27 |
| PDZK1 interacting protein 1 | IPI00011858 | 28 |
| PRIC285 | IPI00249305 | 29 |
| Prostaglandin-H2 D-isomerase | IPI00013179 | 30 |
| Rcl | IPI00007926 | 31 |
| S100-A9 | IPI00027462 | 32 |
| Serum amyloid A protein | IPI00552578 | 33 |
| SLC13A3 | IPI00103426 | 34 |
| SLC2A1 | IPI00220194 | 35 |
| SLC2A2 | IPI00003905 | 36 |
| SLC4A1 | IPI00022361 | 37 |
| SLC9A3 | IPI00011184 | 38 |
| SORBS1 | IPI00002491 | 39 |
| SPRX2 | IPI00004446 | 40 |
| Supervillin | IPI00412650 | 41 |
| TGFbeta2R | IPI00383479 | 42 |
| TTYH3 | IPI00749429 | 43 |
| VA0D1 | IPI00034159 | 44 |
| Vascular adhesion molecule 1 | IPI00018136 | 45 |
| Versican | IPI00009802 | 46 |
| VIP36 | IPI00009950 | 47 |
| α-1-acid glycoprotein 2 | IPI00020091 | 48 |
| β-1,3-galactosyltransferase | IPI00032034 | 49 |

In one embodiment, the reference level or reference value is a level of a appendicitis biomarker in a urine sample of a healthy human not having acute appendicitis, or not having been diagnosed with acute appendicitis. A healthy human is any person who exhibits no symptom which commonly known to be associated with acute appendicitis as described herein. In another embodiment, the reference value is an average level of the appendicitis biomarker in a plurality of urine samples from a population of healthy humans not having acute appendicitis or not having been diagnosed with acute appendicitis. A population of healthy subjects that have not been diagnosed with acute appendicitis is at least five healthy humans, at least 10 healthy humans, preferably 20 or more healthy humans. The average urine level of an appendicitis biomarker can be obtained by taking the sum of the level of an appendicitis biomarker from a number of humans divided by the number of humans.

In one embodiment, the reference level or reference value is a normalized level of the appendicitis biomarker in a urine sample of a healthy human not having acute appendicitis, wherein the normalization is performed against the level of albumin in the urine sample of a healthy human not having acute appendicitis, or not having been diagnosed with acute appendicitis. The normalized reference value for leucine α-2 glycoprotein (LRG), calgranulin A (S100-A8), α-1-acid glycoprotein 1 (ORM), plasminogen (PLG), mannan-binding lectin serine protease 2 (MASP2), Zinc-α-2-glycoprotein (AZGP1), α-1-antichymotrypsin (SERPINA3) and apolipoprotein D (ApoD) is 0.001. When the normalized value for any of the described biomarker from a human is at least one order of magnitude greater that the normalized reference value, i.e. 0.01 and greater, this is indicative that the human has acute appendicitis.

In one embodiment, the urine sample is collected in mid-stream.

In one embodiment, the urine sample is obtained by depositing the urine on to a test strip. In one embodiment, the test strip is a lateral flow immunoassay test, also known as the immunochromatographic assay. In some embodiments, the lateral flow immunoassay is a double antibody sandwich assay, a competitive assay, a quantitative assay or variations thereof (See FIGS. 11-19).

Appendicitis Biomarker Proteins

As discussed herein, in some embodiments, the present invention provides kits or devices for predicting acute appendicitis in a subject, for example, a human subject that is responsive to at least one appendicitis biomarker selected from the list of appendicitis biomarkers listed in Table 1. In one embodiment, the kit or device for predicting acute appendicitis in a subject is responsive to leucine α-2 glycoprotein (LRG). In one embodiment, the kit or device for predicting acute appendicitis in a subject, is responsive to leucine α-2 glycoprotein (LRG) and at least one marker selected from α-1-acid glycoprotein 1 (ORM), and/or mannan-binding lectin serine protease 2 (MASP2).

LRG:

leucine-rich alpha-2-glycoprotein 1 (LRG) is also known in the art as LRG; HMFT1766; LRG1. The leucine-rich repeat (LRR) family of proteins, including LRG1, has been shown to be involved in protein-protein interaction, signal transduction, and cell adhesion and development. LRG1 is expressed during granulocyte differentiation.

In some embodiments, LRG can be detected in the methods, kits and devices using commercially available assay kits, e.g., from Immuno-Biological Laboratories, Inc., Human LRG Assay Kit, catalog number 27769. LRG can also be detected using the kits as disclosed in U.S. patent application Ser. No. 11/627,164 filed Jan. 25, 2007, and provisional patent application 60/761,808 filed Jan. 25, 2006, which are incorporated herein in their entirety by reference.

Commercial polyclonal and monoclonal antibodies against LRG are also useful as protein-binding agents to LRG and are available from a variety of companies, e.g., but not limited to Assay Designs, SIGMA-ALDRICH and Novus Biologicals.

Antibodies or protein binding agents which recognize and specifically bind the LRG1 protein of SEQ ID NO: 1, the sequence of which is reproduced below, can be readily produced by one of ordinary skill in the art and are useful for the methods, kits and devices as disclosed herein. SEQ ID NO: 1 is the polypeptide sequence for LRG (Leucine-rich alpha-2-glycoprotein) and has the amino acid sequence as follows:

```
MSSWSRQRPKSPGGIQPHVSRTLFLLLLLAASAWGVTLSPKDCQVFRSD

HGSSISCQPPAEIPGYLPADTVHLAVEFFNLTHLPANLLQGASKLQELH

LSSNGLESLSPEFLRPVPQLRVLDLTRNALTGLPPGLFQASATLDTLVL

KENQLEVLEVSWLHGLKALGHLDLSGNRLRKLPPGLLANFTLLRTLDLG

ENQLETLPPDLLRGPLQLERLHLEGNKLQVLGKDLLLPQPDLRYLFLNG
```

-continued

```
NKLARVAAGAFQGLRQLDMLDLSNNSLASVPEGLWASLGQPNWDMRDGF

DISGNPWICDQNLSDLYRWLQAQKDKMFSQNDTRCAGPEAVKGQTLLAV

AKSQ
```

S100A8:

S100A8 is also known in the art as synonyms 60B8AG; CAGA; CFAG; CGLA; CP-10; L1Ag; MA387; MIF; Migration inhibitory factor-related protein 8 (MRP8); NIF; OTTHUMP00000015329; OTTHUMP00000015330; P8; S100 calcium-binding protein A8; S100 calcium-binding protein A8 (calgranulin A); S100A8; calgranulin A; cystic fibrosis antigen.

Without wishing to be bound by theory, S100 calcium binding protein A8 (S100 A8), also known as migration inhibitory factor-related protein (MRP-8) belongs to the S-100 family of calcium binding proteins associated with myeloid cell differentiation. They are highly expressed in resting neutrophils, keratinocytes (particularly in psoriasis), in infiltrating tissue macrophages and on epithelial cells in active inflammatory disease. The heterogeneity of macrophage subpopulations in chronic or acute inflammation is reflected by different expression of MRP8 and migration inhibitory factor-related proteins-14 (MRP14). Phagocytes expressing MRP8 and MRP14 belong to the early infiltrating cells, while MRP8 alone is found in chronic inflammatory tissues. The partially antagonistic functions of MRP8, MRP14 and of the $Ca^{2+}$-dependent MRP8/14 heterocomplex makes them versatile mediators.

Human S100A8 (MRP8) has a molecular weight of 11.0 kD, while human MRP14 exists in a 13.3 kD and a truncated 12.9 kD form. $Ca2^{+}$ induces the formation of heterocomplexes of the form (MRP8)(MRP14) (abbreviated MRP8/14), (MRP8)2(MRP14), and (MRP8/14)2. There are two EF-hand motifs each on MRP8 and MRP14. MRP14 shows a higher affinity for calcium than MRP8, and the affinity of the C terminal EF2 is higher than that of the N-terminal EF1. The C-terminal domain also mainly determines the specificity of dimerization. The helix in EF2 undergoes a large conformational change upon calcium binding and may play a role as a trigger for $Ca^{2+}$ induced conformational change.

In some embodiments, S100A8 can be detected in the methods, kits and devices using commercial assays, such as, but without limitation, S100A8 assay kits from R & D Systems's Human MIF QUANTIKINE® ELISA Kit•Catalog number: DMF00; and BMA Biomedicals, MRP8 Enzyme Immunoassay Product Code: S-1007. S100A8 can also be detected using the kits as disclosed in U.S. Pat. No. 7,501,256 and WO/2006/012588 which is incorporated herein in its entirety by reference.

In some embodiments, commercial polyclonal and monoclonal antibodies against S100A8 are also useful as protein-binding agents to S100A8 and are available from a variety of companies, e.g., but not limited to commercial polyclonal and monoclonal antibodies against S100A8 are available from a variety of companies, e.g. Assay Designs, SIGMA-ALDRICH, R & D Systems, Novus Biologicals and Santa Cruz Biotechnology.

Antibodies or protein binding agents which recognize and specifically bind the S100 A8 protein of SEQ ID NO: 2, the sequence of which is reproduced below, can be readily produced by one of ordinary skill in the art and are useful for the methods, kits and devices as disclosed herein.

SEQ ID NO: 2 is the polypeptide sequence for S100 A8 and has the amino acid sequence as follows:

```
MLTELEKALNSIIDVYHKYSLIKGNFHAVYRDDLKKLLETECPQYIRKK

GADVWFKELDINTDGAVNFQEFLILVIKMGVAAHKKSHEESHKE
```

ORM:

alpha-1-acid-glycoprotein 1 (ORM) is also known in the art as orosomucoid 1, AGP1; AGP-A; ORM1. This gene encodes a key acute phase plasma protein. Because of its increase due to acute inflammation, this protein is classified as an acute-phase reactant. The specific function of this protein has not yet been determined; however, it may be involved in aspects of immunosuppression.

In some embodiments, ORM can be detected in the methods, kits and devices using commercial assays, such as, but without limitation, Human Orosomucoid ELISA Quantitation Kit from GenWay Biotech, Inc. catalog No. 40-288-22927F.

In some embodiments, commercial polyclonal and monoclonal antibodies against ORM are also useful as protein-binding agents to ORM and are available from a variety of companies, e.g., but not limited to Assay Designs, SIGMA-ALDRICH, Novus Biologicals, Lifespan Biosciences, R & D Systems, and Santa Cruz Biotechnology Antibodies or protein binding agents which recognize and specifically bind the ORM protein of SEQ ID NO: 3, the sequence of which is reproduced below, can be readily produced by one of ordinary skill in the art and are useful for the methods, kits and devices as disclosed herein. SEQ ID NO: 3 is the polypeptide sequence for ORM and has the amino acid sequence as follows:

```
MALSWVLTVLSLLPLLEAQIPLCANLVPVPITNATLDQITGKWFYIASA

FRNEEYNKSVQEIQATFFYFTPNKTEDTIFLREYQTRQDQCIYNTTYLN

VQRENGTISRYVGGQEHFAHLLILRDTKTYMLAFDVNDEKNWGLSVYAD

KPETTKEQLGEFYEALDCLRIPKSDVVYTDWKKDKCEPLEKQHEKERKQ

EEGES
```

Plasminogen (PLG):

Plasminogen, is also known in the art as PLG or DKFZp779M0222 and is a circulating zymogen that is converted to the active enzyme plasmin by cleavage of the peptide bond between arg560 and val561, which is mediated by urokinase (PLAU; MIM 191840) and tissue plasminogen activator (PLAT; MIM 173370). The main function of plasmin is to dissolve fibrin (see, e.g., FGA, MIM 134820) clots. Plasmin, like trypsin, belongs to the family of serine proteinases.

In some embodiments, PLG can be detected in the methods, kits and devices using commercial assays, such as, but without limitation, commercial assay kits from Human Plasminogen ELISA Kit from Alpco Diagnostics 41-PLAHU-E01; Human Plasminogen ELISA Kit from AMERICAN DIAGNOSTICA, 640; Plasminogen Colorimetric Assay Kit from AMERICAN DIAGNOSTICA, 851; Human Plasminogen total antigen ELISA Assay Kit from Innovative Research, IHPLGKT-TOT. PLG can also be detected using the kits as disclosed in International Patent Application WO/1991/005257 and European Patent Application EP1990914430 which is incorporated herein in its entirety by reference.

In some embodiments, commercial polyclonal and monoclonal antibodies against PLG are also useful as protein-binding agents to PLG and are available from a variety of companies, e.g., but not limited to Rockland, Abcam, Assay Designs, EMD Biosciences, SIGMA-ALDRICH, Novus Biologicals, Lifespan Biosciences, R & D Systems, and Santa Cruz Biotechnology.

Antibodies or protein binding agents which recognize and specifically bind the PLG protein of SEQ ID NO: 4, the sequence of which is reproduced below, can be readily produced by one of ordinary skill in the art and are useful for the methods, kits and devices as disclosed herein. SEQ ID NO: 4 is the polypeptide sequence for PLG and has the amino acid sequence as follows:

```
MEHKEVVLLLLLFLKSGQGEPLDDYVNTQGASLFSVTKKQLGAGSIEEC

AAKCEEDEEFTCRAFQYHSKEQQCVIMAENRKSSIIIRMRDVVLFEKKV

YLSECKTGNGKNYRGTMSKTKNGITCQKWSSTSPHRPRFSPATHPSEGL

EENYCRNPDNDPQGPWCYTTDPEKRYDYCDILECEEECMHCSGENYDGK

ISKTMSGLECQAWDSQSPHAHGYIPSKFPNKNLKKNYCRNPDRELRPWC

FTTDPNKRWELCDIPRCTTPPPSSGPTYQCLKGTGENYRGNVAVTVSGH

TCQHWSAQTPHTHNRTPENFPCKNLDENYCRNPDGKRAPWCHTTNSQVR

WEYCKIPSCDSSPVSTEQLAPTAPPELTPVVQDCYHGDGQSYRGTSSTT

TTGKKCQSWSSMTPHRHQKTPENYPNAGLTMNYCRNPDADKGPWCFTTD

PSVRWEYCNLKKCSGTEASVVAPPPVVLLPDVETPSEEDCMFGNGKGYR

GKRATTVTGTPCQDWAAQEPHRHSIFTPETNPRAGLEKNYCRNPDGDVG

GPWCYTTNPRKLYDYCDVPQCAAPSFDCGKPQVEPKKCPGRVVGGCVAH

PHSWPWQVSLRTRFGMHFCGGTLISPEWVLTAAHCLEKSPRPSSYKVIL

GAHQEVNLEPHVQEIEVSRLFLEPTRKDIALLKLSSPAVITDKVIPACL

PSPNYVVADRTECFITGWGETQGTFGAGLLKEAQLPVIENKVCNRYEFL

NGRVQSTELCAGHLAGGTDSCQGDSGGPLVCFEKDKYILQGVTSWGLGC

ARPNKPGVYVRVSRFVTWIEGVMRNN
```

MASP2:

mannan-binding lectin serine peptidase 2 (MASP2) is also known in the art as aliases sMAP; MAP19; MASP-2; MASP2 and is a Ra-reactive factor (RARF) which is a complement-dependent bactericidal factor that binds to the Ra and R2 polysaccharides expressed by certain enterobacteria. Alternate splicing of this gene results in two transcript variants encoding two RARF components that are involved in the mannan-binding lectin pathway of complement activation. The longer isoform is cleaved into two chains which form a heterodimer linked by a disulfide bond. The encoded proteins are members of the trypsin family of peptidases.

In some embodiments, MASP2 can be detected in the methods, kits and devices using commercial assays, such as, but without limitation, commercial assay kits such as Human MASP-2 ELISA Kit from Cell Sciences, HK326. MASP2 can also be detected using the kits as disclosed in International Patent Application WO/2007/028795 which is incorporated herein in its entirety by reference.

In some embodiments, commercial polyclonal and monoclonal antibodies against MASP2 are also useful as protein-binding agents to MASP2 and are available from a variety of companies, e.g., but not limited to Cell Sciences, USBIO, and Santa Cruz Biotechnology.

Antibodies or protein binding agents which recognize and specifically bind the MASP2 protein of SEQ ID NO: 5, the sequence of which is reproduced below, can be readily produced by one of ordinary skill in the art and are useful for the methods, kits and devices as disclosed herein.
SEQ ID NO: 5 is the polypeptide sequence for MASP5 and has the amino acid sequence as follows:

```
MRLLTLLGLLCGSVATPLGPKWPEPVFGRLASPGFPGEYANDQERRWTL

TAPPGYRLRLYFTHFDLELSHLCEYDFVKLSSGAKVLATLCGQESTDTE

RAPGKDTFYSLGSSLDITFRSDYSNEKPFTGFEAFYAAEDIDECQVAPG

EAPTCDHHCHNHLGGFYCSCRAGYVLHRNKRTCSEQSL
```

AZGP1:

alpha-2-glycoprotein 1 (AZGP1) is also known in the art as aliases zinc-alpha-2-glycoprotein (ZAG); ZA2G; AZGP1, Azgp1, ZNGP1 and lipid-Mobilizing Factor (LMF). AZGP1 is a soluble 41 kDa glycoprotein belonging to the immunoglobuline protein family and consisting of a single polypeptide chain. Human ZAG shares 59% sequence identity with the murine homolog. AZGP1 is closely related to antigens of the class1 major histocompatibility complex (MHC I) and shares 30-40% sequence identity with the heavy chain of MHC I. Most MHC-I members heterodimerize with beta-2-microglobuline (b2m) and bind peptides derived from intracellular proteins to present them to cytotoxic T cells. In contrast, AZGP1 is a soluble protein rather than being anchored to plasma membranes that acts independently on b2m and binds the hydrophobic ligand which may relate to its function in lipid metabolism.

AZGP1 is widespread in body fluids and is also found in various human tissues such as adipose tissue, prostate, breast, skin, salivary gland, trachea, broncheus, lung, gastrointestinal tract, pancreas, liver and kidney. AZGP1 acts as a lipid mobilizing factor to induce lipolysis in adipocytes and plays an important role in lipid utilization and loss of adipose tissue, especially during cachexia, which occurs in patient suffering from cancer, AIDS and other chronic illnesses. The role of AZGP1 in cancer cachexia is also connected with its ability to directly influence expression of uncoupling proteins (UCPs) which are implicated in the regulation of energy balance. In human adipocytes, AZGP1 expression is regulated particularly through TNF-alpha and the PPAR gamma nuclear receptor. AZGP1 expression is also upregulated by glucocorticoides and attenuated by eicosapentaenoic acid (EPA) and beta-3-adrenoreceptor antagonists.

AZGP1 is overexpressed in certain human malignant tumors such as prostate, breast, lung or bladder cancer and can relate to tumor differentiation. Additionally, AZGP1 plays a role in obesity, diabetic kidney disorders, frontotemporal dementia and regulation of melanin production by melanocytes. AZGP1 is proposed to have a therapeutic use in obesity and cachexia. It can be used as a marker for clinical analysis of diabetic nephropathy and as a marker for certain tumors.

In some embodiments, AZGP1 can be detected in the methods, kits and devices using commercial assays, such as, but without limitation, Human Zinc-Alpha-2-Glycoprotein (ZA2G, ZAG) ELISA Kit, HRP Detection, from BioVendor Laboratory Medicine, Inc., RD191093100R, The assay is intended for the determination of human Zinc-alpha-2-glycoprotein in serum, plasma, cerebrospinal fluid, urine and cell lysate; Human/Mouse/Rat ZAG EIA Kit from Raybiotech, Inc or Biovendor lab medicine Inc., EIA-ZAG-1.

In some embodiments, commercial polyclonal and monoclonal antibodies against AZGP1 are also useful as protein-binding agents to AZGP1 and are available from a variety of companies, e.g., but not limited to Abcam (Zinc Alpha 2 Glycoprotein antibody, catalog #ab47116) and Novus Biologicals (AZGP1 Antibody, catalog #H00000563-B01). Cell Sciences, USBIO, and Santa Cruz Biotechnology.

Antibodies or protein binding agents which recognize and specifically bind the AZGP1 protein of SEQ ID NO: 6, the sequence of which is reproduced below, can be readily produced by one of ordinary skill in the art and are useful for the methods, kits and devices as disclosed herein.
SEQ ID NO: 6 is the polypeptide sequence for AZGP1 and has the amino acid sequence as follows:

```
MVRMVPVLLSLLLLLGPAVPQENQDGRYSLTYIYTGLSKHVEDVPAFQA

LGSLNDLQFFRYNSKDRKSQPMGLWRQVEGMEDWKQDSQLQKAREDIFM

ETLKDIVEYYNDSNGSHVLQGRFGCEIENNRSSGAFWKYYYDGKDYIEF

NKEIPAWVPFDPAAQITKQKWEAEPVYVQRAKAYLEEECPATLRKYLKY

SKNILDRQDPPSVVVTSHQAPGEKKKLKCLAYDFYPGKIDVHWTRAGEV

QEPELRGDVLHNGNGTYQSWVVVAVPPQDTAPYSCHVQHSSLAQPLVVP

WEAS
```

APOD: Apolipoprotein D (ApoD or APOD) is a polypeptide which is a high density lipoprotein that has no marked similarity to other apolipoprotein sequences. It has a high degree of homology to plasma retinol-binding protein and other members of the alpha 2 microglobulin protein superfamily of carrier proteins, also known as lipocalins. This glycoprotein is closely associated with the enzyme lecithin: cholesterol acyltransferase—an enzyme involved in lipoprotein metabolism.

In some embodiments, ApoD can be detected in the methods, kits and devices using as disclosed in International Patent Application WO/1996/019500 or U.S. Pat. No. 5,804,368 or 5,804,368 or European Patent EP0301667 which are incorporated herein in their entirety by reference.

Antibodies or protein binding agents which recognize and specifically bind the ApoD protein of SEQ ID NO: 7, the sequence of which is reproduced below, can be readily produced by one of ordinary skill in the art and are useful for the methods, kits and devices as disclosed herein.
SEQ ID NO: 7 is the polypeptide sequence for ApoD and has the amino acid sequence as follows:

```
MVMLLLLLSALAGLFGAAEGQAFHLGKCPNPPVQENFDVNKYLGRWYE

IEKIPTTFENGRCIQANYSLMENGKIKVLNQELRADGTVNQIEGEATP

VNLTEPAKLEVKFSWFMPSAPYWILATDYENYALVYSCTCIIQLFHVD

FAWILARNPNLPPETVDSLKNILTSNNIDVKKMTVTDQVNCPKLS
```

SERPINA3:

α-1-antichymotrypsin (SERPINA3) is also known in the art as aliases serpin peptidase inhibitor, Glade A (alpha-1 antiproteinase, antitrypsin), member 3, ACT; AACT; GIG24; GIG25 and MGC88254. The SERPINA3 polypeptide is a plasma protease inhibitor and member of the serine protease inhibitor class. Polymorphisms in this protein appear to be tissue specific and influence protease targeting.

Variations in this protein's sequence have been implicated in Alzheimer's disease, and deficiency of this protein has been associated with liver disease. Mutations have been identified in patients with Parkinson disease and chronic obstructive pulmonary disease.

In some embodiments, SERPINA3 can be detected in the methods, kits and devices using as disclosed in International Patent Application WO/2005/039588 which is incorporated herein in its entirety by reference.

In some embodiments, commercial polyclonal and monoclonal antibodies against SERPINA3 are also useful as protein-binding agents to SERPINA3 and are available from a variety of companies, e.g., but not limited to Proteintech Group, Lifespan Biosciences, and Santa Cruz Biotechnology.

Antibodies or protein binding agents which recognize and specifically bind the SERPINA3 protein of SEQ ID NO: 8, the sequence of which is reproduced below, can be readily produced by one of ordinary skill in the art and are useful for the methods, kits and devices as disclosed herein.

SEQ ID NO: 8 is the polypeptide sequence for SERPINA3 and has the amino acid sequence as follows:

```
MKIHYSRQTALESTSYIQLPEAELRMERMLPLLALGLLAAGFCPAVLC

HPNSPLDEENLTQENQDRGTHVDLGLASANVDFAFSLYKQLVLKAPDK

NVIFSPLSISTALAFLSLGAHNTTLTEILKGLKFNLTETSEAEIHQSF

QHLLRTLNQSSDELQLSMGNAMFVKEQLSLLDRFTEDAKRLYGSEAFA

TDFQDSAAAKKLINDYVKNGTRGKITDLIKDLDSQTMMVLVNYIFFKA

KWEMPFDPQDTHQSRFYLSKKKWVMVPMMSLHHLTIPYFRDEELSCTV

VELKYTGNASALFILPDQDKMEEVEAMLLPETLKRWRDSLEFREIGEL

YLPKFSISRDYNLNDILLQLGIEEAFTSKADLSGITGARNLAVSQVVH

KAVLDVFEEGTEASAATAVKITLLSALVETRTIVRFNRPFLMIIVPTD

TQNIFFMSKVTNPKQA
```

Measuring Levels of Appendicitis Biomarker Proteins

In embodiments of the invention, the level of appendicitis biomarker proteins, such as those disclosed in Table 1, and in particular, the following appendicitis biomarker: leucine α-2 glycoprotein (LRG), calgranulin A (S100-A8), α-1-acid glycoprotein 1 (ORM), plasminogen (PLG), mannan-binding lectin serine protease 2 (MASP2), zinc-α-2-glycoprotein (AZGP1), α-1-antichymotrypsin (SERPINA3) or apolipoprotein D (ApoD), is measured to obtain a determination of whether a human patient has acute appendicitis. A urinary biomarker protein level can be measured using any assay known to those of ordinary skilled in the art, including, but not limited to, Enzyme-Linked Immunosorbent Assay (ELISA), immunoprecipitation assays, radioimmunoassay, mass spectrometry, Western Blotting, and via dipsticks using conventional technology.

For purposes of comparison, the levels of an appendicitis biomarker protein in a urine sample from the patient should be measured in the same manner as the reference value is measured. For example, the levels of appendicitis biomarker proteins can be represented in arbitrary units dependent upon the assay used to measure the levels of appendicitis biomarker proteins, e.g., the intensity of the signal from the detectable label can correspond to the amount of appendicitis biomarker proteins present (e.g. as determined by eye, densitometry, an ELISA plate reader, a luminometer, or a scintillation counter).

The levels of an appendicitis biomarker protein present in a urine sample can be determined using any protein-binding agent. In some embodiments, a protein-binding agent is a ligand that specifically binds to an appendicitis biomarker protein, and can be for example, a synthetic peptide, chemical, small molecule, or antibody or antibody fragment or variants thereof. In some embodiments, a protein-binding agent is a ligand or antibody or antibody fragment, and in some embodiments, a protein-binding agent is preferably detectably labeled.

In one embodiment of the invention, immunoassays using antibodies are used to measure the levels of biomarker proteins in urine. As used herein, the term "antibody" is intended to include immunoglobulin molecules and immunologically active determinants of immunoglobulin molecules, e.g., molecules that contain an antigen binding site which specifically binds (immunoreacts with) to the appendicitis biomarker to be measured. The term "antibody" is intended to include whole antibodies, e.g., of any isotype (IgG, IgA, IgM, IgE, etc), and includes fragments thereof which are also specifically reactive with the appendicitis biomarker proteins to be measured, e.g. leucine α-2 glycoprotein (LRG), calgranulin A (S100-A8), α-1-acid glycoprotein 1 (ORM), plasminogen (PLG), mannan-binding lectin serine protease 2 (MASP2), zinc-α-2-glycoprotein (AZGP1), α-1-antichymotrypsin (SERPINA3) or apolipoprotein D (ApoD). Antibodies can be fragmented using conventional techniques. Thus, the term "antibody" includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody" includes polyclonal, monoclonal, or other purified preparations of antibodies and recombinant antibodies. The term "antibody" is further intended to include humanized antibodies, bispecific antibodies, and chimeric molecules having at least one antigen binding determinant derived from an antibody molecule. In one embodiment, the antibody is detectably labeled.

Antibodies to the appendicitis biomarker proteins can be generated using methods known to those skilled in the art. Alternatively, commercially available antibodies can be used. Antibodies to LRG, S100-A8, ORM1, PLG, MASP2, AZGP1, ApoD and SERPINA3 are commercially available.

As used herein "detectably labeled", includes antibodies that are labeled by a measurable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, HIS, or biotin.

In the diagnostic methods of the invention that use an antibody for the detection of biomarker proteins levels, the level of biomarker proteins present in the urine samples correlates to the intensity of the signal emitted from the detectably labeled antibody.

In one embodiment, the antibody is detectably labeled by linking the antibody to an enzyme. The enzyme, in turn, when exposed to it's substrate, will react with the substrate in such a manner as to produce a chemical moiety which can be detected, for example, by spectrophotometric, fluorometric, or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. Chemiluminescence is another method that can be used to detect an antibody.

Detection can also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by audoradiography. Isotopes which are particularly useful for the purpose of the present invention are $^{3}H$, $^{131}I$, $^{35}S$, $^{14}C$, and preferably $^{125}I$.

It is also possible to label an antibody with a fluorescent compound. When the fluorescently labeled antibody is exposed to light of the proper wave length, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as $^{152}Eu$, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

In one embodiment, the levels of biomarker proteins in urine are detected by an immunoassay. Immunoassays include but are not limited to enzyme immunoassay (EIA), also called enzyme-linked immunosorbant assay (ELISA), radioimmunoassay (RIA), diffusion immunoassay (DIA), fluoroimmunoassay (FIA), chemiluminescent immunoassay (CLIA), counting immunoassay (CIA), lateral flow tests or immunoassay (LFIA), also known as lateral flow immunochromatographic assays, and magnetic immunoassay (MIA).

An immunoassay is a biochemical test that measures the concentration of a substance in a biological sample, typically serum or urine, using the reaction of an antibody or antibodies to its antigen. The assay takes advantage of the specific binding of an antibody to its antigen. Monoclonal antibodies are often used as they only usually bind to one site of a particular molecule, and therefore provide a more specific and accurate test, which is less easily confused by the presence of other molecules. The antibodies picked must have a high affinity for the antigen (if there is antigen available, a very high proportion of it must bind to the antibody).

For numerical results, the response of the biological sample being measured must be compared to standards of a known concentration. This is usually done through the plotting of a standard curve on a graph, the position of the curve at response of the unknown is then examined, and so the quantity of the unknown found. Alternatively, a defined amount of antibody is used in the assay where the defined amount of antibody binds completely to a fixed amount of antigen. This fixed amount of antigen is the reference level of biomarker in the urine. Thus, this defined amount of antibody is used to indicate whether the amount of antigen in the biological sample is at least at, below or above the reference level of biomarker (See FIGS. 11-12).

Detecting the quantity of antigen in the biological sample can be achieved by a variety of methods. One of the most common is to label either the antigen or the antibody. The label can consist of an enzyme (see enzyme immunoassay (EIA)), colloidal gold (lateral flow assays), radioisotopes such as I-$^{125}$ Radioimmunoassay (RIA), magnetic labels (magnetic immunoassay—MIA) or fluorescence. Other techniques include agglutination, nephelometry, turbidimetry and Western Blot.

In one embodiment, the immunoassay is a competitive immunoassay. In another embodiment, the immunoassay is a noncompetitive immunoassay.

Immunoassays can be divided into those that involve labeled reagents and those which involve non-labeled reagents. Those which involve labeled reagents are divided into homogenous and heterogeneous (which require an extra step to remove unbound antibody or antigen from the site, usually using a solid phase reagent) immunoassays. Heterogeneous immunoassays can be competitive or non-competitive.

In a competitive immunoassay, the antigen in the unknown sample competes with labeled antigen to bind with antibodies. The amount of labeled antigen bound to the antibody site is then measured. In this method, the response will be inversely proportional to the concentration of antigen in the unknown. This is because the greater the response, the less antigen in the unknown was available to compete with the labeled antigen.

In noncompetitive immunoassays, also referred to as the "sandwich assay," antigen in the unknown, e.g. urine sample, is bound to a first antibody site, then second antibody that is labeled is bound to the antigen, forming a sandwich. The amount of labeled antibody on the site is then measured. Unlike the competitive method, the results of the noncompetitive method will be directly proportional to the concentration of the antigen. This is because labeled antibody will not bind if the antigen is not present in the unknown sample, e.g urine sample.

In one embodiment, the levels of biomarker proteins in urine are detected by ELISA assay. There are different forms of ELISA which are well known to those skilled in the art, e.g. standard ELISA, competitive ELISA, and sandwich ELISA. The standard techniques for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

Enzyme-linked immunosorbent assay, also called ELISA, enzyme immunoAssay or EIA, is a biochemical technique used mainly in immunology to detect the presence of an antibody or an antigen in a sample. The ELISA has been used as a diagnostic tool in medicine and plant pathology, as well as a quality control check in various industries. For the methods described herein, in the ELISA a known amount of anti-biomarker antibody is affixed to a solid surface, and then the sample, e.g. urine, containing the biomarker of interest is washed over the surface so that the antigen biomarker can bind to the immobilized antibodies (a first antibody). The surface is washed to remove any unbound biomarker and also any non-biomarker proteins present in the urine sample. A detection antibody (a second antibody) is applied to the surface. The detection antibody is specific to antibodies from the subject. For example, if the subject is a human, the detection antibody should be an anti-human IgG antibody. If the subject is a dog, the detection antibody then should an anti-dog IgG antibody. This detection antibody can be linked to an enzyme, and in the final step a substance is added that the enzyme can convert to some detectable signal. For example, in the case of fluorescence ELISA, when light is shone upon the sample, any antigen/antibody complexes will fluoresce so that the amount of antibodies in the sample can be measured.

The following is a general standard protocol for setting up and performing an indirect enzyme-linked immunosorbent assay. Using 96-well microtiter plates (Falcon Pro-Bindassay plate 3915; Becton Dickinson, Paramus, N.J.), test wells are coated with anti-biomarker antibody by incubation with 100 μl of purified anti-LRG antibody (31 g/ml in PBS) per well overnight at room temperature, with PBS substituted for the antibody in control wells. After the plates have been washed three times with PBS-Tween, 250 μl of 2% BSA in PBS is added to each well, and the plates are incubated for 1 h at room temperature. The plates are washed three times with PBS-Tween and incubated for 1 h at room temperature with test urine sample and control urine sample from healthy individuals diluted 1:100 in PBS-Tween-BSA; each urine sample is tested in triplicate in anti-LRG antibody-coated wells as well as in PBS control wells. The plate is then assayed (with appropriate controls) for the presence and/or the level of LRG by incubation for 1 h at room temperature with 100 μl of goat anti-LRG IgG conjugated with horseradish peroxidase (Bio-Rad, Richmond, Calif.) per well diluted 1:2,000 in PBS-Tween-BSA. After three washes in PBS-Tween, the substrate solution (o-phenylenediamine dihydrochloride; Sigma) is added to each well. The plates are then incubated for 30 min at room temperature in darkness, and the reaction is terminated by the addition of 2N sulfuric acid. The optical density values at 490 nm (OD490) are measured in a micro plate ELISA reader. For each urine sample, mean OD490 readings are calculated for the test wells and for the antigen control wells, the latter being subtracted from the former to obtain the net ELISA value.

Performing an ELISA involves at least one antibody with specificity for a particular biomarker. A known amount of anti-biomarker antibody is immobilized on a solid support (usually a polystyrene micro titer plate) either non-specifically (via adsorption to the surface) or specifically (via capture by another antibody specific to the anti-biomarker antibody, in a "sandwich" ELISA). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified anti-biomarker antibody is coated on the solid phase of multi-wells. Urine sample, a defined amount of purified biomarker and horseradish peroxidase labeled with anti-biomarker antibody (secondary detection conjugated antibody) are added to coated wells to form competitive combination. After incubation, if the biomarker level in the urine sample is high, a complex of biomarker-anti-biomarker antibody-anti-biomarker antibody labeled with HRP will form. Washing the wells will remove the complex. Incubation with TMB (3,3',5,5'-tetramethylbenzidene) will result in color development substrate for the localization of horseradish peroxidase-conjugated antibodies in the wells. There will be no color change or little color change. If the biomarker level in the urine sample is low, there will be much color change. Such a competitive ELSA test is specific, sensitive, reproducible and easy to operate.

In one embodiment, the levels of appendicitis biomarker proteins are determined by contacting a urine sample with a first antibody that specifically binds to a biomarker protein to be measured under conditions permitting formation of a complex between the antibody and the appendicitis biomarker proteins (e.g. LRG, S100-A8, ORM1, PLG, MASP2, AZGP1, ApoD and SERPINA3). The amount of complex formed is then measured as a measure of the level of the appendicitis biomarker protein, and the amount of complex formed is compared to the amount of complex formed between the first antibody and a predetermined reference amount of the appendicitis biomarker protein. This predetermined reference level amount of the appendicitis biomarker protein is the amount found in the urine of healthy humans. A level above the reference level amount of an appendicitis biomarker protein indicates that the human has acute appendicitis.

In one embodiment, the first antibody is detectably labeled. Detectably labeling the first antibody is appropriate for use, for example, in standard ELISA assays where biomarker protein is absorbed to an ELISA plate, or in Western Blot analysis, or certain LFIA dipstick analyses.

In one embodiment, the first antibody is immobilized on a solid support, for example, when using a "Sandwich ELISA" or a dipstick analysis, then the amount of complex formed can measured by detecting binding of a second antibody that specifically binds to the appendicitis biomarker protein (e.g. LRG, S100-A8, ORM1, PLG, MASP2, AZGP1, ApoD and SERPINA3) under conditions permitting formation of a complex between the second antibody and the appendicitis biomarker protein, wherein the second antibody does not substantially cross-react with the first antibody, and wherein the second antibody is detectably labeled.

Any solid support can be used, including but not limited to, nitrocellulose, solid organic polymers, such as polystyrene, or laminated dipsticks such as described in U.S. Pat. Nos. 5,550,375 and 5,656,448, which is specifically incorporated herein by reference in their entirety.

In one embodiment, the levels of two appendicitis biomarker proteins defining a first and a second appendicitis biomarker protein, are measured using at least two antibodies specific to each appendicitis biomarker protein to be measured. Each antibody specifically reacts either the first appendicitis biomarker protein or the second appendicitis biomarker protein to be measured while not substantially cross-reacting with the other appendicitis biomarker proteins to be measured.

In one embodiment, the levels of three biomarker proteins defining a first biomarker protein, a second biomarker protein, and a third biomarker protein, are measured using at least three antibodies specific to each biomarker protein to be measured, wherein each antibody specifically reacts either the first biomarker protein, the second biomarker protein, or the third biomarker protein to be measured while not substantially cross-reacting with the other biomarker proteins to be measured.

In one embodiment, the levels of four biomarker proteins defining a first, a second, a third and a fourth biomarker protein, are measured using at least four antibodies specific to each biomarker protein to be measured, wherein each antibody specifically reacts either the first biomarker protein, the second biomarker protein, the third biomarker protein, or the fourth biomarker protein to be measured while not substantially cross-reacting with the other biomarker proteins to be measured.

In one embodiment, the appendicitis biomarker proteins are selected from the group consisting of LRG, S100-A8, ORM1, PLG, MASP2, AZGP1, ApoD and SERPINA3.

In one embodiment, the levels of biomarker proteins in urine are detected by a lateral flow immunoassay test (LFIA), also known as the immunochromatographic assay, or strip test. LFIAs are a simple device intended to detect the presence (or absence) of a target antigen in a fluid sample. There are currently many LFIA tests are used for medical diagnostics either for home testing, point of care testing, or laboratory use. LFIA tests are a form of immunoassay in which the test sample flows along a solid substrate via capillary action. After the sample is applied to the test it encounters a coloured reagent which mixes with the sample and transits the substrate encountering lines or zones which have been pretreated with an antibody or antigen. Depending upon the antigens present in the sample the coloured reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be use on site in the field.

LFIA tests can be operated as either competitive or sandwich assays. Sandwich LFIAs are similar to sandwich ELISA. The sample first encounters coloured particles which are labeled with antibodies raised to the target antigen. The test line will also contain antibodies to the same target, although it may bind to a different epitope on the antigen. The test line will show as a coloured band in positive samples. Example 5 illustrates a sandwich LFIA in the test strip format. Competitive LFIAs are similar to competitive ELISA. The sample first encounters coloured particles which are labeled with the target antigen or an analogue. The test line contains antibodies to the target/its analogue. Unlabelled antigen in the sample will block the binding sites on the antibodies preventing uptake of the coloured particles. The test line will show as a coloured band in negative samples.

A typical test strip consists of the following components: (1) sample application area comprising an absorbent pad (i.e. the matrix or material) onto which the test sample is applied; (2) conjugate or reagent pad—this contains antibodies specific to the target antigen conjugated to coloured particles (usually colloidal gold particles, or latex microspheres); test results area comprising a reaction membrane—typically a hydrophobic nitrocellulose or cellulose acetate membrane onto which anti-antigen antibodies are immobilized in a line across the membrane as a capture zone or test line (a control zone may also be present, containing antibodies specific for the conjugate antibodies); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly. FIGS. 11-19 show the various components and embodiments of several test strips.

In some embodiments, the lateral flow immunoassay is a double antibody sandwich assay, a competitive assay, a quantitative assay or variations thereof. FIGS. 15, 16, 17, Example 5 and Example 6 exemplify double antibody sandwich LFIA in a test strip format.

Figure 14:
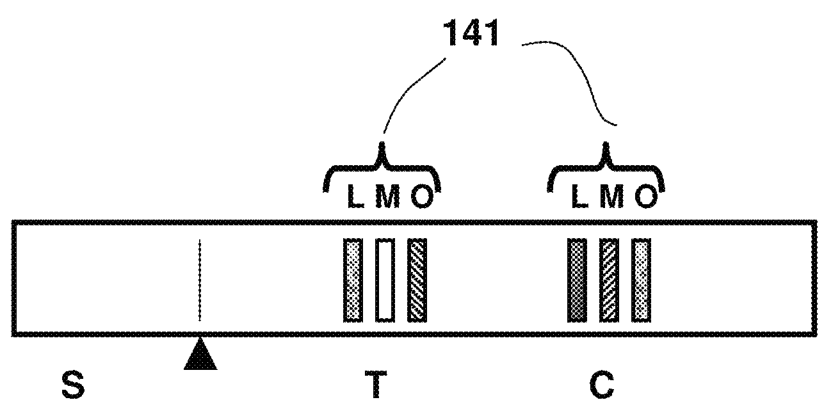
FIG. 14 shows a schematic diagram of how the levels of three biomarker proteins are determined simultaneously on the same LFIA test strip. A diagnostic kit can comprise a single composite or multiplex LFIA test strip for determining the levels of several biomarker proteins simultaneously. The single composite test trip has three distinct protein binding agent specific respectively for three appendicitis biomarker proteins.
Figure 19:
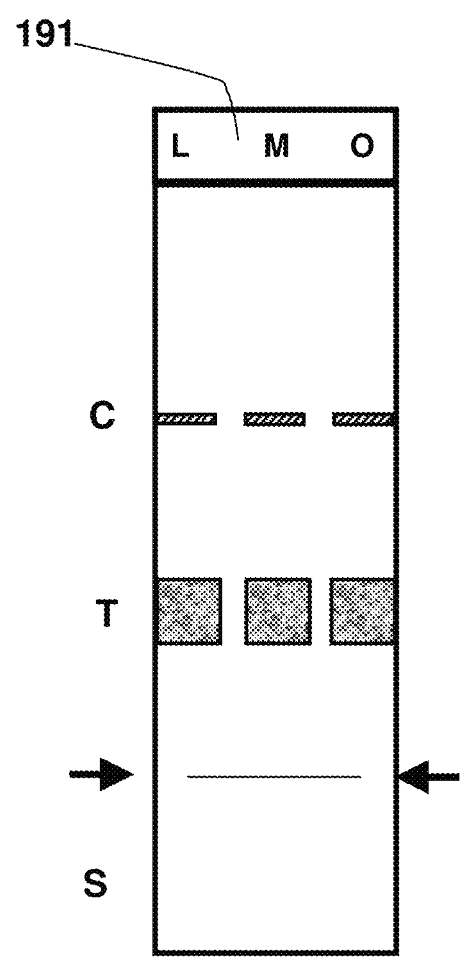
FIG. 19 shows a schematic diagram of an alternative version how the levels of three biomarker proteins are determined simultaneously on the same LFIA test strip. A diagnostic kit can comprise a single composite LFIA test strip for determining the levels of several biomarker proteins.

There are a number of variations on lateral flow technology. It is also possible to apply multiple capture zones to create a multiplex test. FIGS. 14 and 19 exemplify a multiplex LFIA in a test strip format. In one embodiment, a diagnostic kit can comprise multiple LFIA test strips, one strip for a different biomarker protein. In another embodiment, a diagnostic kit can comprise a single composite LFIA test strip for determining the levels of several biomarker proteins. Such diagnostic kits and LFIA test strips can be used as POCT in the field.

The use of "dip sticks" or LFIA test strips and other solid supports have been described in the art in the context of an immunoassay for a number of antigens. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick.

A urine dipstick is a colorimetric chemical assay that can be used to determine the pH, specific gravity, protein, glucose, ketone, bilirubin, urobilinogen, blood, leukocyte, and nitrite levels of an individual's urine. It consists of a reagent stick-pad, which is immersed in a fresh urine specimen and then withdrawn. After predetermined times the colors of the reagent pad are compared to standardized reference charts.

The urine dipstick offers an inexpensive and fast method to perform screening urinalyses, which help in identifying the presence of various diseases or health problems. A urine dipstick provides a simple and clear diagnostic guideline and can be used in the methods and kits as described herein. Accordingly, one aspect of the presents invention relates to a method for detecting acute appendicitis using a device, such as a dipstick, to test for the presence of appendicitis biomarkers as described herein. Dipsticks useful in the present invention can be used to test for at least one appendicitis biomarker, for example LRG or multiple biomarkers, such as any combination selected from the group of leucine-rich α-2-glycoprotein (LRG); S100-A8 (calgranulin); α-1-acid glycoprotein 1 (ORM); plasminogen (PLG); mannan-binding lectin serine protease 2 (MASP2); zinc-α-2-glycoprotein (AZGP1); apolipoprotein D (ApoD); α-1-antichymotrypsin (SERPINA3), or alternatively, multiple biomarkers selected from any combination listed in Table 1. Combination dipsticks can be used to test for at least two appendicitis biomarkers selected from the group of leucine-rich α-2-glycoprotein (LRG); S100-A8 (calgranulin); α-1-acid glycoprotein 1 (ORM); plasminogen (PLG); mannan-binding lectin serine protease 2 (MASP2); zinc-α-2-glycoprotein (AZGP1); apolipoprotein D (ApoD); α-1-antichymotrypsin (SERPINA3), or alternatively, multiple biomarkers selected from any combination listed in Table 1. Examples of combinations of two appendicitis biomarkers are LRG and ORM; LRG and S100-A8; LRG and PLG; LRG and MASP2; LRG and AZGP1; LRG and ApoD; LRG and SERPINA3; ORM and S100-A8; ORM and PLG; ORM and MASP2; ORM and ApoD; ORM and SERPINA3; S100-A8 and PLG; S100-A8 and MASP2; S100-A8 and ApoD; S100-A8 and SERPINA3; PLG and MASP2; PLG and ApoD; PLG and SEPRINA3; MASP2 and ApoD; MASP2 and SERPINA3; and Apo and SERPINA3. Combination dipsticks can be used to test for at least three appendicitis biomarkers, at least four appendicitis biomarkers, at least five appendicitis biomarkers, or at least six appendicitis biomarkers selected from the group of leucine-rich α-2-glycoprotein (LRG); S100-A8 (calgranulin); α-1-acid glycoprotein 1 (ORM); plasminogen (PLG); mannan-binding lectin serine protease 2 (MASP2); zinc-α-2-glycoprotein (AZGP1); apolipoprotein D (ApoD); α-1-antichymotrypsin (SERPINA3), or alternatively, multiple biomarkers selected from any combination listed in Table 1. Combination dipsticks can be used to test for at least seven appendicitis biomarkers selected from the group of leucine-rich α-2-glycoprotein (LRG); S100-A8 (calgranulin); α-1-acid glycoprotein 1 (ORM); plasminogen (PLG); mannan-binding lectin serine protease 2 (MASP2); zinc-α-2-glycoprotein (AZGP1); apolipoprotein D (ApoD); α-1-antichymotrypsin (SERPINA3), or alternatively, multiple biomarkers selected from any combination listed in Table 1. An example of a combination of seven appendicitis biomarkers is LRG, ORM, S100-A8, PLG, MASP2, ApoD, and SERPINA3. Uses of dipsticks are commonly known in the art, and are described in U.S. Pat. No. 5,972,594 to Heine, which is incorporated herein in its entirety by reference which is used to detect the presence of neutrophil defensins to diagnose reproductive tract inflammation and preeclampsia.

Other dipsticks and related components are well known in the art, for example dipsticks to detect leukocytes and leukocyte enzymes in body fluids have been patented. For example, U.S. Pat. No. 5,656,448 to Kang et al, which is incorporated herein in its entirety discloses a dipstick encompassed for use in the present invention. Additionally, U.S. Pat. No. 4,758,508 to Schnabel, et al. describes an agent and a method for detecting esterolytic and/or proteolytic enzymes in body fluids. U.S. Pat. No. 4,637,979 to Skjold, et al. describes a composition and test device for determining the presence of leukocytes in test samples including body fluids such as urine. U.S. Pat. No. 4,645,842 describes pyrrole compounds, and U.S. Pat. No. 4,704,460 (both to Corey) describes novel compounds for detecting the presence of hydrolytic analytes including leukocytes, esterase, and protease, in a test sample, including urine. U.S. Pat. No. 4,774,340 to Corey describes a method for preparing 3-hydroxy pyrroles and esters thereof, which are used to test samples including urine. A composition and test device for determining the presence of leukocytes, esterase, and protease in a body fluid including urine is described in U.S. Pat. No. 4,657,855 to Corey, et al. A method for determining the concentration of white blood cells in urine or other biological fluid is described in U.S. Pat. No. 5,663,044 to Noffsinger, et al. A method for preparing an ester used to detect leukocyte cells, esterase, and protease in body fluids such as urine is described in U.S. Pat. No. 4,716,236 to Ward, et al. All of these patents, which are incorporated herein in their entirety by reference, identify an abnormally high level of leukocytes in a patient's urine and produce a signal to indentify likelihood that the subject from which the urine was obtained has a pathological condition such as kidney or urogenital tract infection or other dysfunction.

In some embodiments, the present invention provides a LFIA device such as a dipstick to identify appendicitis biomarkers in a urine test sample. In one embodiment is a method for detecting acute appendicitis using a LFIA device, such as a dipstick, having diagnostic test reagents to detect acute appendicitis. The diagnostic test reagents react with the test sample, such as urine test sample to produce a change upon contact with the test sample, such as urine. Another embodiment of the invention is a device, such as a dipstick, that has (1) a positive indication for the presence of acute appendicitis and (2) a negative indication for the absence of acute appendicitis. The difference between the positive indication and the negative indication is pre-determined.

In some embodiments, the present invention also provides a method for determining if a subject has a likelihood of acute appendicitis. In some embodiments, the method begins with obtaining a urine sample from a subject, such as a symptomatic patient for appendicitis. Symptomatic patients for appendicitis are described herein. Once the sample is obtained, a device having diagnostic test reagents that detect the presence of at least one appendicitis biomarker, such as leucine-rich α-2-glycoprotein (LRG); S100-A8 (calgranulin); α-1-acid glycoprotein 1 (ORM); plasminogen (PLG); mannan-binding lectin serine protease 2 (MASP2); zinc-α-2-glycoprotein (AZGP1); apolipoprotein D (ApoD); α-1-antichymotrypsin (SERPINA3) or any listed from Table 1 is contacted with the urine sample. Depending on the type of device used, a certain amount of time might have to pass before the device is read. For example, as a general guideline but not as a limitation, when using a MULTISTIX-2 by Bayer Aktiengesellschaft (Fed. Rep. Germany) two minutes pass between the time that the device is contacted with the sample and when it is read to produce an experimental test result. The MULTISTIX-2 dipstick is sold to test urine. The experimental test result is then compared to pre-determined test results that indicate either the presence or absence of acute appendicitis.

In some embodiments, the method to diagnose acute appendicitis in a subject uses a quantitative device (such as, for example, the MULTISTIX-2, MULTISTIX-10, URISTIX-4, or any appendicitis biomarker-detecting device as disclosed herein) or the subject inventive device that has two indications, one for a positive result and one for a negative result. When using such a quantitative device, it produces a range of results. For example, the MULTISTIX-2 produces quantitative results of 0, trace, +1, +2 and +3. Quantitative results also include "Between +1 and +2" and "Between +2 and +3." A test result of 0, trace, and +1 corresponds to the absence of acute appendicitis). A test result of "Between +1 and +2", "Moderate (+2)", "Between +2 and +3", and "Large (+3)" corresponds to the presence of acute appendicitis). The pre-determination is done using a study where the range of the urine marker presence is determined based on the range in urine from confirmed appendicitis subjects as compared to the range of urine maker in the urine from healthy (i.e. confirmed non-appendicitis) subjects.

In some embodiments, a device, such as a dipstick immunological device as disclosed herein can includes (1) a matrix (preferably filter paper) with diagnostic test reagents and (2) a mounting substrate (preferably polystyrene film), which typically does not absorb the test (e.g. urine) sample, such that the user can hold onto the substrate without contacting the sample. The device produces a visual change in the matrix upon contact with the urine sample. In some embodiments, the matrix has two indicators-a first that indicates the presence of acute appendicitis and a second that indicates the absence of appendicitis. The first indicator produces a positive test result and the second indicator produces a negative result. The test result is positive when the test result is pre-determined to correspond with a level of the appendicitis biomarker which is indicative of acute appendicitis. Conversely, a test result is negative when the test result is pre-determined to be below the level of an appendicitis biomarker which indicates the absence of acute appendicitis. The device, such as a dipstick device determines the presence of acute appendicitis with the positive test result, and the absence of acute appendicitis with the negative test result.

In some embodiments, the diagnostic test reagents may be associated with the matrix by any physical or chemical means, including, for example impregnation, coating, linking, and covalent attachment. The matrix may take any convenient physical form, such as a card, pad, strip, or dipstick. Such diagnostic test reagents include the compositions of the above-referenced patents, including an ester (preferably a chromogenic ester) and a diazonium salt such as those described in U.S. Pat. No. 4,637,979. Another preferred reagent is a derivatized pyrrole amino acid ester, a diazonium salt, a buffer, and non-reactive ingredients as described in U.S. Pat. Nos. 4,645,842; 4,637,979; 4,657,855; 4,704,460; 4,758,508; and 4,774,340. The preferred amounts of these ingredients is based on dry weight at the time of impregnation and is as follows: about 0.4% w/w derivatized pyrrole amino acid ester, about 0.2% w/w diazonium salt, about 40.9% w/w buffer, and about 58.5% w/w non-reactive ingredients.

In one embodiment, the test reagent, e.g. the anti-antigen antibody of the immunoassay is detectably labeled. In some embodiments, the detectable label is selected from a group consisting of enzyme, fluorescent, biotin, gold, latex, hapten and radioisotope labeling. A detectable-hapten includes but is not limited to biotin, fluorescein, digoxigenin, dinitrophenyl (DNP). Other labels include but are not limited to colloidal gold and latex beads. The latex beads can also be colored. Methods of labeling antibodies, antibody-based moiety, or proteins are known in the art, for example, as described in "Colloidal Gold. Principles. Methods and Applications", Hayat M A (ed) (1989-91). Vols 1-3, Academic press, London; in "Techniques in Immunocytochemistry", Bullock G R and Petrusz P (eds) (1982-90) Vols 1, 2, 3, and 4, Academic Press, London; in "Principles of Biological Microtechnique", Baker J R (1970), Methuen, London; Lillie R D (1965), Histopathologic Technique and practical Histochemistry, 3rd ed, McGraw Hill, New York; Berryman M A, et al (1992), J. Histochem Cytochem 40, 6, 845-857, all of which are incorporated hereby reference in their entirety.

In one embodiment, the detectable label is a dye. A "dye" refers to a substance, compound or particle that can be detected, particularly by visual, fluorescent or instrumental means. A dye can be, for example, but not limited to, a pigment produced as a coloring agent or ink, such as Brilliant Blue, 3132 Fast Red 2R and 4230 Malachite Blue Lake, all available from Hangzhou Hongyan Pigment Chemical Company, China. The "dye" can also be a particulate label, such as, but not limited to, blue latex beads or gold particles. The particulate labels may or may not be bound to a protein, depending upon if it is desired for the particles to move in the test strip or not. If the particles are to be immobilized in the test strip, the particles may be conjugated to a protein, e.g. the anti-antigen antibody, which in turn is bound to the test strip by either physical or chemical means.

In colloidal gold labeling technique, the unique red color of the accumulated gold label, when observed by lateral or transverse flow along a membrane on which an antigen is captured by an immobilized antibody, or by observation of the red color intensity in solution, provides an extremely sensitive method for detecting sub nanogram quantities of proteins in solution. A colloidal gold conjugate consists of a suspension of gold particles coated with a selected protein or macromolecule (such as an antibody or antibody-based moiety). The gold particles may be manufactured to any chosen size from 1-250 nm. This gold probe detection system, when incubated with a specific target, such as in a tissue section, will reveal the target through the visibility of the gold particles themselves. For detection by eye, gold particles will also reveal immobilized antigen on a solid phase such as a blotting membrane through the accumulated red color of the gold sol. Silver enhancement of this gold precipitate also gives further sensitivity of detection. Suppliers of colloidal gold reagents for labeling are available from SPI-MARK™. Polystyrene latex Bead size 200 nm colored latex bead coated with antibody SIGMA ALDRICH®, Molecular Probes, Bangs Laboratory Inc., and AGILENT® Technologies.

Other detection systems can also be used, for example, a biotin-streptavidin system. In this system, the antibodies immunoreactive (i.e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e.g. from DAKO; Carpinteria, Calif.

Protein binding agents described herein such as antibodies and antibody-based moiety can alternatively be labeled with any of a number of fluorescent compounds such as fluorescein isothiocyanate, europium, lucifer yellow, rhodamine β isothiocyanate (Wood, P. In: Principles and Practice of Immunoasay, Stockton Press, New York, pages 365-392 (1991)) for use in immunoassays. In conjunction with the known techniques for separation of antibody-antigen complexes, these fluorophores can be used to quantify the biomarker of interest. The same applies to chemiluminescent immunoassay in which case antibody or biomarker of interest can be labeled with isoluminol or acridinium esters (Krodel, E. et al., In: Bioluminescence and Chemiluminescence: Current Status. John Wiley and Sons Inc. New York, pp 107-110 (1991); Weeks, I. et al., Clin. Chem. 29:1480-1483 (1983)). Radioimmunoassay (Kashyap, M. L. et al., J. Clin. Invest, 60:171-180 (1977)) is another technique in which antibody can be used after labeling with a radioactive isotope such as $^{125}$I. Some of these immunoassays can be easily automated by the use of appropriate instruments such as the IMX™ (Abbott, Irving, Tex.) for a fluorescent immunoassay and Ciba Coming ACS 180™ (Ciba Corning, Medfield, Mass.) for a chemiluminescent immunoassay.

A "LFIA test strip" or "dip stick" can include one or more bibulous or non-bibulous materials or matrices. In reference to a "LFIA test strip" or "dip stick", the terms "material" and "matrix" are used interchangeably. If a test strip comprises more than one material, the one or more materials are preferably in fluid communication. One material of a test strip may be overlaid on another material of the test strip, such as for example, filter paper overlaid on nitrocellulose membrane. Alternatively or in addition, a test strip can include a region comprising one or more materials followed by a region comprising one or more different materials. In this case, the regions are in fluid communication and may or may not partially overlap one another. Suitable materials for test strips include, but are not limited to, materials derived from cellulose, such as filter paper, chromatographic paper, nitrocellulose, and cellulose acetate, as well as materials made of glass fibers, nylon, dacron, PVC, polyacrylamide, cross-linked dextran, agarose, polyacrylate, ceramic materials, and the like. The material or materials of the test strip may optionally be treated to modify their capillary flow characteristics or the characteristics of the applied sample. For example, the sample application region of the test strip may be treated with buffers to correct the pH or specific gravity of an applied urine sample, to ensure optimal test conditions.

The material or materials can be a single structure such as a sheet cut into strips or it can be several strips or particulate material bound to a support or solid surface such as found, for example, in thin-layer chromatography and may have an absorbent pad either as an integral part or in liquid contact. The material can also be a sheet having lanes thereon, capable of spotting to induce lane formation, wherein a separate assay can be conducted in each lane. The material can have a rectangular, circular, oval, triagonal or other shape provided that there is at least one direction of traversal of a test solution by capillary migration. Other directions of traversal may occur such as in an oval or circular piece contacted in the center with the test solution. However, the main consideration is that there be at least one direction of flow to a predetermined site.

The support for the test strip, where a support is desired or necessary, will normally be water insoluble, frequently non-porous and rigid but may be elastic, usually hydrophobic, and porous and usually will be of the same length and width as the strip but may be larger or smaller. The support material can be transparent, and, when a test device is assembled, a transparent support material can be on the side of the test strip that can be viewed by the user, such that the transparent support material forms a protective layer over the test strip where it may be exposed to the external environment, such as by an aperture in the front of a test device. A wide variety of materials, both natural and synthetic, and combinations thereof, may be employed provided only that the support does not interfere with the capillary action of the material or materials, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly(vinyl butyrate), glass, ceramics, metals, and the like. Elastic supports may be made of polyurethane, neoprene, latex, silicone rubber and the like.

In some embodiments, a dipstick device has one indication of the presence of acute appendicitis and a second indication for the absence of acute appendicitis. The two indications preferably are a negative (−) symbol and a positive (+) symbol, but could be any two indications. In one embodiment, the device has the negative indication (e.g., the "−" portion of a possible "+" symbol) containing reagents that reacts with all samples. That is, the diagnostic test reagents react to some constituent analyte, such as urea which is present in all urine samples. Alternatively, the diagnostic test reagents test an aspect of the sample, such as pH, that every sample has. The positive indication (e.g., the "|" portion of a "+" symbol) contains a reagent that the reacts only with a sample containing the presence of a test appendicitis biomarker which is above a certain pre-defined level, such that it reacts in urine samples which only contain the presence of the appendicitis biomarker (i.e. of a LRG biomarker) above a certain level, i.e. above a pre-defined level of the appendicitis biomarker. Another embodiment has the negative indicator (e.g., the "−" portion of a possible "+" symbol) which contains reagents that reacts with the sample which either has the absence of the test appendicitis biomarker (i.e. absence of a LRG biomarker) or the level of the test appendicitis biomarker (i.e. the LRG biomarker) below a certain pre-defined or threshold level. The positive indication (e.g., the "|" part of the "+" symbol) has a lower sensitivity to the presence of a test appendicitis biomarker (i.e. LRG biomarker) and thus such the reagents react only with urine samples containing level of the urine marker (i.e. LRG biomarker) above a pre-defined level.

In some embodiments, a test device, such as a dipstick device has text on the device in two places. In one place the text indicates a positive result (i.e. the likelihood the subject has acute appendicitis). In another, it indicates a negative result (i.e. the likelihood the subject does not have acute appendicitis). Next to the indications are matrices having the appropriate diagnostic test reagents. For example, next to the negative indication is a matrix having diagnostic test reagents that react with all urine samples, regardless of the content of appendicitis biomarkers as disclosed herein. Next to the positive indication is a matrix having diagnostic test reagents that react only with samples that have the presence of the test appendicitis biomarker, (e.g. LRG, or any or any combination of appendicitis biomarkers listed in Table 1) above a pre-defined level. In some embodiments, such a device such as one discussed in FIG. 12, does not require a chart, such as a coloration chart, to interpret the results. In some embodiments of this aspect of the invention, this enables the detection device, such as a dipstick device (and the corresponding method) to be used easily by one without special training and provides a more rapid diagnostic (and method) for determining if a subject is likely to have acute appendicitis. In some embodiments of this aspect of the invention, such a device is ideal for point-of-care testing application.

Production and manufacturer of dipsticks are well known by ordinary skill in the art. Dipsticks are commercially available from Bayer Corporation of Elkhart, Ind., as well as other commercial sources. The dipstick is dipped into a well mixed urine sample, and after a time period, for example between about thirty seconds (30 s) to about two minutes (2 mins) or more, the various reagent bands are visually or optically examined for color changes. The bands can be visually compared to a preprinted color chart in order to determine the amount of each of the constituents or parameters being measured. It is also possible to optically scan using a machine or optical scanner the dipstick and thereby obtain instrument readings of color intensity or wave length through the use of a particular instrument adapted for reading the reagents and color of the dipstick. Examples of such instruments or machines are manufactured by Ames. Examples of useful machines or instruments for optically scanning the dipstick bands are able to distinguish between positive and negative reaction or reagent bands, was well as differences in color distribution of the reagent bands in the presence (i.e. above a certain threshold level) or absence (or below a certain threshold level) of the test appendicitis biomarker(s). In some embodiments, the instrument is capable of quantify a number of reagent bands as well as quantify the overall color intensity sensed on the band.

In some embodiments, the immunoassays operate on a purely qualitative basis. However it is possible to measure the intensity of the test line to determine the quantity of antigen in the sample when using an immunoassay such a LFIA. Implementing a magnetic immunoassay (MIA) in the lateral flow test form also allows for getting a quantified result.

Figure 8:
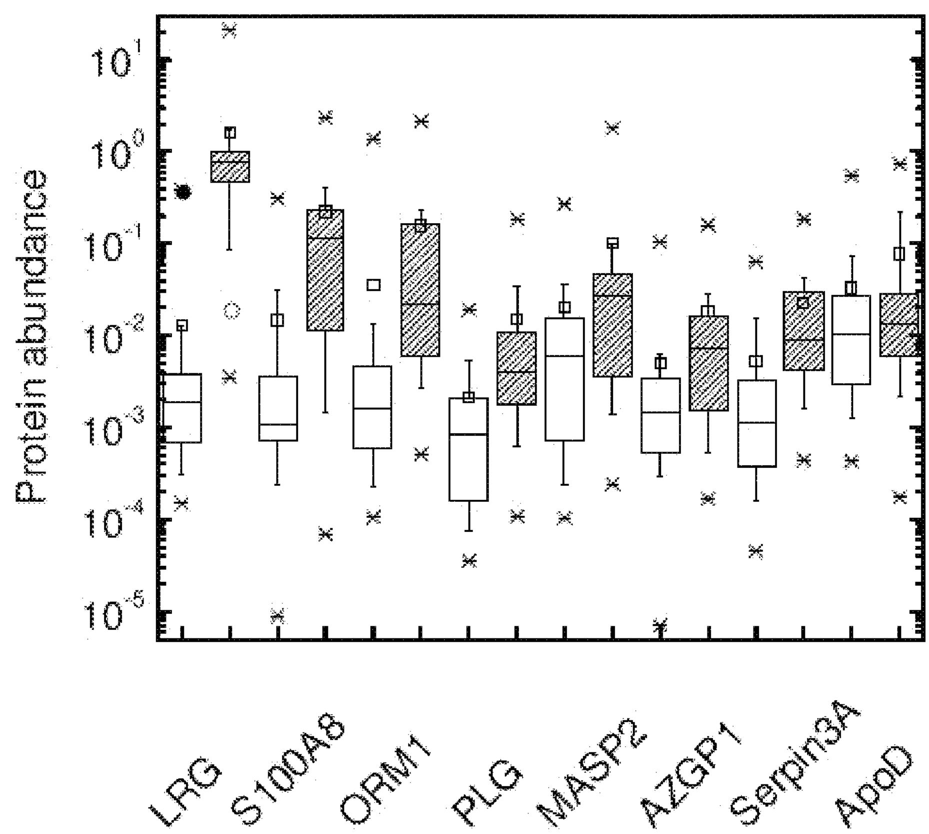
FIG. 8 is a boxplot showing the relative urine protein abundance (logarithm normalized ion current units) of the validated diagnostic markers for the non-appendicitis (open) and appendicitis (hatched) patient groups. Normalized value of 1 corresponds to the apparent abundance of internal reference standard. Boxes contain the 25-75% interquartile range, with the dividing bars representing means, whiskers representing 10-90% range, and crosses representing 1-99% range. Square symbols represent medians. Abundance of LRG in patients with pyelonephritis (solid dot, ●) and those who underwent appendectomies with findings of histologically normal appendices (open dot, ○).

Instruments have been developed which both determine the chemical constituents of the urine and also assist in the microscopic analysis, for example the instrument disclosed in U.S. Pat. No. 6,004,821 which is incorporated herein in its entirety by reference. Such an instrument is the Yellow IRIS, which automatically places the sample on the urine dipstick and then reads the chemical results. FIG. 8 of U.S. Pat. No. 6,004,821 shows a schematic depiction of such an automated calorimetric microscopical instrument assembly (which is denoted generally by the numeral 54), and which can be used to scan a urine sample, and can, without significant human intervention, colorometrically analyze the wavelengths of the colors imparted to the dipstick by the urine in the chamber 14, either colorometrically and/or morphometrically. Accordingly, such an instrument, which is specifically adapted to scan the reaction of the dipstick after contact with a urine sample for the presence of the appendicitis biomarkers (such as at least one selected from Table 1) is encompassed for use in the present invention.

In some embodiments, the dipstick uses reagents such as copper-creatinine and iron-creatinine complexes have peroxidase activity. Other dipstick reagents can use reagents such as 3,3',5,5'-tetramethylbenzidine (TMB), and diisopropyl benzene dihydroperoxide (DBDH) which are used with peroxidase. In some embodiments, a dipstick for use to detect the presence of appendicitis biomarkers is based upon the first-generation devices which relied on the same colorimetric reaction used for assessing the presence of glucose test strips for urine. Besides glucose oxidase, a test kit for use herein can contain a benzidine derivative, which is oxidized to a blue polymer by the hydrogen peroxide formed in the oxidation reaction. Care must be taken if such a dipstick is generated to ensure the test strip is developed after a precise interval after contact with the urine test sample as well as frequent calibration of the meter to read the test result. The same principle is used in test strips that have been commercialized for the detection Diabetic ketoacidosis (DKA). These test strips use a beta-hydroxybutyrate-dehydrogenase enzyme instead of a glucose oxidizing enzyme and have been used to detect and help treat some of the complications that can result from prolonged hyperglycaemia. Blood alcohol sensors using the same approach but with alcohol dehydrogenase enzymes have been developed.

In another embodiment, the device, such as a dipstick device uses an electrochemical method. Test strips contain a capillary that sucks up a reproducible amount of urine. The presence of an appendicitis biomarker such as any or a combination of those listed in Table 1 in the urine reacts with an enzyme electrode containing protein-binding agents with the test appendicitis biomarker. The coulometric method is a technique where the total amount of charge generated by the specific binding of the appendicitis biomarker to the specific protein-binding agent reaction is measured over a period of time. This is analogous to throwing a ball and measuring the distance it has covered so as to determine how hard it was thrown. The amperometric method is used by some meters and measures the electrical current generated at a specific point in time. This is analogous to throwing a ball and using the speed at which it is travelling at a point in time to estimate how hard it was thrown. The coulometric method can allow for variable test times, whereas the test time on a meter using the amperometric method is always fixed. Both methods give an estimation of the concentration of the appendicitis biomarker in the urine sample.

In one embodiment, the levels of appendicitis biomarker proteins in urine are detected by a magnetic immunoassay (MIA). MIA is a type of diagnostic immunoassay using magnetic beads as labels in lieu of conventional enzymes (ELISA), radioisotopes (RIA) or fluorescent moieties (fluorescent immunoassays). This assay involves the specific binding of a protein binding agent to an appendicitis biomarker protein, such as an antibody binding to its antigen, where a magnetic label is conjugated to one element of the pair. The presence of magnetic beads is then detected by a magnetic reader (magnetometer) which measures the magnetic field change induced by the beads. The signal measured by the magnetometer is proportional to the antigen or biomarker quantity in the initial sample.

Magnetic beads are made of nanometric-sized iron oxide particles encapsulated or glued together with polymers. These magnetic beads can range from 35 nm up to 4.5 μm. The component magnetic nanoparticles range from 5 to 50 nm and exhibit a unique quality referred to as superparamagnetism in the presence of an externally applied magnetic field. Magnetic labels exhibit several features very well adapted for such applications: they are not affected by reagent chemistry or photo-bleaching and are therefore stable over time; the magnetic background in a biomolecular sample is usually insignificant; sample turbidity or staining have no impact on magnetic properties; and magnetic beads can be manipulated remotely by magnetism.

The use of MIA is well known in the art, for example, Dittmer W U and colleagues (J Immunol Methods. 2008, 338:40-6) described a sensitive and rapid immunoassay for detection and measurement parathyroid hormone using magnetic particle labels and magnetic actuation. The assay involves a 1-step sandwich immunoassay with no fluid replacement steps. The detection limit is the 10 pM range and the assay took only 15 minutes; Kuma H and colleagues (Rinsho Byori. 2007, 55:351-7) developed a sensitive immunoassay system using magnetic nanoparticles made from $Fe_3O_4$; and Kuramitz H. reviews the current state of concerning electrochemical immunoassays using magnetic microbeads as a solid phase in Anal Bioanal Chem. 2009, 394:61-9. U.S. Pat. Nos. 5,252,493; 5,238,811; 5,236,824; 7,604,956; U.S. Patent Application No. 20090216082; 20090181359; and 20090263834 all describe various improvements and versions of MIA. These references are all incorporated herein by reference in their entirety.

Magnetometers are instruments that can detect the presence and measure the total magnetic signal of a sample. An effective MIA is one that is capable of separating naturally occurring magnetic background (noise) from the weak magnetically labeled target (signal). Various approaches and devices have been employed to achieve a meaningful signal-to-noise ratio (SNR) for bio-sensing applications:giant magneto-resistive sensors and spin valves, piezo-resistive cantilevers, inductive sensors, superconducting quantum interference devices, anisotropic magneto-resistive rings, and miniature Hall sensors. MIA that exploits the non-linear magnetic properties of magnetic labels can effectively use the intrinsic ability of a magnetic field to pass through plastic, water, nitrocellulose, and other materials, thus allowing for true volumetric measurements in various immunoassay formats. Unlike conventional methods that measure the susceptibility of superparamagnetic materials, a MIA based on non-linear magnetization eliminates the impact of linear dia- or paramagnetic materials such as sample matrix, consumable plastics and/or nitrocellulose. Although the intrinsic magnetism of these materials is very weak, with typical susceptibility values of −10-5 (dia) or +10-3 (para), when one is investigating very small quantities of superparamagnetic materials, such as nanograms per test, the background signal generated by ancillary materials cannot be ignored. In MIA based on non-linear magnetic properties of magnetic labels the beads are exposed to an alternating magnetic field at two frequencies, f1 and f2. In the presence of non-linear materials such as superparamagnetic labels, a signal can be recorded at combinatorial frequencies, for example, at $f=f1\pm2\times f2$. This signal is exactly proportional to the amount of magnetic material inside the reading coil. Ultrasensitive magnetic biosensor for homogeneous immunoassay have been described by Y. R. Chemla, et al., Proc Natl Acad Sci USA. 2000, 97:14268-14272. This is incorporate hereby reference in its entirety.

In one embodiment, the levels of biomarker proteins in urine are detected by a diffusion immunoassay (DIA). In this assay, the transport of molecules perpendicular to flow in a microchannel, e.g. in a microfluidic chip, is affected by binding between antigens and antibodies. By imaging the steady-state position of labeled components in a flowing stream, the concentration of very dilute analytes, in this invention, the urine biomarkers, can be measured in a few microliters of sample in seconds. Microfluidics is the manipulation of microliter volumes in channels with sub-millimeter dimensions. Microfluidic diffusion immunoassays for the detection of analytes or biomarkers in fluid samples have been described in the art, for example, in U.S. Pat. Nos. 6,541,213; 6,949,377; 7,271,007; U.S. Patent Application No. 20090194707; 20090181411; in Hatch et al., 2001, Nature Biotechnology 19(5): 461-465; K. Scott Phillips and Quan Cheng, Anal. Chem., 2005, 77:327-334; J. Hsieh, et al., Nanotech 2007 Vol. 3, Technical Proceedings of the 2007 NSTI Nanotechnology Conference and Trade Show, Chapter 4: Micro and Nano Fluidics, pp 292-295; Frank Y. H. Lin et al., Clinical and Diagnostic Laboratory Immunology, 2005, 12:418-425; and A. Bhattacharyya and C. M. Klapperich, 2007, Biomedical Microdevices, 9: 245-251. These are incorporated herein by reference in their entirety. U.S. Pat. No. 6,541,213 describes the use of a credit-card sized microfluidic device to perform competitive immunoassays. The ability to perform assays in this microscale dimension affords an extremely rapid, homogenous, and cost effective alternative to current methods used commercially today. The credit-card sized microfluidic device can be integrated into the development of point-of-use systems that allow real-time answers to health questions while at the physician's office, home, workplace, school, shopping mall and other public places. These systems include portable and handheld instruments with integrated laboratory-tests-on-a-card ("lab cards"), as well as stand alone, single use lab cards being developed to provide rapid on-site results in infectious diseases testing, nucleic acid testing, blood type analysis, cancer testing, and respiratory disease testing.

In one embodiment, the levels of biomarker proteins in urine are detected by an on-the-spot assay also known as point-of-care assay. Point-of-care testing (POCT) is defined as diagnostic testing at or near the site of patient care. Currently majority of the detection and diagnostic testing for analytes, toxin, pathogen toxins and antigens in samples are largely restricted to centralized laboratories because of the need for long assay times, complex and expensive equipment, and highly trained technicians. POCT brings the test conveniently and immediately to the patient. This increases the likelihood that the patient will receive the results in a timely manner. POCT is accomplished through the use of transportable, portable, and handheld instruments (e.g., blood glucose meter, nerve conduction study device) and test kits (e.g., CRP, HBA1C, Homocystein, HIV salivary assay, etc.). POCTs are well known in the art, especially immunoassays. For example, the LFIA test strip or dip sticks can easily be integrated into a POCT diagnostic kit. One skilled in the art would be able to modify immunoassays for POCT using different format, e.g. ELISA in a microfluidic device format or a test strip format. For example, U.S. Patent Application No. 2009/0181411 describes a microfluidic device-based point-of-care immunoassay for biomarker molecules associated with pathology in a vertebrate host, man or animal. The microfluidic devices such as chips are formatted to either hand-held cartridges (also termed "cards"), or cartridges for automated or semi-automated, machine-aided testing. Microfluidic device-based assays enable small-volume sampling, with point-of-care results from a broad variety of biological fluids and samples in real time. In addition, the assay cartridges can be single use reagent packs, or be fully self-contained and operable entirely by hand. This reference is incorporated herein by reference in its entirety.

Embodiments of the invention further provide for diagnostic kits and products of manufacture comprising the diagnostic kits. The kits can comprise a means for predicting acute appendicitis in a human.

In one embodiment, the kit comprises an indicator responsive to the level of biomarker protein in a sample of urine, wherein the appendicitis biomarker protein is selected from the group consisting of LRG, S100-A8, ORM1, PLG, MASP2, AZGP1, ApoD and SERPINA3. In some embodiments, the indicator is in the form of a LFIA test strip or a microfluidic device. In one embodiment, a diagnostic kit can comprise multiple LFIA test strips, one strip for a different biomarker protein. In another embodiment, a diagnostic kit can comprise a single composite LFIA test strip for determining the levels of several biomarker proteins. In one embodiment, a diagnostic kit can comprise a single multichannel microfluidic device for determining the levels of several biomarker proteins. In another embodiment, a diagnostic kit can comprise several microfluidic devices for determining the levels of several biomarker proteins, one microfluidic device for a different biomarker protein.

The kits can further comprise cups or tubes, or any other collection device for sample collection of urine.

In one embodiment, the kit can optionally further comprise at least one diagram and/or instructions describing the interpretation of test results.

Protein-Binding Agents, Antibodies or Antisera Against Biomarker Proteins

In one embodiment, the methods disclosed herein uses antibodies or anti-sera for detecting, quantifying, and/or labeling LRG, S100-A8, ORM1, PLG, MASP2, AZGP1, ApoD and SERPINA3 described herein. The antibodies can be obtained from a commercial source. These commercial antibodies can also be conjugated with labels, e.g. Cy3 or FITC.

Antibodies for use in the methods described herein can also be produced using standard methods to produce antibodies, for example, by monoclonal antibody production (Campbell, A. M., Monoclonal Antibodies Technology: Laboratory Techniques in Biochemistry and Molecular Biology, Elsevier Science Publishers, Amsterdam, the Netherlands (1984); St. Groth et al., J. Immunology, (1990) 35: 1-21; and Kozbor et al., Immunology Today (1983) 4:72). Antibodies can also be readily obtained by using antigenic portions of the protein to screen an antibody library, such as a phage display library by methods well known in the art. For example, U.S. Pat. No. 5,702,892 (U.S.A. Health & Human Services) and WO 01/18058 (Novopharm Biotech Inc.) disclose bacteriophage display libraries and selection methods for producing antibody binding domain fragments.

Methods for the production of antibodies are disclosed in PCT publication WO 97/40072 or U.S. Application. No. 2002/0182702, which are herein incorporated by reference. The processes of immunization to elicit antibody production in a mammal, the generation of hybridomas to produce monoclonal antibodies, and the purification of antibodies may be performed by described in "Current Protocols in Immunology" (CPI) (John Wiley and Sons, Inc.) and Antibodies: A Laboratory Manual (Ed Harlow and David Lane editors, Cold Spring Harbor Laboratory Press 1988) which are both incorporated by reference herein in their entireties; Brown, "Clinical Use of Monoclonal Antibodies," in BIOTECHNOLOGY AND PHARMACY 227-49, Pezzuto et al. (eds.) (Chapman & Hall 1993).

For example, to generate a polyclonal antibody against human LRG, S100-A8, ORM1, PLG, MASP2, AZGP1, ApoD or SERPINA3. Methods of making recombinant proteins are well known in the art. For example, full-length cDNAs of LRG, S100-A8, ORM1, PLG, MASP2, AZGP1, ApoD and SERPINA3 (Genbank Accession Nos. NM_052972.2, NM_002964.3, NM_000607.2, NM_000301.2, NM_006610.2, NM_001185.2, NM_001647.3, and NM_001085.4 respectively) can be cloned into the pQE30 vector containing an N-terminal hexa-histidine tag (QIAGEN, GmbH, Hilden, Germany), and then transformed into *E. coli* strain JM109 cells. Recombinant proteins is expressed and purified by affinity chromatography using Ni-nitriloacetic acid agarose (QIAGEN) according to the manufacturer's instructions. The final preparation yielded a single calculated molecular weight of 89707 kDa band on SDS-PAGE and is used for the immunization of rabbits.

Detection of anti-antibodies to the appendicitis biomarkers can be achieved by direct labeling of the antibodies themselves, with labels including a radioactive label such as $^{3}H$, $^{14}C$, $^{35}S$, $^{125}I$, or $^{131}I$, a fluorescent label (e.g. Cy3, Cy5, FITC), a hapten label such as biotin, heavy metal such as gold, or an enzyme such as horse radish peroxidase or alkaline phosphatase. Such methods are well known in the art. Alternatively, unlabeled primary antibody is used in conjunction with labeled secondary antibody, comprising antisera, polyclonal antisera or a monoclonal antibody specific for the primary antibody. In another embodiment, the primary antibody or antisera is unlabeled, the secondary antisera or antibody is conjugated with biotin and enzyme-linked strepavidin is used to produce visible staining for histochemical analysis.

In one embodiment, the levels of the appendicitis biomarker proteins described herein in a sample can be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference in their entirety.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition, Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection and quantification of the appendicitis biomarker proteins will typically depend on the detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the appendicitis biomarker WIZARD program (Ciphergen Biosystems, Inc., Fremont, Calif.) can be used to aid in analyzing mass spectra. The mass spectrometers and their techniques are well known to those of skill in the art.

Diagnostic Imaging of Acute Appendicitis

In some embodiments, described herein is a method of diagnosing likelihood of acute appendicitis in a subject by in situ histochemical imaging of an appendix using at least a protein binding agent that bind specifically to a biomarker selected from the group consisting of leucine-rich α-2-glycoprotein (LRG); S100-A8 (calgranulin); α-1-acid glycoprotein 1 (ORM); plasminogen (PLG); mannan-binding lectin serine protease 2 (MASP2); zinc-α-2-glycoprotein (AZGP1); apolipoprotein D (ApoD); and α-1-antichymotrypsin (SERPINA3).

In other embodiments, the method further comprises at least one additional different protein-binding agent that bind specifically to a biomarker selected from the group consisting AMBP; amyloid-like protein 2; angiotensin converting enzyme 2; BAZ1B; carbonic anhydrase 1; CD14; chromogranin A; FBLN7; FXR2; hemoglobin α; hemoglobin β; interleukin-1 receptor antagonist protein; inter-α-trypsin inhibitor; lipopolysaccharide binding protein; lymphatic vessel endothelial hyaluronan acid receptor 1; MLKL; nicastrin; novel protein (Accession No: IPI00550644); PDZK1 interacting protein 1; PRIC285; prostaglandin-H2 D-isomerase; Rcl; S100-A9; serum amyloid A protein; SLC13A3; SLC2A1; SLC2A2; SLC4A1; SLC9A3; SORBS1; SPRX2; supervillin; TGFbeta2R; TTYH3; VA0D1; vascular adhesion molecule 1; versican; VIP36; α-1-acid glycoprotein 2; and β-1,3-galactosyltransferase. In other embodiments, the method further comprises at least one additional different protein-binding agent that bind specifically to a biomarker selected from Table 1.

In one embodiment, the method for diagnosing likelihood of acute appendicitis in a subject comprise (a) introducing a protein-binding agent into the subject via a physiologically compatible vehicle in an amount effective for detection, wherein the protein binding agent in detectably labeled; (b) detecting the location of the protein-binding agent at the appendix with an extracorporeal detection means capable of detecting the labeling means; and (c) quantifying the protein-binding agent concentration in order to determine the presence and extent of inflammation in the appendix. In one embodiment, the intensity of the label is directly proportional to the concentration of the protein-binding agent that binds specifically to an appendicitis biomarker protein.

In some embodiment, the protein-binding agent concentration measured by extracorporeal detection means in a patient is compared to the protein-binding agent concentration in a healthy individual, wherein in the detectable label and the imaging method are the same for both the patient and the healthy individuals. In some embodiments, the patient has at least one symptom associated with acute appendicitis as disclosed herein or as known to one skilled in the art such as a physician. In some embodiments, the protein-binding agent concentration at the appendix of a patient is compared to the protein-binding agent concentration that is the average obtained for a population, i.e. more than two individuals, preferably ten or more, of healthy individuals, wherein in the detectable label and the imaging method are the same for both the patient and the healthy individual.

In one embodiment, the protein-binding agent is introduced into the vascular system of the subject, for example, intravenously. In one embodiment, the protein-binding agent is introduced into the abdomen cavity of the subject, preferably within the vicinity of the appendix at the lower right abdomen. In one embodiment, the protein-binding agent is introduced into the peritoneal cavity, preferably within the vicinity of the appendix at the lower right abdomen.

In one embodiment, a fixed amount of time is allowed to lapse before imaging is performed.

In one embodiment, the protein-binding agent is an antibody or fragment thereof. In one embodiment, the protein-binding agent is a monoclonal antibody or active fragment thereof. In one embodiment, the protein-binding agent is a polyclonal antibody or active fragment thereof. For example, the protein-binding agent is an anti-LRG antibody or fragments thereof. In some embodiments, the protein-binding agent is an antibody that is specifically immunoreactive (i.e. binds specifically to) to a biomarker protein selected from the group consisting of leucine-rich α-2-glycoprotein (LRG); S100-A8 (calgranulin); α-1-acid glycoprotein 1 (ORM); plasminogen (PLG); mannan-binding lectin serine protease 2 (MASP2); zinc-α-2-glycoprotein (AZGP1); apolipoprotein D (ApoD); α-1-antichymotrypsin (SERPINA3); AMBP; amyloid-like protein 2; angiotensin converting enzyme 2; BAZ1B; carbonic anhydrase 1; CD14; chromogranin A; FBLN7; FXR2; hemoglobin α; hemoglobin β; interleukin-1 receptor antagonist protein; inter-α-trypsin inhibitor; lipopolysaccharide binding protein; lymphatic vessel endothelial hyaluronan acid receptor 1; MLKL; nicastrin; novel protein (Accession No: IPI00550644); PDZK1 interacting protein 1; PRIC285; prostaglandin-H2 D-isomerase; Rcl; S100-A9; serum amyloid A protein; SLC13A3; SLC2A1; SLC2A2; SLC4A1; SLC9A3; SORBS1; SPRX2; supervillin; TGFbeta2R; TTYH3; VA0D1; vascular adhesion molecule 1; versican; VIP36; α-1-acid glycoprotein 2; β-1,3-galactosyltransferase and a biomarker selected from Table 1.

In one embodiment, the protein-binding agent is conjugated to a label for extracorporeal detection of the protein binding agent located in the body of the subject.

In some embodiments, the detectable label on the protein-binding agent is selected from the group comprising of radioisotopes, paramagnetic labels, echogenic liposomes, biotin, and fluorescence.

In some embodiments, the extracorporeal detection method is selected from the group comprising magnetic resonance imaging (MRI), computer axial tomography (CAT) scan, positron emission tomography (PET) scan, electron beam, computed tomography (CT) scan, single photon emission computed tomography (SPECT) imaging, gamma imaging, angiography, abdominal ultrasound, and abdominal radioactive and fluorescent detection.

In one embodiment, radionuclide is used as the labeling means and the step of detecting the location of the protein binding agent within the subject further includes detecting radiation therefrom with a radiation detector. In one embodiment, a radionuclide is the detectable label conjugated to the protein binding agent.

In one embodiment, step of detecting radiation further includes employing a gamma camera to detect and make an image of gamma radiation emitted by the labeling means of the protein binding reagent.

Suitable radionuclides include Co-57, Cu-67, Ga-67, Ga-68, Ru-97, Tc-99m, In-111, In-113m, I-123, I-125, I-131, Hg-197, Au-198, and Pb-203. The radionuclides can be linked by direct labeling (e.g., by acidic buffered reactions or oxidative procedures) or by ligand exchange or chelation. The radionuclides are preferably imaged with a radiation detection means capable of detecting gamma radiation, such as a gamma camera or the like. Methods of radiolabeling of proteins for imaging are well known to one skilled in the art, for examples, D. Hnatowich, et al., 1983, Science 220:613-615; M. R. McDevitt, et al., 2000, Cancer Res. 60:6095-6100; DA Scheinberg, et al., 1982, Science, 215:1511-1513; and W. J. McBride, et al., 2009, J. Nucl. Med. 50, 991-998; and R. Macklis, B. et al., 1988, Science 240:1024-1026; U.S. Pat. Nos. 4,472,509; 4,454,106; 4,634,586; 4,994,560; 5,286,850; U.S. Patent Application Nos. 2008/0241967 and 20090297620. These are all incorporated herein by reference in their entirety.

Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The invention can also be practiced with non-radioactive labeling means, such as magnetic contrast agents capable of detection in magnetic resonance imaging (MRI) systems. In such systems, a strong magnetic field is used to align the nuclear spin vectors of the atoms in a patient's body. The field is then disturbed and an image of the patient is read as the nuclei return to their equilibrium alignments. In the present invention, the protein binding agent can be linked to diamagnetic contrast agents, such as gadolinium, cobalt, nickel, manganese or copper complexes, to form conjugate diagnostic reagents that are imaged extracorporeally with an MRI system. Other imaging techniques include plethysmography, thermography and ultrasonic scanning In one embodiment, the protein binding agent such as an antibody can be genetically or chemically engineered to contain $^{99m}$Tc binding sites for nuclear scintigraphy imaging. In vivo localized quantitative imaging is performed (SPECT imaging) can be carried out on the subject.

In one embodiment, the protein binding agent can be labeled with gadolinium or echogenic liposomes for magnetic resonance and abdomen ultrasound imaging, respectively.

Methods and regents such as detectably labeled antibodies for in situ imaging are been described and are well known in the art, for example, U.S. Pat. Nos. 3,899,675; 4,660,563; 4,877,599; 4,647,445; 5,605,831; 6,716,410; U.S. Patent Application Nos. 2009/0016965 and 20070059775. Additional methods and regents for in situ imaging are described in JH Tseng, 2001, Abdominal Imaging, 26: 171-177; Liu, Qing-Yu, 2009, Abdominal Imaging, in press; DA Scheinberg, et al., 1982, Science, 215:1511-1513; and W. J. McBride, et al., 2009, J. Nucl. Med. 50, 991-998. These are all incorporated herein by reference in their entirety.

Conjugation of Protein Binding Agent, e.g. Antibody to Echogenic Liposomes for Ultrasound Imaging Antibody-conjugated echogenic liposomes have been developed for site-specific intravascular (30 MHz) and transvascular (15 MHz) image enhancement. As examples, anti-fibrinogen and anti-intercellular adhesion molecule-1 (anti-ICAM-1) antibodies have been conjugated to acoustically reflective liposomes and images obtained in animal models of thrombi and atherosclerotic lesions. These acoustic liposomes consist of a 60:8:2:30 molar mixture of phosphatidylcholine:phosphatidyl-ethanolamine:phosphatidylglycerol: cholesterol and are prepared by a dehydration/rehydration mixture. They are multilamellar with well separated lipid bilayers and internal vesicles which confers echogenicity. Their mean size is ~800 nm as measured by quasielastic light scattering. These liposomes are stable in circulation, do not trap gas, pass through pulmonary capillaries and retain their properties at 37° C., even after conjugation with antibodies. Antibodies are modified by the addition of cysteines to the C- or N-terminus of the protein and conjugated to liposomes. A 12 MHz imaging catheter (Acuson) is used for imaging (resolution<1 mm). The antibodies are thiolated with N-succinimidyl-3-(2-pyridyldithio) propionate, reduced, and conjugated with the liposomes by creating a thioether linkage between the antibody and phospholipid. The conjugated antibodies are stable and have a long shelf half-life. Imaging is by ultrasound.

Gadolinium(Gd3)-Labeled Protein Binding Agent, e.g. scFv Antibodies (MAbs)

An alternative imaging method that provides enhanced resolution (<0.5 mm), magnetic resonance imaging (MRI) is using Gd3-labeling protein binding agent as a contrast agent. MRI has the advantages of rapid acquisition, increased resolution, and absence of radioactivity However, because free Gd3 as a contrast agent is toxic, it is used in clinical MRI imaging bound to diethylenetriaminepentaacetic acid (DTPA). Precedent exists for conjugating Gd3 to MAbs by reacting cyclic-diaminetriaminepentaacetic acid anhydride (c-DTPA) with the MAb. Polylysine-DTPA-Gd3-coupled antibodies have been used for tumour imaging with up to 30 Gd3 ions conjugated without significantly affecting antigen affinity. Previous studies using Gd3-labeled MAbs have either directly bound Gd3 to available $NH_2$ groups or chemically conjugated polylysine. The natural site for coupling DTPA is limited in scFv (single chain antibody) molecules. Therefore, genetic fusion of several clusters of polylysine groups (6-30 in length) to the N-terminal or C-terminal of scFv MAb can be used and this fusion can be reacted with c-DTPA. Although other amino groups may potentially react, the availability of polylysine in the tail of the molecule should allow preferential site-directed labeling. The bioengineering of the polylysine site was done by PCR using primers encoding six lysine residues and restriction site for cloning at both 5' and 3' ends.

Imaging with $^{99m}$Tc-Labeled Protein Binding Agent, e.g. Antibody $^{99m}$Tc-labeling of oxidation specific antibodies has been previously described (Tsimikas et al., 1999, J Nucl Cardiol. 1999; 6:41-53). $^{99m}$Tc-protein binding agent specific for the biomarkers described herein can be intravenously injected into the patient and is analyzed for the pharmacokinetics, organ distribution and appendix uptake. For in vivo imaging, 1-5 mCi are intravenously injected in the patient and imaging can be performed with a dual detector ADAC vertex model gamma camera set to a 20% window for $^{99m}$Tc (VXUR collimator) equipped with ADAC Pegasys™ computer software. In vivo images planar (anterior, posterior and 45° oblique positions) and SPECT can be acquired on a 256×256×12 matrix for a minimum of $1\times10^6$ counts at 10 minutes post injection. Repeat imaging can be performed for 3-500,000 counts at various time points based on the optimal target to background ratio derived from in vivo uptake data. Previous imaging studies using whole monoclonal antibody have shown that whole monoclonal antibody often give a low signal to noise ratio due to the prolonged half-life of the $^{99m}$Tc-MAb in the circulation. The use of Fab, scFv, or smaller fragments can abrogate this problem under certain imaging conditions as the Fabs and scFvs have a very short half lives (<30 minutes). When the signal to noise ratio is not favorable, injections of MDA-LDL, Cu-OxLDL, or other appropriate antigen can be injected to clear the background signal.

Imaging with Gd3-Labeled Protein Binding Agent, e.g. Antibody

Labeling of Gd3 to an antibody-DTPA complex has been previously described (Lister-James, et al, 1996, J Nucl Med. 1996; 40:221-233; Wu et al, 1995, Arterioscler Thromb Vasc Biol. 1995; 15:529-533). Initial testing by in vivo uptake assays can be carried out with 153 Gd-antibody in mice and rabbits and the pharmacokinetics, biodistribution and aortic plaque uptake of antibody is determined. In vivo imaging can be performed in rabbits with a 1.5 T GE MRI scanner with a small surface coil.

Computer Systems and Computer Readable Media to Assay Appendicitis Biomarkers in Urine Samples.

One aspect of the present invention relates to a system for analyzing a urine biological sample from a subject, where the system comprises: (a) a determination module configured to receive a urine biological sample and to determine an appendicitis biomarker level information, wherein the appendicitis biomarker level information comprises determination of at least one appendicitis biomarker level, i.e. at the level or amount of an appendicitis biomarker, such as LRG, or any or a combination of appendicitis biomarkers listed in Table 1; (b) a connection from the determination module to transmit the appendicitis biomarker level information to an electronic computer, wherein the computer comprises a storage device, a comparison module and a display module; (c) the storage device configured to store appendicitis biomarker level information from the determination module; (d) the comparison module adapted to compare the appendicitis biomarker level information stored on the storage device with reference data, and to provide a comparison result, wherein the comparison result comprises; (i) a comparison of the appendicitis biomarker level in the urine biological sample with the reference appendicitis biomarker level, and (ii) a determination of the appendicitis biomarker level in the biological sample above or below a threshold level relative to the reference appendicitis biomarker level, wherein a appendicitis biomarker level above the threshold level for that biomarker is indicative of acute appendicitis (i.e. a positive test result); and wherein a appendicitis biomarker level below the threshold level is indicative of absence of acute appendicitis (i.e. a negative test result); and (e) the display module for displaying a content based in part on the comparison result for the user, wherein the content is a signal indicative of the likelihood of a subject having acute appendicitis (i.e. a positive test result) or unlikely to have acute appendicitis (i.e. a negative test result).

Another aspect of the present invention relates to a computer readable medium having computer readable instructions recorded thereon to define software modules including a comparison module and a display module for implementing a method on a computer, the method comprising: (a) comparing with the comparison module the data stored on a storage device with reference data to provide a comparison result, wherein the comparison result is the appendicitis biomarker level information in the urine biological above a threshold level relative to a reference appendicitis biomarker level for that biomarker tested which is indicative of acute appendicitis; and (b) displaying a content based in part on the comparison result for the user, wherein the content is a signal indicative of acute appendicitis.

In some embodiments, the appendicitis biomarker threshold level which is used in the system, computer-readable medium and methods as disclosed herein that is indicative of acute appendicitis is at a level of at least about two-fold (2×) above the control or reference appendicitis biomarker level for that biomarker. For example, if the appendicitis biomarker is LRG, if the level of LRG in the test urine sample from the subject is at least about 2-fold above the reference LRG biomarker level, it is indicative of a subject likely to have or be at risk of acute appendicitis. In some embodiments a threshold level is at least about 3-fold, or at least about 4-fold, or at least about 5-fold, or at least about 6-fold, or at least about 7-fold, or at least about 8-fold, or at least about 9-fold, or at least about 10-fold or more than 10-fold above the reference level for that biomarker, and thus a the level of the appendicitis biomarker in the test urine sample above the threshold level it is indicative of a subject likely to have or be at risk of acute appendicitis.

In some embodiments, the system, computer-readable media and methods as disclosed herein is used to measure an appendicitis biomarker level in a biological sample, where the appendicitis biomarker level is the level of a polypeptide biomarker, for example any biomarker of Table 1 or of any SEQ ID NOs 1-49. In some embodiments, the level of at least one biomarker protein is measured by immuno assay, for example western blot analysis or ELISA, or a high-through-put protein detection method, for example but are not limited to automated immunohistochemistry apparatus, for example, robotically automated immunohistochemistry apparatus which in an automated system section the tissue or biological sample specimen, prepare slides, perform immunohistochemistry procedure and detect intensity of immunostaining, such as intensity of an antibody binding to a biomarker protein in the urine sample and produce output data. Examples of such automated immunohistochemistry apparatus are commercially available, for example such Autostainers 360, 480, 720 and Labvision PT module machines from LabVision Corporation, which are disclosed in U.S. Pat. Nos. 7,435,383; 6,998,270; 6,746,851, 6,735, 531; 6,349,264; and 5,839; 091 which are incorporated herein in their entirety by reference. Other commercially available automated immunohistochemistry instruments are also encompassed for use in the present invention, for example, but not are limited BOND™ Automated Immunohistochemistry & In Situ Hybridization System, Automate slide loader from GTI vision. Automated analysis of immunohistochemistry can be performed by commercially available systems such as, for example, IHC Scorer and Path EX, which can be combined with the Applied spectral Images (ASI) CytoLab view, also available from GTI vision or Applied Spectral Imaging (ASI) which can all be integrated into data sharing systems such as, for example, Laboratory Information System (LIS), which incorporates Picture Archive Communication System (PACS), also available from Applied Spectral Imaging (ASI) (see world-wide-web: spectral-imaging.com). Other a determination module can be an automated immunohistochemistry systems such as NexES® automated immunohistochemistry (IHC) slide staining system or BenchMark® LT automated IHC instrument from Ventana Discovery SA, which can be combined with VIAS™ image analysis system also available Ventana Discovery. BioGenex Super Sensitive MultiLink® Detection Systems, in either manual or automated protocols can also be used as the detection module, preferably using the BioGenex Automated Staining Systems. Such systems can be combined with a BioGenex automated staining systems, the i6000™ (and its predecessor, the OptiMax® Plus), which is geared for the Clinical Diagnostics lab, and the GenoMx 6000™, for Drug Discovery labs. Both systems BioGenex systems perform "All-in-One, All-at-Once" functions for cell and tissue testing, such as Immunohistochemistry (IHC) and In Situ Hybridization (ISH).

As an example, a determination module used in the system, computer-readable media and methods as disclosed herein for determining appendicitis biomarker level measures the level of at least one appendicitis biomarker polypeptide, for instance the determination module is configured to detect the total level (i.e. amount) of at least one appendicitis biomarker polypeptide of Table 1 using any known systems for automated protein expression analysis, including for example, but not limited Mass Spectrometry systems including MALDI-TOF, or Matrix Assisted Laser Desorption Ionization—Time of Flight systems; SELDI-TOF-MS ProteinChip array profiling systems, e.g. Machines with Ciphergen Protein Biology System II™ software; systems for analyzing gene expression data (see for example U.S. 2003/0194711); systems for array based expression analysis, for example HT array systems and cartridge array systems available from Affymetrix (Santa Clara, Calif. 95051) AutoLoader, Complete GeneChip® Instrument System, Fluidics Station 450, Hybridization Oven 645, QC Toolbox Software Kit, Scanner 3000 7G, Scanner 3000 7G plus Targeted Genotyping System, Scanner 3000 7G Whole-Genome Association System, GeneTitan™ Instrument, GeneChip® Array Station, HT Array; an automated ELISA system (e.g. DSX® or DK® form Dynax, Chantilly, Va. or the ENEA-SYSTEM III®, Triturus®, The Mago® Plus); Densitometers (e.g. X-Rite-508-Spectro Densitometer®, The HYRYS™ 2 densitometer); automated Fluorescence in situ hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, Becton Dickinson); and radio isotope analyzers (e.g. scintillation counters).

In some embodiments, the appendicitis biomarker level is the appendicitis biomarker polypeptide level of any biomarker listed in Table 1. In some embodiments, the appendicitis biomarker level is LRG polypeptide (SEQ ID NO:1). In some embodiments, the appendicitis biomarker level is ORM (SEQ ID NO:3) or MASP2 (SEQ ID NO:5).

In some embodiments, the system, computer-readable media and methods as disclosed herein is used to measure at least one appendicitis biomarker level in the biological sample such as a urine sample.

In some embodiments, the system, computer-readable media and methods as disclosed herein is used to measure at least one appendicitis biomarker level in urine biological sample which is obtained from a mammalian subject, for example a human subject. In some embodiments, the subject has at least one symptom of appendicitis as discussed herein.

In some embodiments, the system, computer-readable media and methods as disclosed herein is used to measure at least one appendicitis biomarker level in biological sample obtained from a subject who has experienced one or more symptoms of acute appendicitis include pain starting centrally (periumbilical) before localizing to the right iliac fossa (the lower right side of the abdomen); loss of appetite and fever; nausea or vomiting; the feeling of drowsiness; the feeling of general bad health; pain beginning and staying in the right iliac fossa, diarrhea and a more prolonged, smoldering course; increased frequency of urination; marked retching; tenesmus or "downward urge" (the feeling that a bowel movement will relieve discomfort); positive Rovsing's sign, Psoas sign, and/or Obturator sign.

In some embodiments, the system, computer-readable media and methods as disclosed herein comprises a determination module which has been configured to determine the level of an additional agent in the biological sample, for example, albumin.

In some embodiments, the system, computer-readable media and methods as disclosed herein is used to measure at least one appendicitis biomarker level in a urine biological sample to indicate if a subject has, or is at risk of acute appendicitis. Accordingly, in some embodiments, the system, computer-readable media and methods as disclosed herein is used to identify if a subject is has acute appendicitis.

In some embodiments, the system, computer-readable media and methods as disclosed herein is used to measure at least one appendicitis biomarker level in a urine biological sample obtained from a subject.

Another aspect of the present invention relates to a method of treating a subject identified to have acute appendicitis comprising; (a) determining if the subject has, or is likely to have or is at risk of having acute appendicitis by measuring at least one appendicitis biomarker level in a urine sample obtained from the subject, and if high levels (e.g. at least about 2-fold above a reference level for the measured biomarker) of the appendicitis biomarker protein exists in the urine biological sample from the subject, it indicates that the subject is likely to have acute appendicitis, and (b) administering an appropriate treatment to a subject determined to likely have acute appendicitis, where an appropriate treatment can be determined by an ordinary physician, for example by surgical resection of the appendix (i.e. appendectomy) if the appendicitis is severe, or antibiotics if the appendicitis is not severe.

In one embodiment, the method is performed on a subject who has experienced or exhibited symptoms of acute appendicitis or one or more of the following symptoms or risk factors: pain starting centrally (periumbilical) before localizing to the right iliac fossa (the lower right side of the abdomen); loss of appetite and fever; nausea or vomiting; the feeling of drowsiness; the feeling of general bad health; pain beginning and staying in the right iliac fossa, diarrhea and a more prolonged, smoldering course; increased frequency of urination; marked retching; tenesmus or "downward urge" (the feeling that a bowel movement will relieve discomfort); positive Rovsing's sign, Psoas sign, and/or Obturator sign.

In one embodiment, the diagnostic tool or device is used to test a urine sample from a subject who has experienced or exhibited symptoms of acute appendicitis or one or more of the following symptoms or risk factors: pain starting centrally (periumbilical) before localizing to the right iliac fossa (the lower right side of the abdomen); loss of appetite and fever; nausea or vomiting; the feeling of drowsiness; the feeling of general bad health; pain beginning and staying in the right iliac fossa, diarrhea and a more prolonged, smoldering course; increased frequency of urination; marked retching; tenesmus or "downward urge" (the feeling that a bowel movement will relieve discomfort); positive Rovsing's sign, Psoas sign, and/or Obturator sign.

The device or methods as disclosed herein can be used to assess the urine sample from a subject at one or more indicated times following specific experienced symptoms of the subject, such as initial symptoms (e.g., at about 1 hour, 2-5 hours, 10 hours, 12 hours, 24 hours, 36 hours, 48 hours, and/or 72 hours.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Definitions of Terms

Unless otherwise explained, all technical and scientific terms used herein have the same meaning as commonly understood by one of ordinary skill in the art to which this disclosure belongs. Definitions of common terms in urology, endocrinology, biochemistry and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in Molecular Biology 149) by Crowther J. R. (2000); Fundamentals of RIA and Other Ligand Assays by Jeffrey Travis, 1979, Scientific Newsletters; and Immunology by Werner Luttmann, published by Elsevier, 2006.

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); A. R. Kimmerl Eds., Academic Press Inc., San Diego, USA (1987)) and Current Protocols in Immunology (CPI) (John E. Coligan, et. al., ed. John Wiley and Sons, Inc.), which are all incorporated by reference herein in their entireties.

As used herein, the term "biomarker" is a biological characteristic that is measured and evaluated objectively as an indicator of normal biological or pathogenic processes (a diagnostic biomarker), or a pharmacological response to therapeutic intervention (a therapeutic biomarker). A "biomarker" can be any patient parameter that can be measured, for example, mRNA expression profiles, proteomic signatures, protein, hormone or lipid levels, imaging methods or electrical signals. Typically, the term "biomarker" as used herein refers to a protein, polypeptide or peptide in the sample.

The term "protein binding agent" is used interchangeably herein with "protein binding molecule" or protein binding moiety" and refers to any entity which has specific affinity for a protein. The term "protein-binding molecule" also includes antibody-based binding moieties and antibodies and includes immunoglobulin molecules and immunologically active determinants of immunoglobulin molecules, e.g., molecules that contain an antigen binding site which specifically binds (immunoreacts with) to the Psap proteins. The term "antibody-based binding moiety" is intended to include whole antibodies, e.g., of any isotype (IgG, IgA, IgM, IgE, etc), and includes fragments thereof which are also specifically reactive with the Psap proteins. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled. In some embodiments, a "protein-binding agent" is a co-factor or binding protein that interacts with the appendicitis biomarker protein to be measured, for example a co-factor or binding protein or ligand to the appendicitis biomarker protein.

The term "labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of a appendicitis biomarker protein present in a urine samples correlate to the intensity of the signal emitted from the detectably labeled antibody.

The term "specific affinity" or "specifically binds" or "specific binding" are used interchangeably herein refers to an entity such as a protein-binding molecule or antibody that recognizes and binds a desired polypeptide (e.g. a specific appendicitis biomarker protein) but that does not substantially recognize and bind other molecules in the sample, i.e. a urine sample. In some embodiments, the term "specifically binds" refers to binding with a $K_d$ of 10 micromolar or less, preferably 1 micromolar or less, more preferably 100 nM or less, 10 nM or less, or 1 nM or less.

The term "antibody" is meant to be an immunoglobulin protein that is capable of binding an antigen. Antibody as used herein is meant to include antibody fragments, e.g. $F(ab')_2$, Fab', Fab, capable of binding the antigen or antigenic fragment of interest.

The term "humanized antibody" is used herein to describe complete antibody molecules, i.e. composed of two complete light chains and two complete heavy chains, as well as antibodies consisting only of antibody fragments, e.g. Fab, Fab', $F(ab')_2$, and Fv, wherein the CDRs are derived from a non-human source and the remaining portion of the Ig molecule or fragment thereof is derived from a human antibody, preferably produced from a nucleic acid sequence encoding a human antibody.

The terms "human antibody" and "humanized antibody" are used herein to describe an antibody of which all portions or majority (at least 80%) of the antibody molecule are derived from a nucleic acid sequence encoding a human antibody. Such human antibodies are most desirable for use in antibody therapies; as such antibodies would elicit little or no immune response in the human subject.

The term "chimeric antibody" is used herein to describe an antibody molecule as well as antibody fragments, as described above in the definition of the term "humanized antibody." The term "chimeric antibody" encompasses humanized antibodies. Chimeric antibodies have at least one portion of a heavy or light chain amino acid sequence derived from a first mammalian species and another portion of the heavy or light chain amino acid sequence derived from a second, different mammalian species. In some embodiments, a variable region is derived from a non-human mammalian species and the constant region is derived from a human species. Specifically, the chimeric antibody is preferably produced from a nucleotide sequence from a non-human mammal encoding a variable region and a nucleotide sequence from a human encoding a constant region of an antibody.

In the context of this invention, the term "probe" refers to a molecule which can detectably distinguish between target molecules differing in structure. Detection can be accomplished in a variety of different ways depending on the type of probe used and the type of target molecule, thus, for example, detection may be based on discrimination of activity levels of the target molecule, but preferably is based on detection of specific binding. Examples of such specific binding include antibody binding and nucleic acid probe hybridization. Thus, for example, probes can include enzyme substrates, antibodies and antibody fragments, and preferably nucleic acid hybridization probes.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "agent" as used herein refers to a chemical entity or biological product, or combination of chemical entities or biological products. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. The term "agent" refers to any entity selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "support" refers to conventional supports such as beads, particles, dipsticks, fibers, filters, membranes and silane or silicate supports such as glass slides.

The terms "reduced" or "reduce" or "decrease" as used herein generally means a decrease by a statistically significant amount relative to a reference. However, for avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e. absent level as compared to a reference sample), or any decrease between 10-100% as compared to a reference level, as that term is defined herein.

The term "low" as used herein generally means lower by a statically significant amount; for the avoidance of doubt, "low" means a statistically significant value at least 10% lower than a reference level, for example a value at least 20% lower than a reference level, at least 30% lower than a reference level, at least 40% lower than a reference level, at least 50% lower than a reference level, at least 60% lower than a reference level, at least 70% lower than a reference level, at least 80% lower than a reference level, at least 90% lower than a reference level, up to and including 100% lower than a reference level (i.e. absent level as compared to a reference sample).

The terms "increased" or "increase" as used herein generally mean an increase by a statically significant amount; for the avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "high" as used herein generally means a higher by a statically significant amount relative to a reference; for the avoidance of doubt, "high" means a statistically significant value at least 10% higher than a reference level, for example at least 20% higher, at least 30% higher, at least 40% higher, at least 50% higher, at least 60% higher, at least 70% higher, at least 80% higher, at least 90% higher, at least 100% higher, at least 2-fold higher, at least 3-fold higher, at least 4-fold higher, at least 5-fold higher, at least 10-fold higher or more, as compared to a reference level.

As used herein, the terms "treat," "treating," and "treatment" refer to the alleviation or measurable lessening of one or more symptoms or measurable markers of a disease or disorder; while not intending to be limited to such, disease or disorders of particular interest include ischemic or ischemia/reperfusion injury and diabetes. Measurable lessening includes any statistically significant decline in a measurable marker or symptom.

As used herein, the terms "prevent," "preventing" and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the complete avoidance or prevention of symptoms or markers, but also a reduced severity or degree of any one of those symptoms or markers, relative to those symptoms or markers arising in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

As used herein the term "reference level" is used interchangeably herein with "reference value" and refers to a level in a particular appendicitis biomarker which provides a baseline against which to compare the measured appendicitis biomarker protein level from the test urine biological sample. As an illustrative example, the reference level for a particular appendicitis biomarker protein can be calculated as the average level of that appendicitis biomarker protein level from a plurality of urine biological samples obtained from a plurality of subjects with similar demographics (i.e. age, gender, weight, ethnicity and the like) which do not have appendicitis. As another illustrative example only, a reference level for a particular appendicitis biomarker protein can be from a plurality of subjects that do not have appendicitis. As another illustrative example only, a reference level for a particular appendicitis biomarker protein can be from the same subject taken at an earlier timepoint. Typically, a reference level is normalized to "0" value, and an increase, for example at least about a 2-fold increase in the particular appendicitis biomarker protein measured by the determination module or in the system and methods as disclosed herein relative to the reference level would indicate a subject would likely have appendicitis (i.e. a positive appendicitis test result). A reference appendicitis biomarker level can be from an individual not affected by a given pathology (i.e. not affected with appendicitis or having a symptom of appendicitis), or, alternatively, from the same individual being tested, where the urine for the reference appendicitis biomarker level was taken at an at least one earlier time point (i.e. $t_0$, $t_1$, $t_2$ etc) when the subject did not exhibit a symptom of appendicitis. A reference appendicitis biomarker level can also be a pooled sample, taken from a plurality of individuals not affected by appendicitis. Where appropriate, a reference appendicitis biomarker level can also be a fixed reference level of an appendicitis biomarker level, where a test appendicitis biomarker level above the fixed reference level (i.e. at least about 2-fold above the fixed reference level) identifies a subject likely to have appendicitis. It is preferred that a reference sample be from an individual or group of individuals of similar characteristics to the tested individual, e.g., that the reference be taken from individuals of similar age, gender, rave or ethnic background, etc. In some embodiments, other reference levels can also be used, for example a positive reference appendicitis biomarker level can be used as a positive control for a subject having a risk of acute appendicitis. Typically, where a positive reference level is used, if the appendicitis biomarker level in the test urine biological sample is substantially the same or close in the value of the positive reference appendicitis biomarker level, it would indicate a positive test result for acute appendicitis.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip.

The term "software" can refer to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

The term "proteomics" may refer to the study of the expression, structure, and function of proteins within cells, including the way they work and interact with each other, providing different information than genomic analysis of gene expression.

As used herein the term "consisting essentially of" refers to those elements required for a given embodiment. The term permits the presence of elements that do not materially affect the basic and novel or functional characteristic(s) of that embodiment of the invention.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

As used herein, the term "comprising" means that other elements can also be present in addition to the defined elements presented, whether essential or not. The use of "comprising" indicates inclusion rather than limitation.

As used herein the term "consisting essentially of" refers to those elements required for a given embodiment. The term permits the presence of elements that do not materially affect the basic and novel or functional characteristic(s) of that embodiment of the invention.

The term "consisting of" refers to kits and methods thereof as described herein, which are exclusive of any element not recited in that description of the embodiment.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention can be defined by any of the following alphabetized paragraphs:

[A] A device for detecting at least one appendicitis biomarker protein in a urine sample from a subject to identify if the subject is likely to have acute appendicitis, the device comprising: (a) at least one protein-binding agent which specifically binds to at least one appendicitis biomarker protein selected from the group of: leucine α-2 glycoprotein (LRG), mannan-binding lectin serine protease 2 (MASP2), α-1-acid glycoprotein 1 (ORM); and (b) at least one solid support for the at least one protein binding-agent in (a), wherein the protein-binding agent is deposited on the solid support.

[B] The device of paragraph [A], wherein the protein-binding agent deposited on the solid support specifically binds the polypeptide of leucine α-2 glycoprotein (LRG) of SEQ ID NO: 1.

[C] The device of paragraph [A], wherein the protein-binding agent deposited on the solid support specifically binds to the polypeptide of α-1-acid glycoprotein 1 (ORM) of SEQ ID NO: 3.

[D] The device of paragraph [A], wherein the protein-binding agent deposited on the solid support specifically binds to the polypeptide of mannan-binding lectin serine protease 2 (MASP2) of SEQ ID NO: 5.

[E] The device of paragraph [A], wherein the device further comprises at least one additional different protein-binding agent deposited on the solid support, wherein the additional protein-binding agent specifically binds to an appendicitis biomarker protein selected from the group consisting of: leucine-rich α-2-glycoprotein (LRG); S100-A8 (calgranulin); α-1-acid glycoprotein 1 (ORM); lasminogen (PLG); mannan-binding lectin serine protease 2 (MASP2); zinc-α-2-glycoprotein (AZGP1); apolipoprotein D (ApoD); α-1-antichymotrypsin (SERPINA3).

[F] The device of paragraph [A], wherein the device further comprises at least one additional different protein-binding agent deposited on the solid support, wherein the additional protein-binding agent specifically binds to an appendicitis biomarker protein selected from the group consisting of: Adipocyte specific adhesion molecule; AMBP; Amyloid-like protein 2; Angiotensin converting enzyme 2; BAZ1B; Carbonic anhydrase 1; CD14; chromogranin A; FBLN7; FXR2; Hemoglobin α; Hemoglobin β; Interleukin-1 receptor antagonist protein; Inter-α-trypsin inhibitor; Lipopolysaccharide binding protein; Lymphatic vessel endothelial hyaluronan acid receptor 1; MLKL; Nicastrin; Novel protein (Accession No: IPI00550644); PDZK1 interacting protein 1; PRIC285; Prostaglandin-H2 D-isomerase; Rcl; S100-A9; Serum amyloid A protein; SLC13A3; SLC2A1; SLC2A2; SLC4A1; SLC9A3; SORBS1; SPRX2; Supervillin; TGFbeta2R; TTYH3; VA0D1; Vascular adhesion molecule 1; Versican; VIP36; α-1-acid glycoprotein 2; and 13-1,3-galactosyltransferase.

[G] The device of paragraph [A], wherein the solid support is in the format of a dipstick, microfluidic chip or a cartridge.

[H] The device of any of paragraphs [A] to [G], wherein the protein-binding agent is an antibody, antibody fragment, aptamer, small molecule or variant thereof

[I] The device of any of paragraphs [A] to [H], wherein the subject is a human subject.

[J] The device of any of paragraphs [A] to [I], wherein the subject is a subject with at least one symptom of appendicitis.

[K] The device of any of the paragraphs [A] to [J], wherein the protein-binding agent deposited on the device specifically binds to the appendicitis biomarker protein when the level of the appendicitis biomarker protein is at least 2-fold above a reference level for that biomarker protein.

[L] A device of paragraph [K], wherein the reference level is an average level of the appendicitis biomarker protein in a plurality of urine samples from a population of healthy humans not having acute appendicitis.

[M] Use of the device of any of paragraphs [A] to [L] to identify if a subject to have acute appendicitis, wherein if at least one appendicitis biomarker protein specifically binds to at least one protein-binding agent, the subject is likely to have acute appendicitis.

[N] A kit comprising: (a) a device according to any of paragraphs [A] to [L]; and (b) a first agent, wherein the first agent produces a detectable signal in the presence of a protein-binding agent which deposited on the device is specifically bound to an appendicitis biomarker protein.

[O] The kit of paragraph [N], further comprising a second agent, wherein the second agent produces a different detectable signal in the presence of a second protein-binding agent deposited on the device which is specifically bound to a second appendicitis biomarker protein.

[P] A method to identify the likelihood of a subject to have acute appendicitis comprising: (a) measuring the level of at least one appendicitis biomarker protein selected from the group listed in Table 1 in a urine sample from the human subject; (b) comparing the level of the at least one appendicitis biomarker protein measured in step (a) to a reference level for the measured biomarker; wherein if the level of the measured appendicitis biomarker protein is at least 2-fold increased than the reference level for the appendicitis biomarker protein, it identifies the subject is likely to have acute appendicitis.

[Q] The method of paragraph [P], further comprising determining the level of albumin in the urine sample from the human subject.

[R] The method of any of paragraphs [P]-[Q], wherein the human exhibits at least one symptom of acute appendicitis.

[S] The method of any of paragraphs [P]-[R], wherein the measuring is completed with the use of an immunoassay or an automated immunoassay.

[T] The method of any of paragraphs [P]-[S], wherein the appendicitis biomarker protein is leucine α-2 glycoprotein (LRG).

[U] The method of any of paragraph [P]-[T], wherein the appendicitis biomarker is α-1-acid glycoprotein 1 (ORM).

[V] The method of any of paragraphs [P]-[U], wherein the appendicitis biomarker protein is mannan-binding lectin serine protease 2 (MASP2)

[W] The method of any of paragraphs [P]-[S], wherein the appendicitis biomarker protein is selected from a group consisting of leucine α-2 glycoprotein (LRG), calgranulin A (S100-A8), α-1-acid glycoprotein 1 (ORM), plasminogen (PLG), mannan-binding lectin serine protease 2 (MASP2), Zinc-α-2-glycoprotein (AZGP1), α-1-antichymotrypsin (SERPINA3) and apolipoprotein D (ApoD).

[X] The method of any of paragraphs [P]-[W], wherein the reference level is a level of the appendicitis biomarker protein in a urine sample of a healthy human not having acute appendicitis.

[Y] The method of any of paragraphs [P]-[W], wherein the reference level is an average level of the appendicitis biomarker protein in a plurality of urine samples from a population of healthy humans not having acute appendicitis.

[Z] The method of any of paragraphs [P]-[W], wherein the reference level is a normalized level of the appendicitis biomarker protein in a urine sample of a healthy human not having acute appendicitis, wherein the normalization is performed against the level of albumin in the urine sample of a healthy human not having acute appendicitis.

[AA] The method of any of paragraphs [P]-[Z], wherein the urine sample is collected in mid-stream.

[BB] The method of any of paragraph [P]-[Z], wherein the urine sample is obtained by depositing the urine on to a test strip.

This invention is further illustrated by the following examples which should not be construed as limiting. The contents of all references, patents, and patent applications cited throughout this application, as well as the figures and table are incorporated herein by reference.

Example 1

Urine Proteomics for Profiling of Human Disease Using High Accuracy Mass Spectrometry Knowledge of the biologically relevant components of human tissues has enabled the invention of numerous clinically useful diagnostic tests, as well as non-invasive ways of monitoring disease and its response to treatment. By virtue of tissue perfusion, blood serum is the most useful material for the discovery of such biomarkers in general. However, the relatively high concentration of serum proteins, as well as their wide range of concentrations, spanning at least 9 orders of magnitude, often limit the study of serum biomarkers [1], though several recent approaches are promising [2-4].

On the other hand, of the biological fluids amenable to routine clinical evaluation, urine has the advantage of being frequently and non-invasively available, abundant, and as a result of being a filtrate of serum, relatively simple in its composition. Consequently, detection of urinary proteins has been used to identify markers of disease affecting the kidney and the urogenital tract [5, 6], as well as distal organs such as the brain and the intestine [7, 8]. However, the current understanding of the human urinary proteome is incomplete, specifically with respect to its overall composition and dynamics, not to mention the identity of variable components that may dependent on physiologic state and disease.

Several approaches have been used to characterize the human urinary proteome. Initial studies using electrophoresis and immunoblotting were able to identify tens of abundant and rare urinary proteins [9]. Recently, Pisitkun and colleagues applied ultracentrifugation and liquid chromatography (LC)-tandem mass spectrometry (MS/MS) to identify 295 highly abundant unique proteins isolated from urinary exosomes [10]. Sun and colleagues identified 226 soluble proteins by using multidimensional LC-MS/MS [11]. For an overview, see Pisitkun et al [12]. And most recently, Adachi and colleagues identified more than 1,500 unique proteins from ultrafiltered urine with a high degree of accuracy by using a hybrid linear ion trap-Orbitrap (LTQ-Orbitrap) mass spectrometer [13].

The inventors herein extend the current characterization of the human urinary proteome by extensively fractionating urine using ultracentrifugation, gel electrophoresis, ion exchange and reverse phase chromatography, effectively reducing mixture complexity while minimizing loss of material. By using high accuracy mass measurements of the LTQ-Orbitrap mass spectrometer and LC-MS/MS of peptides generated from such extensively fractionated specimens, the inventors identified over 2,000 unique proteins in routinely collected individual urine specimens. The inventors provide assessments of the physical and tissue origins of the urinary proteome, as well as dependence of its detection on instrumental and individual variables. Finally, by using text mining and machine learning the inventors annotate the urinary proteome with respect to 27 common and more than 500 rare human diseases, thereby establishing a widely useful resource for the study of human pathophysiology and biomarker discovery.

Materials and Methods for Example 1

Sample Collection.

Urine was collected as clean catch, mid stream specimens as part of routine evaluation of 12 children and young adults (ages 1-18 years, median 11) presenting with acute abdominal pain in the Children's Hospital Boston's Emergency Department. Upon obtaining informed consent, urine was frozen at −80° C. in 12 ml aliquots in polyethylene tubes. All samples were frozen within 6 hours of collection.

Reagents.

All reagents were of highest purity available and purchased from Sigma Aldrich unless specified otherwise. HPLC-grade solvents were purchased from Burdick and Jackson.

Urine Sedimentation.

Aliquots were thawed and centrifuged at 17,000 g for 15 minutes at 10° C. to sediment cellular debris. Absence of intact cells in the sediment was confirmed by light microscopy (data not shown). Subsequently, supernatant was centrifuged at 210,000 g for 60 minutes at 4° C. to sediment vesicles and high molecular weight complexes. Resultant pellets were resuspended in 0.5 ml of 0.1× Laemmli buffer, concentrated 10-fold to 0.05 ml by vacuum centrifugation and stored at −80° C.

Cation Exchange Chromatography.

Supernatant remaining after ultracentrifugation was diluted 5-fold with 0.1 M acetic acid, 10% (v/v) methanol, pH 2.7 (Buffer A) and incubated with 1 ml 50% (v/v) slurry of SP Sephadex (40-120 .im beads, Amersham) for 30 minutes at 4° C. to adsorb peptides that are <30 kDa molecular weight. Upon washing the beads twice with Buffer A, peptides were eluted by incubating the beads in 5 ml of 0.5 M ammonium acetate, 10% (v/v) methanol, pH 7 for 30 minutes at 4° C. Eluted peptides were purified by reverse phase chromatography by using PepClean C-18 spin columns, according to manufacturer's instructions (Pierce). Residual purification solvents were removed by vacuum centrifugation and small proteins and peptides were resuspended in aqueous 50 mM ammonium bicarbonate buffer (pH 8.5).

Protein Precipitation.

Proteins remaining in solution after cation exchange were precipitated by adding trichloroacetic acid to 20% (w/v), with deoxycholate to 0.02% (w/v) and Triton X-100 to 2.5% (v/v) as carriers, and incubating the samples for 16 hours at 4° C. Precipitates were sedimented at 10,000 g for 15 minutes at 4° C. and pellets were washed twice with neat acetone at 4° C. with residual acetone removed by air drying. Dried pellets were resuspended in 0.1 ml of 1× Laemmli buffer.

Gel Electrophoresis.

Laemmli buffer suspended fractions (from 17,000 g and 210,000 g centrifugation, and from protein precipitation) were incubated at 70° C. for 15 min and separated by using NuPage 10% polyacrylamide Bis-Tris gels according to manufacturer's instructions (Invitrogen). Gels were washed three times with distilled water, fixed with 5% (v/v) acetic acid in 50% (v/v) aqueous methanol for 15 minutes at room temperature, and stained with Coomassie. Each gel lane was cut into 6 fragments and each fragment was cut into roughly 1 $mm^3$ particles, which were subsequently washed 3 times with water and once with acetonitrile.

Protein Reduction, Alkylation and Trypsinization.

Protein containing gel particles and cation exchange purified proteins were reduced with 10 mM dithiotreitol in 50 mM ammonium bicarbonate (pH 8.5) at 56° C. for 45 minutes. They were subsequently alkylated with 55 mM iodoacetamide in 50 mM ammonium bicarbonate (pH 8.5) at room temperature in darkness for 30 minutes. Gel particles were washed 3 times with 50 mM ammonium bicarbonate (pH 8.5) prior to digestion. Alkylated peptides were purified by using PepClean C-18 spin columns as described above to remove residual iodoacetamide from the cation exchange fraction. They were then digested with 12.5 ng/μl sequencing grade bovine trypsin in 50 mM ammonium bicarbonate (pH 8.5) at 37° C. for 16 hours. Tryptic products were purified by using PepClean C-18 spin columns as described above, vacuum centrifuged and stored at −80° C.

Mass Spectrometry and Liquid Chromatography.

Fractions containing tryptic peptides dissolved in aqueous 5% (v/v) acetonitrile and 0.1% (v/v) formic acid were resolved and ionized by using nanoflow high performance liquid chromatography (nanoLC, Eksigent) coupled to the LTQ-Orbitrap hybrid mass spectrometer (Thermo Scientific). Nanoflow chromatography and electrospray ionization were accomplished by using a 15 cm fused silica capillary with 100 mm inner diameter, in-house packed with Magic C18 resin (200 Å, 5 μm, Michrom Bioresources). Peptide mixtures were injected onto the column at a flow rate of 1000 nl/min and resolved at 400 nl/min using 45 min linear acetonitrile gradients from 5 to 40% (v/v) aqueous acetonitrile in 0.1% (v/v) formic acid. Mass spectrometer was operated in data dependent acquisition mode, recording high accuracy and high resolution survey Orbitrap spectra using the lock mass for internal mass calibration, with the resolution of 60,000 and m/z range of 350-2000. Six most intense multiply charged ions were sequentially fragmented by using collision induced dissociation, and spectra of their fragments were recorded in the linear ion trap, with the dynamic exclusion of precursor ions already selected for MS/MS of 60 sec.

Spectral Processing and Peptide Identification.

Custom written software was used to extract the 200 most intense peaks from each MS/MS spectrum and to generate mascot generic format files. Peak lists were searched against the human International Protein Index database (version 3.36, at the World Wide Website of "ebi.ac.uk/IPI") by using Mascot (version 2.1.04; Matrix Science), allowing for variable formation of N-pyroglutamate, Asn and Gln deamidation, N-acetylation, and methionine oxidation, requiring full trypsin cleavage of identified peptides with 2 possible miscleavages, and mass tolerances of 5 ppm and 0.8 Da for the precursor and fragment ions, respectively. Searches allowing semi-tryptic peptides did not affect overall search yields (data not shown). Spectral counts were calculated by summing the number of fragment ion spectra assigned to each unique precursor peptide.

Data Analysis.

Assessment of identification accuracy was carried out by searching a decoy database composed of reversed protein sequences of the target IPI database. Frequency of apparent false positive identifications was calculated by merging individual target and decoy searches for each sample. An initial estimate of the apparent false positive rate was obtained by dividing the number of peptide identifications with a Mascot score greater than the identity score obtained from the target search by the number of peptide identifications with a score higher than the identity score threshold extracted from the decoy search [37]. Only proteins identified on the basis of more than 2 peptides were included in the comparison. Parsimonious protein grouping was performed by remapping all peptide identifications onto their corresponding proteins as listed in the IPI. This step was necessary to generate a minimal, non-redundant list of proteins that explain all of the identified peptides, while excluding proteins that could not be unambiguously unidentified. This parsimonious list of proteins was used for comparisons of various samples at the protein level. For Gene Ontology annotation, the inventors used GO slim terms version 1.8, accessed by using GOfact (at the World Wide Website of "hupo.org.cn/GOfact"). For annotation of tissue expression of detected proteins, the inventors used version 2 of the GNF gene expression atlas (at the World Wide Website of "expression.gnf.org"), accessed by using BioMart (at the World Wide Website of "biomart.org").

Disease Annotations.

The inventors linked proteins found in the urine proteome to published articles that associate a protein with a human disease, as well articles that associate a disease with a protein. For the former, the inventors derived sets of diseases from OMIM [38], MeSH (at the World Wide Website of "nlm.nih.gov/mesh/"), and a short list of common diseases of interest not described in OMIM or MeSH (Additional Files, at the World Wide Website of "childrenshospital.org/research/steenlab"). The inventors extracted disease names from MeSH by selecting MeSH concepts with Descriptor Record Descriptor Class=1, and marked by SemanticTypeName 'Disease or Syndrome'. Synonym disease names were obtained from the content of Term or TermList elements for the main concept. For OMIM, documents matching an OMIM entry were obtained by searching Medline with a query of the form (Term1 OR Term2 . . . Termk), where Termk include the 100 lowest frequency terms in a given OMIM entry. These OMIM disease queries were executed by using Twease with the BM25EC scorer against abstracts in Medline [39], accessed Jul. 7, 2008. Documents that matched the query with a BM25EC score above a Z-score of 10 were considered matching the OMIM disease [40]. Each MeSH disease name and synonyms were expressed as a query of the form ("disease name" "alias 1"|"alias 2"| . . . ). Common disease names were expressed as a single phrase query.

To determine diseases that are associated with a given protein, the inventors queried BioMart by using IPI identifiers for proteins in the urine proteome to obtain corresponding protein descriptions and gene names. Queries of the form (IPI-id|"description"|GeneName) were generated for each protein, where IPI-id is the IPI identifier, and description is the description phrase retrieved from BioMart. These queries were run against Medline by using Twease with the slider parameter set to 0. Lists of documents matching protein names were stored and overlapped with lists of documents matching diseases. Pairs of disease associated proteins that matched less than 5 documents were discarded (manual examination indicated that this level of overlap frequently happens as an artifact of the search procedure). To further increase stringency of the protein disease literature associations, the inventors estimated the odds that the number of overlapping documents found between a given disease and protein could occur by chance, considering the number of documents matching either the disease or the proteins in Medline. Only protein name/disease name pairs with odds ratio greater than 2,000 were reported. Lists of overlapping documents were formatted in HTML files organized in hierarchies of diseases or proteins.

List of Abbreviations.

Liquid chromatography-tandem mass spectrometry (LC-MS/MS), linear ion trap (LTQ).

Results

Exhaustive Protein Capture from Routinely Collected Human Urine

In order to identify medically useful urinary proteins, the inventors obtained urine as routinely collected clean catch, mid stream urine specimens, collected at the time of clinical evaluation. The inventors examined urine samples from 12 children and young adults evaluated for abdominal pain in our Emergency Department, all of whom were previously healthy. Also examined were the urine samples from asymptomatic patients evaluated 6-8 weeks after they underwent appendectomies. All urines exhibited normal profiles without evidence of renal disease or infection, as assessed by using clinical urinalysis (data not shown). All urine specimens were frozen within 6 hours of collection, consistent with earlier temporal analysis of whole urine specimens which indicated that no detectable degradation occurred for as long as 24 hours of 4° C. refrigerated storage with subsequent freezing at −80° C. [14-16]. This is expected given the fact that urine is stored in situ for many hours in the bladder, reaching a physiologic equilibrium prior to collection.

Urine is a complex mixture with abundant proteins such as albumin and uromodulin obscuring the identification of less concentrated, biologically more informative proteins such as secreted cytokines and hormones for example. Thus, the inventors adopted a fractionation method that reduced mixture complexity while minimizing loss of material by first ultracentrifugating to fractionate urinary exosomes and other high molecular weight complexes from soluble peptides and proteins, subsequently capturing the latter by using size excluded cation exchange chromatography and trichloroacetic acid precipitation, respectively, which has been shown to capture more than 95% of proteins under similar conditions [17, 18].

Secondary and tertiary fractionations of thus captured proteins and peptides were achieved by using one dimensional SDS-PAGE of the ultracentrifugation and precipitation fractions, and liquid chromatography of the tryptic peptides of SDS-PAGE resolved proteins, respectively. As a result, high abundance proteins such as albumin and uromodulin, which would otherwise comprise more than 99% of the mixture, can be separated effectively from the bulk of the proteome (FIG. 1). Though the composition and concentration of urine varies with physiologic state, there was less than 10±10% (mean±standard deviation) difference in total protein abundance among individual specimens, as ascertained by using gel image densitometry (FIG. 1), similar to earlier studies of urine of children [19-21].

Accurate and Comprehensive Identification of Urinary Proteomes

Figure 3:
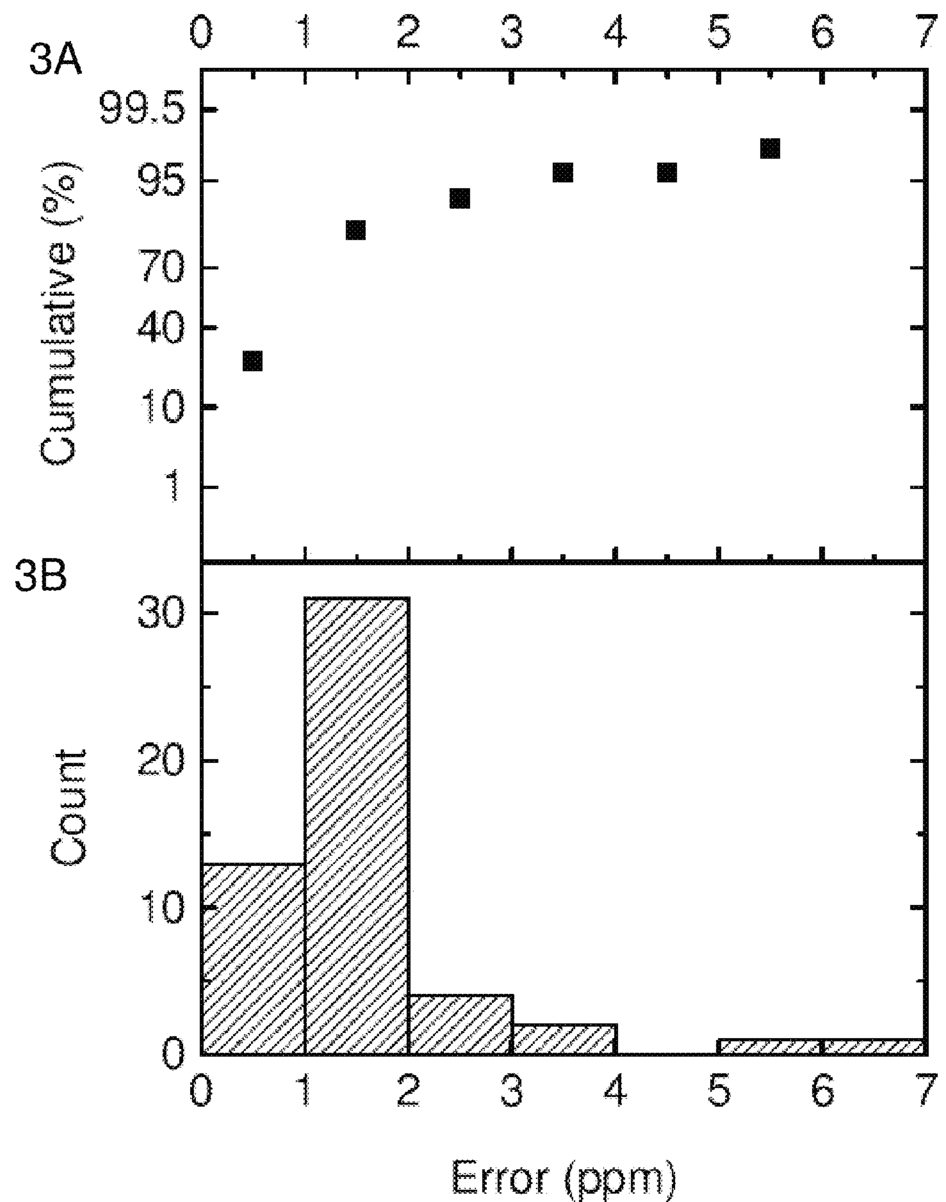
FIGS. 3A-3B shows the apparent mass accuracy error of the LTQ-Orbitrap.

In order to maximize detection sensitivity while minimizing identification errors, the inventors used the recently developed hybrid LTQ-Orbitrap mass spectrometer for tryptic peptide sequencing of the above fractionated proteomes. A representative set of tandem mass spectra is shown in FIG. 2, achieving mass errors of less than 2 ppm for the majority of the LC/MS runs as judged from analysis of trypsin autolysis peptides (FIG. 3). Peptide sequences were identified from tandem mass spectra by using probability based Mascot searches of the human IPI database (Methods). By carrying out simultaneous searches of the data against a decoy database containing reversed protein sequences, and rejecting (false) identifications of spectra that matched decoy sequences, as well as excluding proteins identified on the basis of single peptides, the inventors were able to achieve an apparent false positive protein identification frequency of less than 1%. The median number of unique peptides per identified protein was 10.

Figure 4:
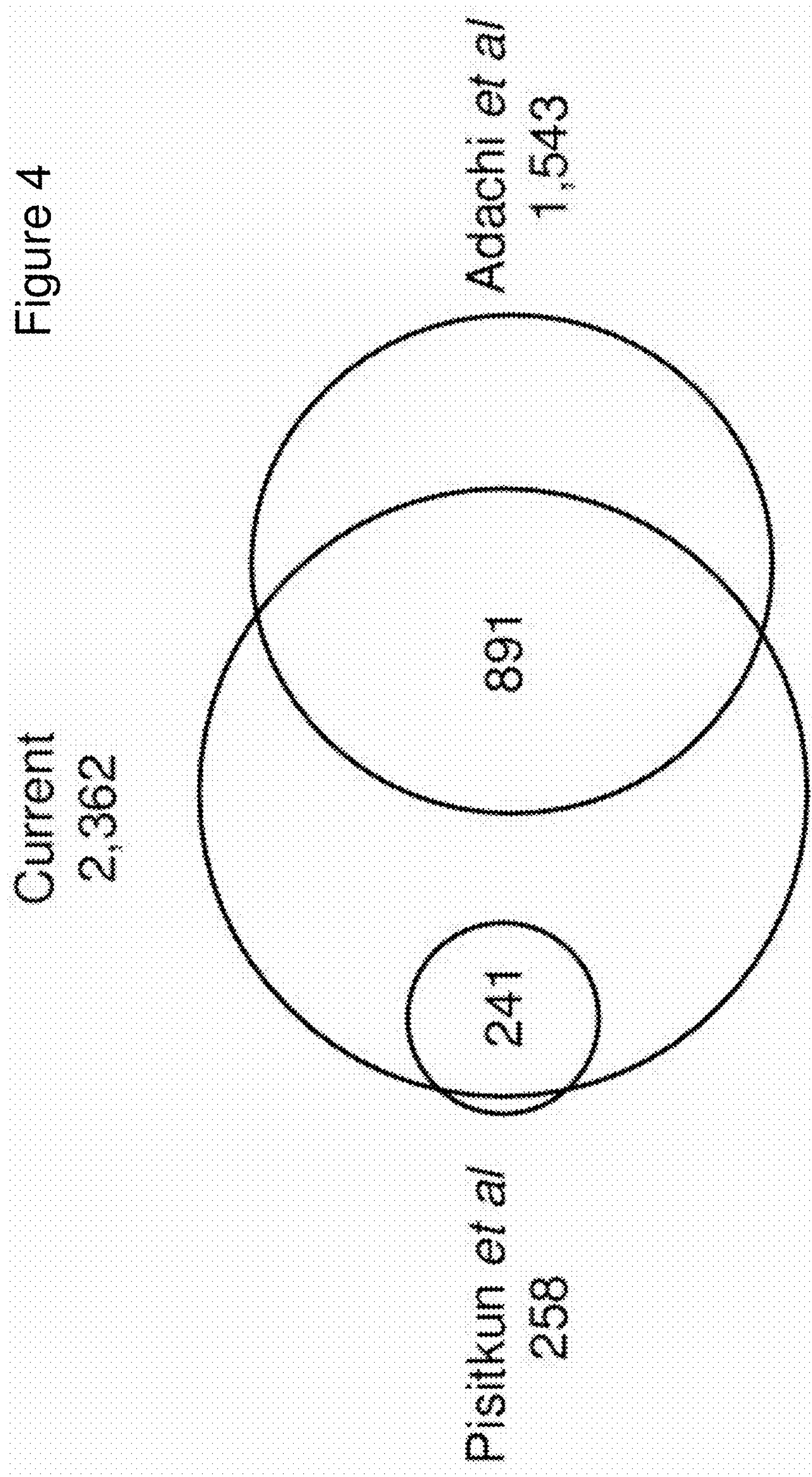
FIG. 4 is a venn diagram showing the comparisons of the observed aggregate urine proteome with those published by Adachi et al [13], and Pisitkun et al [10], demonstrating high concordance with the previous studies of human urine, as well as discovery of not previously observed proteins.

As a result, the inventors identified with high degree of accuracy [12], 126 unique peptides, corresponding to 2,362 proteins. These proteins include 891 proteins identified in an earlier high accuracy study of the human urine proteome [13], and more than 1,000 additional proteins identified for the first time (FIG. 4). These data are provided as Additional Files, and can be accessed publicly from the inventors' server (at the World Wide Website of "childrenshospital.org/research/steenlab").

Origin of the Human Urinary Proteome

The composition of the identified proteomes was characterized with respect to Gene Ontology (GO) annotated biological function, apparent physical origin, and predicted tissue expression. As compared with the entire list of IPI entries, analysis of GO annotated biological function revealed saturation of cellular components such as the cytoplasm, endoplasmic reticulum, golgi, lysosome, and the plasma membrane. Proteins from the nucleus were relatively under-represented, consistent with the general absence of intact cells in human urine. Similar to [13], the inventors observed a relative enrichment of hydrolases, peptidases, carbohydrate and lipid binding proteins, and a relative under-representation of nucleic acid binding proteins.

By comparing whether identified proteins sedimented in the 17,000 g versus 210,000 g ultracentrifugation fractions, were adsorbed onto size exclusion ion exchange resin or were TCA precipitated, the inventors defined them as large or small complexes, and soluble peptides or proteins, respectively. The fractions of proteins identified uniquely from these physical states were 14, 20, 3 and 9%, respectively, demonstrating that individual proteins or their variants exist in multiple physical states. For example, components of the urinary exosomes including the endosomal sorting complex (ESCRT-I), BRO1/ALIX, and VPS4, were detected as both small complexes and soluble proteins. Similarly, insulin-like growth factor binding proteins (IGFBPs) which are low molecular weight circulating hormones were detected as soluble proteins, peptides, and in small complexes. Though the size excluded ion exchange fraction contributed only 3% to the total unique protein identifications, it was substantially enriched for biomedically significant molecules which would not be detected otherwise, including circulating hormones such as hepcidin and chromogranin [22, 23], and shed cell surface molecules such as Ly-6 and platelet glycoproteins [24, 25].

The inventors assessed the probable tissue origin of the identified proteome by comparing it to published tissue expression atlases. As expected, 90% of the proteins detected in the urinary proteome have tissue expression profiles that include organs of the urogenital tract, such as the kidneys and the bladder, from which they likely originate. In addition to these proximal organs, the urinary proteome contains a substantial number of proteins that appear to originate from distal tissues. Among them are 336 proteins that are uniquely expressed in distal tissues such as the nervous system, heart and vasculature, lung, blood and bone marrow, intestine, liver and other intra-abdominal viscera, suggesting that a substantial portion of the urinary proteome is formed as a result of their systemic circulation and serum filtration. For instance, the urinary proteome includes Nogo/reticulon which is involved in the regulation of neurite growth and is expressed in the nervous system but not the urogenital tract [26]. Similarly, the urinary proteome includes angiopoietin-2, involved in angiogenesis and vascular homeostasis, and is expressed by the vascular endothelium [27].

Individual Urinary Proteomes

By virtue of studying individual urinary proteomes, the inventors assessed the extent of similarities and differences among them. For the 12 specimens studied in this example, the inventors detected 1,124±292 (mean±standard deviation) proteins per individual proteome, with the average concordance of 68%, as calculated over all binary comparisons. Highly abundant proteins common to all individual proteomes include molecules involved in renotubular trafficking (uromodulin, cubilin, and megalin (LRP2)), serum filtered enzymes and carriers (bikunin (AMBP), aminopeptidase N, ceruloplasmin, apolipoproteins, and immunoglobulins), extracellular structural components (perlecan, glial fibrillary acidic proteins), as well as a variety of other secreted molecules such as CD44, tetraspanin, and lysosomal associated membrane proteins (LAMPs). Many of these have been detected in human urine previously, and many were identified for the first time. Examples of the latter include claudin, a regulator of tight junctions involved in the maintenance of glomerular and tubular integrity [28], collectrin, a novel homolog of the angiotensin converting enzyme related carboxypeptidase implicated in renal failure and the pathogenesis of polycystic kidney disease [29], SLC5A2, a tubular sodium-glucose transporter which causes autosomal recessive renal glucosuria when defective [30], and numerous other proteins with poorly understood functions such as peflin and trefoil factor 2.

Figure 5:
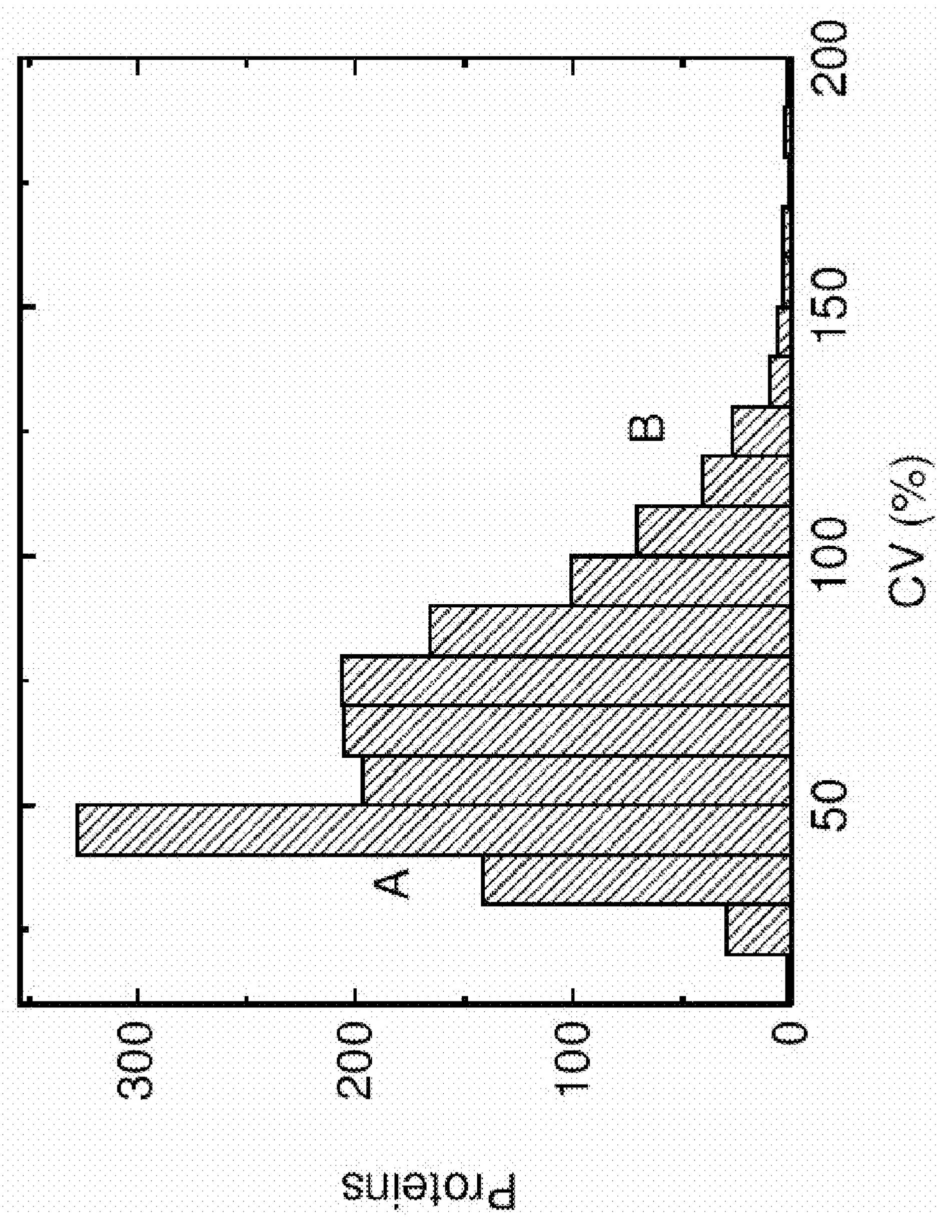
FIG. 5 is a histogram showing the variability in the composition of individual urine proteomes, as assessed by the coefficients of variation of their proteins' spectral counts, demonstrating a broad distribution, including proteins that are relatively invariant (A: Albumin, cubilin, megalin), and those that appear to vary among individual proteomes (B: α1-anti-trypsin, fibrinogen, α2-macroglobulin).

In large part, the variability observed among individual proteomes appears to be multifactorial in origin, as suggested by the multimodal distribution of the coefficients of variation of proteins' apparent detectability, as measured by using spectral counting [31] (FIG. 5; representative proteins are labeled). Proteins with high degree of apparent variability included complement factors, α1-anti-trypsin, protein C inhibitor, galectin (LGALS3BP), CD59, CD14, α-enolase, α2-macroglobulin, gelsolin, haptoglobin, hemopexin, intelectin, fibrinogen, arylsulfatase, serum amyloid A2, cystatin C, angiotensin, and resistin, among others. Many of these proteins are components of the acute phase response [32], consistent with the collection of some of the studied specimens from patients with acute abdominal pain. Other differences among proteomes included components of seminal fluid and other sex specific proteins such as semenogelin.

Urine Proteomics for Profiling of Human Disease

The inventors annotated the identified urinary proteins with respect to possible associations with human disease by using machine learning and text mining of Medline abstracts. Annotations identified for the 26 common and more than 200 rare examined diseases are available in hypertext documents (Additional Files, http://www.childrenshospital.org/research/steenlab), with links to information about the identified proteins and original studies about their role in disease. They include common kidney diseases such as nephrotic syndrome (72 proteins) and nephritis (139), systemic illnesses such as sepsis (42), diseases of distal organs such as pneumonia (34), meningitis (22), and colitis (45). In addition, the proteome was annotated with respect to more than 500 rare diseases, including storage diseases such as Niemann-Pick disease, immune system disorders such as Wiskott-Aldrich syndrome, and diseases of the nervous system such as spinocerebellar ataxia. These associations may be used to develop diagnostic tests or new approaches for the study and monitoring of disease progression.

References cited by number in brackets, i.e. "(#)" in Example 1 are cited below and are incorporate herein in their entirety by reference.

1. N L Anderson, N G Anderson: The human plasma proteome: history, character, and diagnostic prospects. Mol Cell Proteomics 2002, 1:845-67.
2. J N Adkins, S M Varnum, K J Auberry, R J Moore, N H Angell, R D Smith, D L Springer, J G Pounds: Toward a human blood serum proteome: analysis by multidimensional separation coupled with mass spectrometry. Mol Cell Proteomics 2002, 1:947-55.
3. J Stahl-Zeng, V Lange, R Ossola, K Eckhardt, W Krek, R Aebersold, B Domon: High sensitivity detection of plasma proteins by multiple reaction monitoring of N-glycosites. Mol Cell Proteomics 2007, 6:1809-17.
4. H Keshishian, T Addona, M Burgess, E Kuhn, S A Carr: Quantitative, multiplexed assays for low abundance proteins in plasma by targeted mass spectrometry and stable isotope dilution. Mol Cell Proteomics 2007, 6:2212-29.
5. R P Woroniecki, T N Orlova, N Mendelev, I F Shatat, S M Hailpern, F J Kaskel, M S Goligorsky, E O'Riordan: Urinary proteome of steroid-sensitive and steroid-resistant idiopathic nephrotic syndrome of childhood. Am J Nephrol 2006, 26:258-67.
6. W S Oetting, T B Rogers, T P Krick, A J Matas, H N Ibrahim: Urinary beta2-microglobulin is associated with acute renal allograft rejection. Am J Kidney Dis 2006, 47:898-904.

7. R P Berger, P M Kochanek: Urinary S100B concentrations are increased after brain injury in children: A preliminary study. Pediatr Crit. Care Med 2006, 7:557-61.
8. A Propst, T Propst, M Herold, W Vogel, G Judmaier: Interleukin-1 receptor antagonist in differential diagnosis of inflammatory bowel diseases. Eur J GastroenterolHepatol 1995, 7:1031-6.
9. C B Laurell: Composition and variation of the gel electrophoretic fractions of plasma, cerebrosinal fluid and urine. Scand J Clin Lab Invest Suppl 1972, 124:7 1-82.
10. T Pisitkun, R F Shen, M A Knepper: Identification and proteomic profiling of exosomes in human urine. Proc Natl Acad Sci USA 2004, 101:13368-73.
11. W Sun, F Li, S Wu, X Wang, D Zheng, J Wang, Y Gao: Human urine proteome analysis by three separation approaches. Proteomics 2005, 5:4994-5001.
12. T Pisitkun, R Johnstone, M A Knepper: Discovery of appendicitis biomarker s. Mol Cell Proteomics 2006.
13. J Adachi, C Kumar, Y Zhang, J V Olsen, M Mann: The human urinary proteome contains more than 1500 proteins, including a large proportion of membrane proteins. Genome Biol 2006, 7:R80.
14. A Z Traum, M P Wells, M Aivado, T A Libermann, M F Ramoni, A D Schachter: SELDI-TOF MS of quadruplicate urine and serum samples to evaluate changes related to storage conditions. Proteomics 2006, 6:1676-80.
15. H Zhou, P S Yuen, T Pisitkun, P A Gonzales, H Yasuda, J W Dear, P Gross, M A Knepper, R A Star: Collection, storage, preservation, and normalization of human urinary exosomes for biomarker discovery. Kidney Int 2006, 69:1471-6.
16. R S Lee, F Monigatti, A C Briscoe, Z Waldon, M R Freeman, H Steen: Optimizing Sample Handling for Urinary Proteomics. J Proteome Res 2008, 7:4022-4030.
17. C Renard, O Chappey, M P Wautier, M Nagashima, E Lundh, J Morser, L Zhao, A M Schmidt, J M Schumann, J L Wautier: Recombinant advanced glycation end product receptor pharmacokinetics in normal and diabetic rats. Mol Pharmacol 1997, 52:54-62.
18. K P Gudehithlu, A A Pegoraro, G Dunea, J A Arruda, A K Singh: Degradation of albumin by the renal proximal tubule cells and the subsequent fate of its fragments. Kidney Int 2004, 65:2113-22.
19. N Cindik, E Baskin, P I Agras, S T Kinik, M Turan, U Saatci: Effect of obesity on inflammatory markers and renal functions. Acta Paediatr 2005, 94:1732-7.
20. E F De Palo, R Gatti, F Lancerin, E Cappellin, A Sartorio, P Spinella: The measurement of insulin-like growth factor-I (IGF-I) concentration in random urine samples. Clin Chem Lab Med 2002, 40:574-8.
21. A M Skinner, P E Clayton, D A Price, G M Addison, C Y Mui: Variability in the urinary excretion of growth hormone in children: a comparison with other urinary proteins. J Endocrinol 1993, 138:337-43.
22. E Nemeth, M S Tuttle, J Powelson, M B Vaughn, A Donovan, D M Ward, T Ganz, J Kaplan: Hepcidin regulates cellular iron efflux by binding to ferroportin and inducing its internalization. Science 2004, 306:2090-3.
23. K B Helle, A Corti, M H Metz-Boutigue, B Tota: The endocrine role for chromogranin A: a prohormone for peptides with regulatory properties. Cell Mol Life Sci 2007, 64:2863-86.
24. D L Pflugh, S E Maher, A L Bothwell: Ly-6 superfamily members Ly-6A/E, Ly¬6C, and Ly-6I recognize two potential ligands expressed by B lymphocytes. J Immunol 2002, 169:5130-6.
25. D Varga-Szabo, I Pleines, B Nieswandt: Cell adhesion mechanisms in platelets. Arterioscler Thromb Vasc Biol 2008, 28:403-12.
26. R Yan, Q Shi, X Hu, X Zhou: Reticulon proteins: emerging players in neurodegenerative diseases. Cell Mol Life Sci 2006, 63:877-89.
27. T Hato, M Tabata, Y Oike: The role of angiopoietin-like proteins in angiogenesis and metabolism. Trends Cardiovasc Med 2008, 18:6-14.
28. S Angelow, A S Yu: Claudins and paracellular transport: an update. Curr Opin Nephrol Hypertens 2007, 16:459-64.
29. Y Zhang, J Wada: Collectrin, a homologue of ACE2, its transcriptional control and functional perspectives. Biochem Biophys Res Commun 2007, 363:1-5.
30. E M Wright: Renal Na(+)-glucose cotransporters. Am J Physiol Renal Physiol 2001, 280:F10-8.
31. P C Carvalho, J Hewel, V C Barbosa, J R Yates, 3rd: Identifying differences in protein expression levels by spectral counting and feature selection. Genet Mol Res 2008, 7:342-56.
32. R F Ritchie, G E Palomaki, L M Neveux, O Navolotskaia, T B Ledue, W Y Craig:
Reference distributions for the positive acute phase serum proteins, alpha1-acid glycoprotein (orosomucoid), alpha1-antitrypsin, and haptoglobin: a practical, simple, and clinically relevant approach in a large cohort. J Clin Lab Anal 2000, 14:284-92.
33. P Vadas, M Gold, B Perelman, G M Liss, G Lack, T Blyth, F E Simons, K J Simons, D Cass, J Yeung: Platelet-activating factor, PAF acetylhydrolase, and severe anaphylaxis. N Engl J Med 2008, 358:28-35.
34. J S Sanders, H van Goor, R Hanemaaijer, C G Kallenberg, C A Stegeman: Renal expression of matrix metalloproteinases in human ANCA-associated glomerulonephritis. Nephrol Dial Transplant 2004, 19:1412-9.
35. E H Schuchman: The pathogenesis and treatment of acid sphingomyelinase‣deficient Niemann-Pick disease. J Inherit Metab Dis 2007, 30:654-63.
36. A Kentsis, Y Y Lin, K Kurek, M Colicchio, Y Y Wang, F Monigatti, F Campagne, B H Horwitz, H Steen, R G Bachur: Discovery and validation of urine markers of acute appendicitis using high accuracy mass spectrometry. Submitted 2008.
37. J E Elias, S P Gygi: Target-decoy search strategy for increased confidence in large-scale protein identifications by mass spectrometry. Nat Methods 2007, 4:207-14.
38. V A McKusick: Mendelian Inheritance in Man. A Catalog of Human Genes and Genetic Disorders, 12 edn. Baltimore: Johns Hopkins University Press; 1998.
39. K C Dorff, M J Wood, F Campagne: Breaking and fixing BM25 scoring with query expansion, a biologically inspired double mutant recovery experiment. In: TREC; 2006; Gaithersburg, Md., USA. 836-850.
40. F Campagne: Objective and automated protocols for the evaluation of biomedical search engines using No Title Evaluation protocols. BMC Bioinformatics 2008, 9:132.

Example 2

Appendicitis is among many human diseases, for which the diagnosis is complicated by the heterogeneity of its clinical presentation and shortage of diagnostic markers. As such, it remains the most common surgical emergency of children, with initial diagnosis accuracy additionally challenged because of non-specific but similar symptoms of many other childhood conditions (1). Delays in accurate diagnosis lead to increased mortality, morbidity, and costs associated with the complications of appendicitis.

The use of high resolution computed tomography (CT) to identify appendiceal inflammation was hoped to improve both the diagnosis and treatment of acute appendicitis. Though variable, these improvements have been modest at best, with rates of unnecessary appendectomies and ruptures of 3-30% and 30-45%, respectively (2-4). In addition, availability of and experience with CT limit the usefulness of this approach. Furthermore, recently its use has been re-evaluated due to concerns of cancer risk (5).

Thus, several studies sought to identify laboratory markers of acute appendicitis, by studying both markers of the acute phase response, as well as specific inflammatory mediators. The performance of both appeared to be limited (6-11), likely because of the non-specific and unrelated mechanisms of their elevation during acute appendicitis which is characterized specifically by the infiltration of neutrophils and release of distinct cytokines (12, 13).

As disclosed herein, the inventors using an unbiased approach, have profiled the molecular alterations on a proteomic scale, including molecules that are being secreted locally by the diseased tissues themselves or produced systemically in response to local disease. The inventors have identified various urinary markers for appendicitis. Because urine is abundant, obtained frequently and non-invasively, and as a result of being a serum filtrate, is relatively simple in its composition, the inventors have discovered urinary markers for the use in an simple and rapid method to identify a subject with appendicitis.

Recently, advanced mass spectrometry (MS) has been used effectively to discover the protein composition of human urine, (14-16) and to identify markers of diseases affecting the kidney (17) and the urogenital tract (18). Similarly, MS studies of urine have been used to study proteins produced by distal organs such as the brain (19) and the intestine, (20) and to relate them to brain injury and inflammatory bowel disease, respectively.

Here, the inventors demonstrate the use of urine proteome profiling and have discovered urinary markers of acute appendicitis. By using high accuracy mass spectrometry, the inventors identified more than 2,000 unique proteins in urine specimens routinely collected from children and young adults evaluated for acute abdominal pain in the emergency department (ED). Statistical comparisons of individual urine proteomes, pattern recognition class prediction, and gene expression profiling of diseased appendices were used to discover diagnostic markers. By carrying out a blinded, prospective study of these markers, the inventors assessed their diagnostic performance.

Methods Use in Example 2

Study Population.

The inventors studied 67 children and young adults who presented to the ED suspected of having acute appendicitis. Patients were excluded if they had pre-existing autoimmune, neoplastic, renal or urologic disease or were pregnant. Urine was collected as clean catch, mid stream samples as part of routine ED evaluation of abdominal pain. Additional intra-individual control specimens were collected from selected patients with appendicitis after undergoing appendectomies. Informed consent was obtained prior to knowledge of final diagnosis and the urine remaining in the laboratory was retrieved and stored at −80° C. within 6 hours of collection. The expected number of patients was estimated by using the Pearson 2 test to detect a difference at a two-sided statistical significance level of 5% and power of 90% that requires 6 patients in each group, assuming that 80% of the positive samples (5 patients) will contain at least one protein unique to the appendicitis as compared to the non-appendicitis group (21). This study was approved by the Children's Hospital Boston Committee on Clinical Investigation, began in November of 2006, and ended in May of 2008.

Discovery Urine Proteome Profiling and Validation Target Mass Spectrometry.

For the discovery of markers, thawed 10 ml urine aliquots were fractionated by using ultracentrifugation, cation exchange chromatography, protein precipitation, polyacrylamide gel electrophoresis, and reverse phase liquid chromatography. Their protein composition was discovered by using liquid chromatography tandem mass spectrometry (LC-MS/MS) using a nanoflow HPLC system (Eksigent) coupled to a hybrid linear ion trap-Orbitrap (LTQ-Orbitrap) mass spectrometer (Thermo Scientific). The LTQ-Orbitrap enables an unprecedented combination of high detection sensitivity in the attomolar (10-18 M) range, and high mass accuracy of less than 2 parts per million (0.001 Da for a typical 500 Da peptide), as described in detail in the accompanying manuscript (22). Validation of markers was performed using 1 ml aliquots of coded specimens that were blinded to the final outcome. The entire experimental procedure is schematized in FIG. 7.

Analysis.

Urine markers were ranked by calculating relative enrichment ratios (RER) of detection in appendicitis versus non-appendicitis groups by summing individual protein spectral counts normalized to the spectral counts of albumin to account for small differences in total protein abundance, (23) where RER=(appendicitis) $\Sigma C_p/C_a$/(non-appendicitis) $\Sigma C_p/C_a$, with $C_p$ and $C_a$ denoting spectral counts of protein markers and albumin, respectively. Urinary markers were additionally ranked by assessing the prevalence of their detection among different specimens by using a uniformity parameter (U), calculated by dividing the number of appendicitis cases in which they were detected by the total number of appendicitis cases. Urinary markers were filtered to have U>0.7 and RER>5 to identify those that were variably detected or insufficiently enriched, respectively. Support vector machine analysis and comparison of urine protein markers with tissue gene expression profiles of diseased appendices were carried as described herein. The latter was based on a previous study (24). Receiver operating characteristics were calculated using standard methods.

Outcome Measures.

Final diagnosis was determined by the presence or absence of appendicitis on gross and histological examination. All appendectomy specimens were reviewed by a clinical pathologist, and their disease assignments were confirmed by an independent, blinded review. One patient with perforated appendicitis underwent an interval appendectomy, and was not included in the histologic review. Assessment of the histologic severity of appendicitis was done by classifying the specimens as having: no inflammatory changes (normal); foci of neutrophilic infiltration in mucosa or wall (focal); scattered transmural infiltration (mild); dense transmural infiltration with tissue distortion (moderate); dense transmural infiltration with tissue necrosis or wall perforation (severe). For patients who did not undergo appendectomies, the outcome was confirmed via telephone 6-8 weeks after the ED evaluation. All patients enrolled in the study received a final outcome.

Tissue Immunohistochemistry and Urine Immunoblotting.

Immunohistochemical staining of formalin fixed, paraffin embedded appendices was performed by using the rabbit anti-LRG polyclonal antibody at 1:750 dilution (Atlas Antibodies), OmniMap DAB anti-rabbit HRP detection kit and the Ventana Discovery XT automated slide processing platform, according to the manufacturer's instructions (Ventana Medical Systems). Staining specificity was confirmed by using liver and muscle as the positive and negative controls, respectively (data not shown).

For immunoblotting of urine, specimens were precipitated and resolved by SDS-PAGE as described for target mass spectrometry. Western blotting was done blinded to final outcome, as described previously (25), using the rabbit anti-LRG polyclonal antibody at 1:2000 dilution, and the SuperSignal West Pico chemiluminescent reagent (Thermo). Equal total protein loading was assessed by Coomassie staining (22).

Results

Study Population

Over the 18 month course of this study, 67 patients were enrolled who presented to our Emergency department (ED) and underwent evaluation for possible acute appendicitis. In agreement with earlier studies of the epidemiology and presentation of acute appendicitis in pediatric EDs, the mean age of our study population was 11 years, with presenting signs and symptoms described in Table 2. Twenty five patients (37%) received a final diagnosis of appendicitis. All patients with appendicitis underwent appendectomies, 16% of which were found to have a perforation. One patient (4%) who received a pre-operative diagnosis of appendicitis was found to have no gross or histologic evidence of appendicitis upon undergoing appendectomy. Twenty four percent of patients were found to have no specific cause of their abdominal pain, with the remaining patients found to have a variety of common and rare mimicking conditions (Table 3).

TABLE 2

Presenting signs, symptoms and diagnostic studies of 67 patients with acute abdominal pain. Values are reported as mean standard deviation, where appropriate.

| | Final Diagnosis | |
|---|---|---|
| | Appendicitis | Non-appendicitis |
| Number | 25 | 42 |
| Gender (% male) | 56 | 40 |
| Age (years) | 11 ± 3.5 | 11 ± 4.2 |
| Duration of symptoms (days) | 2.7 ± 2.0 | 2.2 ± 1.7 |
| Nausea or vomiting (%) | 72 | 52 |
| Fever (%) | 52 | 48 |
| Pain migration (%) | 36 | 14 |
| RLQ pain or tenderness (%) | 100 | 95 |
| Temperature at triage (° C.) | 36.9 ± 0.6 | 36.6 ± 0.9 |
| Peripheral white blood cell count (K cells/mm$^3$) | 15.7 ± 5.2 | 11.0 ± 6.4 |
| Absolute neutrophil count (K cells/mm$^3$) | 12.8 ± 5.4 | 8.5 ± 6.6 |
| US imaging (%) | 88 | 74 |
| US diagnosis of appendicitis (%) | 64 | 0 |
| CT imaging (%) | 60 | 64 |
| CT diagnosis of appendicitis (%) | 93 | 7.4 |

RLQ (right lower quadrant), US (ultrasound), CT (computer tomography).

TABLE 3

Final diagnosis of the 67 study patients

| | Number of patients |
|---|---|
| Appendicitis | 25 |
| Non specific abdominal pain | 16 |
| Ovarian cyst or torsion | 5 |
| Constipation | 5 |
| Pyelonephritis or Urinary Tract Infection | 5 |
| Renal calculus | 2 |
| Mesenteric adenitis | 2 |
| Gastroenteritis or gastritis | 2 |
| Influenza or scarlet fever | 2 |
| Intussusception | 1 |
| Inflammatory bowel disease | 1 |
| Diverticulitis | 1 |

Discovery of diagnostic markers by using urine proteomic profiling urine markers of appendicitis were identified from the analysis of 12 specimens, collected at the onset of the study, and distributed equally between patients with and without appendicitis. Table 4 lists the 32 markers, identified by ranking their relative enrichment ratios (RER). These proteins include known components of the acute phase response such as α-1-acid glycoprotein (orosomucoid), plasminogen, carbonic anhydrase, angiotensin converting enzyme, and lipopolysaccharide binding protein, consistent with the systemic inflammatory response that accompanies acute appendicitis.

TABLE 4 urine marker proteins identified using relative enrichment ratio analysis.

| Protein | Accession Number* | U[†] | RER[†] |
|---|---|---|---|
| Adipocyte specific adhesion molecule | IPI00024929 | 1.0 | 18 |
| Leucine-rich α-2-glycoprotein | IPI00022417 | 1.0 | 9.5 |
| Zinc-α-2-glycoprotein | IPI00 166729 | 1.0 | 7.3 |
| α-1-acid glycoprotein 2 | IPI00020091 | 1.0 | 5.8 |
| MLKL | IPI00180781 | 1.0 | 5.5 |
| α-1-acid glycoprotein 1 | IPI00022429 | 1.0 | 5.3 |
| Plasminogen | IPI00019580 | 1.0 | 5.1 |
| Carbonic anhydrase 1 | IPI002 15983 | 0.8 | 15 |
| Angiotensin converting enzyme 2 | IPI00465 187 | 0.8 | 12 |
| Nicastrin | IPI00021983 | 0.8 | 12 |
| Lipopolysaccharide binding protein | IPI00032311 | 0.8 | 11 |
| Vascular adhesion molecule 1 | IPI00018 136 | 0.8 | 10 |
| PDZK1 interacting protein 1 | IPI0001 1858 | 0.8 | 7.5 |
| SLC9A3 | IPI00011184 | 0.8 | 7.5 |
| Lymphatic vessel endothelial hyaluronan receptor 1 | IPI00290856 | 0.8 | 6.9 |
| FXR2 | IPI000 16250 | 0.7 | N/A |
| SORBS1 | IPI00002491 | 0.7 | N/A |
| SLC4A1 | IPI00022361 | 0.7 | 44 |
| PRIC285 | IPI00249305 | 0.7 | 14.9 |
| TGFbeta2R | IPI00383479 | 0.7 | 11.3 |
| SLC2A1 | IPI00220194 | 0.7 | 10.7 |
| Rcl | IPI00007926 | 0.7 | 9.7 |
| VA0D1 | IPI00034159 | 0.7 | 8.9 |
| SLC13A3 | IPI00103426 | 0.7 | 7.8 |
| TTYH3 | IPI00749429 | 0.7 | 7.3 |
| SPRX2 | IPI00004446 | 0.7 | 6.4 |
| BAZ1B | IPI00216695 | 0.7 | 6.1 |
| β-1,3-galactosyltransferase | IPI00032034 | 0.7 | 6.1 |
| chromogranin A | IPI00383975 | 0.7 | 5.9 |
| Novel protein | IPI00550644 | 0.7 | 5.5 |
| SLC2A2 | IPI00003905 | 0.7 | 5.2 |
| FBLN7 | IPI00167710 | 0.7 | 5.1 |

[†]Values of U = 1 indicate markers detected in all appendicitis specimens, whereas values of relative enrichment ration (RER) = 1 indicate markers that exhibit no apparent enrichment in appendicitis as compared to non-appendicitis groups.
N/A (not detected) identifies markers not detected in non-appendicitis specimens).
(*International Protein Index (version 3.36, at the World Wide Website of "ebi.ac.uk/IPI").)

The markers also include a number of cell adhesion proteins such as adipocyte specific adhesion molecule, a component of the epithelial and endothelial tight junctions, leucine-rich α-2-glycoprotein (LRG), a marker of neutrophil differentiation involved in cell trafficking, vascular adhesion molecule 1, which mediates lymphocyte-endothelial adhesion, and lymphatic vessel endothelial hyaluronan acid receptor 1 involved in cell migration, consistent with earlier findings of leukocyte trafficking and infiltration into mucosal tissue that accompanies acute appendicitis.

Remaining top ranking markers do not appear to share any known functional or structural similarities, though some of them such as β-1,3-galactosyltransferase and VA0D1 have been shown to function specifically in the colonic epithelium, and therefore, may include components of the local and systemic appendicitis response. Additional markers were identified by using support vector machine (SVM) learning, as well as comparisons with tissue gene expression profiles of diseased appendices (Tables 6 and 7). In total, 49 markers were identified.

TABLE 6 urine marker proteins identified using SVM analysis

| Protein | Accession Number |
|---|---|
| Serum amyloid A protein | IPI00552578 |
| α-1-antichymotrypsin | IPI00550991 |
| Supervillin | IPI00412650 |
| Mannan-binding lectin serine protease 2 | IPI00306378 |
| Inter-α-trypsin inhibitor | IPI00218192 |
| VIP36 | IPI00009950 |
| Prostaglandin-H2 D-isomerase | IPI00013179 |
| α-1-acid glycoprotein 2 | IPI00020091 |
| AMBP | IPI00022426 |
| α-1-acid glycoprotein 1 | IPI00022429 |
| CD14 | IPI00029260 |
| Hemoglobin α | IPI00410714 |
| Apolipoprotein D | IPI00006662 |
| Hemoglobin β | IPI00654755 |
| Leucine-rich α-2-glycoprotein | IPI00022417 |
| Zinc-α-2-glycoprotein | IPI00166729 |

TABLE 7

Urine marker proteins identified by comparisons with corresponding tissue gene overexpression.

| Protein | Accession Number | Affymetrix gene ID* | Fold gene over-expression* |
|---|---|---|---|
| S100-A8 | IPI00007047 | 214370_at | 67 |
| S100-A9 | IPI00027462 | 203535_at | 45 |
| Amyloid-like protein 2 | IPI00031030 | 214456_x_at | 38 |
| Versican | IPI00009802 | 211571_s_at | 11 |
| SPRX2 | IPI00004446 | 205499_at | 8.1 |
| α-1-acid glycoprotein 1 | IPI00022429 | 205041_s_at | 7.8 |
| Interleukin-1 receptor antagonist protein | IPI00000045 | 212657_s_at | 4.3 |
| Lymphatic vessel endothelial hyaluronan acid receptor 1 | IPI00290856 | 220037_s_at | 2.0 |

*From Murphy C G, et al. Mucosal Immunol. 2008; 1: 297-308.

Validation of Urine Protein Markers by Using Target Mass Spectrometry

In order to assess their diagnostic performance, the inventors determined their concentrations in urine of all enrolled patients in a prospective fashion, with experimental measurements blinded to the patients' outcomes. Proteins detected with sufficient uniformity among the 67 specimens examined are listed in Table 5. The remaining proteins were detected in less than half of specimens, likely as a result of differences in processing of the discovery and validation specimens. Comparison of differences in urinary concentration between the appendicitis and non-appendicitis patient groups revealed LRG, S100-A8, and α-1-acid glycoprotein 1 (orosomucoid) as exhibiting substantial apparent enrichment in the urines of patients with appendicitis (FIG. 8).

TABLE 5

Urine marker proteins validated by target mass spectrometry.

| Protein | ROC AUC | AUC 95% confidence interval |
|---|---|---|
| Leucine-rich α-2-glycoprotein (LRG) | 0.97 | 0.93-1.0 |
| calgranulin A (S100-A8) | 0.84 | 0.72-0.95 |
| α-1-acid glycoprotein 1 (ORM) | 0.84 | 0.72-0.95 |
| Plasminogen (PLG) | 0.79 | 0.67-0.91 |
| Mannan-binding lectin serine protease 2 (MASP2) | 0.74 | 0.61-0.88 |
| Zinc-α-2-glycoprotein (AZGP1) | 0.74 | 0.60-0.88 |
| α-1-antichymotrypsin (SERPINA3) | 0.84 | 0.73-0.94 |
| Apolipoprotein D (ApoD) | 0.53 | 0.38-0.69 |

ROC (receiver operating characteristic), AUC (area under the curve).

Figure 9A:
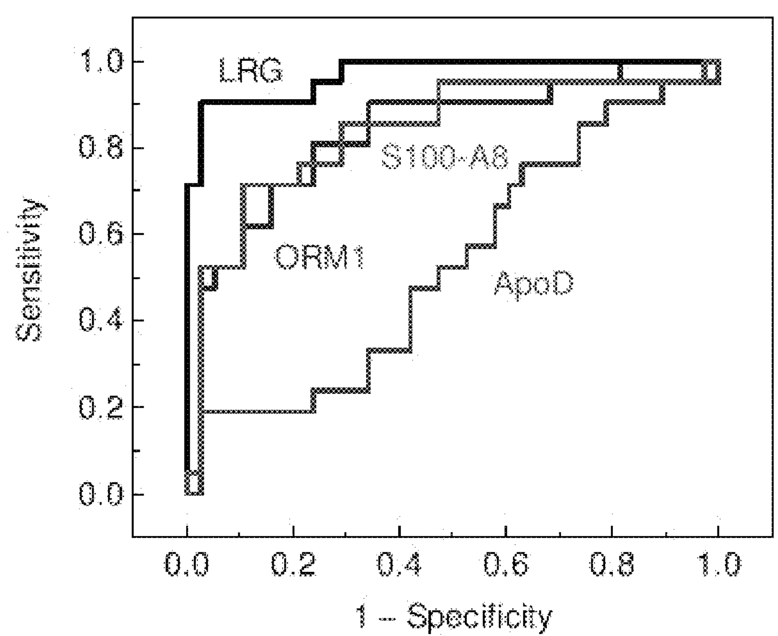
FIGS. 9A-9B show validation of selected appendicitis biomarkers.

Indeed, receiver operating characteristic (ROC) curves for these markers exhibited excellent performance, with LRG and S100-A8 having area under the curve (AUC) values of 0.97 and 0.84, respectively (FIG. 9, Table 5). Other prospectively validated markers with apparently good performance included orosomucoid and α-1-antichymotrypsin (serpin A3); plasminogen, mannan-binding lectin serine protease 2 (MASP2), zinc-α-2-glycoprotein (AZGP) exhibited intermediate performance, and apolipoprotein D exhibited poor performance. These findings are consistent with most of these proteins being components of the general acute phase response, during which they may be upregulated by a variety of infectious and inflammatory conditions, including some that are represented in the non-appendicitis group (Table 3).

The inventors assessed the relationship between apparent urine protein abundance of markers and the apparent severity of appendicitis by classifying appendectomy specimens with respect to the degree of neutrophil infiltration (12). As can be seen from FIG. 10, LRG appears to be a marker of focal appendicitis, whereas S100-A8 appears to be a marker of progressive disease, reaching a peak level with moderate appendicitis. In addition to exhibiting excellent diagnostic performance, LRG was detected strongly in diseased as compared to normal appendices by using tissue immunohistochemistry (FIG. 10), consistent with its biological function and proposed role in appendicitis. Its enrichment in urine of patients with appendicitis relative to those with other conditions was confirmed by using Western immunoblotting (FIG. 9B), demonstrating that clinical diagnostic immunoassays can be used as a method to identify the urinary markers disclosed herein.

As disclosed herein, the inventors used urine proteome profiling to discover urinary markers of acute appendicitis. Usage of exhaustive protein capture and fractionation coupled with high accuracy mass spectrometry allowed the inventors to detect more than 2,000 unique proteins in routinely collected urine specimens, constituting the largest and most comprehensive characterization of protein composition of human urine to date (22). The discovered urinary diagnostic markers (Tables 4, 6, and 7) were subsequently validated in a prospective, blinded study of children suspected of having acute appendicitis, identifying several with statistically significant enrichment in the urine of children with histologically proven appendicitis as compared to those without (Table 5).

The use of high resolution CT and US has led to substantial improvements in the diagnosis of acute appendicitis, with respect to both the rates of complications and unnecessary appendectomies (2-4). However, significant diagnostic challenges remain, largely because of the non-specific nature of signs and symptoms of many conditions that can mimic acute appendicitis. Similarly, CT and US findings can often be indeterminate or equivocal (26). Finally, limited availability and experience with dedicated CT protocols for appendicitis, as well as future risk of cancer, can often limit its usefulness (5).

Numerous studies have sought to identify biomarkers to aid the diagnosis of appendicitis, with the absolute blood neutrophil count and serum C-reactive protein levels being most useful, but still limited with respect to their sensitivity and specificity (27, 28).

Recent attempts to identify new and improved diagnostic markers, such as CD44, interleukin-6, interleukin-8, and 5-hydroxy indole acetate, produced limited improvements as compared to the existing ones (6-11), likely as a result of being closely correlated with the existing markers of the general acute phase response, or not specific for the distinct immune mechanisms that characterize acute appendicitis.

By taking advantage of the latest generation of mass spectrometers that combine high accuracy with high sensitivity, and carrying out exhaustive protein capture and fractionation of routinely collected urine specimens, the inventors developed a method that enables unbiased discovery and validation of multiple diagnostic markers, thereby overcoming the limitations of conventional approaches based on single hypothesis testing. Because of the depth of discovery achieved, identifying more than 2,000 unique proteins in total, urine proteomic profiling, like gene expression profiling, may be susceptible to noise and selection bias. In order to minimize these potential problems (12), discovery urine proteomes were compared not only between patients with histologically proven appendicitis and those without, but also with the same patients after they recovered from appendectomies, thereby minimizing individual differences due to age, gender, physiologic state or genetic variation. High stringency identification criteria were used, essentially eliminating false identifications (22). The discriminatory power of diagnostic markers was assessed by examining the level and uniformity of their enrichment in patients with appendicitis (Table 4), by using pattern recognition class prediction learning algorithms (Table 6), and by comparing discovered urine protein markers with tissue gene expression profiles of diseased appendices (Table 7) (24).

As a result, the 49 discovered urinary markers constitute an extensive characterization of the molecular response that accompanies acute appendicitis, including both systemically and locally produced molecules. Among the former are known components of the acute phase response, such as orosomucoid, plasminogen, angiotensin converting enzyme, carbonic anhydrase, TGF β, lipopolysaccharide binding protein, serum amyloid A, α-1-antichymotrypsin, AMBP (bikunin), and mannan-binding lectin serine protease (2). Numerous cell adhesion molecules that may participate in the local generation of the systemic inflammatory response or its localization to the appendiceal tissue were identified, including the vascular adhesion molecule 1, lymphatic vessel endothelial hyaluronan acid receptor 1, adipocyte specific adhesion molecule, supervillin, CD14, and leucine-rich α-2-glycoprotein. Likewise, several potential local inflammatory mediators and cytokines were identified such as chromogranin A, β-1,3-galactosyltransferase, interleukin-1 receptor antagonist protein, and S100-A8.

Figure 9B:
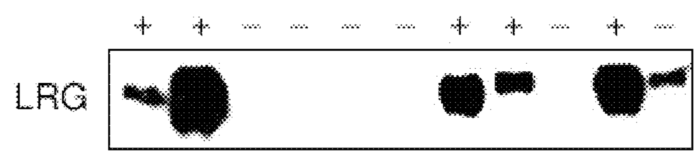
Figure 10A:
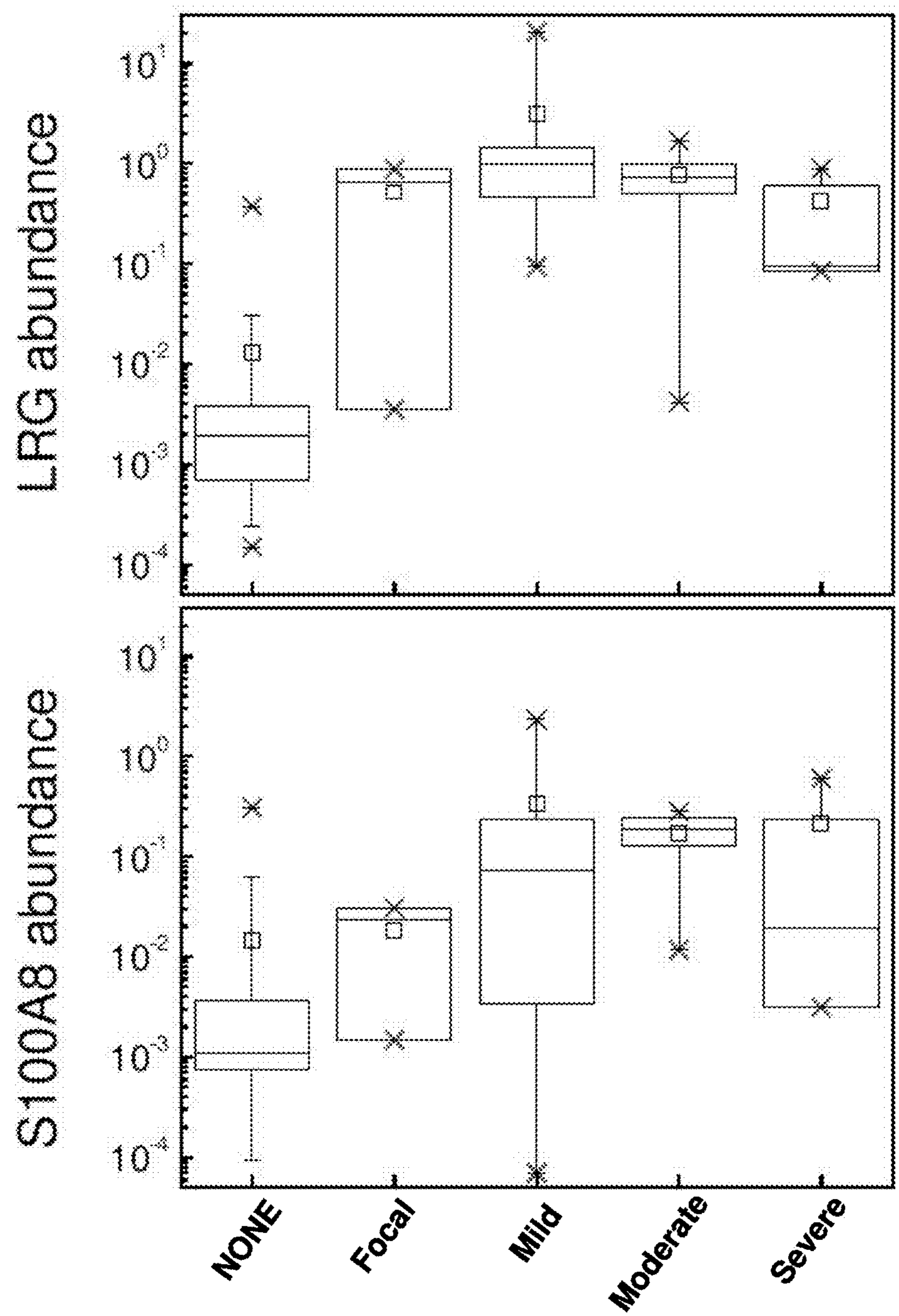
FIGS. 10A-10B show clinical validation of selected appendicitis biomarkers.
Figure 10B:
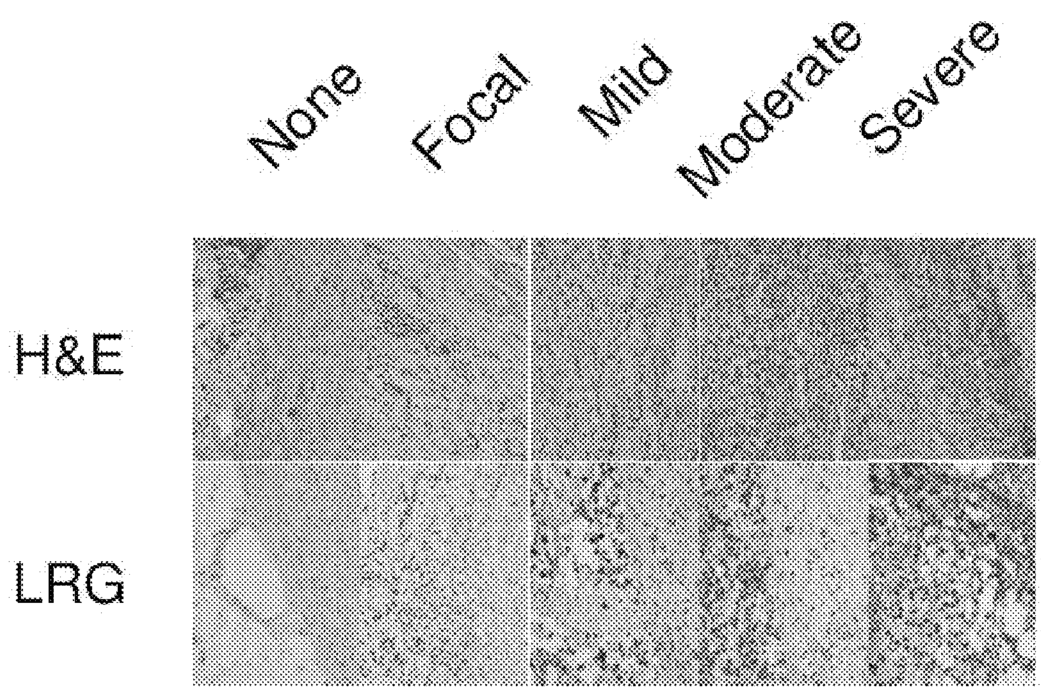

The discovered urinary diagnostic markers were validated in their ability to accurately diagnose acute appendicitis by measuring their urinary concentrations in a prospective and blinded study of 67 patients who were suspected to have acute appendicitis, with the final diagnosis verified by blinded histologic examination of removed appendices. Seven markers were successfully validated, including LRG, S100-A8, and ORM which exhibited excellent diagnostic performance (FIG. 9, Table 5). The enrichment of LRG in urine of patients with appendicitis was confirmed by using Western immunoblotting (FIG. 9B), and its enrichment in diseased as compared to normal appendices was demonstrated by using tissue immunohistochemistry (FIG. 10).

LRG is expressed by differentiating neutrophils, liver, and high endothelial venules of the mesentery, including the meso-appendix, functioning in leukocyte activation and chemotaxis, respectively (29, 30). Its enrichment in the urine of patients with acute appendicitis demonstrates that it may be shed by locally activated neutrophils and/or local inflammatory sites such as the meso-appendix through which they likely traffic (FIG. 10). As such, it is likely a specific marker of local inflammatory processes such as those that specifically characterize acute appendicitis, as opposed to general markers of systemic response such as the acute phase reactants, and macroscopic markers of local inflammation such as those observed using US and CT imaging.

LRG appears to be enriched in the urine of patients with appendicitis in the absence of macroscopic inflammatory changes, as evidenced by its accurate diagnosis of appendicitis of 2 patients who exhibited normal imaging findings but had evidence of acute appendicitis on histologic examination, as well as its accurate diagnosis of the absence of appendicitis in a patient without histologic evidence of appendicitis, but who underwent appendectomy as a result of findings of appendiceal enlargement on CT. Lastly, LRG appears to be enriched in the urine of patients with pyelonephritis, consistent with its proposed role in local inflammatory processes. Consequently, LRG will be useful to diagnose acute appendicitis following ruling out other local tissue infections, such as pyelonephritis, abscesses, and pelvic inflammatory disease (31). Importantly, LRG appears to be strongly expressed in diseased appendices, demonstrating that it may underlie a principal pathway of appendiceal inflammation by localizing or sustaining the local neutrophilic infiltration that specifically characterizes acute appendicitis (12, 13, 24).

The inventors have not tested urine protein markers of acute appendicitis in patients evaluated in settings other than the emergency department, as well as in older adult patients, who may include other causes of abdominal pain from those observed in the study cohort. The inventors' demonstration of urinary markers for appendicitis establishes a useful paradigm for the identification of other clinically useful urinary markers of human disease, including infectious, endocrine, autoimmune and neoplastic diseases.

References cited in Example 2 and disclosed in italicized brackets (i.e. "(#)") are below and each are incorporated herein in their entirety by reference.

1. Addiss D G, Shaffer N, Fowler B S, Tauxe R V. The epidemiology of appendicitis and appendectomy in the United States. Am J Epidemiol 1990; 132:910-25.

2. Rao P M, Rhea J T, Novelline R A, Mostafavi A A, McCabe C J. Effect of computed tomography of the appendix on treatment of patients and use of hospital resources. N Engl J Med 1998; 338:141-6.

3. Peck J, Peck A, Peck C. The clinical role of noncontrast helical computed tomography in the diagnosis of acute appendicitis. Am J Surg 2000; 180:133-6.
4. Partrick D A, Janik J E, Janik J S, Bensard D D, Karrer F M. Increased CT scan utilization does not improve the diagnostic accuracy of appendicitis in children. J Pediatr Surg 2003; 38:659-62.
5. Brenner D J, Hall E J. Computed tomography—an increasing source of radiation exposure. N Engl J Med 2007; 357:2277-84.
6. Taha A S, Grant V, Kelly R W. Urinalysis for interleukin-8 in the non-invasive diagnosis of acute and chronic inflammatory diseases. Postgrad Med J 2003; 79: 159-63.
7. Bolandparvaz S, Vasei M, Owji A A, et al. Urinary 5-hydroxy indole acetic acid as a test for early diagnosis of acute appendicitis. Clin Biochem 2004; 37:985-9.
8. Apak S, Kazez A, Ozel S K, Ustundag B, Akpolat N, Kizirgil A. Spot urine 5-hydroxyindoleacetic acid levels in the early diagnosis of acute appendicitis. J Pediatr Surg 2005; 40: 1436-9.
9. Rivera-Chavez F A, Peters-Hybki D L, Barber R C, et al. Innate immunity genes influence the severity of acute appendicitis. Ann Surg 2004; 240:269-77.
10. Paajanen H, Mansikka A, Laato M, Ristamaki R, Pulkki K, Kostiainen S, Novel serum inflammatory markers in acute appendicitis. Scand J Clin Lab Invest 2002; 62:579-84.
11. Kafetzis D A, Velissariou I M, Nikolaides P, et al. Procalcitonin as a predictor of severe appendicitis in children. Eur J Clin Microbiol Infect Dis 2005; 24:484-7.
12. Tsuji M, Puri P, Reen D J. Characterisation of the local inflammatory response in appendicitis. J Pediatr Gastroenterol Nutr 1993; 16:43-8.
13. Mazzucchelli L, Hauser C, Zgraggen K, et al. Expression of interleukin-8 gene in inflammatory bowel disease is related to the histological grade of active inflammation. Am J Pathol 1994; 144:997-1007.
14. Rai A J, Stemmer P M, Zhang Z, et al. Analysis of Human Proteome Organization
15. Plasma Proteome Project (HUPO PPP) reference specimens using surface enhanced laser desorption/ionization-time of flight (SELDI-TOF) mass spectrometry: multi-institution correlation of spectra and identification of biomarkers. Proteomics 2005; 5:3467-74.
16. Pisitkun T, Johnstone R, Knepper M A. Discovery of appendicitis biomarker s. Mol Cell Proteomics 2006.
17. Adachi J, Kumar C, Zhang Y, Olsen J V, Mann M. The human urinary proteome contains more than 1500 proteins, including a large proportion of membrane proteins. Genome Biol 2006; 7:R80.
18. Woroniecki R P, Orlova T N, Mendelev N, et al. Urinary proteome of steroid-sensitive and steroid-resistant idiopathic nephrotic syndrome of childhood. Am J Nephrol 2006; 26:258-67.
19. Oetting W S, Rogers T B, Krick T P, Matas A J, Ibrahim H N. Urinary beta2-microglobulin is associated with acute renal allograft rejection. Am J Kidney Dis 2006; 47:898-904.
20. Berger R P, Kochanek P M. Urinary S100B concentrations are increased after brain injury in children: A preliminary study. Pediatr Crit. Care Med 2006; 7:557-61.
21. Propst A, Propst T, Herold M, Vogel W, Judmaier G. Interleukin-1 receptor antagonist in differential diagnosis of inflammatory bowel diseases. Eur J Gastroenterol Hepatol 1995; 7:1031-6.
22. Campbell M J. Estimating sample sizes for binary, ordered categorical, and continuous outcomes in two group comparisons. British Medical Journal 1995; 3 11:1145-48.
23. Kentsis A, Monigatti F, Dorff K, Campagne F, Bachur R G, Steen H. Urine proteomics for profiling of human disease using high accuracy mass spectrometry. Submitted 2008.
24. Carvalho P C, Hewel J, Barbosa V C, Yates J R, 3rd. Identifying differences in protein expression levels by spectral counting and feature selection. Genet Mol Res 2008; 7:342-56.
25. Murphy C G, Glickman J N, Tomczak K, et al. Acute Appendicitis is Characterized by a Uniform and Highly Selective Pattern of Inflammatory Gene Expression. Mucosal Immunol 2008; 1:297-308.
26. Kentsis A, Topisirovic I, Culjkovic B, Shao L, Borden K L. Ribavirin suppresses eIF4E-mediated oncogenic transformation by physical mimicry of the 7-methyl guanosine mRNA cap. Proc Natl Acad Sci USA 2004; 101:18105-10.
27. Kharbanda A B, Taylor G A, Bachur R G. Suspected appendicitis in children: rectal and intravenous contrast-enhanced versus intravenous contrast-enhanced CT. Radiology 2007; 243:520-6.
28. Okamoto T, Sano K, Ogasahara K. Receiver-operating characteristic analysis of leukocyte counts and serum C-reactive protein levels in children with advanced appendicitis. Surg Today 2006; 36:515-8.
29. Bundy D G, Byerley J S, Liles E A, Perrin E M, Katznelson J, Rice H E. Does this child have appendicitis? Jama 2007; 298:438-5 1.
30. O'Donnell L C, Druhan L J, Avalos B R. Molecular characterization and expression analysis of leucine-rich alpha 2-glycoprotein, a novel marker of granulocytic differentiation. J Leukoc Biol 2002; 72:478-85.
31. Saito K, Tanaka T, Kanda H, et al. Gene expression profiling of mucosal
32. addressin cell adhesion molecule-1+ high endothelial venule cells (HEV) and identification of a leucine-rich HEV glycoprotein as a HEV marker. J Immunol 2002; 168:1050-9.
33. Bini L, Magi B, Marzocchi B, et al. Two-dimensional electrophoretic patterns of acute-phase human serum proteins in the course of bacterial and viral diseases. Electrophoresis 1996; 17:612-6.

Example 3

Discovery and Validation of Urine Markers of Acute Appendicitis Using High Accuracy Mass Spectrometry Discovery of Diagnostic Markers by Using Urine Proteomic Profiling In order to identify candidate urinary markers of acute appendicitis, the inventors assembled a discovery urine proteome dataset, derived from the analysis of 12 specimens, without any clinical urinalysis abnormalities, collected at the onset of the study, and distributed equally between patients with and without appendicitis. Six of these specimens were collected from patients who were found to have histologic evidence of appendicitis (2 mild, 3 moderate, 1 severe). Three specimens were collected from patients without appendicitis (1 with non-specific abdominal pain, 1 with constipation, 1 with mesenteric adenitis). From the 3 patients with appendicitis, the inventors collected additional control specimens at their routine post-surgical evaluation 6-8 weeks after undergoing appendectomies, at which time they were asymptomatic and in their usual state of health. These specimens were included in the analysis in order to minimize the potential effect of individual variability in urinary composition that may arise due to age, gender, physiologic state or possible genetic variation.

Figure 7:
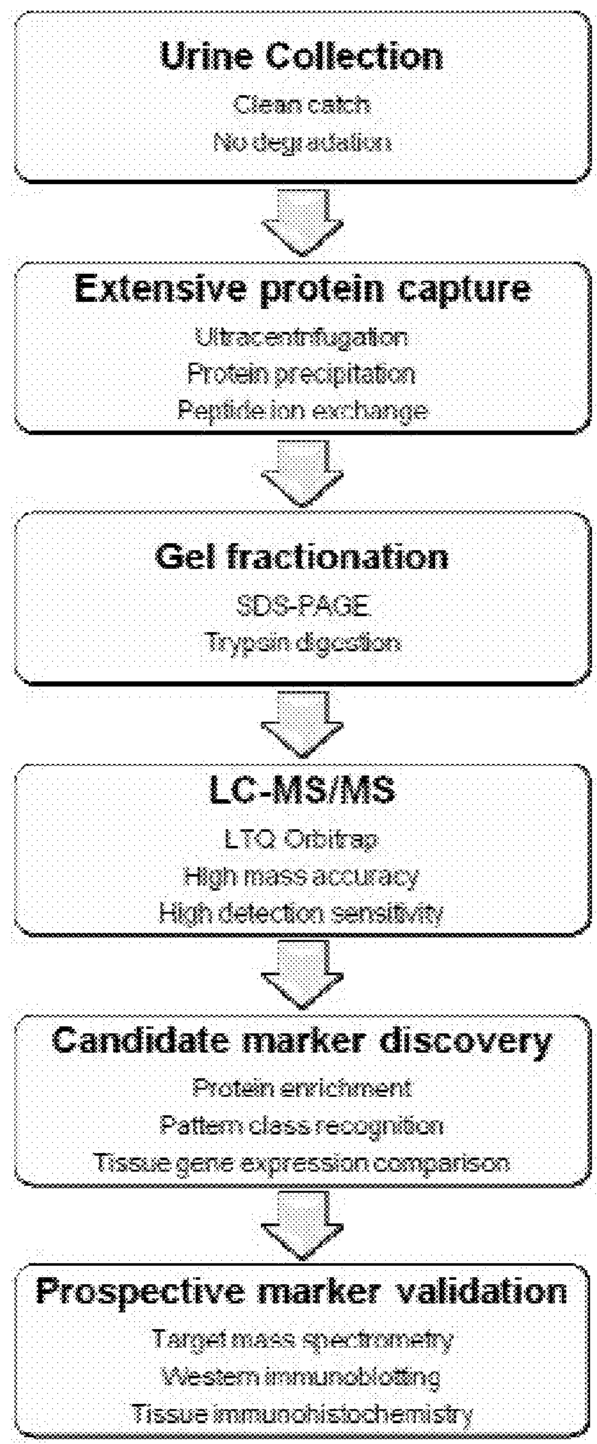
FIG. 7 is a flow diagram showing an experimental scheme, outlining methods used for protein capture and fractionation, of the identification and discovery of appendicitis biomarkers using urine proteomics, and the validation of appendicitis diagnostic biomarkers.

The urine proteome composition of these 12 specimens was discovered by using protein capture and fractionation coupled with high accuracy mass spectrometry, as described in detail in the accompanying study,[1] and schematized in FIG. 7. As urine is a complex mixture with abundant proteins such as albumin obscuring the detection of less concentrated, potentially diagnostic proteins such as secreted cytokines and mediators of the inflammatory response, the inventors devised a fractionation method that reduced mixture complexity while minimizing loss of material (FIG. 7).

As a result, the inventors were able to identify 2,362 proteins in routinely collected urine specimens with the apparent rate of false identifications of less than 1%,[1] as ascertained from decoy database searching.[2] More than 1,200 identified proteins have not been detected in previous proteomic studies of urine, and more than 300 proteins appear to be filtered from serum and expressed in distal tissues, including the intestine. For the discovery of candidate appendicitis markers, the inventors further increased the stringency of peptide identifications to less than 0.1% false identifications, yielding essentially no false protein identifications for proteins identified on the basis of multiple peptides. For example, proteins identified on the basis of 10 unique peptides (median for the entire dataset), have an approximate identification error frequency of 10-19.

In order to identify candidate markers of appendicitis, the inventors took advantage of the quantitative information provided by tandem mass spectrometry by recording the number of fragment ion spectra assigned to each unique precursor peptide, which are proportional to peptide abundance,[3] and have been used for relative quantification of components of complex protein mixtures.[4] Though the composition and concentration of urine varies with physiologic state, there was less than 10±10% (mean±standard deviation) difference in total protein abundance among individual specimens, similar to earlier studies of urine of children.[5-7] Individual protein spectral counts, calculated by summing spectral counts of unique peptides assigned to distinct proteins, were normalized relative to the spectral counts of albumin to account for these small differences in total protein abundance.[4]

In order to maximize the depth of candidate marker discovery, the inventors subjected the discovery urine proteome to support vector machine (SVM) learning in order to identify candidate urine markers that may be enriched as a group but not necessarily individually, as required by the relative expression ration (RER) analysis above. This approach is implemented in a biomarker discovery program BDVAL that uses cross-validation to identify predictive biomarkers (Fabien Campagne, unpublished results, at the World Wide Website of "icb.med.cornell.edu/wiki/index-.php/BDVAL"), similar to established methods for microarray class discovery.[8] Because of the low number of samples, the inventors performed cross-validation with four folds, repeated 5 times with random fold assignments (12 samples total, 6 cases, 6 controls). In this setting, 20 individual evaluation models (5×4) were trained. Each model was trained with a set of 50 features (normalized protein abundance levels). In each split, consisting of 9 training samples and 3 test samples, a Student t-test pre-filtering step prioritized up to 400 features whose average value differed the most between cases and controls in the training set. The 400 intermediate features were ranked by decreasing support vector machine weights and the top 50 features were used to train the evaluation model (models were implemented as a support vector machine, implemented in libSVM with linear kernel, and margin parameter C=1). At the end of the evaluation, the lists of features were inspected to determine how many times a given feature has been used in any one of the 20 evaluation models. The inventors considered features for validation only if they were found in at least 50% of the evaluation models generated (10 models in this case).

Table 6 lists 17 proteins identified by SVM analysis, which include several proteins that were identified by RER analysis, as well as many that were not, including additional components of the acute phase response, such as serum amyloid A, α-1-antichymotrypsin, and bikunin (AMBP). Notably, exclusion of control specimens collected from asymptomatic patients after they underwent appendectomies increased the number of candidate markers to 273 by additionally including a variety of proteins unlikely to be related to the appendicitis response, such as the universal tyrosine kinase Src for example, suggesting that individually variant factors such as those that influence protein filtration and urine production may significantly affect biomarker discovery studies.

Candidate Validation Target Mass Spectrometry

Thawed 1 ml urine aliquots were precipitated by adding trichloroacetic acid to 20% (w/v), and incubating the samples for 1 hour at 4° C. Precipitates were sedimented at 10,000 g for 15 minutes at 4° C. and pellets were washed twice with neat acetone at 4° C., with residual acetone removed by air drying. Dried pellets were resuspended in Laemmli buffer, resolved by SDS-PAGE, alkylated and digested with trypsin as described.[1] To each sample, 0.4 μg of single stranded binding (SSB) protein purified from *Escherichia coli* (USB) was added to serve as a reference standard. Target nanoLC-MS/MS was accomplished by using the LTQ-Orbitrap mass spectrometer, using the parameters described,[1] but operated in an inclusion list dependent acquisition mode, searching detected precursor ions against m/z values of candidate marker peptides with a tolerance of 0.05 Da, using an inclusion list of masses and charges of candidate marker peptides, derived from the analysis of the discovery proteomes. Six most intense matched ions were sequentially fragmented by using collision induced dissociation, and spectra of their fragments were recorded in the linear ion trap, with the dynamic exclusion of precursor ions already selected for MS/MS of 60 sec. Such an approach is superior to conventional data dependent acquisition methods by minimizing the detection of non-target peptides.[9] Differences in apparent protein abundance were normalized relative to exogenously added SSB reference standard to account for instrumental variability. Absence of SSB from urine specimens without its addition was confirmed by searching the data against database of *E. coli* proteins (data not shown).

Recorded mass spectra were processed and identified, as described.[1] The accuracy of peptide identification was assessed by decoy database searching,[1] enforcing a false peptide discovery rate of less than 1%, which corresponds to essentially zero false protein discovery rate, given that all of the candidate diagnostic marker proteins were identified on the basis of at least 9 peptides, which corresponds to an apparent false identification frequency of less than 10-18.

For example, leucine-rich α-2-glycoprotein (LRG) was identified on the basis of 55 unique peptides.

Urine Markers of Appendiceal Inflammatory Response

Figure 6:
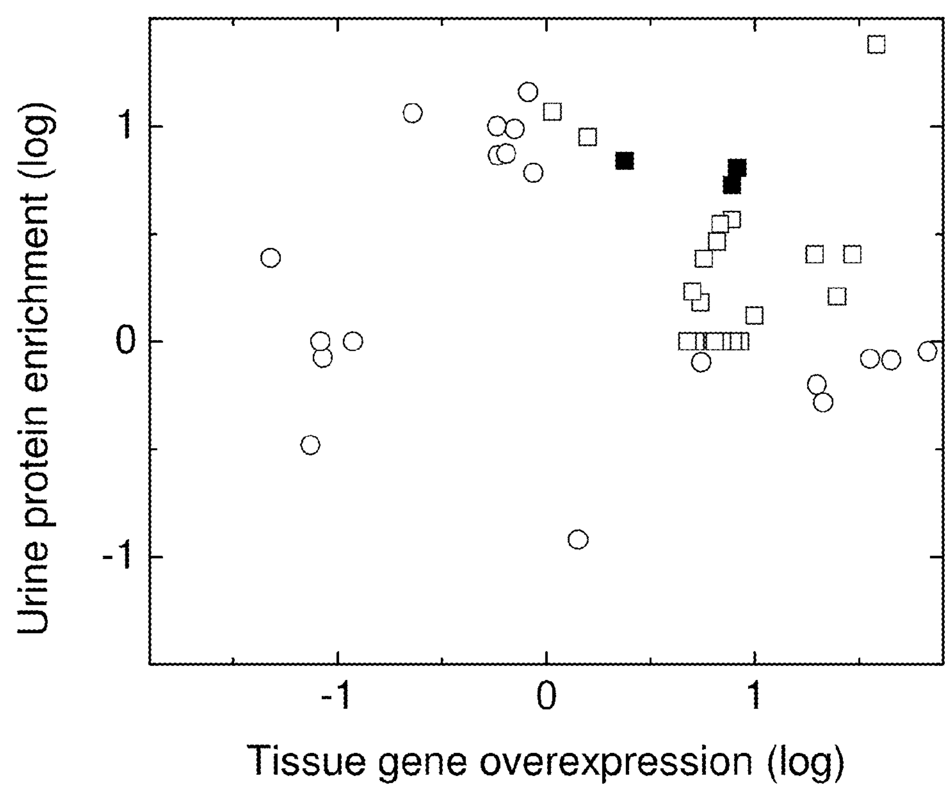
FIG. 6 is a scatter plot showing the relative enrichment of appendicitis protein biomarkers as a function of appendicitis tissue overexpression of the corresponding genes, demonstrating that more than 50% of markers with tissue overexpression exhibit urine enrichment (□), but that only 3 of these (■) were identified as markers by urine proteome profiling.

Because acute appendicitis is characterized by the increased expression of distinct chemoattractants in the gut mucosa,[10] and specific infiltration of neutrophils,[11] the inventors wondered if markers of acute appendicitis identified from studies of appendiceal tissue may be detected in the urine of patients with appendicitis. To this end, the inventors compared candidate urine protein markers as identified by using urine proteome profiling (Table 4) with tissue markers identified in a different study by using microarray gene expression of diseased appendices.[12] FIG. 6 plots RER values of the 40 most uniformly detected (U>0.7) candidate urine markers as a function of the tissue overexpression of their respective microarray profiled genes. Of these, more than 50% exhibit a positive correlation between tissue overexpression and urine enrichment (FIG. 6) demonstrating that tissue gene expression profiles are useful to identify disease markers. However, only 3 of the genes that are overexpressed in diseased as opposed to normal appendices were also identified as candidate markers by urine proteome profiling: SPRX2, lymphatic vessel endothelial hyaluronan acid receptor 1 (LYVE1), and α-1-acid glycoprotein 1 (orosomucoid 1), demonstrating that detection of markers of local disease in the urine is not solely dependent on tissue overexpression, but likely also requires other factors, such as shedding, circulation in blood, and accumulation in urine. Table 7 lists urine protein markers that were enriched in the urines of patients with appendicitis with corresponding genes that were overexpressed in diseased appendices.

In contrast to LRG which is expressed exclusively by the neutrophils, liver and the mesentery, S100-A8 is a cytokine expressed by diverse tissues, including a variety of endothelial and epithelial cells.[13,14] It is upregulated specifically in inflammatory states, including the processes of neutrophil activation and migration. Findings of its overexpression in appendiceal tissue during acute appendicitis,[12] and enrichment in the urine of appendicitis patients demonstrate that like LRG, it is also a marker of local inflammation, though its expression in a wide variety of tissues may affect its diagnostic specificity, consistent with its slightly reduced dynamic range and performance as compared to those of LRG (Table 5, FIG. 9). Accordingly, it has been found to be upregulated in a wide variety of conditions, including inflammatory bowel disease,[15] arthritis,[16] Kawasaki vasculitis'[17] cancer,[18] and sepsis.[19]

References cited in Example 3 and disclosed as superscript (i.e. "[1]") are listed below and each are incorporated herein in their entirety by reference.

1. Kentsis A, Monigatti F, Dorff K, Campagne F, Bachur R G, Steen H. Urine proteomics for profiling of human disease using high accuracy mass spectrometry. Submitted 2008.
2. Elias J E, Gygi S P. Target-decoy search strategy for increased confidence in large-scale protein identifications by mass spectrometry. Nat Methods 2007; 4:207-14.
3. Old W M, Meyer-Arendt K, Aveline-Wolf L, et al. Comparison of label-free methods for quantifying human proteins by shotgun proteomics. Mol Cell Proteomics 2005; 4:1487-502.
4. Carvalho P C, Hewel J, Barbosa V C, Yates J R, 3rd. Identifying differences in protein expression levels by spectral counting and feature selection. Genet Mol Res 2008; 7:342-56.
5. Cindik N, Baskin E, Agras P I, Kinik S T, Turan M, Saatci U. Effect of obesity on inflammatory markers and renal functions. Acta Paediatr 2005; 94:1732-7.
6. De Palo E F, Gatti R, Lancerin F, Cappellin E, Sartorio A, Spinella P. The measurement of insulin-like growth factor-I (IGF-I) concentration in random urine samples. Clin Chem Lab Med 2002; 40:574-8.
7. Skinner A M, Clayton P E, Price D A, Addison G M, Mui C Y. Variability in the urinary excretion of growth hormone in children: a comparison with other urinary proteins. J Endocrinol 1993; 138:337-43.
8. Radmacher M D, McShane L M, Simon R. A paradigm for class prediction using gene expression profiles. J Comput Biol 2002; 9:505-11.
9. Jaffe J D, Keshishian H, Chang B, Addona T A, Gillette M A, Carr S A. Accurate inclusion mass screening: a bridge from unbiased discovery to targeted assay development for biomarker verification. Mol Cell Proteomics 2008.
10. Mazzucchelli L, Hauser C, Zgraggen K, et al. Expression of interleukin-8 gene in inflammatory bowel disease is related to the histological grade of active inflammation. Am J Pathol 1994; 144:997-1007.
11. Tsuji M, Puri P, Reen D J. Characterisation of the local inflammatory response in appendicitis. J Pediatr Gastroenterol Nutr 1993; 16:43-8.
12. Murphy C G, Glickman J N, Tomczak K, et al. Acute Appendicitis is Characterized by a Uniform and Highly Selective Pattern of Inflammatory Gene Expression. Mucosal Immunol 2008; 1:297-308.
13. Passey R J, Xu K, Hume D A, Geczy C L. S100A8: emerging functions and regulation. J Leukoc Biol 1999; 66:549-56.
14. Foell D, Wittkowski H, Vogl T, Roth J. S100 proteins expressed in phagocytes: a novel group of damage-associated molecular pattern molecules. J Leukoc Biol 2007; 81:28-37.
15. Fagerberg U L, Loof L, Lindholm J, Hansson L O, Finkel Y. Fecal calprotectin: a quantitative marker of colonic inflammation in children with inflammatory bowel disease. J Pediatr Gastroenterol Nutr 2007; 45:414-20.
16. de Seny D, Fillet M, Ribbens C, et al. Monomeric calgranulins measured by SELDI-TOF mass spectrometry and calprotectin measured by ELISA as biomarkers in arthritis. Clin Chem 2008; 54:1066-75.
17. Hirono K, Foell D, Xing Y, et al. Expression of myeloid-related protein-8 and -14 in patients with acute Kawasaki disease. J Am Coll Cardiol 2006; 48:1257-64.
18. Hiratsuka S, Watanabe A, Aburatani H, Maru Y. Tumour-mediated upregulation of chemoattractants and recruitment of myeloid cells predetermines lung metastasis. Nat Cell Biol 2006; 8:1369-75.
19. Payen D, Lukaszewicz A C, Belikova I, et al. Gene profiling in human blood leucocytes during recovery from septic shock. Intensive Care Med 2008; 34:1371-6.

Example 4

Diagnostic Lateral Flow Immunoassay Test Strips-Design 1

Figure 11A:
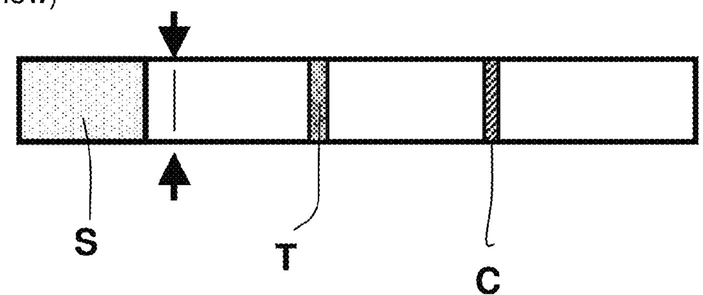
FIGS. 11A (top view) and 11B (side view) shows the schematic diagrams of an exemplary lateral flow immunoassay (LFIA) dipstick test strip for determining that the level of an appendicitis biomarker protein in urine is greater than (or increased as compared to) a predetermined reference level.

The levels of biomarker proteins described herein can be determined using lateral flow immunoassay (LFIA) test strips as illustrated in FIG. 11-12. This test strip can be used in point-of-care testing (POCT). The test strip has a sample (S) position at one end of the test strip and a control (C) position found at the opposite end the test strip (FIG.

11A). There is a test (T) position located at the middle of the test strip, between S and T. For this embodiment of a test strip, the solid support 101 can be made of plastic or other non porous material, supporting the matrix 103. Located at S is a defined quantity of dehydrated anti-biomarker protein antibody. The defined quantity of dehydrated anti-biomarker protein antibody, when rehydrated, will bind at saturation a fixed amount of biomarker antigen, meaning that this fixed amount of biomarker protein will completely occupy all of the Fv binding sites of that defined quantity of antibody. If there is additional biomarker protein in excess of the fixed amount of biomarker that is required to bind all of the amount of antibody from position S, the excess biomarker proteins will be free and are not bound to any antibody in the form of an antibody-biomarker complex. The fixed amount of biomarker protein is the predetermined reference level of biomarker protein which is the level found in healthy individuals who do not have acute appendicitis. The antibody at position S can be conjugated to colloidal gold beads or colored latex beads for visualization purposes. At position T, there is a defined quantity of biomarker protein immobilized on the test strip. This is the same biomarker protein that binds the antibody deposited at position S. At position C, there is another immobilized protein, an antibody immunoreactive to the anti-biomarker protein antibody located at the S position (FIG. 11).

The following is a description on how to use and interpret the results obtained for the test strip shown in FIG. 11. A sample of urine is applied at S. The water in the urine rehydrates the dehydrated anti-biomarker protein antibody that has been deposited at S. The dehydrated anti-biomarker protein antibody can be labeled with colloidal gold beads or colored latex beads. The biomarker protein in the urine binds to this rehydrated anti-biomarker protein antibody to form an antibody-biomarker complex. Any biomarker protein in the urine that is in excess of the rehydrated anti-biomarker protein antibody deposited at S will be free and is not bound to any antibody. A mixture of antibody-biomarker complex and free antibody or free biomarker will move by capillary action away from position S and will move toward the T position and subsequently to the C position. When the biomarker protein of interest is below the reference level, the mixture of antibody and biomarker protein will contain free anti-biomarker protein antibody and antibody-biomarker protein complexes. At position T, any free anti-biomarker protein antibody will bind to the immobilized biomarker protein at T. The localized concentration of free anti-biomarker protein antibody that is colloidal gold or latex bead labeled will become visible as a colored line at the T position (FIG. 12B). There is free antibody only when the biomarker protein in the urine is below the threshold reference value found in healthy humans, which is the predetermined reference level of biomarker protein. When the protein of interest is at or above the predetermined reference level, the mixture of antibody and biomarker protein will contain all antibody-biomarker protein complexes and no free anti-biomarker protein antibody. At the T position, there will be no anti-biomarker protein antibody captured by the immobilized biomarker protein. Thus there will be no colloidal gold or latex bead labeled anti-protein antibody accumulation, and the area remains clear (FIG. 12A). At position C, the antibody-biomarker complex formed initially at S will be bound and captured by the immobilized antibody immunoreactive against the anti-protein antibody coming from the S position. This will in turn result in a concentration of a colloidal gold or latex bead labeled anti-protein antibody accumulated at the C position and will become visible as colored line at the C position. The C position result serves as a test control to indicate that there is functional anti-protein antibody in the test material and should always be present (FIGS. 12A and 12B). When sufficient amount of labeled anti-biomarker protein antibody from the complex accumulates at C, a band becomes visible here. A band at C indicates that labeled antibody from S had moved to C. Therefore, a band at C indicates that the band at T is not a false positive. Arrowheads indicate the boundary limit that a urine sample should not cross on the test strip.

Figure 12A:
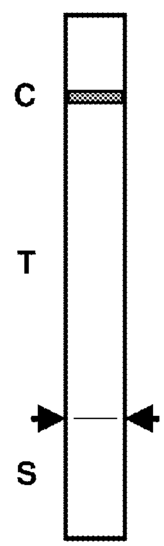
FIG. 12A-D are schematic diagrams of the top views of exemplary LFIA dipstick test strips shown in FIG. 11, showing the different results that can obtained using the simple test strip shown in FIG. 11.
Figure 12B:
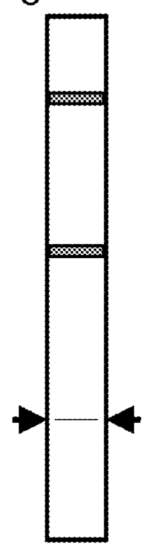
Figure 12C:
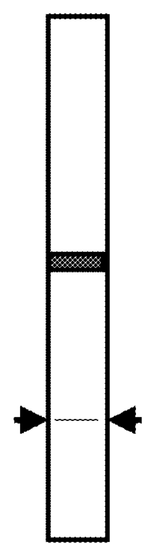
Figure 12D:
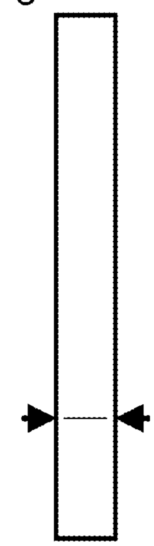

FIG. 12A-12D show the possible outcomes and interpretations of the results for such a test strip. FIG. 12A shows no band at position T but a distinct band at position C, indicating that the biomarker protein level is above predetermined reference level. Acute appendicitis is indicated. FIG. 12B shows a band at position T and a distinct band at position C, indicating that the biomarker protein level is below predetermined reference level. Acute appendicitis is not indicated. FIG. 12C shows a band at position T but no band at position C, indicating that the data at T may be a false positive. FIG. 12D shows no band at either positions T and C, indicating the data at T may be a false negative. Both FIGS. 12C and 12D indicate invalid data and the lateral flow immunoassay should be repeated with a new test strip.

The defined quantity of dehydrated anti-protein antibody at S position is such that there is just enough antibody to bind the biomarker protein from the sample (e.g. urine) when the biomarker protein is at the reference/control level. The reference/control level can be the level of the biomarker found in the samples of healthy individuals. Therefore, when the biomarker protein is at or above the reference level, all of the anti-biomarker antibody at the S position will be bound to the biomarker protein in the form of biomarker protein-antibody complex; there will be no free anti-biomarker protein antibody present.

The choice of the anti-biomarker protein antibody placed at the S position can be any antibody that is specifically immunoreactive to any of the proteins of interest, e.g. biomarker described herein. The antibody can be monoclonal, polyclonal, or a mixture of both monoclonal and polyclonal antibodies. Antibody-based moiety can also be used.

Figure 13:
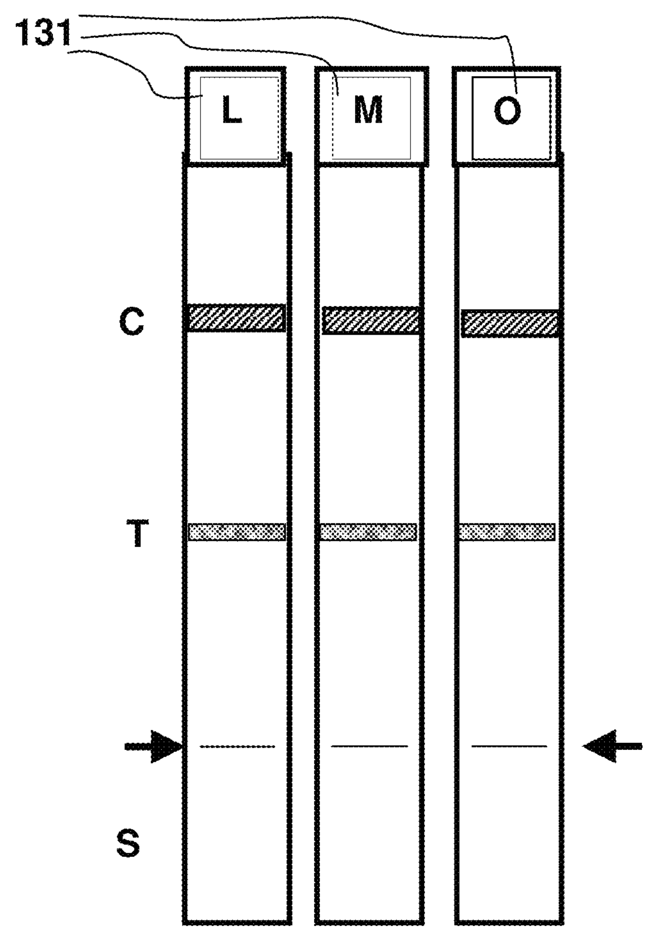
FIG. 13 shows a schematic diagram of how the levels of three biomarker proteins can be determined simultaneously using three independent LFIA test strips, one test strip for a different biomarker protein. A diagnostic kit can comprise several LFIA test strips, one strip for a different biomarker protein.

When only one biomarker protein is studied, the S position should have only one anti-biomarker protein antibody that specifically immunoreactive with just that one biomarker of interest (FIG. 13). A kit comprising test strips for use as POCT can have several single biomarker protein test strips. The kit can test for only one biomarker or more then one biomarker proteins. In this embodiment, the test strip can be labeled 131 on one end to identify the biomarker protein the test strip is used for, e.g. the label “L” represents leucine α-2 glycoprotein (LRG); “M” represents mannan-binding lectin serine protease 2 (MASP2); and “O” represents α-1-acid glycoprotein 1 (ORM) (see FIG. 13). On the other hand, if more than one, e.g. three biomarker proteins are to be studied simultaneously, the S position can have three different types of anti-biomarker protein antibodies, each type specifically immunoreactive to one biomarker protein and does not exhibit cross-reactivity with the other two non-ligand proteins (FIG. 14). Arrowheads indicate the boundary limit that sample should not cross on the membrane. At positions T or C, up to three bands can be visible, each band corresponding to each of the biomarker protein that is being tested. When three proteins are to be studied simultaneously, all three protein types can be represented at the T position and at their respective quantities (FIG. 14). FIG. 14 shows an alternative design where three proteins can be studied simultaneously on the same test strip. The positions of the expected results in the T and C positions for each biomarker are indicated 141.

Figure 11B:
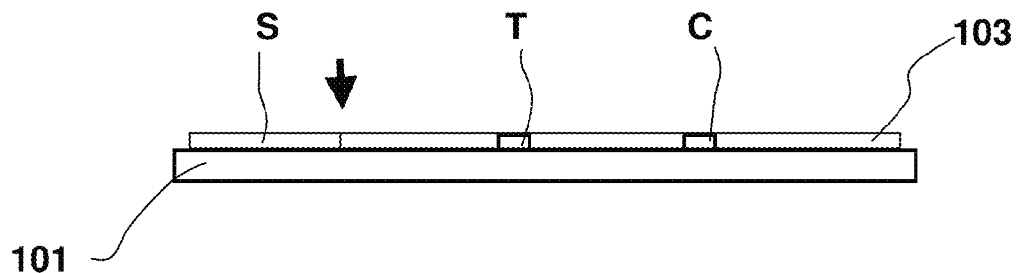

The test strip can be designed in a form of a dipstick test strip (FIG. 11B). As a dipstick test strip, the strip is dipped into a sample (e.g. urine) at the S position end with sample level not to exceed the boundary limit. The strip is then laid horizontally with the membrane surface facing up on a flat surface. A fixed amount of time is given for the antibody re-hydration, capillary action, and antibody biomarker protein binding reaction to take place. At the end of the fixed time, there should be visible bands at the C position and depending on the level of the protein of interest, there may or may not be a visible band at the T position (FIG. 12). FIG. 13 shows a method of using three separate dipstick test strips to test for the three biomarkers of interest. Each dipstick test strip is labeled 131 to indicate which biomarker protein is being tested. A diagnostic kit can comprise multiple types of single biomarker test strips, a type for each biomarker of interest.

Example 5

Diagnostic Lateral Flow Immunoassay Test Strips-Design 2

An alternative embodiment of the lateral flow immunoassay (LFIA) test strips for determining the level of biomarker protein level is illustrated in FIG. 15A-D. This test strip can be used in point-of-care testing. Here the test strip contains two different anti-biomarker protein antibodies specific for the same biomarker, each antibody binds the biomarker at a different epitope. This is a double sandwich LFIA test strip. The first antibody is labeled (e.g. colored latex beads), deposited on the solid support matrix but is not immobilized on it, (i.e. the antibody is mobile), and is deposited in excess at the S position. The second anti-biomarker protein antibody is not labeled but is immobilized and is in excess at position T. This second anti-biomarker protein antibody binds an epitope on the biomarker that is not affected by the binding of the first antibody. At position C, there is an excess of non-labeled antibody against the anti-biomarker antibody deposited at the S position. The antibody at C serves to capture any free labeled anti-biomarker antibody migrating from S. When sufficient free labeled anti-biomarker antibody is accumulated at C, a visible band appears. The band is a control to confirm that the band(s) observed on the test strip at T are due to the mobile antibody at the S position.

Figures 15A, 15B, 15C, 15D:
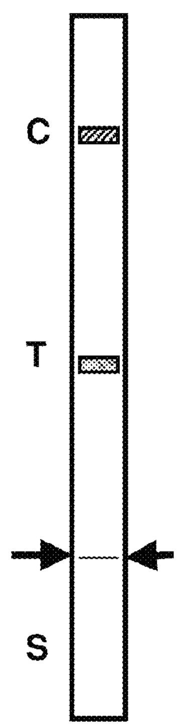
FIG. 15A-D are schematic diagrams of an alternative embodiment of an exemplary LFIA dipstick test strip shown in FIG. 11 for determining whether the level of a biomarker protein in a fluid sample is above or below a reference/control value for that biomarker and the interpretation of the results obtained. Two different anti-biomarker antibodies are used on the test strip.
Figure 16A:
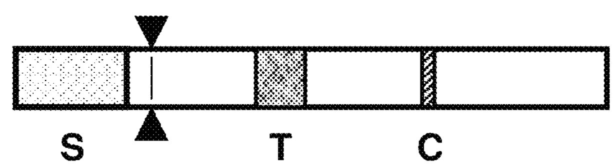
FIGS. 16A (top view) and 16B (side view) shows a schematic diagram of an alternative embodiment of a LFIA test strip for determining the level of a biomarker protein in a fluid sample and comparing the determined level with a reference value. S, T, C definition are as in FIG. 11.

Initially before use, there is no visible band at position T and C of the test strip (FIG. 15B). When a fluid sample (e.g. urine) is place at the S position, the water in the urine rehydrates the dehydrated anti-biomarker protein antibody that has been deposited at S. The dehydrated anti-biomarker protein antibody can be labeled with colloidal gold beads or colored latex beads. The biomarker protein in the urine binds to this rehydrated anti-biomarker protein antibody to form an antibody-biomarker complex. A mixture of free anti-biomarker antibody and biomarker protein:antibody complexes is formed. The mixture migrates by capillary action towards the T and the C positions. The second anti-biomarker antibody immobilized at T will capture all the biomarker protein: antibody complexes but not the free anti-biomarker protein antibody. The localized concentration of anti-biomarker protein:antibody complexes that is colloidal gold or latex bead labeled will become visible as a colored line at the T position (FIG. 15C). Only when the biomarker protein is at or above the reference level will sufficient labeled antibody be captured at T to produce a visible band (FIG. 15C). When the biomarker is below the reference level, no visible band should appear at the T position (FIG. 15D).

At position C, free anti-biomarker antibody initially from S will be bound and captured by the immobilized antibody immunoreactive against the antibody coming from the S position. This will in turn result in a concentration of a colloidal gold or latex bead labeled anti-protein antibody accumulated at the C position and will become visible as colored line at the C position. The C position result serves as a test control to indicate that there is functional anti-protein antibody in the test material and should always be present. A band at C indicates that labeled antibody from S had moved to C. Therefore, a band at C indicates that the band at T is not a false positive or that the absence of a band at T is a false negative.

Example 6

Diagnostic Lateral Flow Immunoassay Test Strips-Design 3

An alternative embodiment of the lateral flow immunoassay (LFIA) test strips for determining the level of biomarker protein level is illustrated in FIG. 16. This test strip can be used in point-of-care testing. The test strip is as described in FIG. 11 having a sample (S), a test (T), and a control (C) positions, all three spatially arranged as shown in FIG. 11 and FIG. 15. For this embodiment of a test strip, the solid support 161 can be made of plastic or other non porous material, supporting the matrix 163. In this embodiment, the S position contain an excess amount of dehydrate anti-biomarker protein antibody (first antibody) that can be labeled (e.g. colloidal gold or color latex bead). Similar to the embodiments in FIG. 11-14, the anti-biomarker protein antibody at S is mobile; once the antibody is re-hydrated, the antibody moves by capillary action towards the T and C positions.

The T position contains a second anti-biomarker protein antibody that is also immunoreactive to the biomarker protein of interest, but to a different epitope on the biomarker (FIG. 16). This second antibody is in excess and is immobilized on the matrix. This second anti-biomarker protein antibody binds a part of the biomarker protein that is different from the part of the protein that is bound by the first anti-biomarker protein antibody found at the S position. In this embodiment, the second antibody at the T position will bind and capture both free unbound biomarker protein and biomarker protein-antibody complexes, and concentrate them at the T position.

Figure 16B:
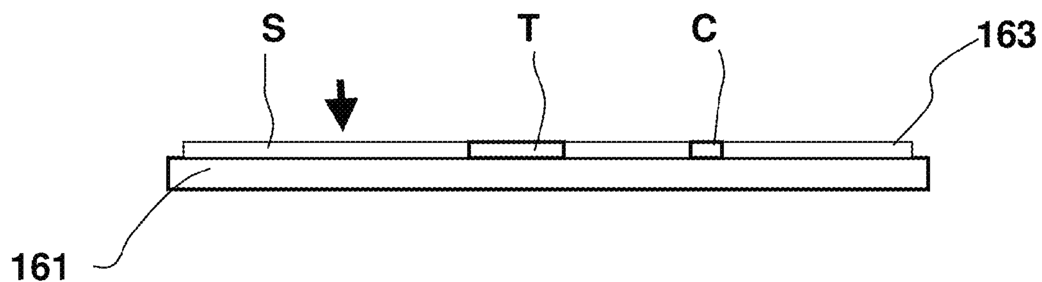
Figure 17A:
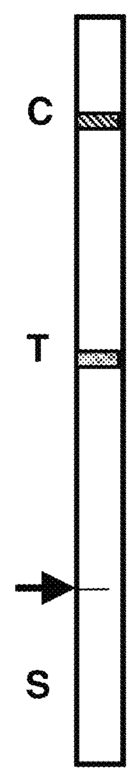
FIG. 17A-F are schematic diagrams showing the different results that can obtained using the LFIA test strip shown in FIG. 16.
Figure 17B:
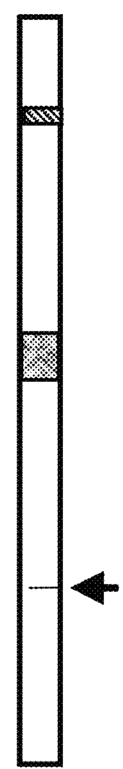

The C position contains a defined quantity of biomarker protein immobilized on the membrane (FIG. 16B). The defined quantity is the predetermined reference value of the biomarker protein being analyzed on the test strip. The reference/control level can be the level of the biomarker found in the samples of healthy men. When the excess free anti-biomarker protein antibody from the S position arrives and bind the immobilized biomarker protein at C, gradually accumulation at C produces a concentration of labeled first antibody will become visible as a colored line at the C position (FIG. 17A, B, D).

An application of a fluid sample (e.g. urine) at the S position will re-hydrate the excess amount of anti-biomarker protein antibody there. All of the biomarker protein of interest should be bound to the excess anti-biomarker protein antibody. A fluid mixture of free biomarker protein antibody and biomarker protein-antibody complex is formed and will move along the membrane by capillary action towards the T position and then subsequently to the C position. At the T position, all of the biomarker protein-antibody complex will be captured and immobilized by the second anti-biomarker protein antibody. The localized concentration of biomarker protein-antibody complexes, wherein the anti-biomarker protein antibody that is colloidal gold or latex bead labeled, will become visible as a colored line at the T position (FIG. 17A, B, D). With increasing amount of biomarker protein-antibody complexes and concentrated at the T position, the colored line expands and develops into a band. The greater the level of biomarker in the sample, the wider the colored band at the T position (FIGS. 17A and B).

Figure 17C:
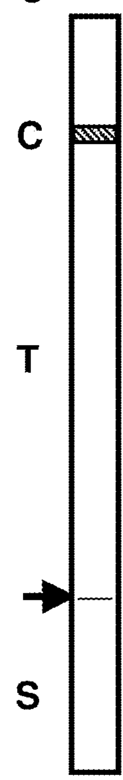
Figure 17D:
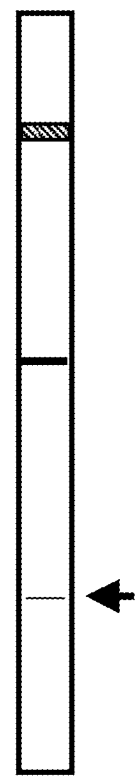
Figures 17E, 17F:
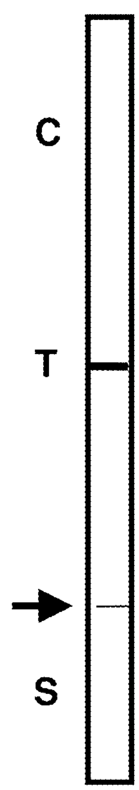

When excess free anti-biomarker protein antibody from the S position arrives to the C position and bind to the immobilized reference amount of biomarker protein there, another color line become visible. Since there is a reference amount of immobilized biomarker protein at the C position, the thickness of the visible colored line at the C position defines the reference value of protein. By comparing the thickness of the color band at the T and C positions on the same test strip, one can estimate whether the biomarker protein level is below or greater than the reference value of the protein. When the biomarker protein level is equal or greater than the reference value, the color band at the T position will be equal or larger than the color band at the C position respectively (FIGS. 17A and B). Acute appendicitis is indicated. When the biomarker protein level is below the threshold level, the color band at the T position will be smaller or even absent than the color band at the C position (FIGS. 17C and D). Acute appendicitis is not indicated. The C position band also serves as a test control to confirm that there is functional anti-protein antibody at the S position and that the functional anti-biomarker protein antibody is derived from the S position (FIGS. 17E and F). FIG. 17E shows a band at position T but no band at position C, indicating that the data at T may be a false positive. FIG. 17F shows no band at either positions T and C, indicating the data at T may be a false negative. Both FIGS. 17E and 17F indicate invalid data and that the lateral flow immunoassay should be repeated with a new test strip.

When only one biomarker protein is studied, the S position should have only one anti-biomarker protein antibody that specifically immunoreactive with just that one biomarker of interest. A kit comprising test strips for use as POCT can have several single biomarker protein test strips. The kit can test for only one biomarker or more then one biomarker proteins. In this embodiment, the test strip can be labeled 181 on one end to identify the biomarker protein the test strip is used for, e.g. the label “L” represents leucine α-2 glycoprotein (LRG); “M” represents mannan-binding lectin serine protease 2 (MASP2); “O” represents α-1-acid glycoprotein 1 (ORM) and “S” represents α-1-antichymotrypsin (SERPINA3) (see FIG. 18). On the other hand, if more than one, e.g. three biomarker proteins are to be studied simultaneously, the S position can have three different types of anti-biomarker protein antibodies, each type specifically immunoreactive to one biomarker protein and does not exhibit cross-reactivity with the other two non-ligand proteins (FIG. 19). FIG. 19 shows an alternative embodiment of a test strip where three biomarker proteins can be studied simultaneously on the same test strip. The positions for each biomarker on the single strip are indicated 191.

Figure 18:
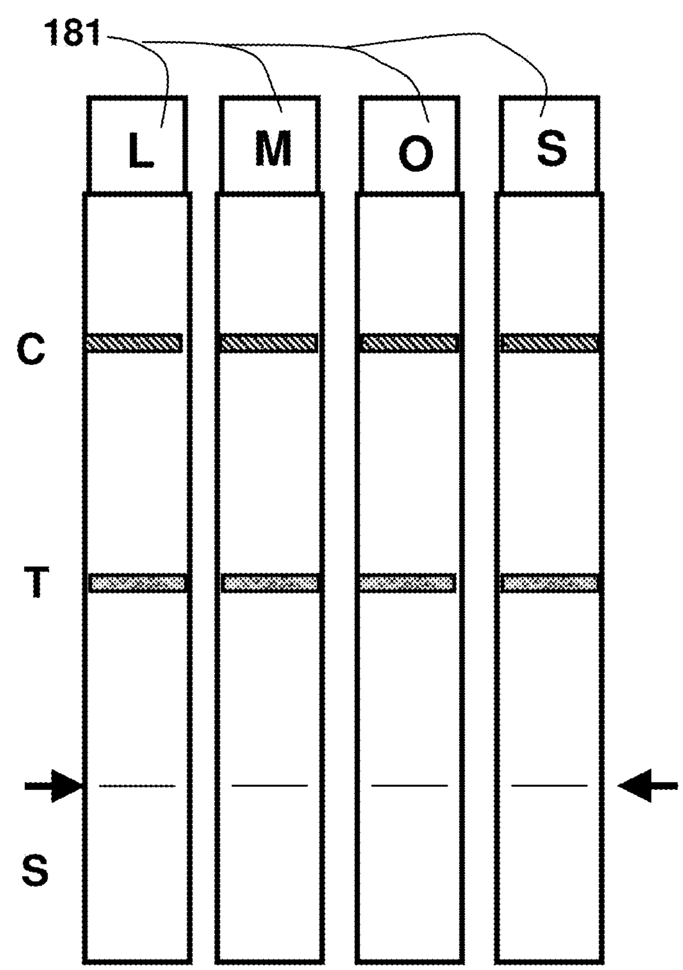
FIG. 18 shows a schematic diagram of an alternative version on how the levels of four biomarker proteins can be determined simultaneously using four separate LFIA test strips, one test strip for a different biomarker protein. A diagnostic kit can comprise multiple LFIA test strips, one strip for a different biomarker protein.

The test strip can be designed in a form of a dipstick test strip (FIG. 16B). As a dipstick test strip, the strip is dipped into a sample (e.g. urine) at the S position end with sample level not to exceed the boundary limit. The strip is then laid horizontally with the membrane surface facing up on a flat surface. A fixed amount of time is given for the antibody re-hydration, capillary action, and antibody biomarker protein binding reaction to take place. At the end of the fixed time, there should be visible bands at the C position and depending on the levels of the biomarker protein(s) of interest, there may or may not be a visible band at the T position (FIGS. 18 and 19) and the bands can be a different thickness. FIG. 18 shows a method of using four separate dipstick test strips to test for the four biomarkers of interest. Such test strip can be the component of a diagnostic kit. Each dipstick test strip is labeled 181 to indicate which biomarker protein is being tested. A diagnostic kit can comprise multiple types of single biomarker test strips, a type for each biomarker of interest.

What is claimed:

1. A method of treating a subject in need thereof comprising:

(a) performing an assay to measure for an increase in the level of a first acute appendicitis protein biomarker α-1-acid glycoprotein 1 (ORM), in a urine sample obtained from the subject, wherein the subject exhibits at least right-lower quadrant abdominal pain or tenderness, a symptom of acute appendicitis, and wherein the subject is suspected of having acute appendicitis;

(b) diagnosing the subject with acute appendicitis when an increased ORM level of at least 2-fold over a reference level is detected, wherein the reference level is the ORM level from a control group of subjects without acute appendicitis and having an appendicitis-like symptom;

(c) selecting the subject with acute appendicitis from step (b) for appendicitis treatment; and (d) administering an appropriate appendicitis treatment comprising surgery.

2. The method of claim 1 further comprising measuring for an increase in the level of at least one second acute appendicitis biomarker protein, wherein the second biomarker protein is selected from a group consisting of calgranulin A (S100-A8), plasminogen (PLG), mannan-binding lectin serine protease 2 (MASP2), Zinc-α-2-glycoprotein (AZGP1), α-1-antichymotrypsin (SERPINA3) and apolipoprotein D (ApoD), adipocyte specific adhesion molecule, AMBP, amyloid-like protein 2, angiotensin converting enzyme 2, BAZ1B, carbonic anhydrase 1, CD14, chromogranin A, FBLN7, FXR2, hemoglobin α, hemoglobin β, interleukin-1 receptor antagonist protein, inter-α-trypsin inhibitor, lipopolysaccharide binding protein, lymphatic vessel endothelial hyaluronan acid receptor 1, MLKL, nicastrin, novel protein (Accession No: IPI00550644), PDZK1 interacting protein 1, PRIC285, prostaglandin-H2 D-isomerase, Rcl, S100-A9, serum amyloid A protein, SLC13A3, SLC2A1, SLC2A2, SLC4A1, SLC9A3, SORBS1, SPRX2, supervillin, TGFbeta2R, TTYH3, VA0D1, vascular adhesion molecule 1, versican, VIP36, α-1-acid glycoprotein 2, and β-1,3-galactosyltransferase.

* * * * *